US010671806B2

(12) United States Patent
Tsabba

(10) Patent No.: US 10,671,806 B2
(45) Date of Patent: Jun. 2, 2020

(54) CUSTOMIZED CUSTOMER RELATIONSHIP MANAGEMENT PLATFORM METHOD AND DEVICES

(71) Applicant: Binyamin Tsabba, Elyachin (IL)

(72) Inventor: Binyamin Tsabba, Elyachin (IL)

(*) Notice: Subject to any disclaimer, the term of this patent is extended or adjusted under 35 U.S.C. 154(b) by 0 days.

(21) Appl. No.: 16/550,197

(22) Filed: Aug. 24, 2019

(65) Prior Publication Data
US 2020/0110796 A1 Apr. 9, 2020

Related U.S. Application Data

(63) Continuation-in-part of application No. 16/214,045, filed on Dec. 8, 2018.

(60) Provisional application No. 62/741,489, filed on Oct. 4, 2018.

(51) Int. Cl.
| G06F 17/00 | (2019.01) |
| G06F 40/174 | (2020.01) |
| G06F 21/40 | (2013.01) |
| G16H 15/00 | (2018.01) |
| G06F 8/38 | (2018.01) |
| G06F 3/0486 | (2013.01) |
| G06F 40/186 | (2020.01) |

(52) U.S. Cl.
CPC .......... *G06F 40/174* (2020.01); *G06F 3/0486* (2013.01); *G06F 8/38* (2013.01); *G06F 21/40* (2013.01); *G06F 40/186* (2020.01); *G16H 15/00* (2018.01)

(58) Field of Classification Search
CPC .... G06F 17/243; G06F 16/211; G06F 17/248; G06F 40/174
See application file for complete search history.

(56) References Cited

U.S. PATENT DOCUMENTS

| 9,258,423 | B1* | 2/2016 | Beall | H04M 3/5158 |
| 2006/0271352 | A1* | 11/2006 | Nikitin | G06F 17/289 |
| | | | | 704/9 |
| 2007/0250769 | A1* | 10/2007 | Bass | G06F 17/243 |
| | | | | 715/234 |
| 2008/0046292 | A1* | 2/2008 | Myers | G06Q 50/24 |
| | | | | 705/3 |
| 2008/0255838 | A1* | 10/2008 | Callaghan | G06Q 10/10 |
| | | | | 704/235 |
| 2013/0097480 | A1* | 4/2013 | Allison | G06Q 10/10 |
| | | | | 715/223 |

(Continued)

*Primary Examiner* — Andrew T McIntosh

(57) ABSTRACT

The embodiments disclose a method including providing a website interface within the customizable application builder with no code visualization tools for an application creation user, providing a form builder for creating at least one form, with at least one form element for receiving form input from an end user, with a conditional rule builder, an auto pdf mapping tool, a manual pdf mapping tool and at least two dynamic pdf mapping tools, wherein each of the pdf mapping tools has no code visualization tools and allows the user to drag and drop form elements onto a pdf format, wherein the auto pdf mapping tool automatically generates a pdf of the entire form, wherein the manual pdf mapping tool automatically generates a customizable pdf of the form, and wherein the dynamic pdf mapping tool user may edit the blank html template and dynamically generates a customizable pdf of the form.

20 Claims, 77 Drawing Sheets

(56) References Cited

U.S. PATENT DOCUMENTS

2013/0174014 A1\* 7/2013 Kwan ...................... G06F 8/36
715/234

\* cited by examiner

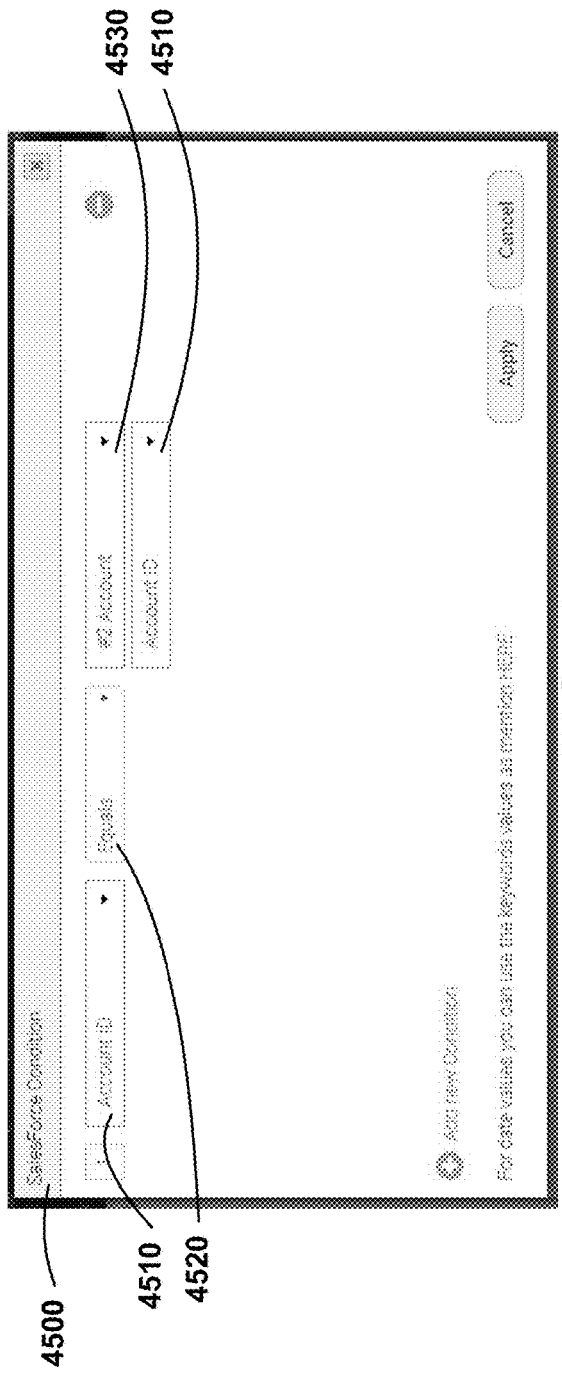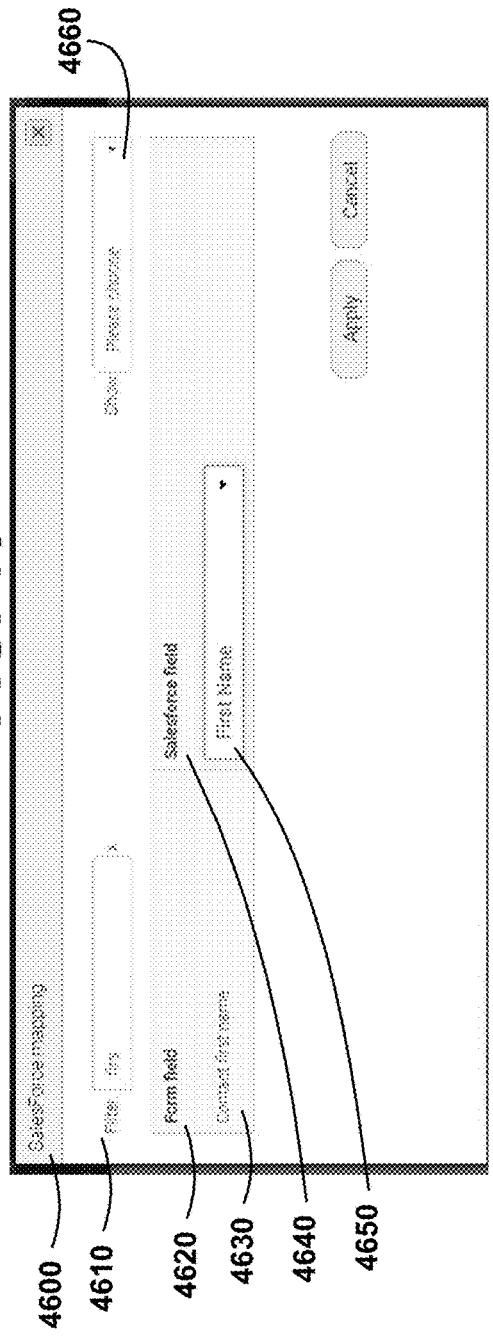

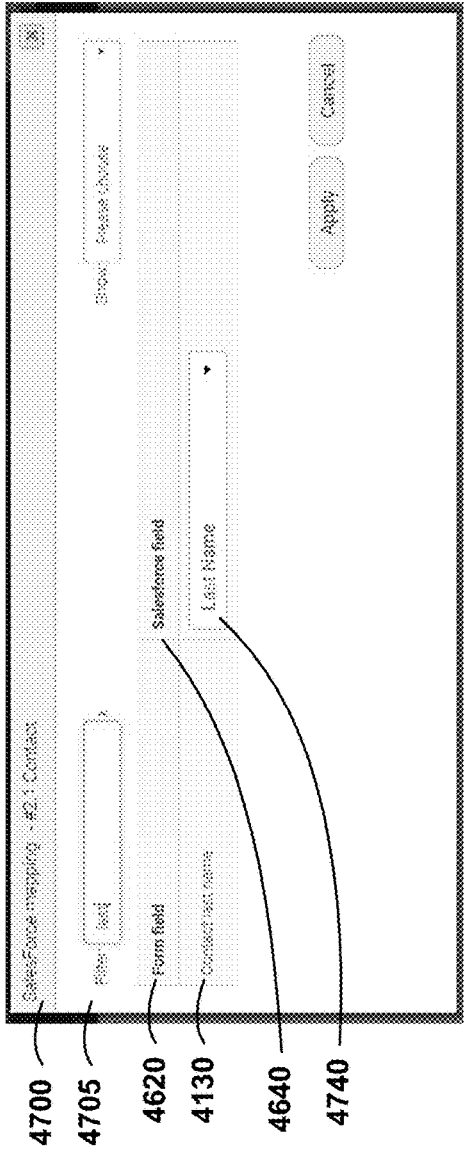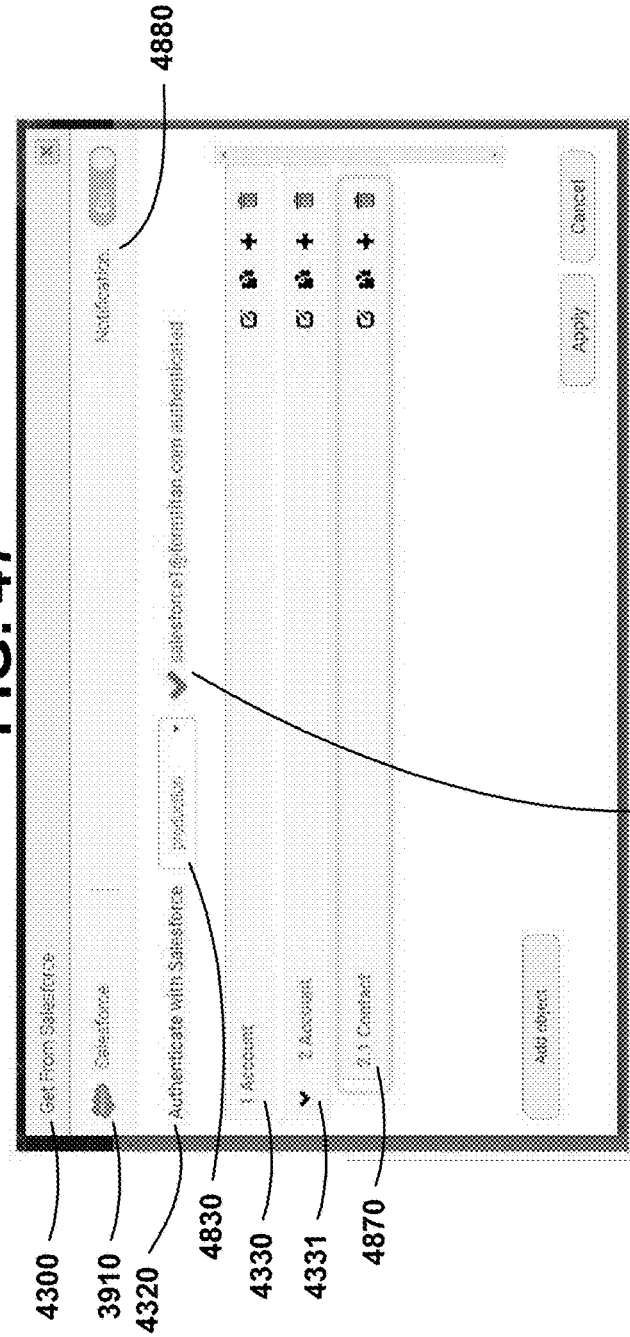
FIG. 47
FIG. 48

7900 — BI DIRECTIONAL, REAL-TIME INTEGRATION WITH SALESFORCE

7910 — BI DIRECTIONAL, REAL-TIME INTEGRATION IS USED TO ALLOW DATA TO SYNC IN ALL THE RELEVANT PLACES, TO HELP MAINTAIN A CLEAN DATABASE, PREVENT DATA DUPLICATION, PROVIDE THE MOST UP TO DATE INFORMATION AND FREE A USER FROM MANUAL DATA ENTRY

7920 — DATA INTEGRATION IS SETTING UP AUTOMATIC RECORD CREATION WITHIN THE USER CRM WHENEVER A POTENTIAL LEAD FILLS OUT THE USER WEBSITE CONTACT FORM

7930 — TO DRAW CONTACT DETAILS FROM A USER SALESFORCE ACCOUNT AND HAVE THE CONTACT DETAILS POPULATED IN THE FORM FIELDS, SO IF THE USER IS ALREADY LISTED IN THE USER CRM THE CONTACT WOULD NOT HAVE TO TYPE IN THEIR DETAILS AGAIN

7940 — TWO DIFFERENT OPERATIONS ARE INCORPORATED INTO THE INTEGRATION SETUP

7942 — READING DATA FROM SALESFORCE OBJECTS, WHICH IS CALLED "GET"

7944 — WRITING DATA TO SALESFORCE OBJECTS, WHICH IS CALLED "PUSH"

7950 — A USER MAY CREATE A FORM WHICH ONLY GETS DATA, OR A FORM THAT ONLY PUSHES DATA OR COMBINE THE TWO OPERTIONS AND CREATE A DUAL INTEGRATION FORM

7960 — THE USER MAY ALSO USE A SPECIAL TABLE ELEMENT FOR WORKING WITH SALESFORCE WHEREIN THE USER SETS UP THE SPECIAL TABLE CONFIGURED TO ONLY RETRIEVE THE "GET" SIDE OF THE INTEGRATION, AND THE "PUSH" SIDE OF THE INTEGRATION IS CREATED AUTOMATICALLY BASED ON THE "GET" DATA

FIG. 79

100 # CUSTOMIZED CUSTOMER RELATIONSHIP MANAGEMENT PLATFORM METHOD AND DEVICES

CROSS-REFERENCE TO RELATED APPLICATIONS

This Patent application claims priority to United States patent application entitled: "CUSTOMIZED CUSTOMER RELATIONSHIP MANAGEMENT PLATFORM METHOD AND DEVICES", U.S. Ser. No. 62/741,489 filed on Oct. 4, 2018, the U.S. patent application being incorporated herein by reference.

BACKGROUND

Methods and devices to create forms have been around a while. Paper forms only provide a rudimentary way to gather data that must be manually processed into a useful management and personnel tool. The advent of computer has elevated the manual task associated with form gathered data to one of more automated systems. But what has been lacking is truly user friendly systems that automate not just the data recovery and organization but expands the ease with which a user can interface with the devices and automated system to not only create a form but to gain more information from the form creation and responses the exists deeper in the content and context. The integration with other systems will assist a user in not having to duplicate the form creation task and broaden the market for gathering data and reducing the time and effort to analyze the data into useful tools for management and customer relations.

BRIEF DESCRIPTION OF THE DRAWINGS

FIG. 45 shows for illustrative purposes only an example of integration Salesforce condition of one embodiment.

FIG. 46 shows for illustrative purposes only an example of integration Salesforce mapping corresponding fields of one embodiment.

FIG. 47 shows for illustrative purposes only an example of integration Salesforce mapping contact of one embodiment.

FIG. 48 shows for illustrative purposes only an example of integration Salesforce get contact of one embodiment.

FIG. 79 shows a block diagram of an overview of bi directional, real-time integration with Salesforce of one embodiment.

DETAILED DESCRIPTION OF THE INVENTION

Figure 1:
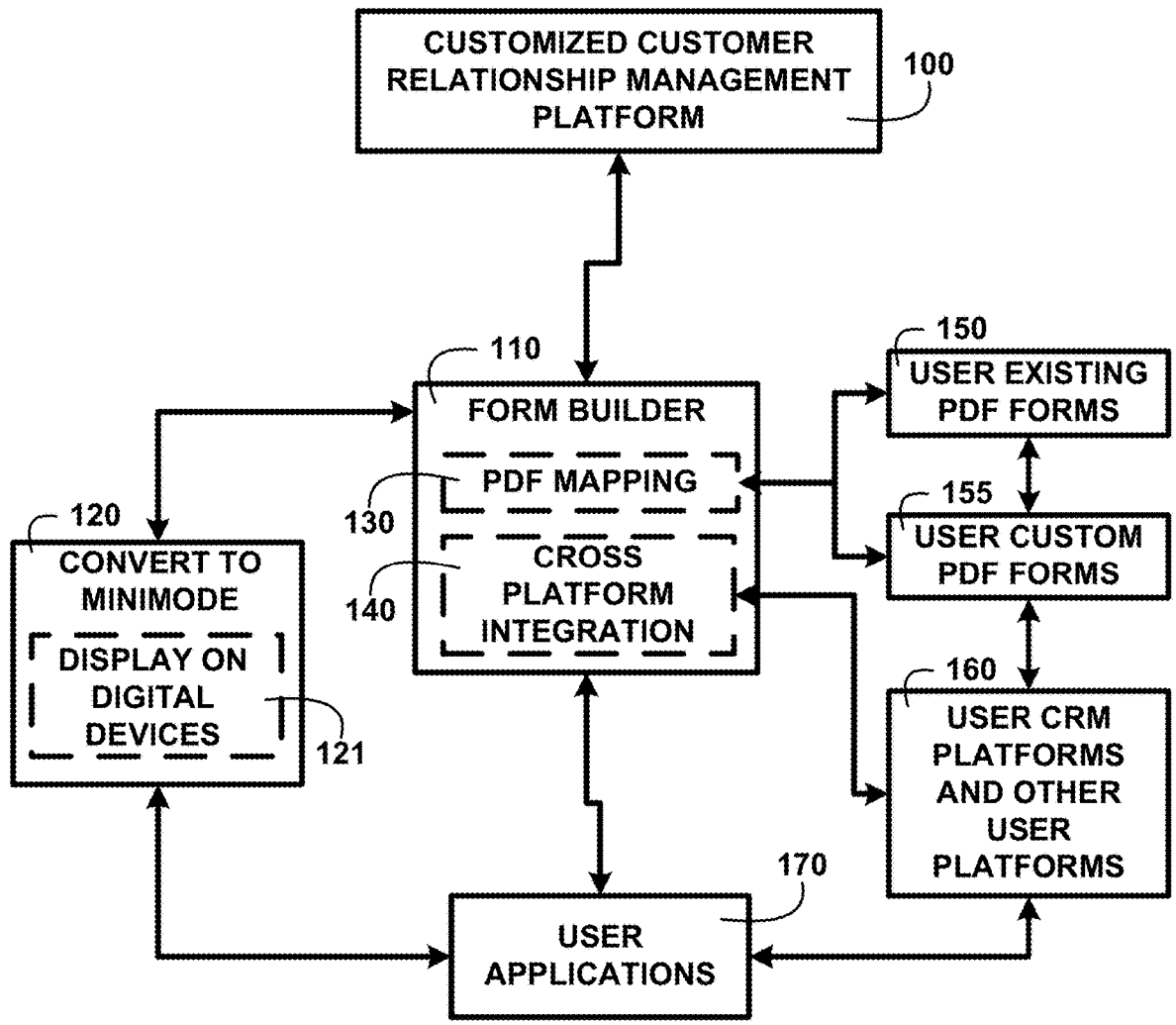
FIG. 1 shows a block diagram of an overview of a customized customer relationship management platform method and devices of one embodiment.

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview:

It should be noted that the descriptions that follow, for example, in terms of customized customer relationship management platform method and devices is described for illustrative purposes and the underlying system can apply to any number and multiple types of application uses. In one embodiment of the present invention, the customized customer relationship management platform method and devices can be configured using a user existing pdf form to overlay interactive pdf mapping elements to create an html interactive pdf form. The customized customer relationship management platform method and devices can be configured to include creating a new html interactive pdf form using a dynamic pdf mapping device and can be configured to include creating an html form using an auto pdf mapping device. The customized customer relationship management platform method and devices can be configured to include integration of the html interactive pdf form created with third party customer relationship management and other types of platforms using the present invention.

"Customized customer relationship management platform method and devices", "Customized customer relationship management platform", "Customized customer relationship management" are terms used herein and can additionally be expressed without any change in meaning as "FormTitan" in any case lower, upper or mixed.

"a form filler" phrase herein means a user filling out entries in a customized customer relationship management form builder created form.

Customized customer relationship management platform method and devices create a powerful cloud based platform for creating online forms, applications, landing pages and portals. Designed for any type of business ranging from small nonprofits to large enterprises. Customized customer relationship management platform method and devices offers Smart integrations, conditional logic, document generation, payments, Lead generation, surveys as well as Innovative bidirectional Salesforce and dynamic CRM integrations. Smart integrations, bidirectional Salesforce and dynamic CRM integrations also include settings including auto save/push, auto pull, auto translate, custom translate, and phone survey.

Auto save/push and auto pull selections for example when selected in the settings will automatically save the data entered in the FormTitan customized form but also simultaneously in the CRM integrated system for example Salesforce without the user having to enter any additional commands. The auto function feature of push and pull will enter, delete and edit any added or edited data automatically without the user having to enter any additional commands on both forms in both FormTitan and the CRM integrated system including Salesforce using the bidirectional feature.

The CRM integrated system includes a PDF Interactive mode for inline editing of PDFs from a PDF preview window. The CRM integrated system includes Smart Validation (Smart V) for Salesforce including additional security for a user's forms configured for 2FA (Two Factor Authentication) and 1FA (One Factor Authentication). The CRM integrated system includes a voice control element configured to allow the text of a user's form to be spoken to a filler pronouncing the names of the fields and their user tips out loud and wherein the voice control element for receiving a filler's spoken input, recognize the filler's speech, enter the filler's oral text in the input boxes of the form, create a new blank form and drag a textbox element and a numeric element into a form. The CRM integrated system includes Conditional logic to affect fields, sections and pages in a form: to Hide/show, enable/disable, set values etc. and use Value rules to determine what values the fields should or should not accept. The CRM integrated system includes at least one form element including a MINI mode element wherein a work area will have a maximum width of 180 px for use on digital devices with narrow display screens.

Auto translate and custom translate settings will allow the user to build their form in a selected language and an online form that needs to be displayed in several languages, you can use our Auto Translate optimization to easily have it presented to your foreign users with in their native language. In some cases you may find the automatic translation insufficient or not precise enough for technical terms, or even simple words with multiple meanings and need to translate things yourself. When using custom translate settings you can control all the labels, captions, user tips, button text in your form, and you can create different translations to as many languages as you want. Other features used in translation include Custom Translation allows Paragraph manual translation, and Translation for Table mandatory message—added to captions. HIPAA, GDPR and other compliances are supported as well of one embodiment.

The phone survey feature allows a user to use account phone numbers from a simple table they have created that includes account phone numbers for example to map for example Salesforce country and State picklists of the account phone numbers. The mapped account phone numbers can then be used to conduct a phone survey on a user selected service or product to determine the picklist accounts sentiments and opinions of the selected service or product of one embodiment.

FIG. 1 shows a block diagram of an overview of a customized customer relationship management platform method and devices of one embodiment. FIG. 1 shows a block diagram of an overview of a customized customer relationship management platform method and devices of one embodiment. FIG. 1 shows a customized customer relationship management platform 100. The customized customer relationship management platform method and devices is a user interface to create interactive pdf forms for use with user applications. The interactive pdf forms are created by a user without the use of coding using the features and elements of the customized customer relationship management platform method and devices to build forms that user clients and other can readily use to enter data that is accessible to the user. Customized customer relationship management platform method and devices can integrate other platforms including customer relationship management (CRM) and other types of platforms to populate the other platforms with the customized customer relationship management platform method and devices created pdf forms quickly and productively for their applications. The customized customer relationship management platform 100 includes features including a form builder 110 with pdf mapping 130 and cross platform integration 140. The customized customer relationship management platform 100 includes a digital process to convert to minimode 120 to display on digital devices 121. The customized customer relationship management platform 100 provides processes for a user to create interactive pdf forms from user existing pdf forms 150, create interactive user custom pdf forms 155, and integrate user CRM platforms and other user platforms 160 into the customized customer relationship management platform 100 to facilitate the use for user applications 170 of one embodiment.

FIG. 1 shows a customized customer relationship management platform method and devices customized customer relationship management platform. The customized customer relationship management platform includes a form builder feature. The form builder feature includes pdf mapping for converting user existing pdf forms into responsive PDF forms and for creating new responsive user custom pdf forms. The form builder feature includes cross platform integration to allow a user to use the form builder created forms on $3^{rd}$ party user CRM platforms and other user platforms. Access to the customized customer relationship management platform can be customized to display without losing any functionality to a display on digital devices a user chooses with a feature to convert to mini mode. The mini mode feature is used to convert the function access to a size that fits the screen size of the user digital device. The customized customer relationship management platform includes a number of different types of forms or user's activities that can be configured into a form format can be created for use on a wide range of user applications. The customized customer relationship management platform includes a number of features including the Form Builder, Account features, Form optimization, Push Integrations, Form design, Data Collection, Data analysis and others. The customized customer relationship management platform includes function products for example for Business including PDF Mapping, Targeting and Workflow, functions for Optimization including CRO, A/B Testing, Auto Translate for multi-lingual conversions, and Online Chat and functions for customer relationship management (CRM) including for example Salesforce, Dynamic 365 and others. A user can use the Online Chat to get assistance and other help functions including Q&A for asking us questions is the fastest and most effective way to get assistance, FAQ for answers to commonly asked questions, TOPICS including a complete index of the FormTitan topics organized by categories, FEATURES for greater detail in the topics directory to find the feature you are looking for and CONTACT to simply send in an inquiry of one embodiment.

Figure 2:
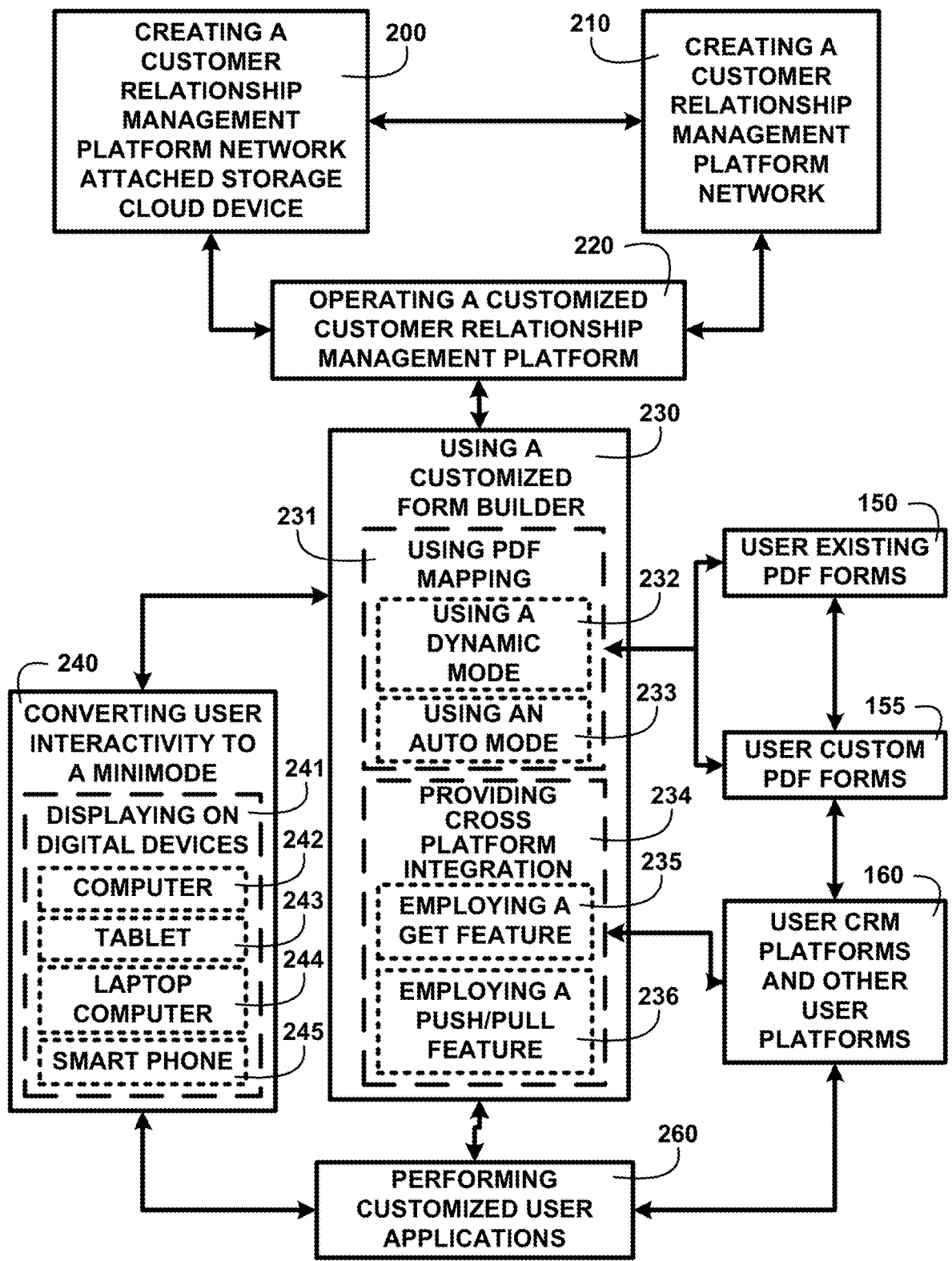
FIG. 2 shows a block diagram of an overview flow chart of a customized customer relationship management platform method and devices of one embodiment.

Overview Flow Chart:

FIG. 2 shows a block diagram of an overview flow chart of a customized customer relationship management platform method and devices of one embodiment. FIG. 2 shows creating a customer relationship management platform network 210 and creating a customer relationship management platform network attached storage cloud device 200. Operating a customized customer relationship management platform 220 includes using a customized form builder 230 with features for using pdf mapping 231, using a dynamic mode 232 and using an auto mode 233. Using a customized form builder 230 includes providing cross platform integration 234 employing a get feature 235 and employing a push/pull feature 236. Converting user interactivity to a minimode 240 for displaying on digital devices 241 includes a computer 242, a tablet 243, a laptop computer 244 and a smart phone 245. Using a customized form builder 230 includes creating interactive pdf forms from user existing pdf forms 150 and user custom pdf forms 155. Using a customized form builder 230 includes integrating user CRM platforms and other user platforms 160 for performing customized user applications 260 of one embodiment.

FIG. 2 shows creating a customized customer relationship management platform network and creating a customized customer relationship management platform network attached storage cloud device. Operating a customized customer relationship management platform providing an interactive interface with the customized customer relationship management platform network and customized customer relationship management platform network attached storage cloud device.

Operating a customized customer relationship management platform includes using a customized form builder for using pdf mapping to create custom responsive PDF forms using a dynamic mode and using an auto mode and converting a user's scanned existing paper form into a responsive PDF form. The customized customer relationship management platform is providing cross platform integration employing a get feature and employing a push/pull feature to apply the form builder created forms on a user CRM platforms and other user $3^{rd}$ party platforms.

Operating a customized customer relationship management platform a user may use many types of digital devices. The display screen for a computer is much larger than a screen on a smart phone. The customized customer relationship management platform includes a mini mode feature for converting user interactivity to a mini mode for displaying on digital devices including a computer, tablet, laptop computer, smart phone or other digital device for users performing customized user applications at their convenience. The customized customer relationship management platform network includes WI-FI and internet connectivity devices for communicating with various user digital devices. The customized customer relationship management platform network includes digital processors, digital servers, digital computers, digital sensors, digital analyzers, and other digitally controlled devices including wireless digital devices. Other features of the Get elements includes Category in Get Integration: Group by for aggregation, Option to Ignore Empty Conditions in Action Button—Get, property in Get—load pick list, and Show Get Integration errors in logs and other features including Sending integration log errors to an additional email, Add group label in Table Add/Edit/View modal windows, Custom labels for Lookup/Table reference, Integration Logs update, and Providing one month of Error log history of one embodiment.

Figure 3:
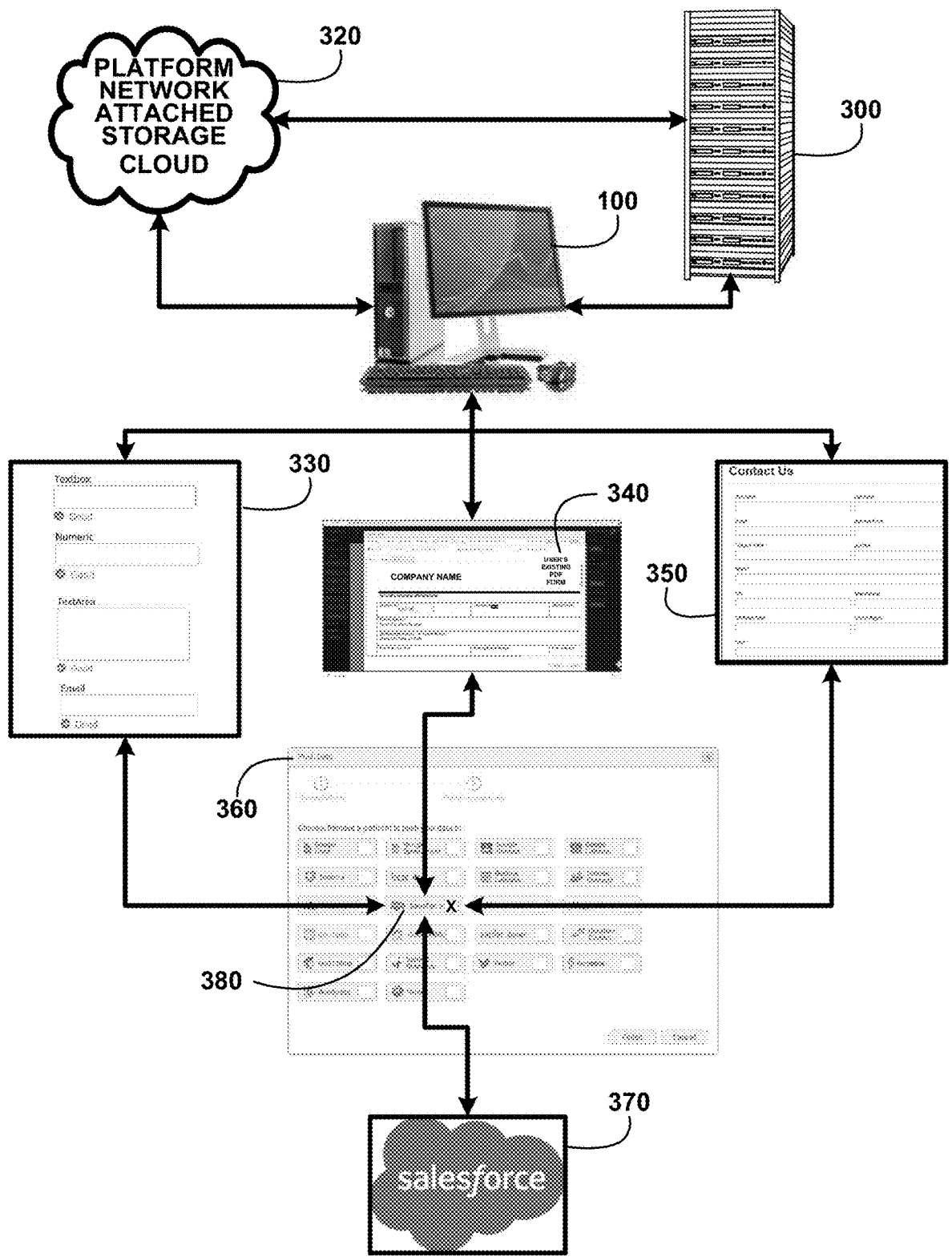
FIG. 3 shows for illustrative purposes only an example of the flow of data in a customized customer relationship management platform method and devices of one embodiment.

The Flow of Data in a Customized Customer Relationship Management Platform Method and Devices:

FIG. 3 shows for illustrative purposes only an example of the flow of data in a customized customer relationship management platform method and devices of one embodiment. FIG. 3 shows a customized customer relationship management platform network 300 including a network server. The customized customer relationship management platform 100 digital device is interactively coupled to the customized customer relationship management platform network 300 network server and a platform network attached storage cloud 320 also interactively coupled to the customized customer relationship management platform network 300 network server. The customized customer relationship management platform 100 digital device is used for operating a customized form builder 330 including pdf mapping to convert existing paper forms into responsive digital pdf forms 340 and creating new pdf forms using a dynamic mode and using an auto mode 350. The customized form builder 330 includes at least one feature including a push data feature for cross platform integration with at least one 3rd party application 360. The at least one 3rd party application 360 includes Salesforce integration with Salesforce get and Salesforce push 380 wherein Salesforce is a built-in integration feature 370 of the customized form builder 330 of one embodiment.

FIG. 3 shows using a customized customer relationship management platform network to pass data between a customized customer relationship management platform network attached storage cloud device and a customized customer relationship management platform. Using the customized customer relationship management platform network attached storage cloud device for storing user generated forms and customized integration and other feature data. Using the customized customer relationship management platform for interfacing with users and the customized customer relationship management platform network for using a customized form builder. The customized form builder is used by users for using pdf mapping to convert existing paper forms into responsive digital PDF forms, creating new form using a dynamic mode and using an auto mode. The customized customer relationship management platform is also providing a push data feature for cross platform integration with at least one 3rd party application a user may be already or planning to use. The customized customer relationship management platform provides a single source of form creation and gathering the response data from the responsive form they have created. A user can easily Integrate Form Builder created forms with a large range of 3rd party applications including DropBox, Box, OneDrive, MailChimp, Gemini, Google Docs, Google Spreadsheets, Google Contacts, Constant Contact, Clinchpad, Twitter, Facebook, WordPress, Outlook Calendar, Outlook Contacts, Custom URL, Salesforce, Google Calendar, Zapier, Solve 360, Zoho, and others of one embodiment.

The customized customer relationship management platform includes features that include elements. Those features include Form Builder with Main Operations, Form Elements including Basic Elements, Advanced Elements, Widgets Elements and Element Settings; Form Properties with Settings and Style; Report Builder feature with Report main operations, Report elements including Basic Elements, Advanced Elements and Widgets Elements; and Report settings. A My Submissions feature includes Main operations. Other features include My Forms, My Account, Account Billing, Security, and Sign in, working with the form builder and Form Embed. Salesforce is a built-in integration feature for this 3$^{rd}$ party application and includes elements including Salesforce Integration with Salesforce Get and Salesforce Push of one embodiment.

Figure 4:
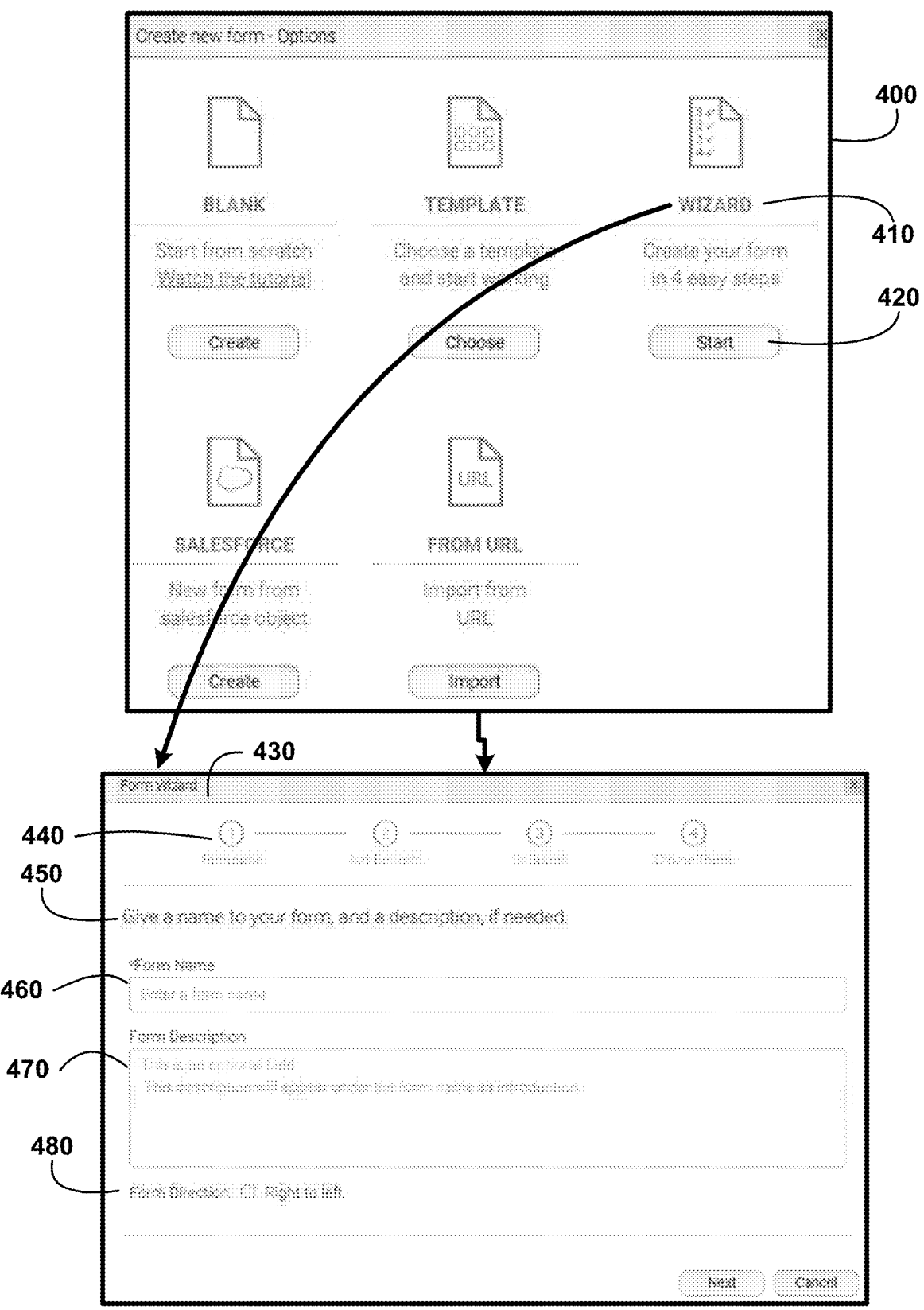
FIG. 4 shows for illustrative purposes only an example of a form builder feature of one embodiment.

Form Builder Feature:

FIG. 4 shows for illustrative purposes only an example of a form builder feature of one embodiment. FIG. 4 shows a form builder feature to create new form—options web page 400. FIG. 4 is showing a blank, template, wizard 410, Salesforce and from URL. The wizard is used to create your form in 4 easy steps 410 including 1. Form name, 2. Add Elements, 3. On Submit, and 4. Choose Theme. The wizard steps begin with a start button 420. Pressing the start button 420 takes the user to the form wizard web page 430. Step 1 enter a form name 440 includes an instruction to give a name to your form, and a description, if needed 450. The input text box to enter a form name 460 is displayed and the user can enter the form name they assign. An input text box to enter a form description 470 is an optional field, this description will appear under the form name as a descriptive introduction. A form direction check box for right to left 480 can be selected for languages that read from right to left of one embodiment.

FIG. 4 shows you can, for example upload an image of a scanned paper form and place the submitted form values above it. This option is available via our basic PDF mapping. You can also create an HTML layout and embed the field values in it. This option is also available using our dynamic PDF mode. But what if you want your PDF to simply look like a screenshot of the filled-in form? This is now possible using our new Auto PDF feature.

Form Builder is a feature that allows a user to easily create powerful forms including elements and sub-features including Field types including Drag and Drop, Responsive, Form wizard, Form Import from URL, Field validations, Unique submissions, Form limits, Mandatory indications, Post submit Redirects, Automatic and custom emails, Element and form Conditional Logic, Save and Resume, Social Autofill, CAPTCHA, Security Seal, Digital Signature, Custom Thank You message, PDF Mapping, Multi Page Form, Valid/Error Indicators, Image Masking Backgrounds, Value Rules, Repeated Section, Field Mask, Advanced Values including in a calculated string mode, DropDown with Hierarchy, Workflow Editor Salesforce Form in one click, Payment Integration, Multiple Selection DropDown, Export the form to another account, Custom Translation, Value Rule with REGEX Validation, Bi-Directional Salesforce Integration, Resubmitting entries back to Salesforce and other 3rd party integrations, Form Rules, Salesforce Table Element, Salesforce Visual Composer Targeting, Allow later editing, Calculated Field, CDN Cache, The Section Element, Collapsible Section, Effected by, Using the Dynamic PDF Mapping, Ignore Mandatory Validation, Address Validation, Auto Submit Your Form, Base your Google map on an address, Version Control feature, PDF Re Generation, Custom mail server, Geo Localization, On Completion Script in Button, Auto PDF, adding a widget to your form, The Salesforce chart, File Upload—Allow Capture, File Upload—Allow Accept, PDF Conditions, Section Repeat with mapped data, PDF Mapping Conditions, PDF Page conditions, PDF Block condition, and Voice Control of one embodiment. Other conditions and conditional rules include conditional results for the HREF element: set value and set value from, Set a CSS class to an element by condition, Enable/Disable condition result options for Checkbox and Radio button, filter in condition window, Adding conditions to your PDF mapping, Filtering data in Get condition based on an integer, Friendly condition, Friendly condition and brackets added to value rule, Functions added to Field condition results, Is empty condition added in Numeric and Price, condition result options: Read only and Read Write, Opposite rule in condition, Optimization for loading times, loading times, CDN cache, conditional logic engine, PDF conditions—If block, Reset radio option in condition results, Show/Hide section tabs via condition, Supporting Boolean conditions, and Supporting special characters in condition of one embodiment.

Other features include feature: voice control, features to Advanced Tools, features to Google Sheets Export, feature for multi page forms: Progress indicator, feature: Auto Submit, Version Control feature, Lock elements in form builder, Hotkeys in form builder for Mac, and Showing validation indicators on form builder canvas of one embodiment.

FormTitan offers all the elements you'll need to create a landing page or online form: Input elements, graphic elements, special elements and widgets. They are all located in the left "Elements" panel and divided into 3 categories: Basic, Advanced and Widgets. Basic elements include Section, Image, Button, Line, Label, Paragraph, Href, Heading, Bullet, Textbox, Numeric, Textarea, Email, URL, File Upload, Dropdown, Radio, and Checkbox. Advanced elements include Address, Full Name, Date & Time, Date, Time, Phone, Price, Star Rating, and Likert. Widgets are elements that include YouTube, Vimeo, Seal, Privacy, Signature, Social Filler, ImageBlock, ImageSlider, HTML, Google Map, Calculated, Hidden, and Page Break of one embodiment.

Figure 5:
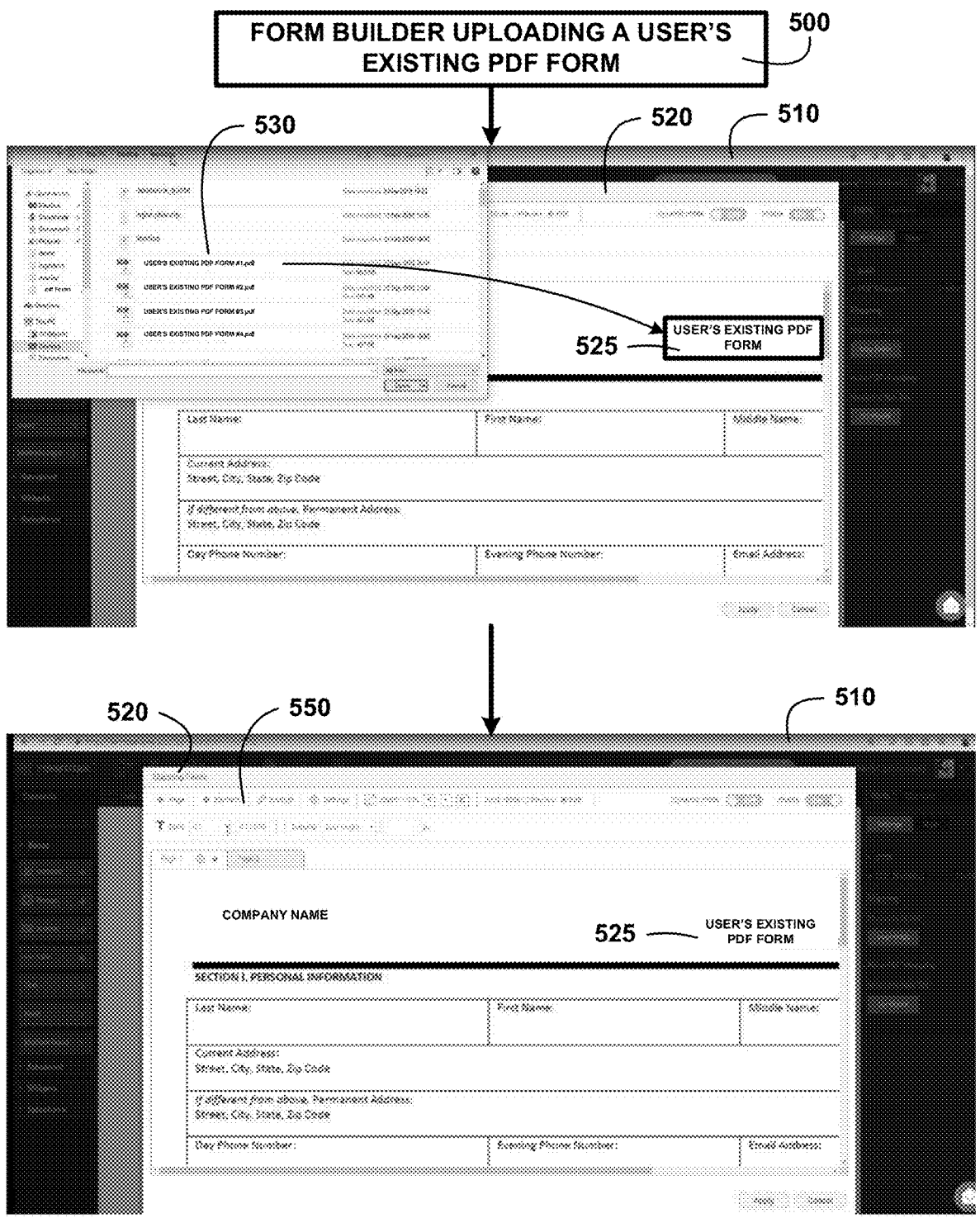
FIG. 5 shows for illustrative purposes only an example of form builder uploading a user's existing pdf form of one embodiment.

Form Builder Uploading a User's Existing Pdf Form:

FIG. 5 shows for illustrative purposes only an example of form builder uploading a user's existing pdf form of one embodiment. FIG. 5 shows the form builder uploading a user's existing pdf form 500. A listing of user existing pdf forms is displayed for selection of an existing pdf form. The user selects user's existing pdf form #1.pdf 530 from the listing. The uploaded user's existing pdf form 525 is displayed on a form builder web page 510 that includes in a header section a mapping fields web page 520. The user can then open an elements 550 tab to make element selections to integrate into the user's existing pdf form 525 of one embodiment.

FIG. 5 shows how to easily convert paper form into a responsive form and automatically output your online form entries into your paper form in one embodiment. 1. SCAN: Scan your paper form and save it as an image or non-responsive pdf. This scanned image will be used in step 3. 2. BUILD: Build an online version of your scanned form using FormTitan form builder. 3. MAP: Upload your scanned form and map your online form fields to it. 4. USE: Start using your online form. Upon data submission a PDF version will be generated. Responsive Form Create a responsive online form to collect data via P.C., tablets and mobile phones. Password Protected Protect your offline form by sealing it with a password. Digital Signatures Collect signatures using an online form. Layouting & Kerning Map the online form to your paper form. Easy to use Simple WYSIWYG online form builder with drag & drop.

Many financial, insurance and legal services still rely on paper forms, which have to be downloaded, printed, manually filled in and sent back via fax. This is an inefficient, inconvenient, time consuming process which leads to negative customer impression and consequently also to low conversion. FormTitan enables you to bypass these shortcomings by collecting the data using an online form, and still receiving it as a PDF in the original layout.

FormTitan provides help with tutorials and specific instruction including GETTING STARTED, Usage Guidelines, Watch a tutorial, Forgot Password, How do I create a form? FORM BUILDER, form builder layout, Apply a theme on my form, Change elements style, Types of forms I can build. MY SUBMISSIONS, Submissions Dashboard, Open form Submissions, Emails sent upon submission, Submissions Page Layout. MY ACCOUNT, My Account Profile, account profile images, Add a collaborator under your account, Change account password. BILLING, My billing information, Billing Transaction Receipt. SECURITY, CAPTCHA, How do I keep my form private?, Make sure no one enters my account. Integration into $3^{rd}$ party applications including Salesforce, Salesforce, Salesforce get integration, How can I track my Salesforce API calls?, Salesforce Push Integration Example #1, Salesforce Get Integration Example #2. A Password Mode Textbox is a feature to use in the protection of a user's privacy of one embodiment.

Figure 6:
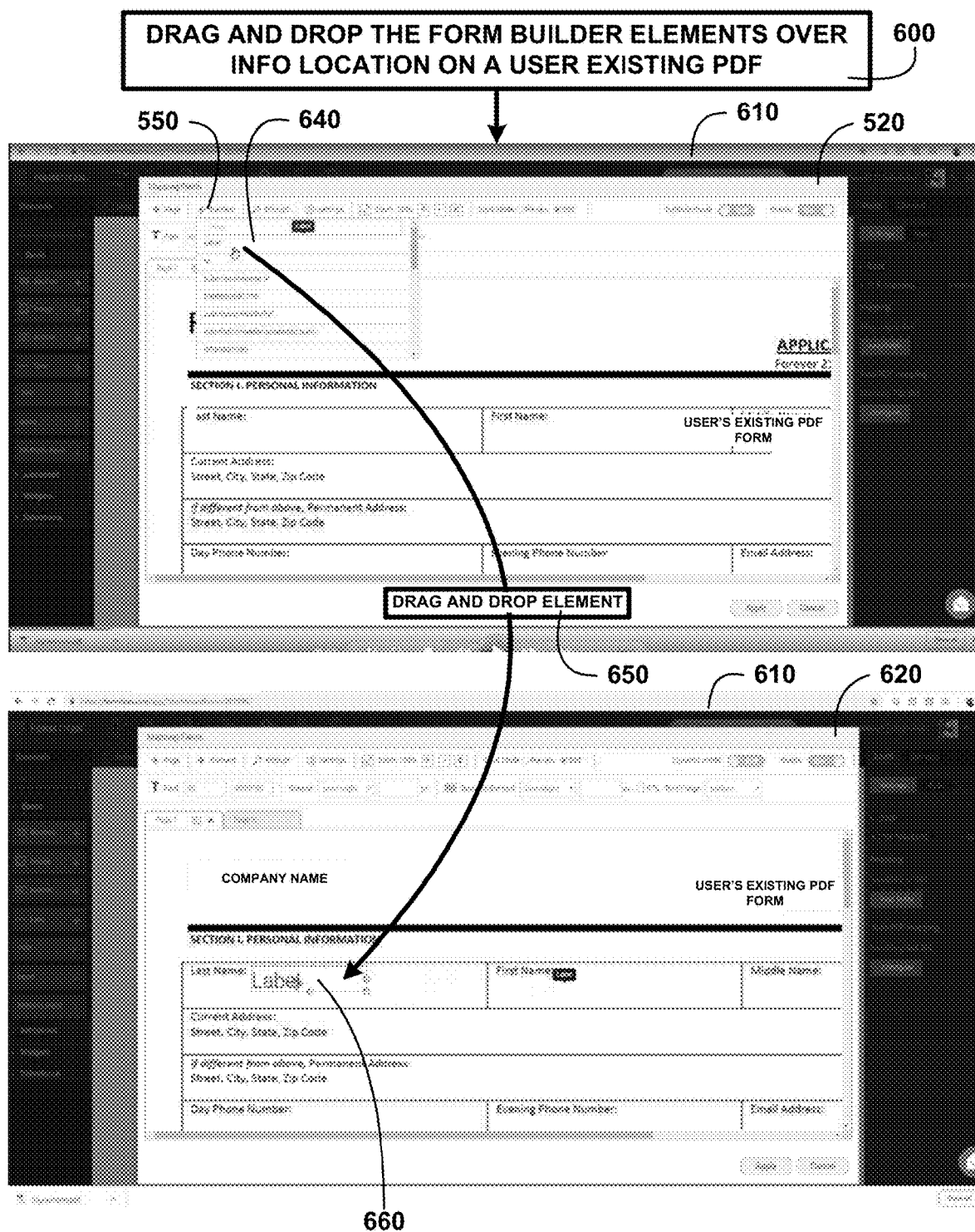
FIG. 6 shows for illustrative purposes only an example of drag and drop the form builder elements over info locations on an existing user scanned paper form of one embodiment.

Drag and Drop the Form Builder Elements Over Info Locations on an Existing User Scanned Paper Form:

FIG. 6 shows for illustrative purposes only an example of drag and drop the form builder elements over info locations on an existing user scanned paper form of one embodiment. FIG. 6 shows drag and drop the form builder elements over info location on a user existing pdf 600. The mapping fields web page 520 is displayed from a FormTitan web site 610. The elements 550 include a drop down elements menu including a label selection. A user drags the label element to the user's existing pdf form 525. A drag and drop element 650 for example a label element 660 is position on a user's existing pdf form and is entered in the mapping fields web page 620 of one embodiment.

FIG. 6 shows how to build an online version of your scanned form using the form builder. PDF Mapping allows a user to 1—upload a PDF and use it as the background to your canvas. 2—select the form fields from the Element Dropdown (one by one) and place them where you want their value to appear.

According to "TechTerms" The drag & drop feature "involves moving the cursor over an object, selecting it, and moving it to a new location". FormTitan form builder is a WYSIWYG tool and it is easy to use. It enables you to create landing pages and forms intuitively by dragging elements from the "Elements" panel on the left, and dropping them in the canvas. The elements may be placed anywhere since the layout is completely flexible. DropDown with Hierarchy. FormTitan, like other form builders, provides a "Dropdown" element you can add to your form to. With this element the form filler can input data in your form by choosing from a list of options. FormTitan, however, provides two types of DropDown: a regular Dropdown called "simple", and a dropdown with a few levels called "Tree" (which is in fact a Dropdown with Hierarchy). How to create a Dropdown with Hierarchy? Following are instructions:

1—Enter the form builder and create a new form or open the form you would like to add it to.

Please note! Since the "simple" Dropdown has only one level, you can always change it to a "tree" by adding Hierarchy to it. However, in this example we will show you how to create a "Tree" Dropdown from scratch.

2—Drag a Dropdown.

3—Once selected go to its properties and change its label text.

"Properties Panel">"Element" tab>Settings>"Basic" category>Label

In the example I have created the dropdown is called "School Kids".

4—Now change the Mode to "Tree"

"Properties Panel">"Element" tab>Settings>Mode Radio button>Tree

5—Press on the "Configure" button

6—A window will open containing all of the Dropdown's default options.

You will see 3 rows. Each row is an item in the highest level of the tree. (Parent)

Each row has its own icons to do the following: Edit—You can change each item's name with the "Edit" Icon. Delete—remove an item by pressing on "Delete". Add—add new options under a specific row (Child) by pressing on the "Add" button (+) in that row. In addition there is an "Add object" button which allows you to add more items to the parent level. In the example I configured a tree with 3 levels: The parent level, which contains schools: Elementary school, Middle school and High school. Under the "Elementary" school option is added another level (child) with 2 options: 'Class 1' and 'Class 2' and under "Class 2" is added another level with 3 kids names.

7—Press "Apply" and save the form.

8—Publish your form so you can see for yourself how the Dropdown will appear to your users. The items on the list will be displayed with an indentation to show the Hierarchy.

9—In addition to this, once data is entered in this dropdown and submitted you will be able to see the data displayed in a Hierarchy, like shown in the screenshot from the submissions page (below). It will be displays like this in your email, submissions page and exported data of one embodiment.

Figure 7:
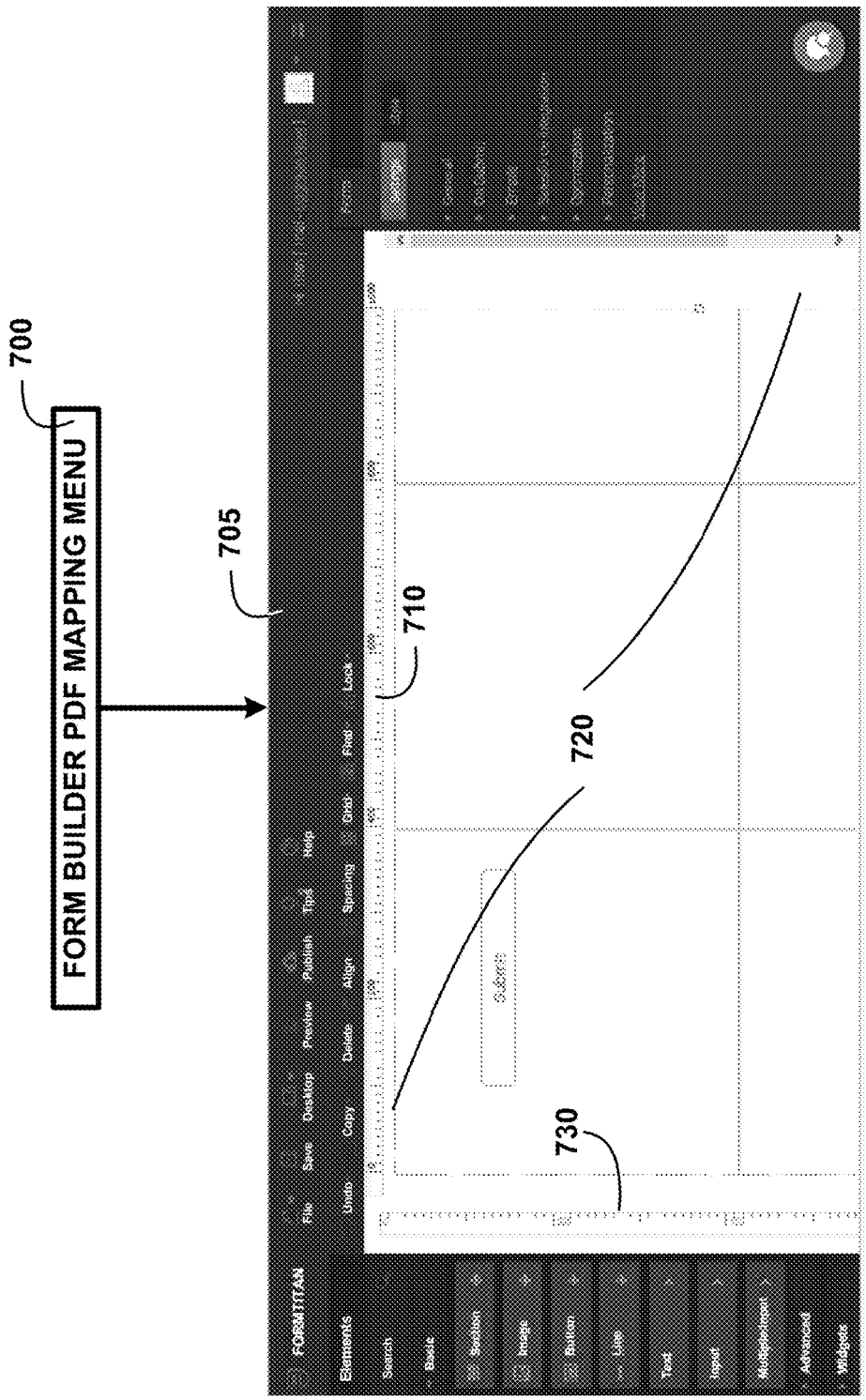
FIG. 7 shows for illustrative purposes only an example of a form builder pdf mapping menu of one embodiment.

A Form Builder Pdf Mapping Menu:

FIG. 7 shows for illustrative purposes only an example of a form builder pdf mapping menu of one embodiment. FIG. 7 shows a form builder pdf mapping menu 700 on a form builder pdf web page 705. The pdf mapping menu 700 includes a form builder pdf grid layout page 720 that includes a horizontal ruler 710 and a vertical ruler 730 of one embodiment.

FIG. 7 shows a form builder pdf mapping menu including a file dropdown, save, desktop dropdown, preview, and publish, tips and help. Using the Dynamic PDF Mapping starts with using the advanced PDF Mode. PDF Mapping, why PDF Mapping? Paper forms have been around for ages. Grant you, today many forms have gone online, however there are still services which rely on paper forms (like law offices, insurance companies, etc.). The problem with paper forms is that they slow things down, they require download, printing, filling in manually, and sending by fax. This becomes a hassle since many people don't have a printer or a fax. In addition, filling in forms by hand can get tiresome when you are required to fill in the same fields over and over again (like your name or signature).

Furthermore, Companies that need to digitally store the data that was collected with their paper forms now have to deal with a heavier work load that includes scanning the forms, typing in the data etc. This is exactly why FormTitan developed this feature: PDF mapping. What is the PDF (Paper Form) Mapping? This feature allows you to collect your data using a responsive online form, and then have a PDF document generated based on the entry, with the data in it. This PDF can be sent to you, the form owner, to your form fillers and it can, of course, be pushed to Salesforce. This is a win-win situation where the data is entered and stored digitally as well as generated into a PDF document in the traditional old way.

FormTitan provides 3 types of PDF mapping: 1—A basic PDF mapping where you need to upload a background, and place your form elements above it. Learn how to use the basic PDF Mapping. 2—A Dynamic PDF where you need to create the layout yourself via editor and HTML code. 3—An auto PDF where the system creates the PDF by capturing an image of the filled in form (sort of like a screenshot) of one embodiment.

Auto Pdf: 1—

Create your form in the form builder. 2—Go to 'Properties' panel>'Form' tab>'Settings' option>'Pdf Mapping' category>Auto PDF. 3—Press on the 'Map Fields' button. 4—A small modal window will open to configure the settings: —Enable auto PDF mapping: this checkbox will activate the auto PDF. —Auto Fit: this will make the screenshot fit the A4 PDF size. —Encrypt PDF: You can have the PDF attached to your emails encrypted, this means that it will only open with a password. With this dropdown you can choose which field will be used as password. —Message with password for PDF: In this text area you can configure a message that will appear when someone tries to open an encrypted PDF. —Custom file name: Here you can enter a name for the PDF you are now creating.

This will be the file name of the PDF attached to the email. —Send to owner/Send to additional/Send to form emails: Checkboxes that determine where this paper form will be sent to. —Enable Condition: if you decide to turn on this Checkbox you will be allowed to add a condition by which this PDF will be generated. Only if the condition terms are met then the PDF will be generated. —Process upon payment only: turning on this checkbox will make sure that the PDF will be generated only if the payment is executed. Since this PDF is a screen capture of your form, there will be no need to create a layout in the editor (like we do in the other 2 PDF options). 5—Save the form and you are set to go. 6—Now you can test your form: —Publish it as URL—Enter data in it and submit the form. Other features are used in the processing of payments including Override of product name in PayPal Payment Integration, Payment Integration Emails, Payment integration with paypal: single and recurring, Payment Integration: Authorized-.Net, payment integration: blue snap, Payment Integration: PaymentHub, payment integration: Pelecard, Payment Integration: YaadPay, payment system USAePAY, Support for Installments in Tranzila Payments, Tranzila payment form now works with Thank you message and Redirect to URL, Attaching the FormTitan purchase transaction invoice to your email, Pelecard invoice: Tamal invoice with dynamic variable, and Pelecard TAMAL Invoice of one embodiment.

Other mapping features include Conditional Logic in the PDF Mapping, Mapping only reference fields in your Table, PDF Mapping: Auto PDF, PDF Mapping Additions, PDF Mapping file name and barcode, Remove auto margin in Dynamic PDF Mapping, Vertical Align Added to Elements in PDF Mapping, Adding conditions to your PDF mapping, Push mapping Condition, Conditional mapping in Repeated and Files, Else added to the Conditional mapping, My submissions filter by PDF mapping, pdf mapping—categories, PDF mapping generated after custom Push, Submission ID in mapping of nested child, and Using the Short State name in Address mapping of one embodiment.

Advanced PDF Mapping Dynamic Mode:

FIGS. 8-19 show features of the Advanced PDF mapping Dynamic mode including elements.

Figure 8:
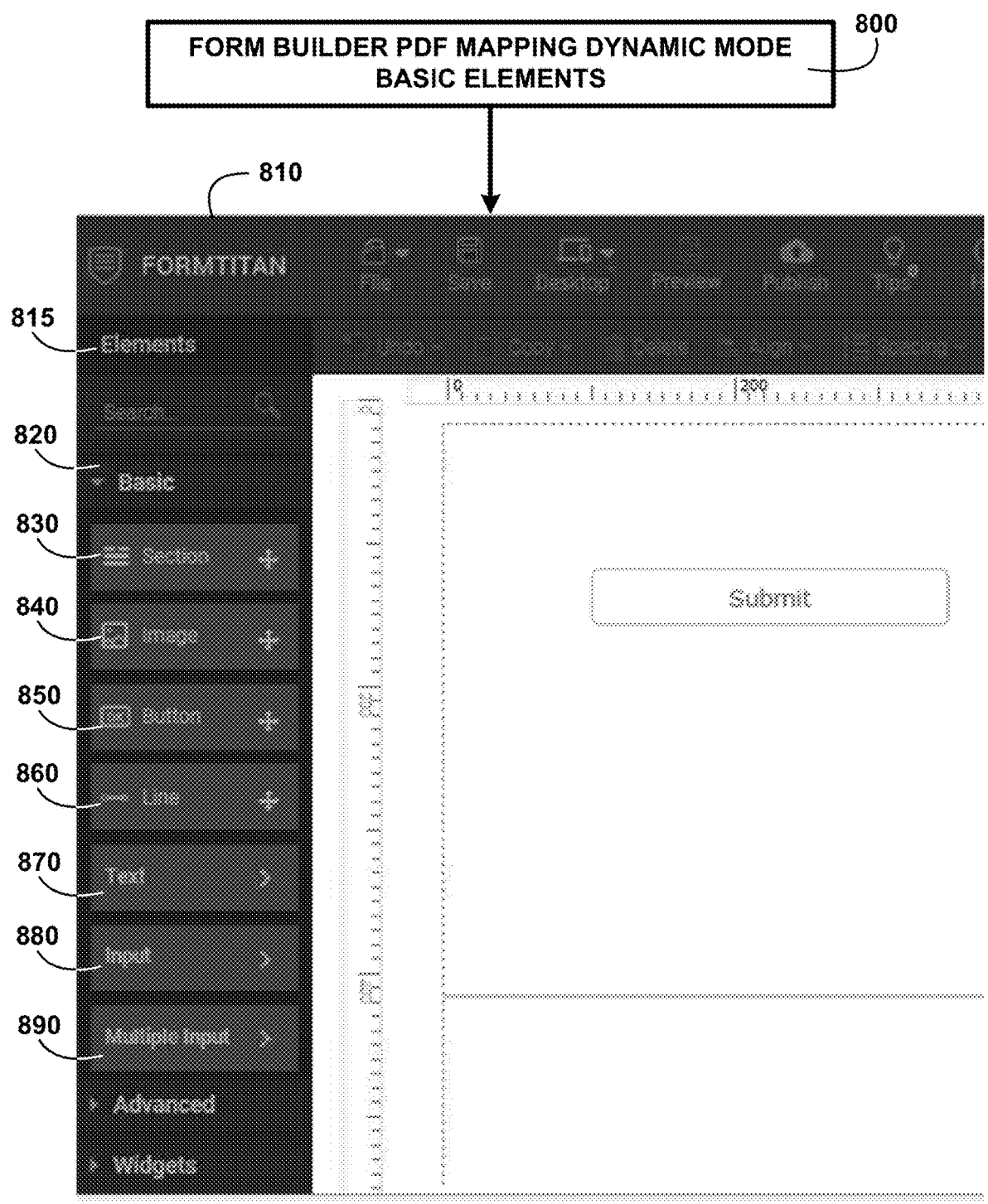
FIG. 8 shows for illustrative purposes only an example of form builder pdf mapping dynamic mode basic elements of one embodiment.

Form Builder Pdf Mapping Dynamic Mode Basic Elements:

FIG. 8 shows for illustrative purposes only an example of form builder pdf mapping dynamic mode basic elements of one embodiment. FIG. 8 shows form builder pdf mapping dynamic mode basic elements 800 on a form builder pdf mapping dynamic mode basic elements menu and grid layout web page 810. An elements menu 815 includes basic elements 820. The basic elements 820 menu includes section 830, image 840, button 850, line 860, text 870, input 880, and multiple input 890 of one embodiment.

FIG. 8 shows when you add PDF Mapping to your form the standard editor opens, allowing you to easily create a PDF by uploading your document, and then placing your form fields above it. It's really simple to do. However, for those who do not want to create their PDF this way we offer a Dynamic Mode. Once you move to this mode, the editor will change, allowing you to insert HTML code, play with styling and even use a table element for displaying your repeated section items dynamically. Wanna' see how it's done? follow this example: 1—Create a new blank form; 2—Move submit button down—so it is located after the section; 3—Drag a few elements on to the canvas. Other Dynamic mode features include Dynamic PDF Mode, Dynamic PDF Background image, Page order in Dynamic PDF, Remove auto margin in Dynamic PDF Mapping, and Setting a Dynamic reply to of one embodiment.

Figure 9:
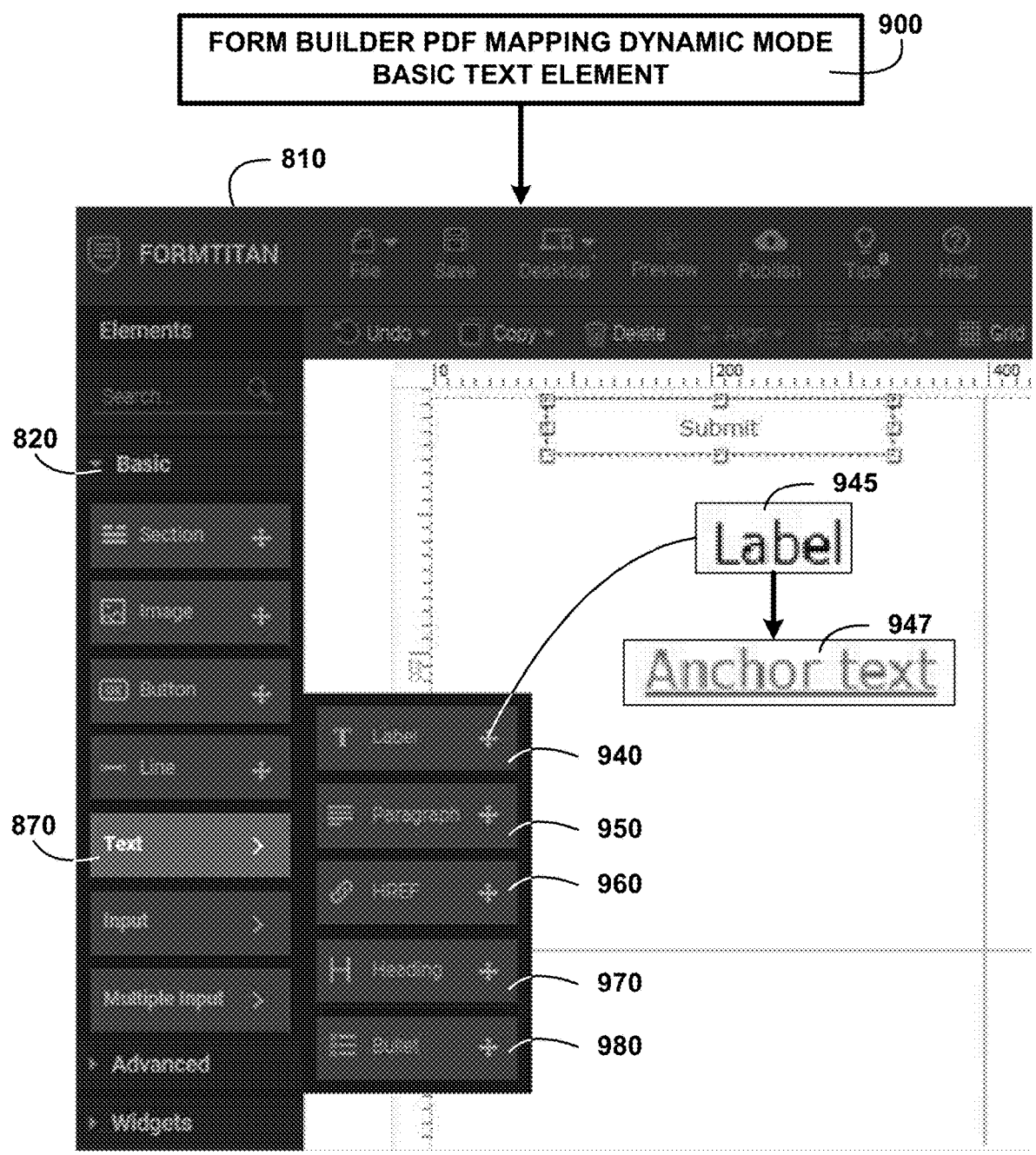
FIG. 9 shows for illustrative purposes only an example of form builder pdf mapping dynamic mode basic text element of one embodiment.

Form Builder Pdf Mapping Dynamic Mode Basic Text Element:

FIG. 9 shows for illustrative purposes only an example of form builder pdf mapping dynamic mode basic text element of one embodiment. FIG. 9 shows for example a form builder pdf mapping dynamic mode basic text element 900 for selection of a sub-element to be positioned on the form builder pdf mapping dynamic mode basic elements menu and grid layout web page 810. A user makes a selection from the basic elements 820 in this example text 870. The text 870 includes a sub-menu that includes Label 940, Paragraph 950, HREF 960, Heading 970, and Bullet 980. In this example a user makes a label selection 945 to position label text box as an anchor text 947 on the grid layout of one embodiment.

FIG. 9 shows a Textbox→change its label to "Parent Name" Drag a Section, and make it wider to fit the 3 following elements:
  textbox→change the label to "Child name"
  numeric→change the label to "Child age"
  textbox→change the label to "favorite color"

Figure 10:
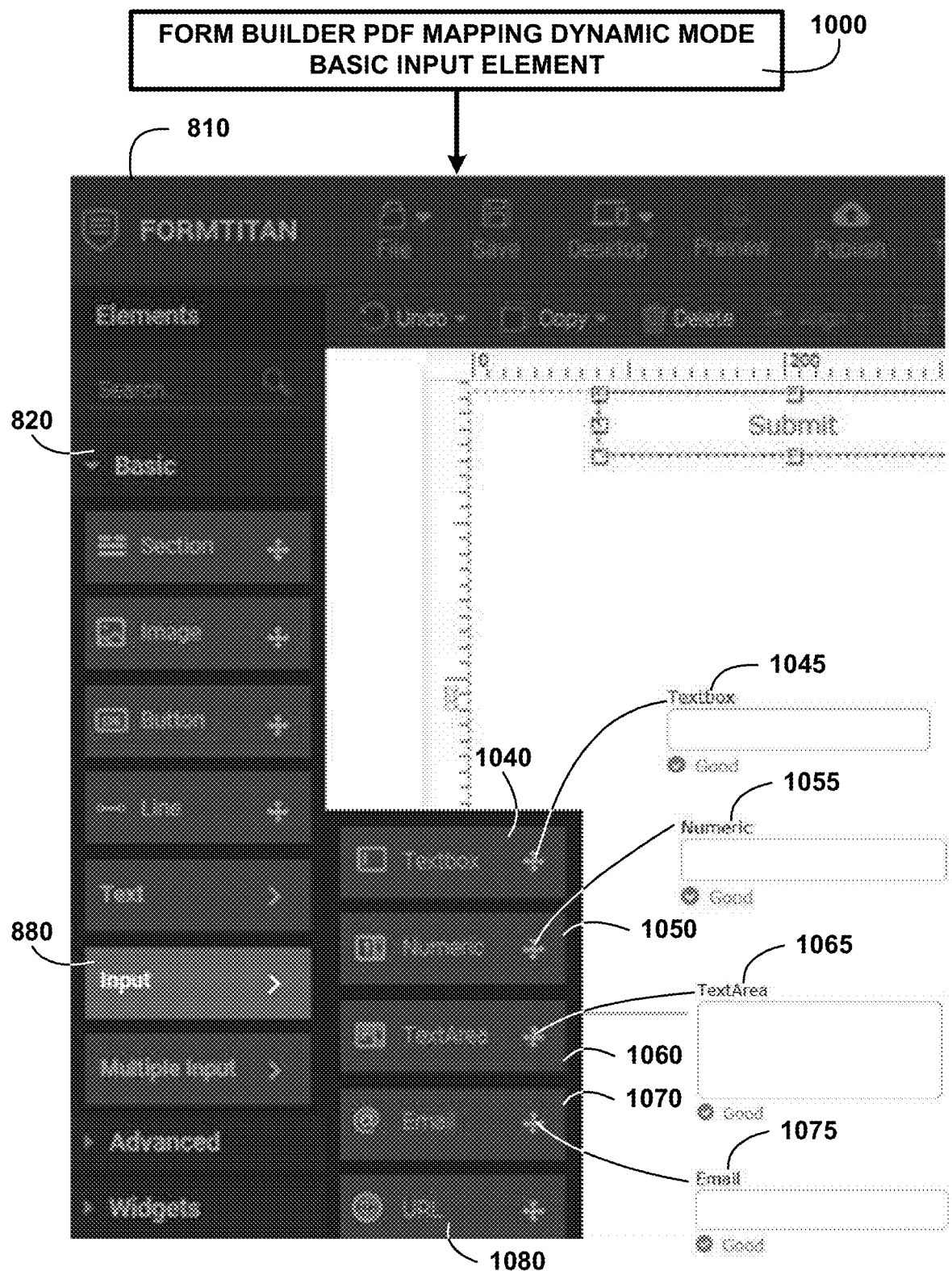
FIG. 10 shows for illustrative purposes only an example of form builder pdf mapping dynamic mode basic input element of one embodiment.

Form Builder Pdf Mapping Dynamic Mode Basic Input Element:

FIG. 10 shows for illustrative purposes only an example of form builder pdf mapping dynamic mode basic input element of one embodiment. FIG. 10 shows a form builder pdf mapping dynamic mode basic input element 1000 on the form builder pdf mapping dynamic mode basic elements menu and grid layout web page 810 basic elements 820 menu. The input 880 menu selection by the user displays a sub-menu that includes selections that include a Textbox 1040, Numeric 1050, TextArea 1060, Email 1070, and URL 1080. The user can for example make selections and place them on to the grid layout including a positioned textbox 1045, positioned numeric box 1055, positioned textarea box 1065 and positioned email box 1075 of one embodiment.

Other elements include label to Section element, default state of the element to Disabled, Custom subject in the Email element, Hover and Selected effects in elements, Infinite scroll in the Section element, element for Salesforce: Chart, element: HTML Editor, target options in the HREF element, Positioning elements with Intelligent Drop, Set Value From—added to radio and dropdown elements, Size per page in pagebreak element, and Styles for buttons in Table element including alignment of one embodiment.

Figure 11:
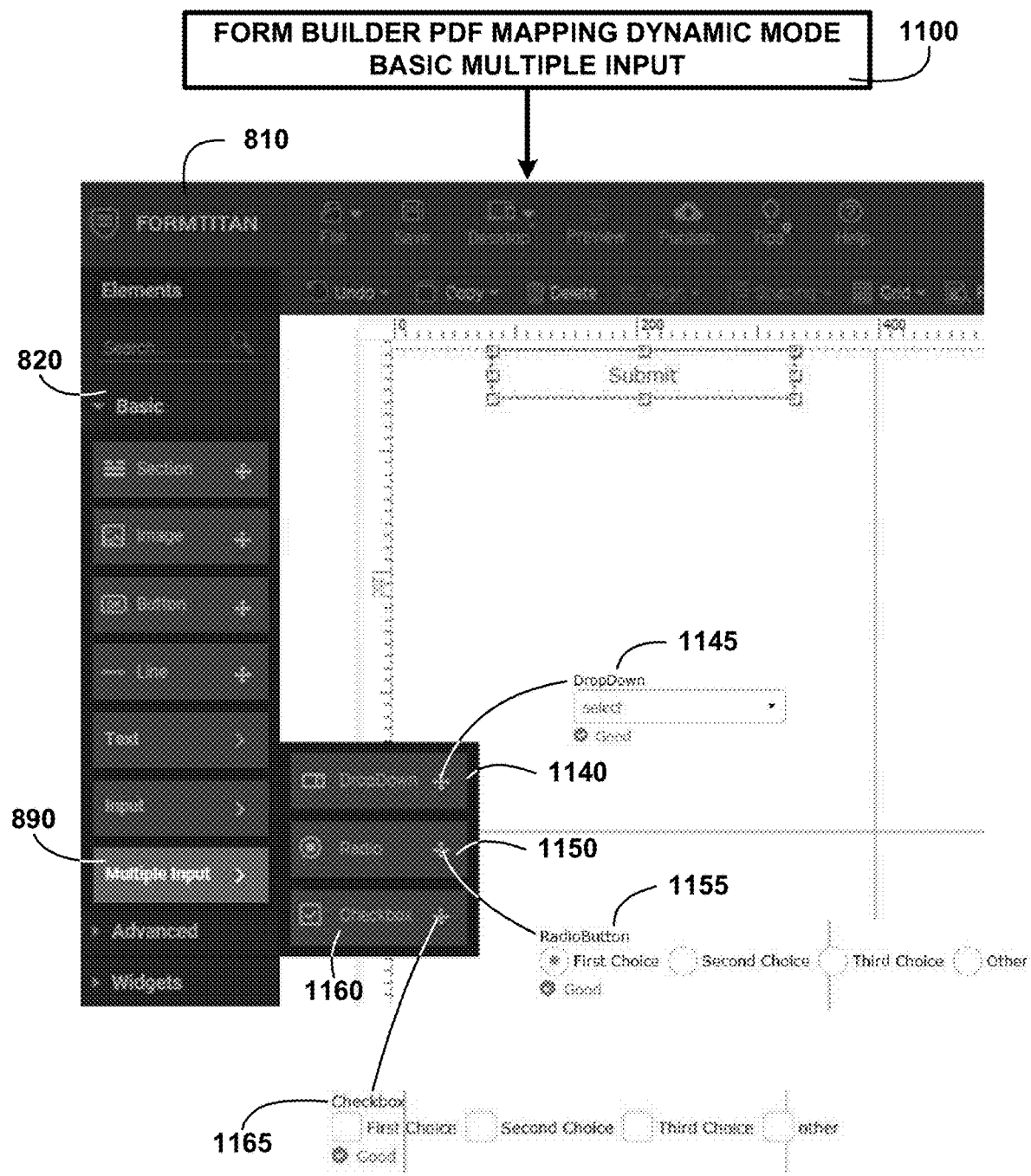
FIG. 11 shows for illustrative purposes only an example of form builder pdf mapping dynamic mode basic multiple input of one embodiment.

Form Builder Pdf Mapping Dynamic Mode Basic Multiple Input:

FIG. 11 shows for illustrative purposes only an example of form builder pdf mapping dynamic mode basic multiple input of one embodiment. FIG. 11 shows a form builder pdf mapping dynamic mode basic multiple input 1100 displayed on the form builder pdf mapping dynamic mode basic elements menu and grid layout web page 810. The user can select from the basic elements 820 menu the multiple input 890. The multiple input 890 selection displays a sub-menu that includes a dropdown 1140, radio 1150, and checkbox 1160 selection. A user can for example place a positioned dropdown selection box 1145 on the grid layout. The user can for example place a positioned radiobutton including first choice second choice third choice and other 1155 on the grid layout. The user can for example place a positioned checkbox including first choice second choice third choice and other 1165. FIG. 10 shows 4—Select the section and go to: "Properties" panel>"Element" tab>"Settings" option>"Basic" category of one embodiment. FIG. 11 shows for illustrative purposes only an example of form builder pdf mapping dynamic mode basic multiple input of one embodiment. FIG. 11 shows turn on the "Repeated" option. This will allow the form filler to add button and enter multiple items instead of just one. Save the form of one embodiment.

Figure 12:
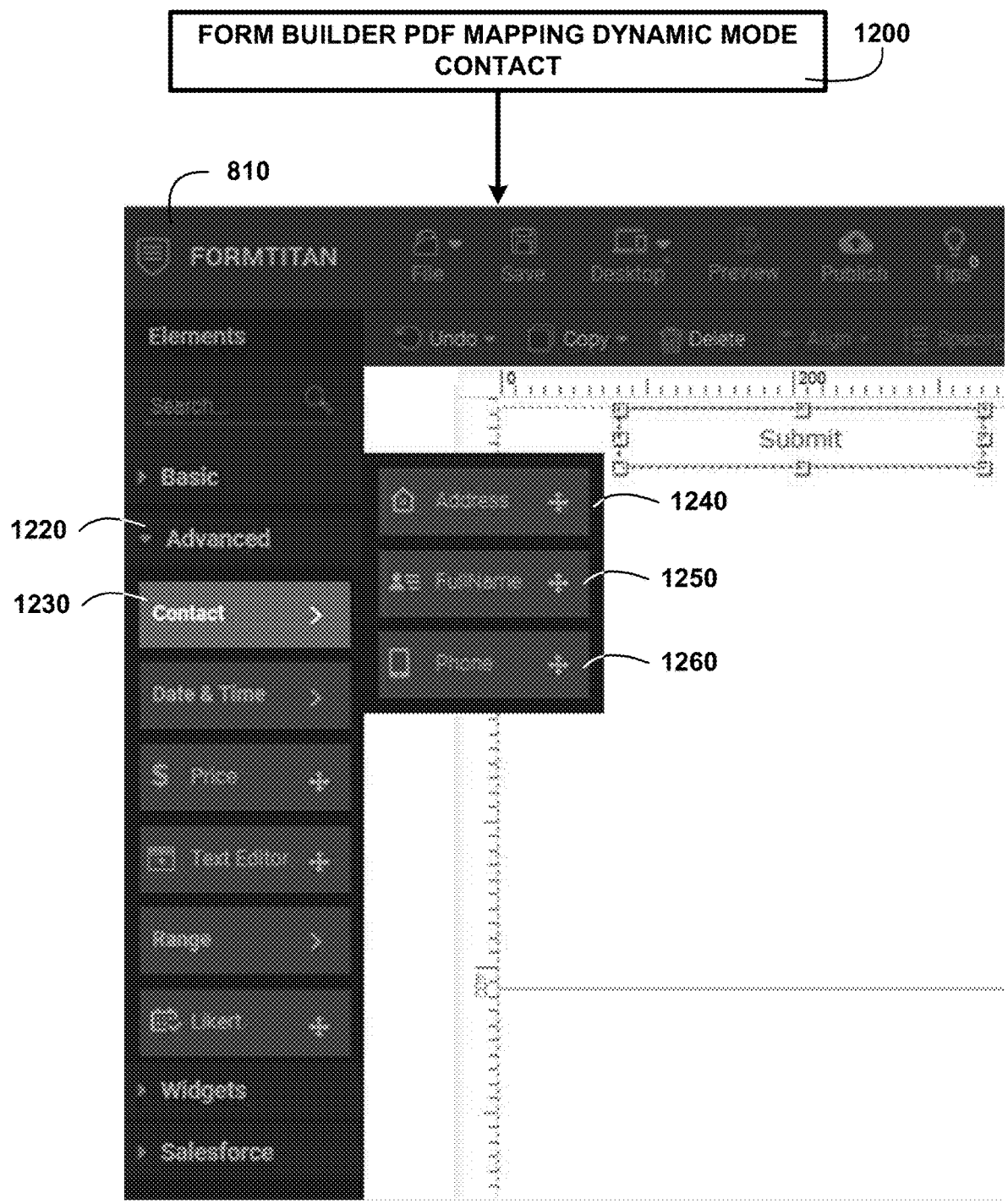
FIG. 12 shows for illustrative purposes only an example of form builder pdf mapping dynamic mode contact of one embodiment.

Form Builder Pdf Mapping Dynamic Mode Contact:

FIG. 12 shows for illustrative purposes only an example of form builder pdf mapping dynamic mode contact of one embodiment. FIG. 12 shows a form builder pdf mapping dynamic mode advanced contact 1200 selection for the user to incorporate into their custom pdf form. The form builder pdf mapping dynamic mode an advanced elements menu and grid layout web page 810 includes advanced 1220 elements for a user to create a contact 1230 section. The contact 1230 section sub-menu includes address 1240, fullname 1250 and phone 1260 selections of one embodiment.

Figure 13:
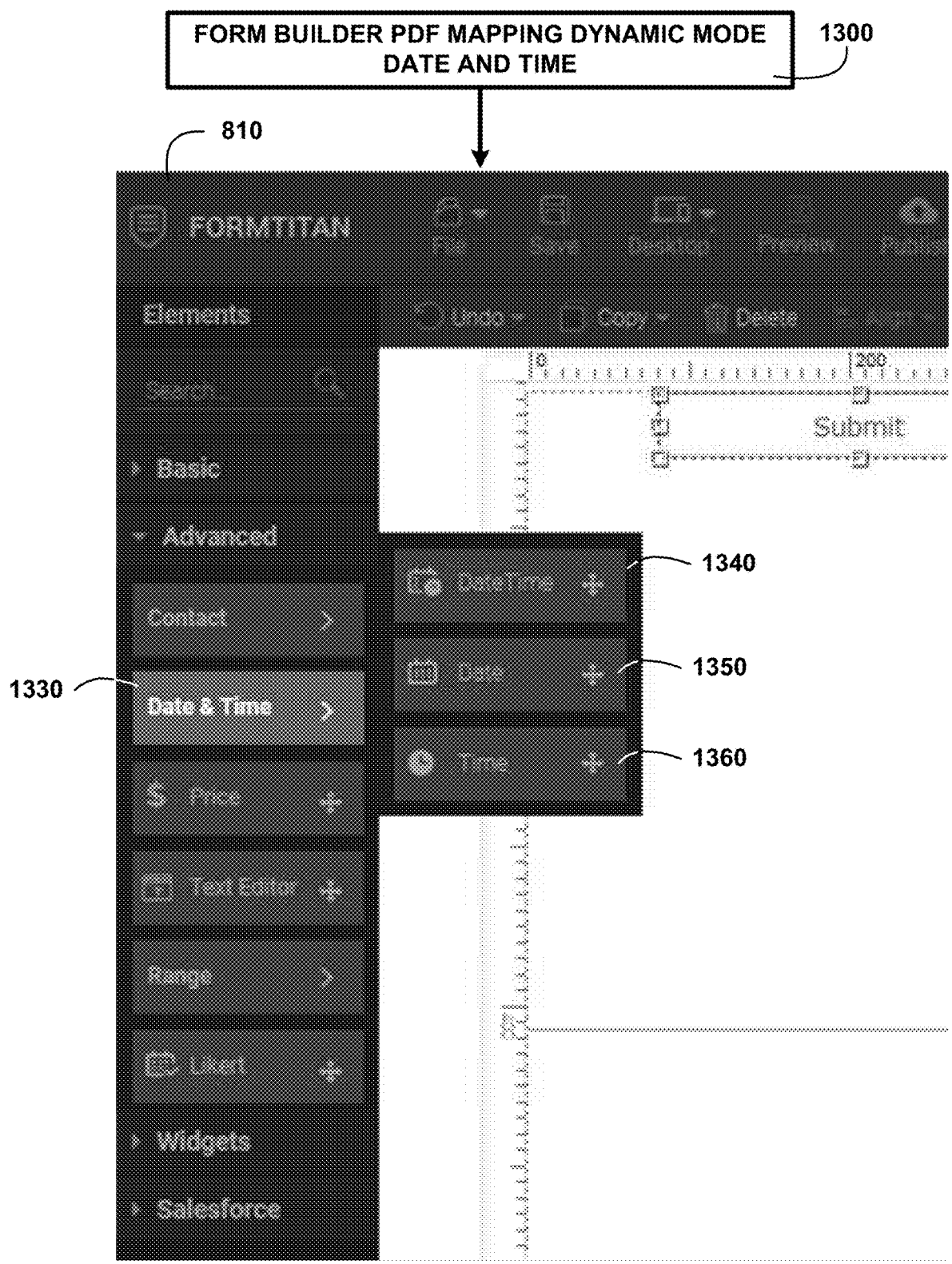
FIG. 13 shows for illustrative purposes only an example of form builder pdf mapping dynamic mode date and time of one embodiment.

Form Builder Pdf Mapping Dynamic Mode Date and Time:

FIG. 13 shows for illustrative purposes only an example of form builder pdf mapping dynamic mode date and time of one embodiment. FIG. 13 shows a form builder pdf mapping dynamic mode advanced date and time 1300 selection for the user to incorporate into their custom pdf form. The form builder pdf mapping dynamic mode an advanced elements menu and grid layout web page 810 includes advanced 1220 elements for a user to create a date & time 1330 section. The date & time 1330 selection includes sub-menu selections including datetime 1340, date 1350, and time 1360 of one embodiment.

Figure 14:
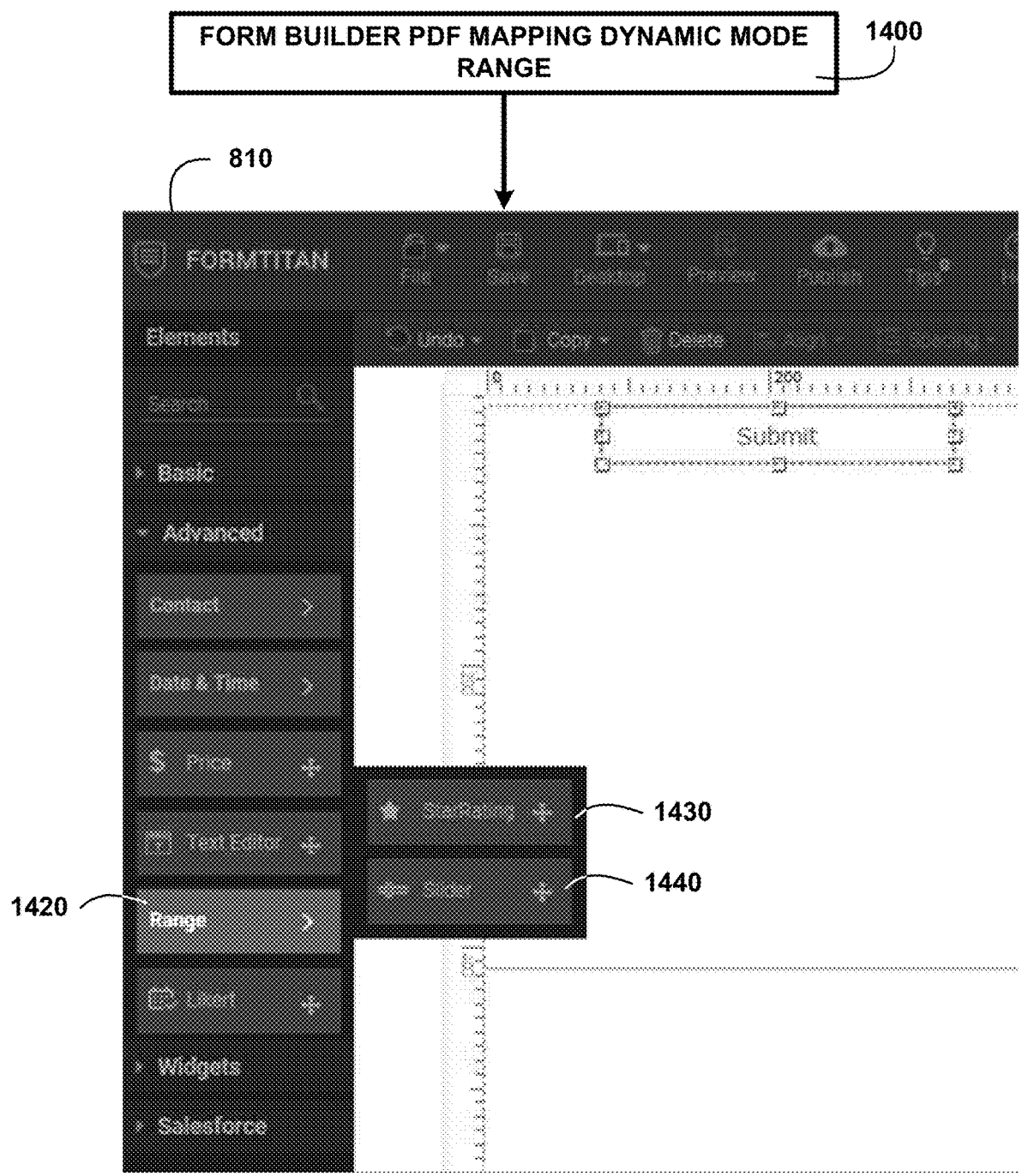
FIG. 14 shows for illustrative purposes only an example of form builder pdf mapping dynamic mode range of one embodiment.

Form Builder Pdf Mapping Dynamic Mode Range:

FIG. 14 shows for illustrative purposes only an example of form builder pdf mapping dynamic mode range of one embodiment. FIG. 14 shows form builder pdf mapping dynamic mode advanced range 1400 section on the form builder pdf mapping dynamic mode advanced elements menu and grid layout web page 810. The range 1420 selection includes a sub-menu including a starrating 1430 and slider 1440 elements of one embodiment.

Figure 15:
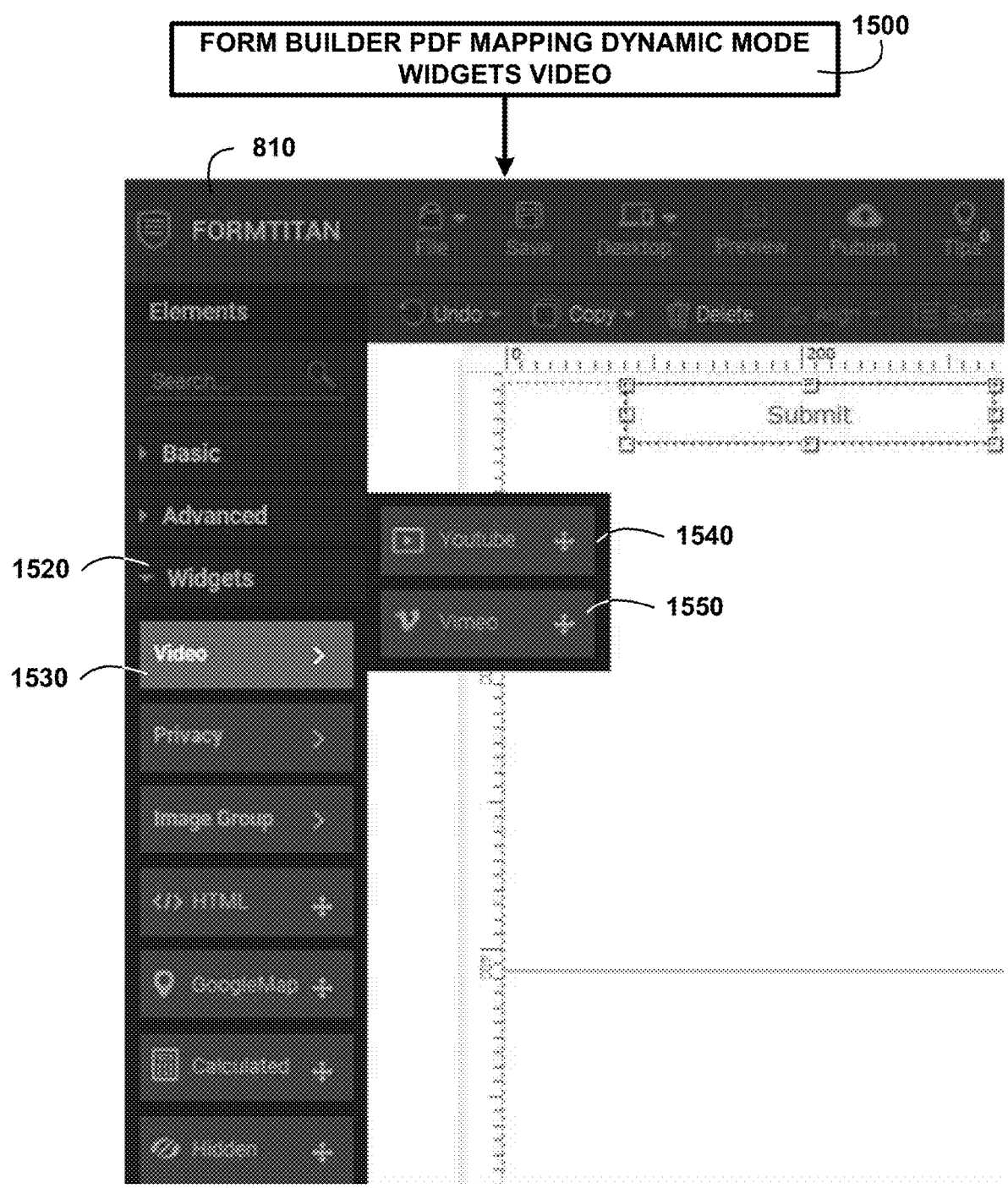
FIG. 15 shows for illustrative purposes only an example of form builder pdf mapping dynamic mode video of one embodiment.

Form Builder Pdf Mapping Dynamic Mode Video:

FIG. 15 shows for illustrative purposes only an example of form builder pdf mapping dynamic mode video of one embodiment. FIG. 15 shows the form builder pdf mapping dynamic mode widgets elements menu and grid layout web page 810. The form builder pdf mapping dynamic mode widgets elements menu includes a video 1500 section. The widgets 1520 video 1530 selection includes a sub-menu including YouTube 1540 and Vimeo 1550 of one embodiment.

Figure 16:
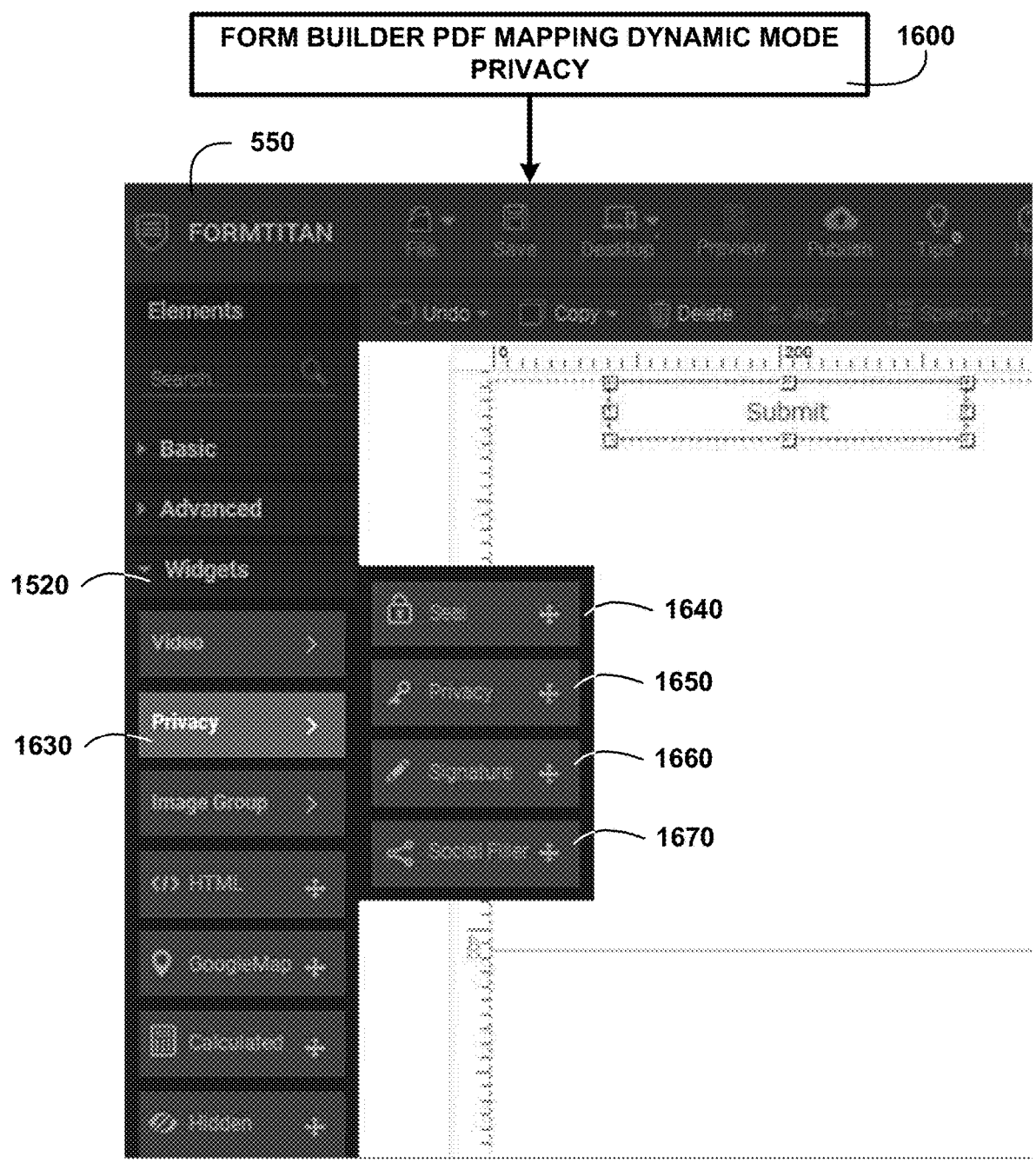
FIG. 16 shows for illustrative purposes only an example of form builder pdf mapping dynamic mode privacy of one embodiment.

Form Builder Pdf Mapping Dynamic Mode Privacy:

FIG. 16 shows for illustrative purposes only an example of form builder pdf mapping dynamic mode privacy of one embodiment. FIG. 16 grid layout web page 810. The form builder pdf mapping dynamic mode widgets elements menu includes a form builder pdf mapping dynamic mode privacy 1600 section. The elements 550 include in the widgets 1520 a privacy 1630 selection. The privacy 1630 selection includes in a sub-menu Seal 1640, Privacy 1650, Signature 1660, and Social Filler 1670 selections of one embodiment.

Figure 17:
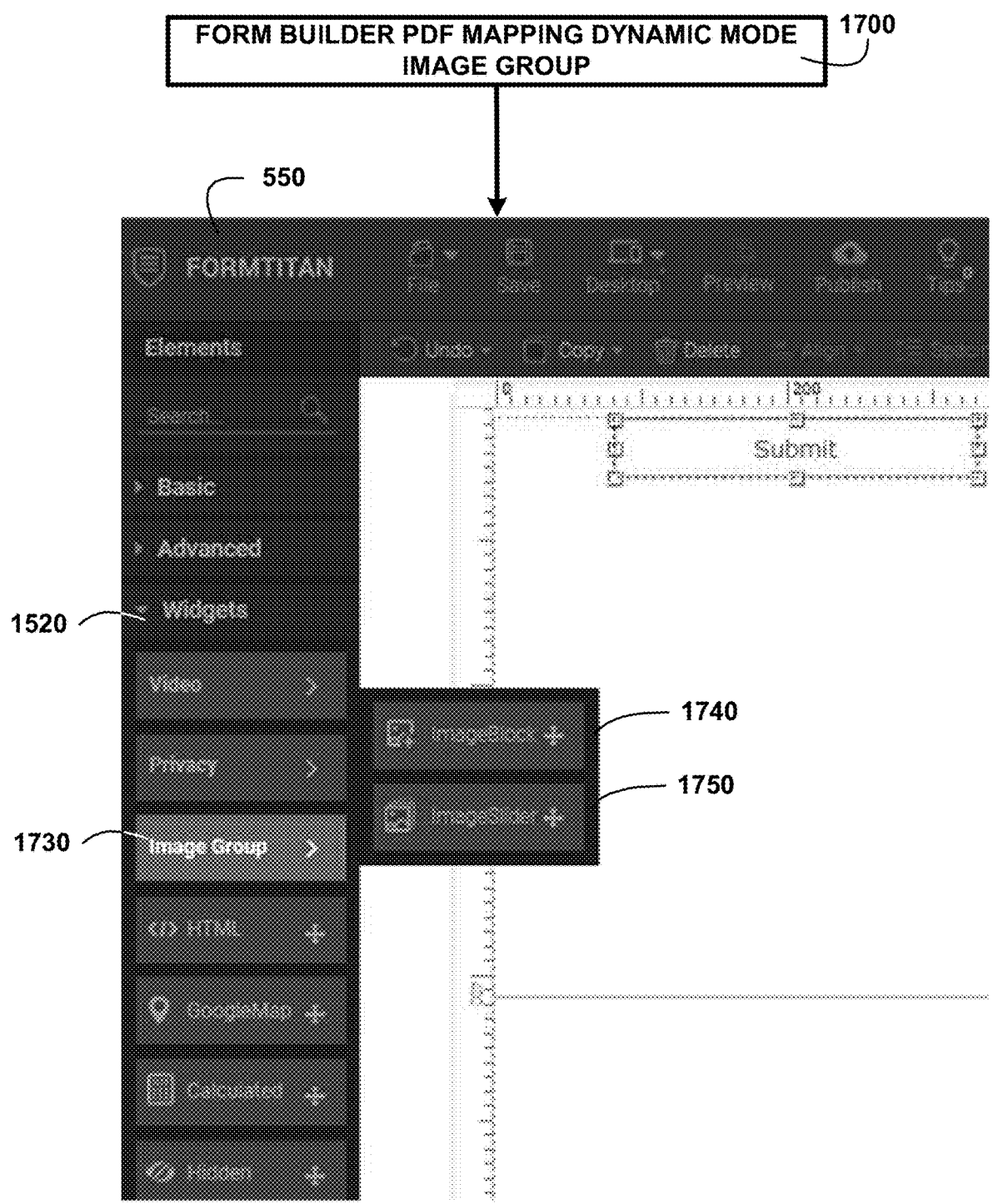
FIG. 17 shows for illustrative purposes only an example of form builder pdf mapping dynamic mode image group of one embodiment.

Form Builder Pdf Mapping Dynamic Mode Image Group:

FIG. 17 shows for illustrative purposes only an example of form builder pdf mapping dynamic mode image group of one embodiment. FIG. 17 shows a form builder pdf mapping dynamic mode image group 1700. In the elements 550 widgets 1520 selections is an image group 1730 that includes in a sub-menu an Imageblock 1740 and Imageslider 1750 for selection by a user of one embodiment.

Figure 18:
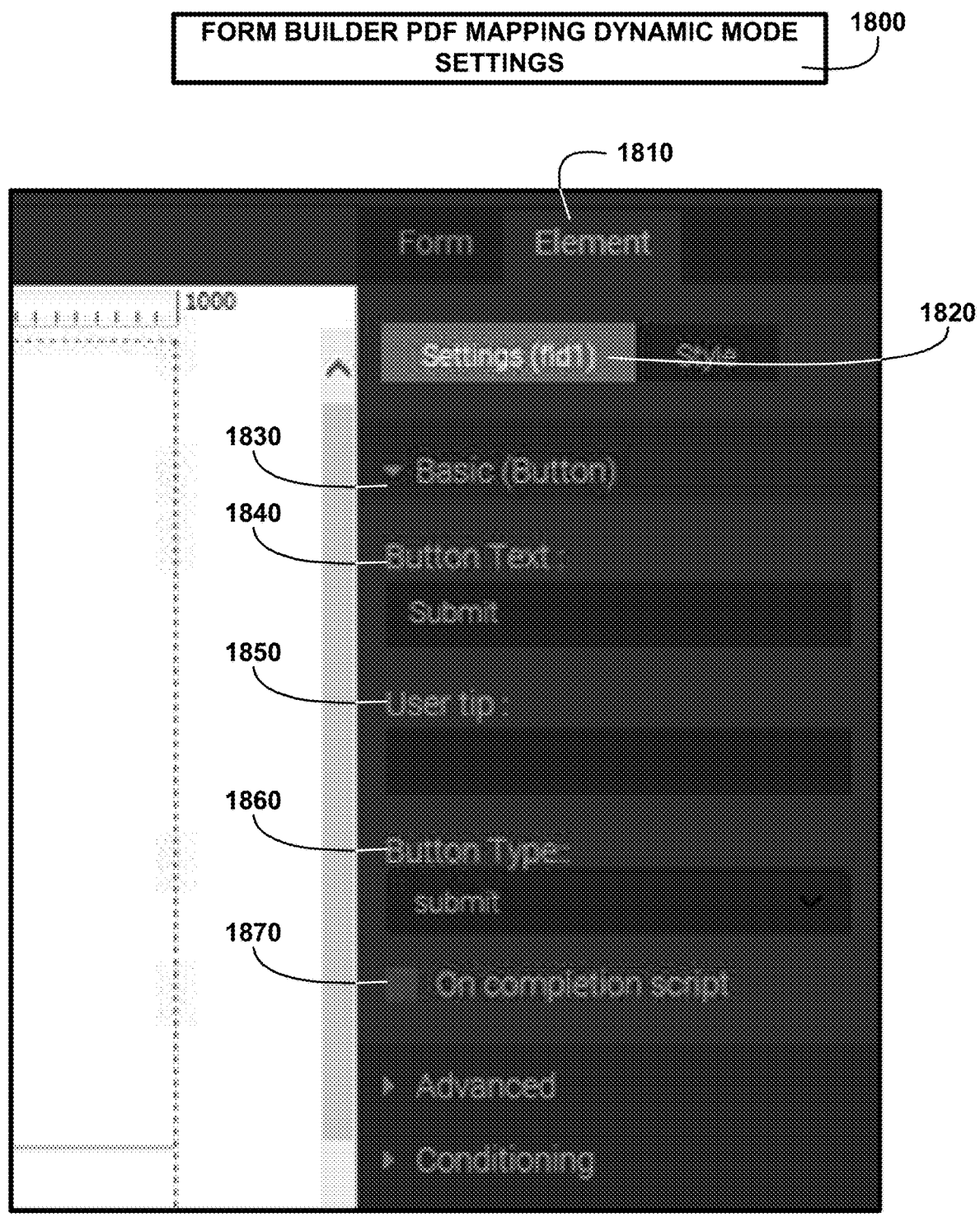
FIG. 18 shows a block diagram of an overview of form builder pdf mapping dynamic mode settings of one embodiment.

Form Builder Pdf Mapping Dynamic Mode Settings:

FIG. 18 shows a block diagram of an overview of form builder pdf mapping dynamic mode settings of one embodiment. FIG. 18 shows form builder pdf mapping dynamic mode settings 1800 elements 550. Under a settings (fld1) 1820 is a basic (button) 1830 selection that includes user selections including button text: 1840, user tip: 1850, button type 1860, and on completion script 1870 selections of one embodiment.

Other features are used for pdf mapping and handling including Adding pages to dynamic PDF, Charts in Auto PDF, Conditional Logic in the PDF Mapping, Generate pdf for all entries in my submission, Maximizing the PDF preview window, Merge attachment and files from Salesforce into PDF, My submissions filter by PDF mapping, page break inside new pdf, PDF Auto preview, PDF generated upon payment, PDF generated upon payment, PDF Interactive mode, PDF kerning works with Interactive mode, pdf mapping—categories, PDF Mapping Additions, PDF Mapping file name and barcode, PDF mapping generated after custom Push, PDF Mapping: Auto PDF, PDF sent to email upon payment, PDF supports letter format, Private content in PDF—Do not include in preview, Processing message for download pdf/auto pdf/file upload in my submissions, Push Signature to Salesforce as attachment without PDF Mapping, Salesforce action Override mode for auto pdf, Vertical Align Added to Elements in PDF Mapping, and View manual/auto PDF information of one embodiment.

Figure 19:
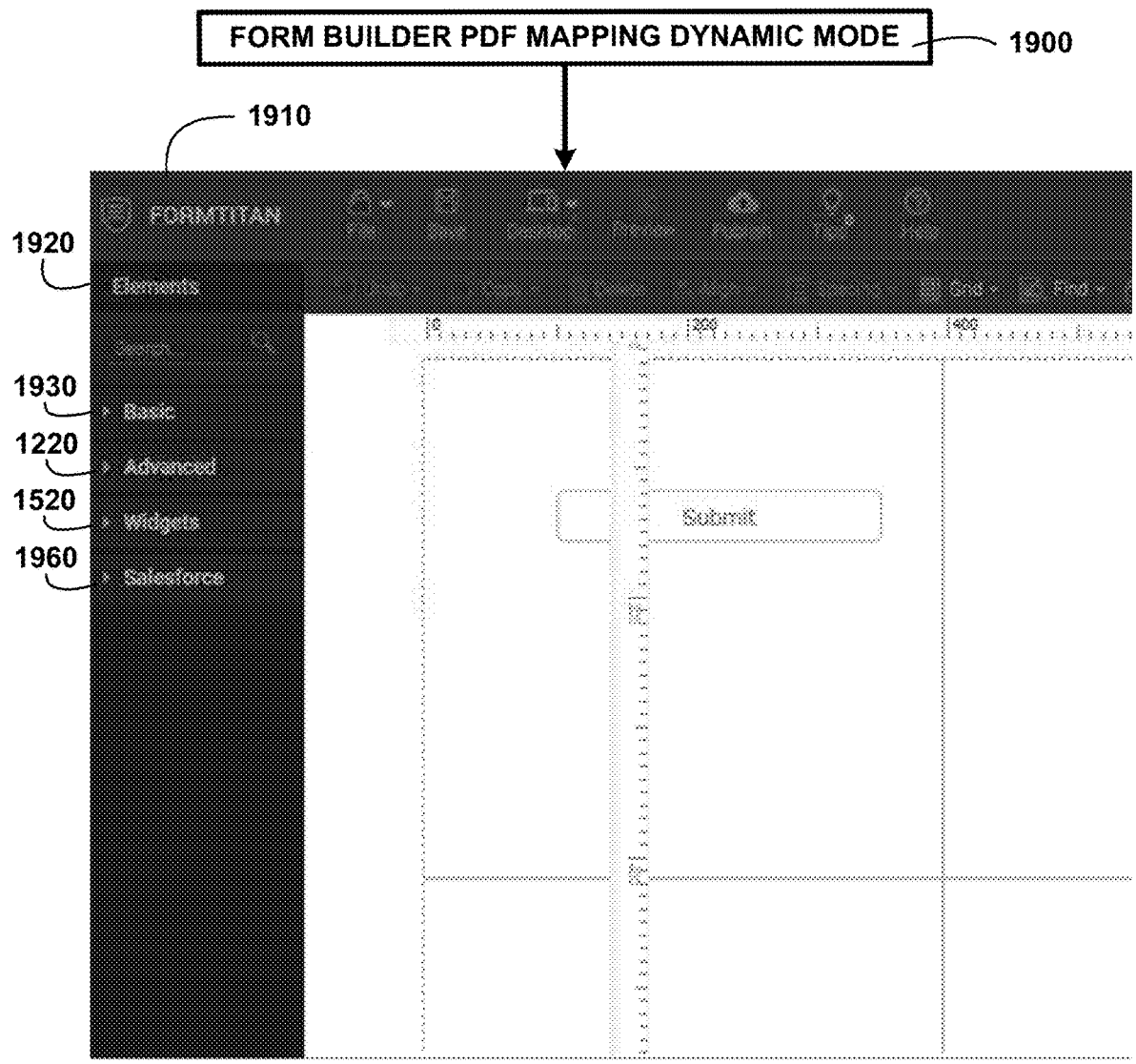
FIG. 19 shows a block diagram of an overview of form builder pdf mapping dynamic mode of one embodiment.

Form Builder Pdf Mapping Dynamic Mode:

FIG. 19 shows a block diagram of an overview of form builder pdf mapping dynamic mode of one embodiment. FIG. 19 shows a form builder pdf mapping dynamic mode 1900 on a FormTitan webpage 1910 that includes an elements selection menu 1920 including basic 1930, advanced 1220, widgets 1520, and Salesforce 1960 of one embodiment.

5—Now let's add the PDF Mapping. Go to: "Properties" panel>"Form" tab>"Settings" option>"Basic" category>Pdf Mapping.
6—Press on the "Map fields" button and a window will open—containing the standard PDF mapping editor. Select the Dynamic mode from the upper toggle.
7—The editor will now switch to the Dynamic PDF editor
8—Now you can Enter your content in the editor. You can make this a multi-page PDF by adding pages. Simply press on the '+Page' in the toolbar and a new page will open in a separate tab.

You can also add pages by inserting a Page break in the PDF editor from the 'Insert' option, and it will divide your PDF into pages. However, this way you will not see the pages in different tabs, but rather a horizontal separation line that will divide the content in the editor. 9—Inserting HTML. Go to Menu>"View">"Source code" and paste your HTML code in the window. 10—Apply Styles. You can enter text and style it: select font, size, color, alignment etc. 11—Adding a table with repeated section data. Go to Menu>"Insert">"Table" and create 1 row and 3 columns. The table will now appear in the editor. It will only have one row, and we will need to just map it to the 3 section fields. but do not worry—more rows will dynamically be added based on the number of rows the form filler added in the repeated section. In the left column—Click inside the column and Enter text: "Child Name:"—Open the "All element" dropdown and Choose the Child name field it will look like this: In the center column—Click inside the column and Enter text: "Child Age:"—Open the "All element" dropdown and Choose the Child Age field it will look like this: In the right column—Click inside the column and Enter text: "Favorite color:"—

Open the "All element" dropdown and Choose the Favorite color field it will look like this: 12—Press on "Settings" in the upper toolbar and configure the PDF properties and set the following: —Open the 'General' category and turn on the "Preview before submit" checkbox. —Open 'Buttons & labels' category and enter a different text for the finish button, Cancel button and preview window title (they already have default values, so this is optional). —Open the 'Emails' category and turn on the "Send to owner" checkbox. This will make sure this PDF is sent to the form owner once the form is submitted. 13—Press on "Apply". 14—One last thing you should know . . . The dynamic PDF you are now creating will be generated in an A4 size document.

The PDF will have default margins on all sides, so if you wish to remove them you can do so by by turning on the 'Remove auto margin' checkbox. If you then decide to add your own margins, you can do this in the Html Source of the PDF. Simply go to: View>Source Code. 15—Save the form. 16—Test your form: Publish it as URL and enter a parent name and details for 3 children. (press twice on "Add" to get three lines). Press on submit—and a preview of the generated PDF will appear. If you press on "Finish" the entry will be submitted and the PDF will be attached to the email sent to the form owner.

Dynamic PDF Mode is designed for users who are using or intend on using the PDF Mapping. In this version we have added a Dynamic Mode to our regular pdf Mapping option. This advanced mode allows you to use HTML code to create your PDF, to play with styles and even add a dynamic table that is populated from a repeated section in your form.

The dynamic PDF mode provides an editor you can create your PDF with. Simply write your text or insert HTML code you have ready. You can then use the editor options to set the styles and last—but most importantly you can now insert a table to this PDF, and map it to a repeated section.

Page Break Inside Dynamic PDF, the dynamic PDF has its own editor that allows you to create a PDF using HTML, styles etc. But what about creating a multi page PDF? This is possible in the regular PDF mode, but can this be done also in the Dynamic mode? In this version we made sure it can—we added the ability to insert a page break to your PDF in the editor. Each time you inset a Page break it will display horizontal lines where the break should be.

Remove auto margin in Dynamic PDF Mapping when using the PDF Mapping, in its dynamic mode, the document is generated to fit an A4 size document and it is given default margins from all sides. In this version we've added an option to remove these default margins. In addition, if you wish to add your own margins you can then do this in the HTML of the PDF (Under the 'View' option in the toolbar).

Adding a Widget to Your Form.

There are times when you want to add a widget/chart or any kind of an external logic into your form. In this scenario you will have to get this external widget to interact with your form fields, whether they are filled manually by the users or populated from Salesforce. To do so, you will have to use a very simple technique: 1—add a HTML widget into your form 2—use the window.parent.FTGetValueByID('FIELD ID')) function. Following is an example to show the exact steps of how to add a gadget to your form. In this example we will show a gauge widget on your form that will respond to a FormTitan slider field. View a live form example Try it for yourself—Let's go: 1—Create new form 2—Add slider element 3—Drag an HTML element 4—paste your widget code in the HTML element: <script type="text/javascript" src="https://www.gstatic.com/charts/loader.js"></script><div id="gauge_div" style="width: 280 px; height:

140 px;"></div><script>google.charts.load('current', {'packages':['gauge']}); google.charts.setOnLoadCallback (drawGauge); var gaugeOptions={min: 0, max: 280, yellowFrom: 200, yellowTo: 250, redFrom: 250, redTo: 250, minorTicks: 5}; var gauge; function drawGauge( ) {gaugeData=new google.visualization.DataTable( ) gaugeData.addColumn('number', 'Speed'); gaugeData.addRows (2); gaugeData.setCell(0, 0, 50); gauge=new google.visualization.Gauge(document.getElementByld('gauge_div')); gauge.draw(gaugeData, gaugeOptions);} setInterval(function( ) {gaugeData.setValue(0, 0, window. parent. FTGetValueByID('FIELD ID')); gauge.draw(gaugeData, gaugeOptions);}, 1000); </script>

5—Replace the FIELD ID with the actual field ID of your slider (OR any other field that you are using) 6—you will then see the widget appear in your HTML element, on canvas Simply resize the HTML element and move it to the right of the Slider field. 7—Select the slider and change its Max number to 200 8—Select the HTML element and remove its border go to: "Properties" panel>'Element' tab>'Style' option>'Border' category>Border style=None 9—Save the form and publish it as URL.

Digital Signature

The "Digital Signature" is an element you can add to your online form when you need your users to sign for identification and Consent (for example: in a legal document, agreements, order forms etc). So if your form requires the form filler's signature—you can easily do so using this feature. Following are steps to add a signature to your form: 1—Enter your form in the form builder 2—Go to the "Elements" panel>"Widgets" category>"Privacy" sub category 3—Drag the "Signature" element. (you can change its style in the "Properties" panel).

Auto Submit Your Form

Seems that there are use cases, in which the form owner does not want the form filler to enter data in the form. He wants to auto populate the fields and have the form automatically submitted. In order for this to be possible we have added a new feature called: "Auto Submit". Following are the steps to make your form auto submit: 1—Enter your form in the form builder. Since this form is intended for auto submit, you should make sure the data is populated in the form automatically when it loads. you can use Params in the URL for this, Salesforce Get integration and conditions to set values in fields based on input. 2—Go to "Properties" panel>Form tab>Settings option>On submit category 3—Turn on the "Allow Auto Submit" checkbox an input box will mow appear below it and you will be required to enter a string of 16 alpha numeric characters. for example: abc234fr48yttr32 4—Save the form 5—Publish the form 6—Add the following to your form URL: ?FTAutoSubmit=abc234fr48yttr32 So it look like this in your Browser address bar: 7 Press on "Enter" and you will then see the form is loaded, populated and finally auto submitted.

Figure 20:
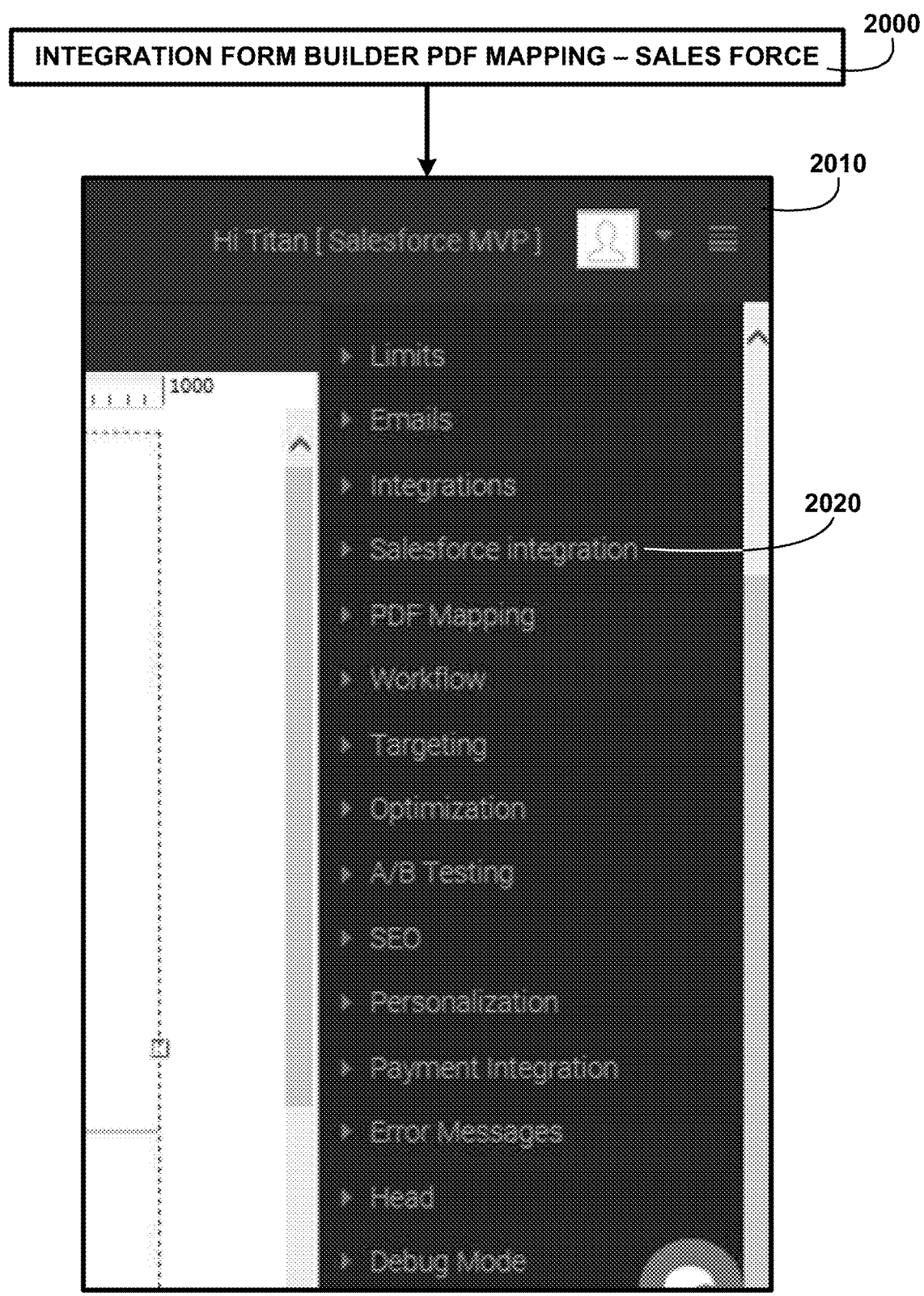
FIG. 20 shows a block diagram of an overview of integration form builder pdf mapping Salesforce of one embodiment.

Integration Form Builder Pdf Mapping Salesforce:

FIG. 20 shows a block diagram of an overview of integration form builder pdf mapping Salesforce of one embodiment. FIG. 20 shows an integration form builder pdf mapping—sales force 2000 Salesforce MVP webpage 2010. The integration form builder pdf mapping—sales force 2000 Salesforce MVP webpage 2010 is used for Salesforce integration 2020 into a user's forms. Other features for Salesforce integration 2020 and functionality include Mapping the Salesforce Checkbox to a Radio button/Dropdown/Multi dropdown, Reset button in Salesforce Push/Get mapping, Salesforce Action button—Now supports Get, Go to Next or Previous Page in Salesforce Action Button, Salesforce Action Button in a multi-page form, Salesforce Action Button per repeated item line, Mapping fields from levels in your Salesforce Table, Mapping the Salesforce Checkbox to a Radio button/Dropdown/Multi dropdown, Mapping the Salesforce Country/State picklists, Push Signature to Salesforce as attachment without PDF Mapping, Controlling which fields may not be editable or creatable in Salesforce mapping, Reset button in Salesforce Push/Get mapping, Salesforce Push mapping to not override in a specific field, Supported boolean in Salesforce table mapping, font—Salesforce Sans, operators for Salesforce Get/Push, Skip Message in Salesforce Get Action, Adding an HREF to The Salesforce Table, Salesforce Table: Mandatory in Edit and Add, Alternative Find In Salesforce Get, Caching object list from Salesforce, Create Upon Payment Label in Salesforce integration, Displaying data from Salesforce in Google map, Document generation (single/bulk) directly from Salesforce, Dynamically Limiting Rows in Salesforce Table with −1, Executing actions after Delete in Salesforce Table, Executing actions after View/Edit/Add in Salesforce Table, Export added to Salesforce Table, Fields Order in Salesforce Form, Go to Next or Previous Page in Salesforce Action Button, Hide Salesforce Table rows footer, Ignore Assignment Rules in Salesforce, Inline editing in the Salesforce Table, Limit num of rows in a Salesforce table based on parameters, Load custom list from Salesforce, Merge attachment and files from Salesforce into PDF, category in Salesforce Get: Translation, publish option: Shadow form (Salesforce web-to-lead), Push Edit later URL to Salesforce, Pushing labels to Salesforce, Replace BR with CRLF in Salesforce Push, Replacing Empty with Null in Salesforce Push, Salesforce Action button—Now supports Get, Salesforce Action Button in a multi-page form, Salesforce Action Button per repeated item line, Salesforce action Override mode for auto pdf, Salesforce Get on load based on a hidden field, Salesforce Table Edit/View/Delete links with Icons, Salesforce Table Max rows per level, Salesforce Table Modal Windows Style, Salesforce translation support for Global Picklist Value Sets, Save as draft working seamlessly with Salesforce integration, Store link to Allow later editing in Salesforce, Submission id in Salesforce push condition upon payment, Supporting Checkbox for multi-picklist in Salesforce, Supporting Child Objects in Salesforce Push Payment, TIME field in Salesforce table—Update and Add, Using a Hyperlink From Salesforce in Your Table, Extended support when mapping Get with Salesforce lookup fields, Refresh Salesforce object list from mapping, element for Salesforce: Chart, Dynamically Limiting Rows in Salesforce Table with −1, Submission id in Salesforce push condition upon payment, Pushing labels to Salesforce, Adding an HREF to The Salesforce Table, Alternative Find In Salesforce Get, Caching object list from Salesforce, category in Salesforce Get: Translation, Create Upon Payment Label in Salesforce integration, Creation Option Added to Salesforce Push—If Multiple Found, Dates format in Salesforce Table View/Edit/New modal windows, Displaying data from Salesforce in Google map, Extended support when mapping Get with Salesforce lookup fields, Fields Order in Salesforce Form, font—Salesforce Sans, Go to Next or Previous Page in Salesforce Action Button, Hide Salesforce Table rows footer, Ignore Assignment Rules in Salesforce, Load custom list from Salesforce, Mapping fields from levels in your Salesforce Table, Mapping the Salesforce Checkbox to a Radio button/Dropdown/Multi dropdown, Mapping the Salesforce Country/State picklists, Move to a specific page using the Salesforce Action button, operators for Salesforce Get/Push, Order of the fields in the Edit Add Salesforce Table windows, publish option: Shadow form (Salesforce web-to-lead), Push Edit later URL to Salesforce, Push logs now reflecting Salesforce Table actions, Replace BR with CRLF in Salesforce Push, Replacing Empty with Null in Salesforce Push, Reset button in Salesforce Push/Get mapping, Salesforce Action button—Now supports Get, Salesforce Action Button in a multi-page form, Salesforce Action Button per repeated item line, Salesforce Get on load based on a hidden field, Salesforce Push mapping to not override in a specific field, Salesforce Table Edit/View/Delete links with Icons, Salesforce Table Max rows per level, Salesforce Table Modal Windows Style, Salesforce Table: Mandatory in Edit and Add, Salesforce translation support for Global Picklist Value Sets, Save as draft working seamlessly with Salesforce integration, Skip Message in Salesforce Get Action, Store link to Allow later editing in Salesforce, Supported boolean in Salesforce table mapping, Supporting Checkbox for multi-picklist in Salesforce, Supporting Child Objects in Salesforce Push Payment, TIME field in Salesforce table—Update and Add, Using a Hyperlink From Salesforce in Your Table, Controlling which fields may not be editable or creatable in Salesforce mapping, Refresh Salesforce object list from mapping, and Salesforce Table with row limit of one embodiment.

Salesforce Get Category—First Steps, Once you press on the "Map Fields" button the "Get from Salesforce" window will open. This is where your integration will be configured and displayed. A few words about Get, "Get" is a very general term that refers to drawing data from one or more Salesforce objects. Each Get action you perform on an Salesforce object will be represented in one integration line, so if you are interested in multiple objects being read you will need to create an integration line for each. The first time you open this window—you will, of course, have no lines and you will need to press on the "Add object" button to create your first integration line.

Once you create your integration line it will be added to this window and you will be able to edit it using four icons on the right side of the line: edit the line, duplicate the line, delete it or add an integration with a child object. First step—Authentication, Now you will be required to do 2 things: 1—Authenticate with your Salesforce account. Simple press on the "Authenticate" button and login to your Salesforce account. If the authentication will succeed a green v icon will appear. 2—Press on "Add object" button to specify the object you want to connect to in your Salesforce account. This will open a window where you will be able to start configuring your get integration. The integration window will open containing 2 categories (out of 7) in an accordion structure. Once you will choose the object the rest of the categories will appear and you will be able to go on with setting your integration.

Salesforce Get Category—Connection is the first category in the accordion, however it mostly informative. This category contains two fields: 1—'Connection' label-specifies the Salesforce account you are currently connected to. 2—"Use different Salesforce connection" checkbox—this is designed for changing your connection to a different account, however you may not use a different connector without a written consent from FormTitan.

Salesforce Get Category—Map Fields, Map Fields is the Seventh category in the accordion and the core of the integration line: this is where you map your form fields to your Salesforce object fields. Map Salesforce fields includes select an object, conditions, rule conditions, sort order, map fields, and messages. This category usually contains one field: 1—'Map fields' button—this button will open a modal window where you will be required to map your form fields to the fields in Salesforce. Simply choose a form field, open the Salesforce field dropdown and choose the field you want to map it to. Please note! This button will only appear if you have more than four fields in your form. If you have four or less the mapping lines will already appear here instead of opening in the modal window. A filter is used to correlate a form field to a corresponding Salesforce field. You can use the filter to look for a specific field, or use the "show" drop down to view "All"/"Mapped fields"/"Not mapped fields".

Salesforce Get Category—Condition is the third category, you will need to fill it in right after 'Salesforce object settings' category. This category contains four fields: 1—'Set Condition' button—this button will open a modal window where you will need to set a condition. If your "get" integration line is not executed on form load (which is flagged in the previous category) you will be required to enter a condition for drawing the data. You wil need to choose: a Salesforce field, an operator and a form field (or other value). For example: Account Name Equals Account, You can press on the "Add new condition" button to add rules or on the minus button to remove rules.

Pressing on the "Show friendly condition" link will let you see the condition is a clearer format. —Turning on the "Remove empty conditions" checkbox—This option makes sure that if a field in your FormTitan form is empty/null it will not add the condition to the query. 2—'If multiple matches found take ID from' radio button—This field will allow you to decide what happens when multiple matches are found. You can choose to use the first result, the last result, use all of the results, or choose "Skip" to pass over mapping altogether. 3—"Limit" numeric textbox—If you chose "All" in the previous radio button you can narrow down the results by drawing only part of them. 4—"ID of section" dropdown—This dropdown contains a list of all the sections in your form. it should be used when you want to display your many results in a repeated section.

Since there are sometimes many section elements in one form, and even sections within sections, It may be hard and even impossible at times to cause a specific section to be repeated automatically. This is where this dropdown comes, allowing you to choose which section will be repeated to display many items. 5—"If not found—run" checkbox—This option is designed for when your integration line returns empty—with no matches found and you want the search to continue by running a different integration line. For example: when you ask for the filler's email to find out if he is a registered contact or lead. You need to look for this email in the contact object first, and if it is not found three, you need to run the next integration line, where you look for it in "Leads" object.

Salesforce Get Category—Rule Condition is the fourth category, There is nothing required in this category. You can use it to create a condition, specifying when this "Get" integration will work. This category contains one field: 1—'Rule Condition' button—this button will open a modal window where you will be able to set a condition. For example: Textbox Contains John. You can of course create a more complex rule by pressing on the "Add new condition" button, using brackets and putting "And"/"Or" between the conditions.

The FormTitan integration feature includes coordination of time zones between the form builder time zone and the time zone wherein the $3^{rd}$ party application is located. In this example to reflect in the form builder created forms the Salesforce time zone to prevent any discrepancy the form builder date time element in the form is mapped to a Date/time field in the Salesforce account.

Adding a chart based on Salesforce data to the form.

The Chart element under the 'Salesforce' category in the 'elements' panel allows you to display information from Salesforce in a graphic way, in real time. This can easily be done—try for yourself! In the following example we will show you how to add a bar chart that shows the number of accounts according to each account type. Following are steps: 1—drag a chart element 2—A chart settings window will automatically open and you will need to choose the chart type. 3—Choose Bar and press on "Next" 4—Press on the "configure Salesforce integration"—Select an object: Account, We will not add a condition this time. 5—Press "Next"—Set the chart as follows: Aggregate By: Count, Count By: Account ID, Chart period: without, Label: Account type, Group By: Account type—Press 'apply' 6—Select the chart on canvas and make it bigger. *While the chart is selected you can always press on the "Map fields" button And change its settings if you want to. *In order to add other types of charts you can do the same exact process, only choose a different chart type. 7—Test the form: Publish it as URL.

Smart Validation for Salesforce. Smart Validation—additional security for your form. The SmartV (short for Smart Validation) is a special element that adds a double verification to your form based on data from Salesforce. It is much like the 2FA (Two Factor Authentication). How does Smart Validation work? When you use the SmartV, a Login window will essentially be create based on the fields you will choose. The form fillers will not be able to access your form. Access will only be granted after 2 steps: First step The authentication window will appear and the form fillers will need to identify themselves, by filling in the required data. If this data They will provide is found comparable with the data in your Salesforce account, an email will be sent to them, containing a secret code.

Second step In the second step the form fillers will need to enter the code in the authentication window. Once all data is confirmed—the form will be accessible. Smart V Session Configurations. Not long ago we released a new feature called Smart V. An element you can use to add a 'Verification window' to your Salesforce integrated forms. Users asked for a way to use the same verification for several forms, and since we found their request legitimate we started working on it. Needless to say, we threw in a few configurations of our own . . . Following are this version's additions to the Smart V element: —Shared session—allows you to it set up the Smart V configuration in one form, and then share this configuration with your other forms. —Enabled Session—lets you set a time frame (in minutes) for your Smart V session. —Captions—enables you to customize the text in the verification window. —Email Settings—allows you to customize the email containing the secret code.

How to add the Smart V to your form. Adding the smart V to your form Following are steps to add a SmartV to your form: 1—Enter your form in the fom builder. 2—Drag a Smart V element from "Elements panel">"Salesforce">"SmartV" 3—Go to "Properties" panel>"Element" tab>"Settings" option>"Basic" category 4—Press on the "Map fields" button to configure your validation. 5—Since the validation is done based on the data in your Salesforce account you will first need to authenticate with Salesforce. 6—Once authenticated press on the "Configure Salesforce integration" button. 7—Choose the Salesforce object you would like to use for this validation—in this example: Contact. 8—Select the fields for the validation by choosing them from the "Add field for display" dropdown, and then press on "Add" button. Please note that you must add an "email" field here so an email with a secret code could be sent to the form filler later on, in the second step of the validation. In this example we have added the following fields from the Salesforce contact object: Email, First name, Secret, Contact ID, Last name. 9—These fields will now be displayed in a table that contains 3 important columns: Email, Value and Secret. You will now have to choose: —which of the the fields will be used for drawing the email address (we chose "email")—which of the fields will be used to hold returned value (we chose "contact id")—which of the fields will be used to store your secret code (we chose "secret") 10—Once this is done press on "Apply" and save your form. 11—In order to do check this LIVE you will need to create a test contact in your Salesforce account. Beforehand and make sure it contains: —You first and last name, —a "Secret" field (create a custom text field for this)—your email address (so that the code is sent to you) You will now see the Smart validation window. Choose a real contact from your Salesforce account and enter its details in this window: the email address, first name and last name. 12—Publish your form as "URL" to test it. You will now see the Smart Validation window. Enter the email, last name and first name of your Test Contact. You will now see a second window, in which you will be required to enter a code. 13—Go to your inbox and copy the code that was sent to you. 14—Paste this code in the window and submit—and the form will open right after. Smart V logout. The Smart V is a 2 factor authentication you can add to your form, and it enables you to make sure that only those you allow will be able to access your form. You can also specify how long the filler's session will last before the form he will need to authenticate again. But what about providing the filler with the option to Logout from the session? In this version we've added a 'Logout' option to the Smart V feature. By dragging a button element and changing its type to 'SmartV Logout' you will enable your form filler to sign out of the session.

Figure 21:
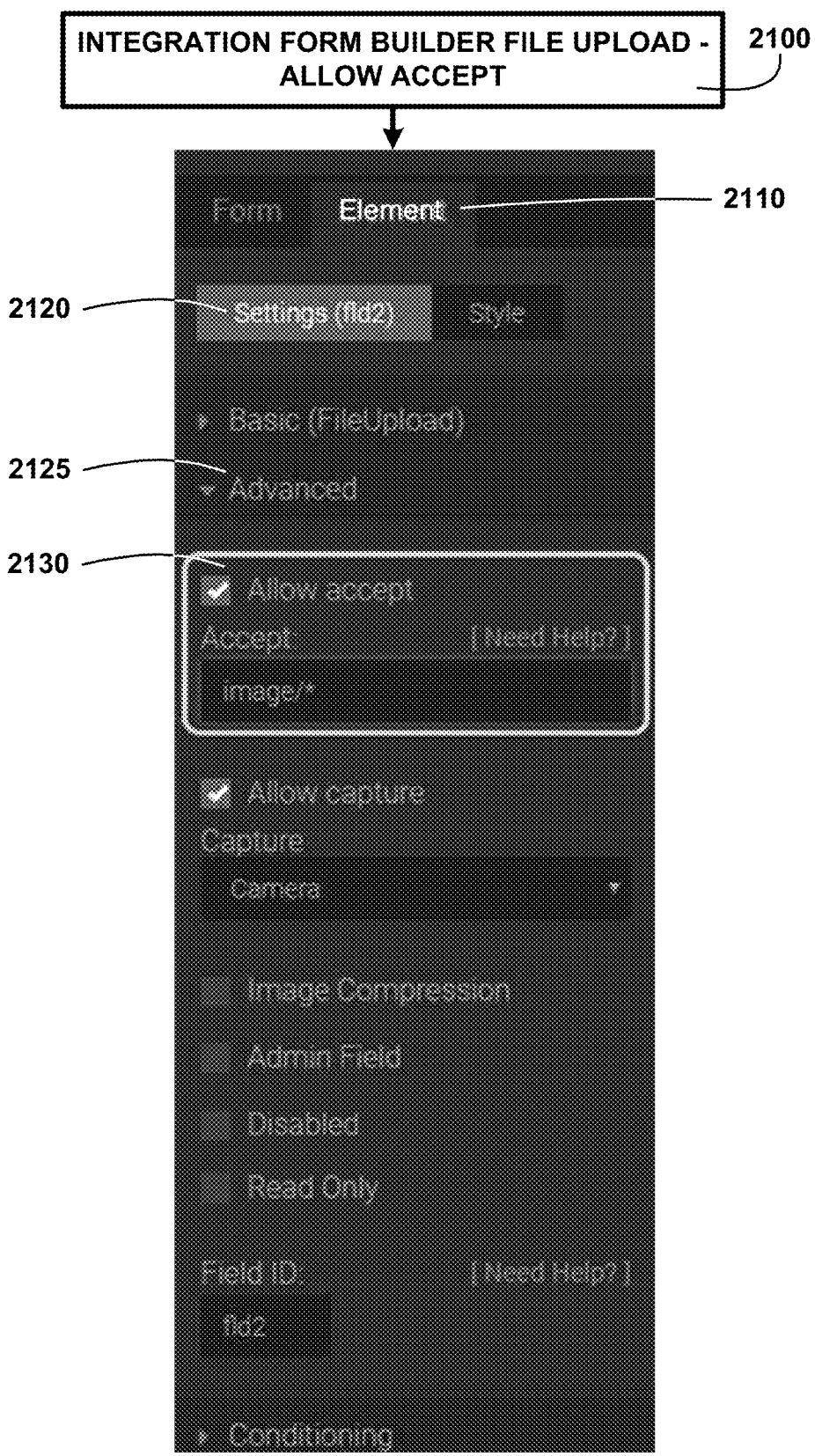
FIG. 21 shows a block diagram of an overview of integration form builder file upload—allow accept of one embodiment.

Integration Form Builder File Upload—Allow Accept:

FIG. 21 shows a block diagram of an overview of integration form builder file upload—allow accept of one embodiment. FIG. 21 shows an integration form builder file upload—allow accept 2100 element 2110 for a settings (fld2) 2120. The advanced 2125 element includes an allow accept 2130 of a file-upload by a user of one embodiment.

File Upload—Allow Accept, We all know how to use a File upload field, right? the filler simply needs to click on the file upload and a browse window opens, and displays his personal computer files, to choose from. It usually displays all of his file types, however you can narrow it down and filter out the files that are not relevant. This is exactly what the file upload 'Allow accept' property does—it adds a filter to the brows window and displays accepted file types according to your request. For example: If you wish for your form filler to upload an image (a GIF, PNG or JPG), there would be no point in displaying irrelevant file types like Doc, CSV, PDF, HTML etc. Following are steps to use the 'Allow Accept' option?

1—Select the file upload element on canvas. 2—Go to ?roperties' panel>'Element' tab>'Advanced' category Turn on the "Allow accept" checkbox. 3—Specify the file types you wish the filler to see. Make sure to start each file type with a dot and separated multiple file types with a comma—like so: .jpg, .png. 4—Save your form and test it—Publish your form as URL, —Click on the file upload field, —The browse window will then open—you will see that it displays either JPG or PNG file types.

File Upload—Allow Capture is an element for a user uploading files and attaching them to the form created using form builder. Form builder includes a file upload element to enable a user to upload files using a 'Capture' property that extends this function of the file upload element. The capture property allows a user to capture an image, an audio or video right then and there, and attach it to your form. File Upload—Allow Capture The file upload element enables your form fillers to upload files and attach them to the form. The 'Capture' property extends this functionality, because it allows the filler to capture an image, an audio or video right then and there, and attach it to your form. When the form filler clicks on the File upload field—this immediately opens the relevant application and enables him to capture his file. Following are steps to use the 'Allow capture' option? 1—Select the file upload element on canvas. 2—Go to ?roperties' panel>'Element' tab>'Basic' category. Turn on the 'Include in email' checkbox. 3—Go to 'Properties' panel>'Element' tab>'Advanced' category, Turn on the "Allow capture" checkbox. 4—You will then get three options: —Camera: used to capture images, —Microphone: used to capture audio and—Camcorder: used to capture a video. 5—Choose one of these options—in this example: Camera. 6—Turn on the "Allow accept" checkbox and enter a suitable value: If you chose Camera→Type: image/*, If you chose Microphone→Type: audio/*, If you chose Camcorder→Type: video/*. Since we chose "Camera" in the previous step—please type: image/*. 7—Save your form and test it, —Publish your form as URL, —send it to yourself and open it in your Mobile phone browser. —Click on the File upload field and the relevant application will automatically open (the camera, the audio recorder or the video camera). —Once you've finished—Press on 'OK' and the file you just captured will be attached to the form's File Upload field. —Submit the form—Check your inbox and you will receive the submission, which includes your captured file of one embodiment.

Figure 22:
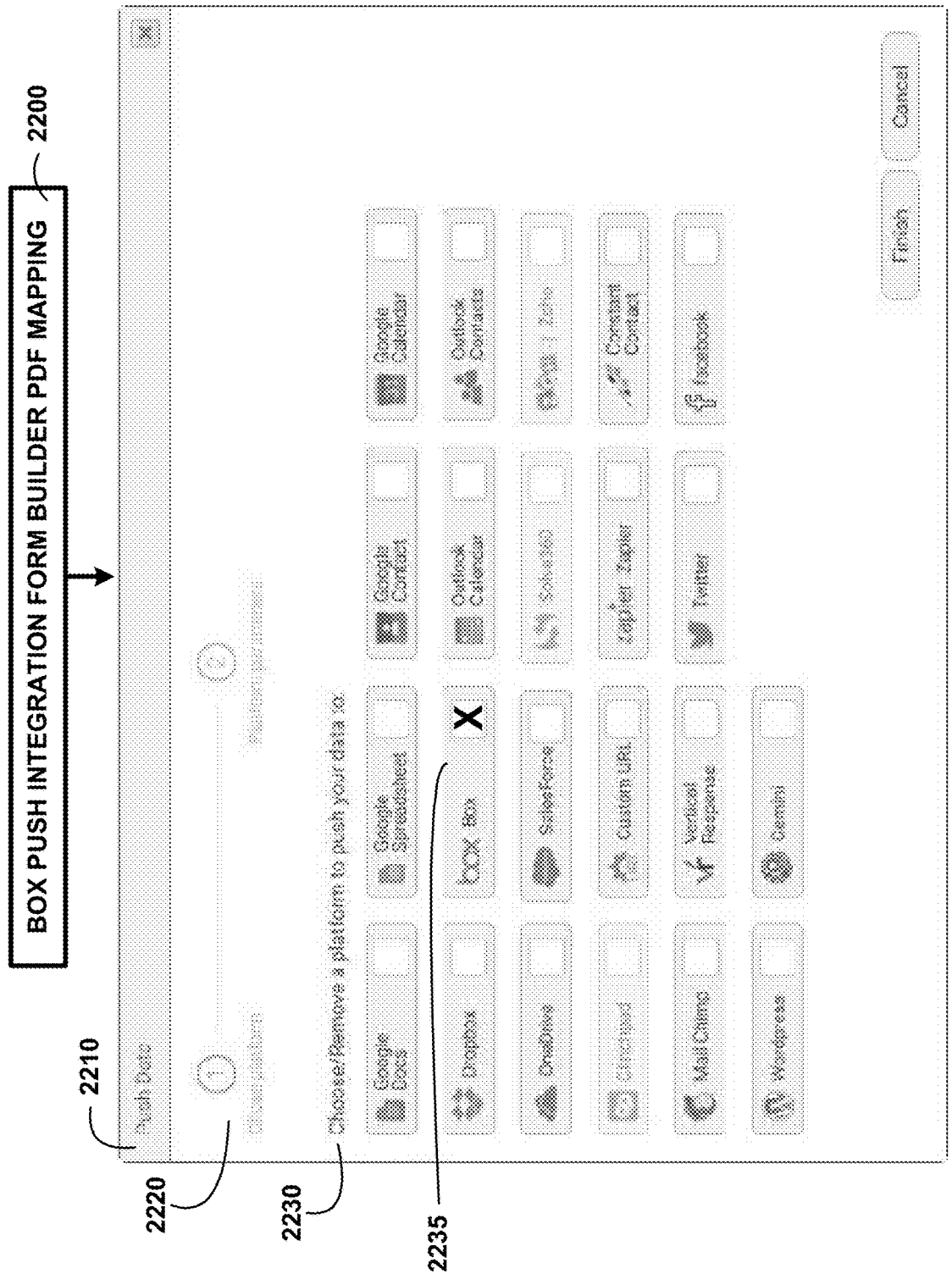
FIG. 22 shows for illustrative purposes only an example of box push integration form builder pdf mapping of one embodiment.

Box Push Integration Form Builder Pdf Mapping:

FIG. 22 shows for illustrative purposes only an example of box push integration form builder pdf mapping of one embodiment. FIG. 22 shows box push integration form builder pdf mapping 2200 to push data 2210 to an integrated platform. Step 1—choose platform 2220 allows a user to choose/remove a platform to push your data to: 2230. For example the user may choose "box Box" by clicking on the input box to place an "X" 2235 for the choice selection of one embodiment.

FIG. 22 shows box push integration form builder pdf mapping. Box offers secure content management and collaboration for individuals, teams and businesses, enabling secure file sharing and access to your files online. By using the customized customer relationship management platform method and devices Push option you can automatically update your Box account.

Following are steps to integrate with Box

1—Open the form you would like to integrate in the Form Builder.

2—Go to "Properties Panel">"Form" tab>"Settings">"Integrations" Category>"Push notification"—Press on "Set Notifications"

3—In the first wizard step: Choose Platform, select "Box".

4—In order to push data to your Dropbox you first will need to "Authenticate with Box".

5—Once authenticated you will be required to enter Box Parameters: File Prefix—This field is not mandatory, but you can choose to add a prefix to the file name created in Box. Folder—Enter a folder name, which will be set up in your Box account and will store your entries. This field is mandatory.

6—Turn on the notification toggle and Press on "Finish".

Example for how the integration works

Now that your form is configured to integrate with Box—a user will fill in your form and then:

1—Once you enter your Box account you will find the folder you configured in the push process and the entries will be stored under it.

Figure 23:
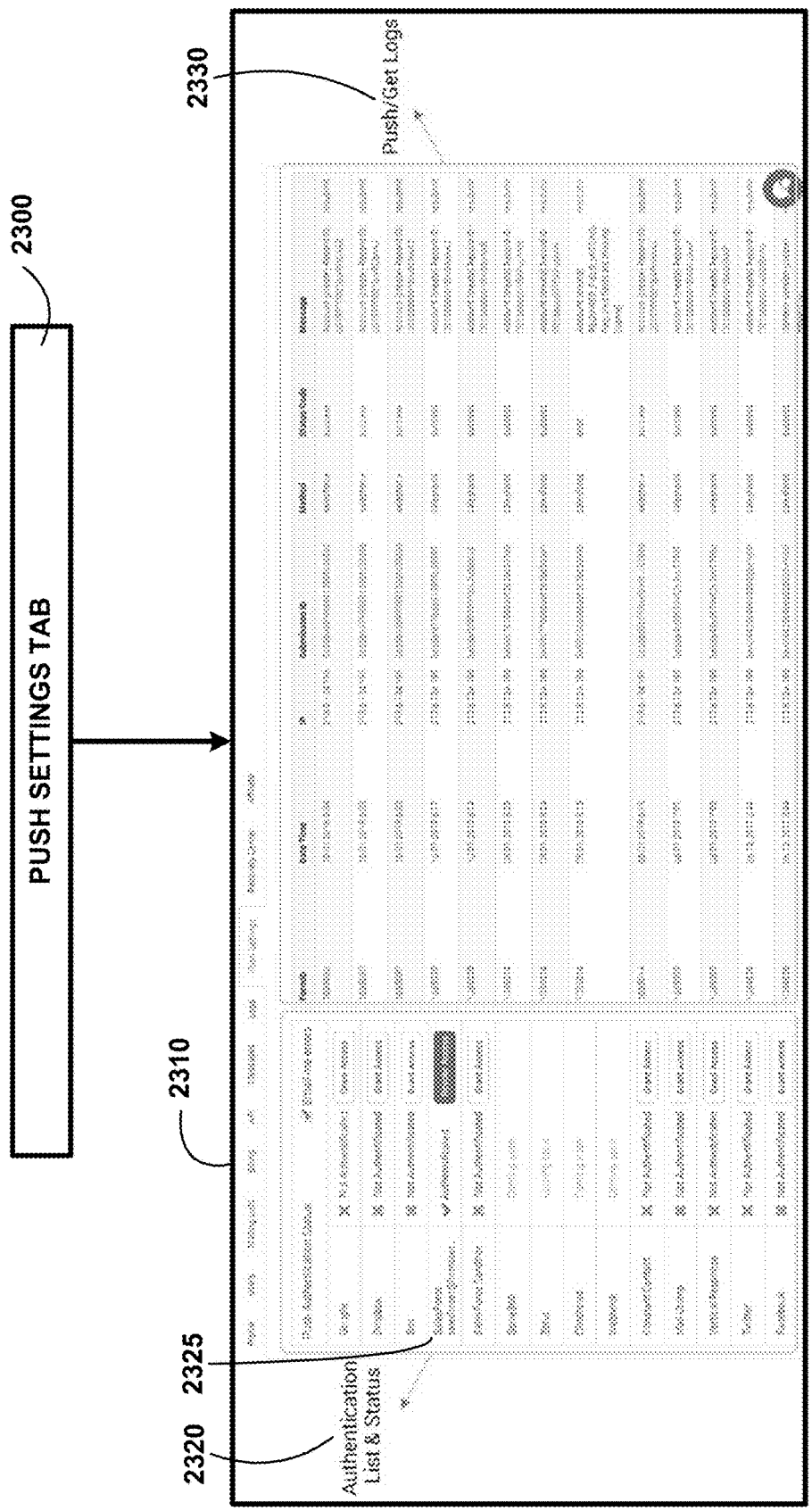
FIG. 23 shows for illustrative purposes only an example of push settings tab of one embodiment.

Push Settings Tab:

FIG. 23 shows for illustrative purposes only an example of push settings tab of one embodiment. FIG. 23 shows a push settings tab 2300 on a push settings tab webpage 2310. The user makes selections for an authentication list & status 2320 of a platform for example Salesforce . . . Salesforce @ FormTitan 2325 to receive automatically Push/Get Logs 2330 from the integrated Salesforce platform.

Other push features include error messages for skip in push, Map fields in get—made wide like in push, No override of empty fields in push, Redirect only after push is complete, All option added to Push Update, error message in Push logs: FT Request Limit, Errors from Push to Box are now in Logs, filter in Push Logs, Form Name in Push Logs, Ignore mandatory and validations in Custom Push, Push logs available in my submissions, Push mapping Condition, Redirect in Custom Push and Get, Twilio integration—Push to SMS and WhatsApp, and Values of Hidden fields now shown after custom Push of one embodiment.

FIG. 23 shows Push Settings Tab wherein "My Account" gives you quick access to settings and tools for managing your customized customer relationship management platform method and devices account. It is divided into nine tabs and "Push Settings" tab is the eighth.

This tab is divided into 2 main areas:

1—Push Authentication List & Status—on the left

2—Push Logs—on the right

Figure 24:
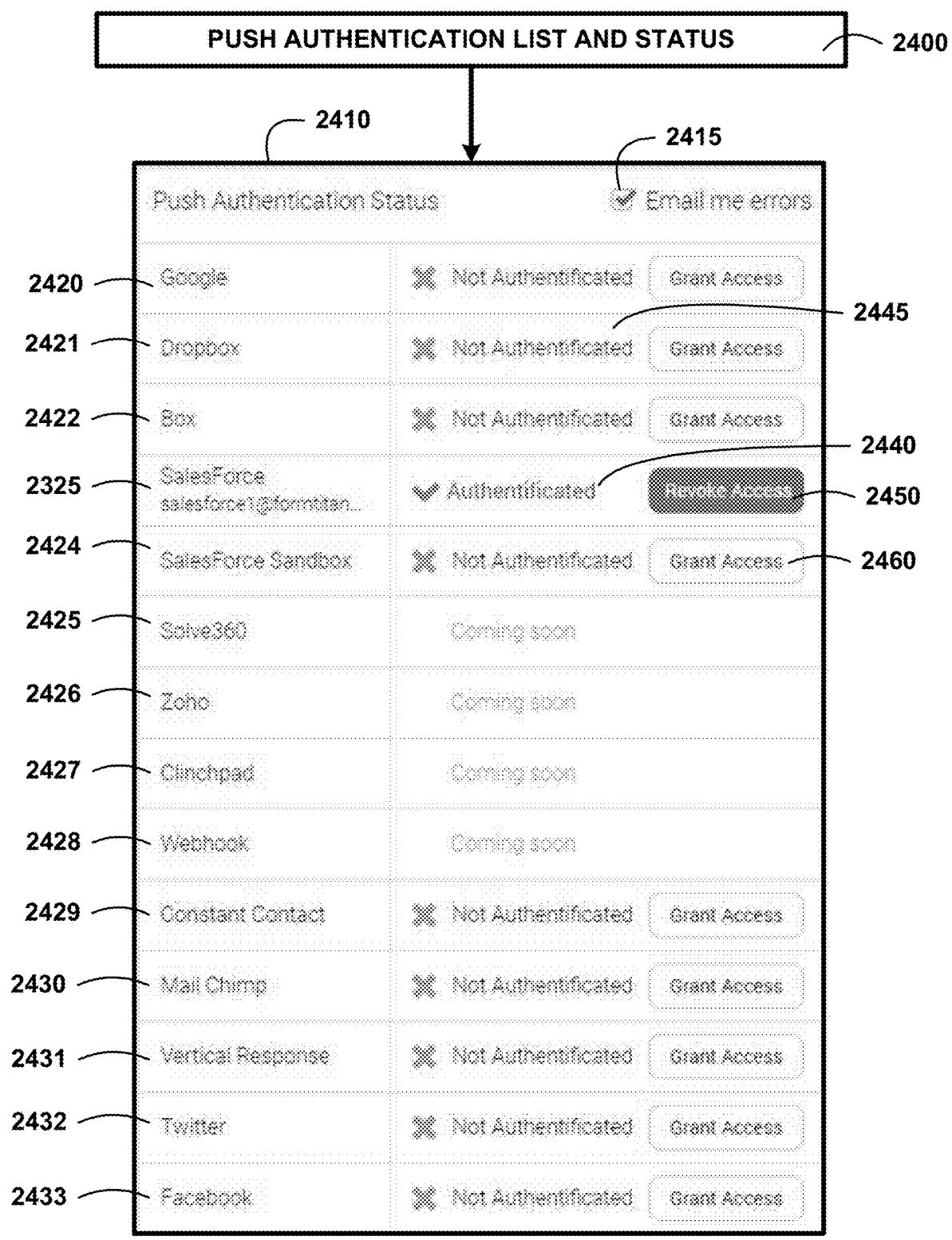
FIG. 24 shows for illustrative purposes only an example of push authentication list and status of one embodiment.

Push Authentication List and Status:

FIG. 24 shows for illustrative purposes only an example of push authentication list and status of one embodiment. FIG. 24 shows a push authentication list and status 2400 with which a user can check the push authentication status 2410 of various platforms they may have chosen. The platforms can include for example Google 2420, Dropbox 2421, Box 2422, for example Salesforce . . . Salesforce @ FormTitan 2325, Salesforce Sandbox 2424, Solve 360 2425, Zoho 2426, Clinchpad 2427, Webhook 2428, Constant Contact 2429, Mail Chimp 2430, Vertical Response 2431, Twitter 2432, and Facebook 2433. The push authentication status 2410 provides a user with a selection to email me errors 2415. The push authentication list and status 2400 provides information and selections for a user showing the status of platforms including not authentificated 2445 or authentificated 2440. The user can select features to revoke access 2450 or grant access 2460 to a platform of one embodiment.

FIG. 24 shows a Push Authentication List & Status including a list of all the 3rd party integrations FormTitan provides, also called "Push integrations" (because we "push" the data out).

We offer all the push integrations you can think of:
    integrations made through Zapier Zap.
    integrations made through FotrmTitan, which currently
        include: Salesforce, Dynamics 365, Google docs, Google spreadsheets, Google contacts, Google calendar, Dropbox, Box, Outlook calendar, Outlook contacts, OneDrive, Custom URL, Constant contact, Mail chimp, Vertical response, Twitter, Facebook, Wordpress, Gemini and Zapier Hook. In this list you can see the 3rd parties you are currently authenticated with. You can also authenticate or revoke access from here. Read more on how to revoke an integration, and how to authenticate an integration. At the top of the list there is an "Email me errors" checkbox, which is turned on by default. This makes sure that if errors occur while users submit a form that is integrated you will receive an email containing this error.

Figure 25:
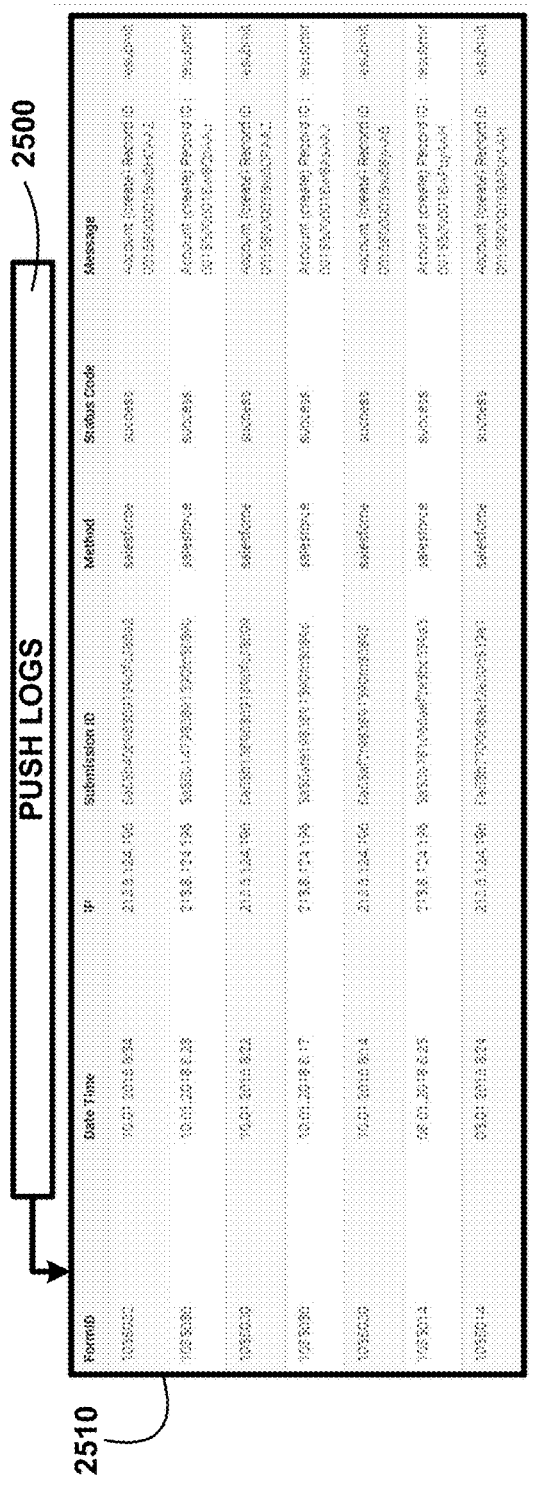
FIG. 25 shows for illustrative purposes only an example of push logs of one embodiment.

Push Logs:

FIG. 25 shows for illustrative purposes only an example of push logs of one embodiment. FIG. 25 shows push logs 2500 a user can select to check data pushed. The push logs 2500 can provide a user with a listing of data pushed to for example Salesforce 2510 of one embodiment.

FIG. 25 shows Push Logs. The table is called a 'Push/Get log'. It contains all the integration action rows for both your push and get integrations.

Each time an action is taken—either get or push—an action row is created in the log containing:
Form Id: what form the action belongs to
Date time: Date of the action
IP: the form filler IP
Submission ID: the submission Idthe action belongs to. This is also a link that displays the submission in "My submissions" page.
Method: Integration party. for example: Salesforce.
Status code: Success or error
Message: Each message contains:
the object used in the action (for example 'Account' or 'Contact')
the action that was taken (Create/Update/Delete . . . )
The error description
a link to the object in Salesforce/or another 3rd party
Resubmit: When an action fails and there is an error—then data is not synced with the 3rd party like it should. However, do not worry, for the information is not lost. and after you make the required fix in your form—you can press on this "Resubmit" link and have the missing data added.

Figure 26:
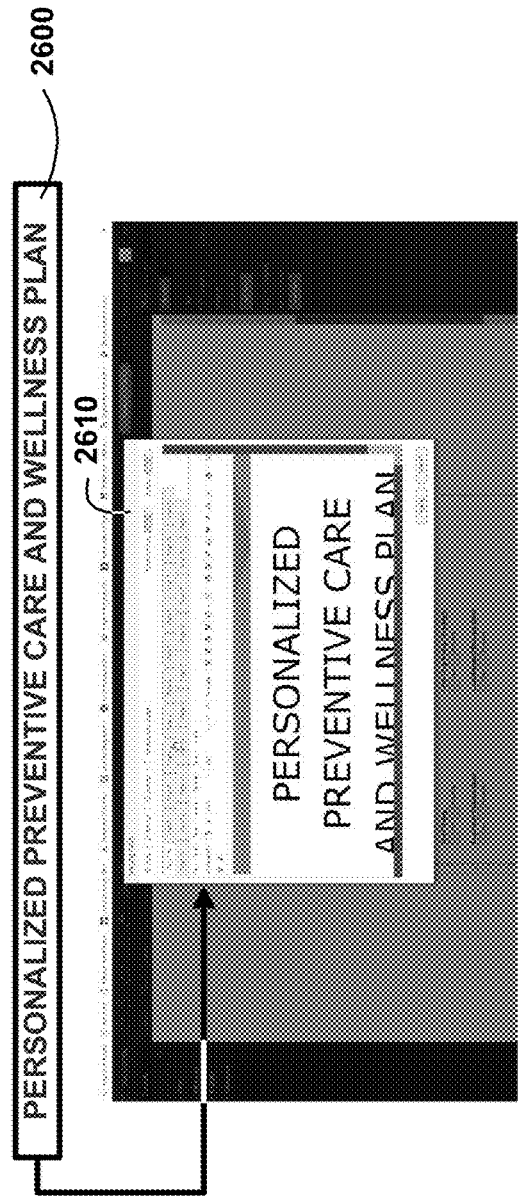
FIG. 26 shows for illustrative purposes only an example of personalized preventive care and wellness plan of one embodiment.

Personalized Preventive Care and Wellness Plan:

FIG. 26 shows for illustrative purposes only an example of personalized preventive care and wellness plan of one embodiment. FIG. 26 shows a personalized preventive care and wellness plan 2600. A user can for example open a personalized preventive care and wellness plan description 2610 to review and revise as they see fit of one embodiment.

The customized customer relationship management platform can be used in health care user applications. The health care industry uses a great deal of forms from initial patient intake, exams, lab test, diagnostics and so forth. The customized customer relationship management platform form builder can reduce workloads by automating data collection using form builder responsive forms that gather the data directly rather than have manual entry of the data. Many health care companies have multiple locations and even nationally distributed locations. Some of those same location may use different $3^{rd}$ party applications which further complicates data collection. In addition the federal requirements for maintaining electronic health records need standardization within a company to prevent non-compliance issues. The customized customer relationship management platform functionality and integration capability can allow a company to standardize data collection while maintaining different $3^{rd}$ party application thereby saving the replace cost of the applications.

Figure 27:
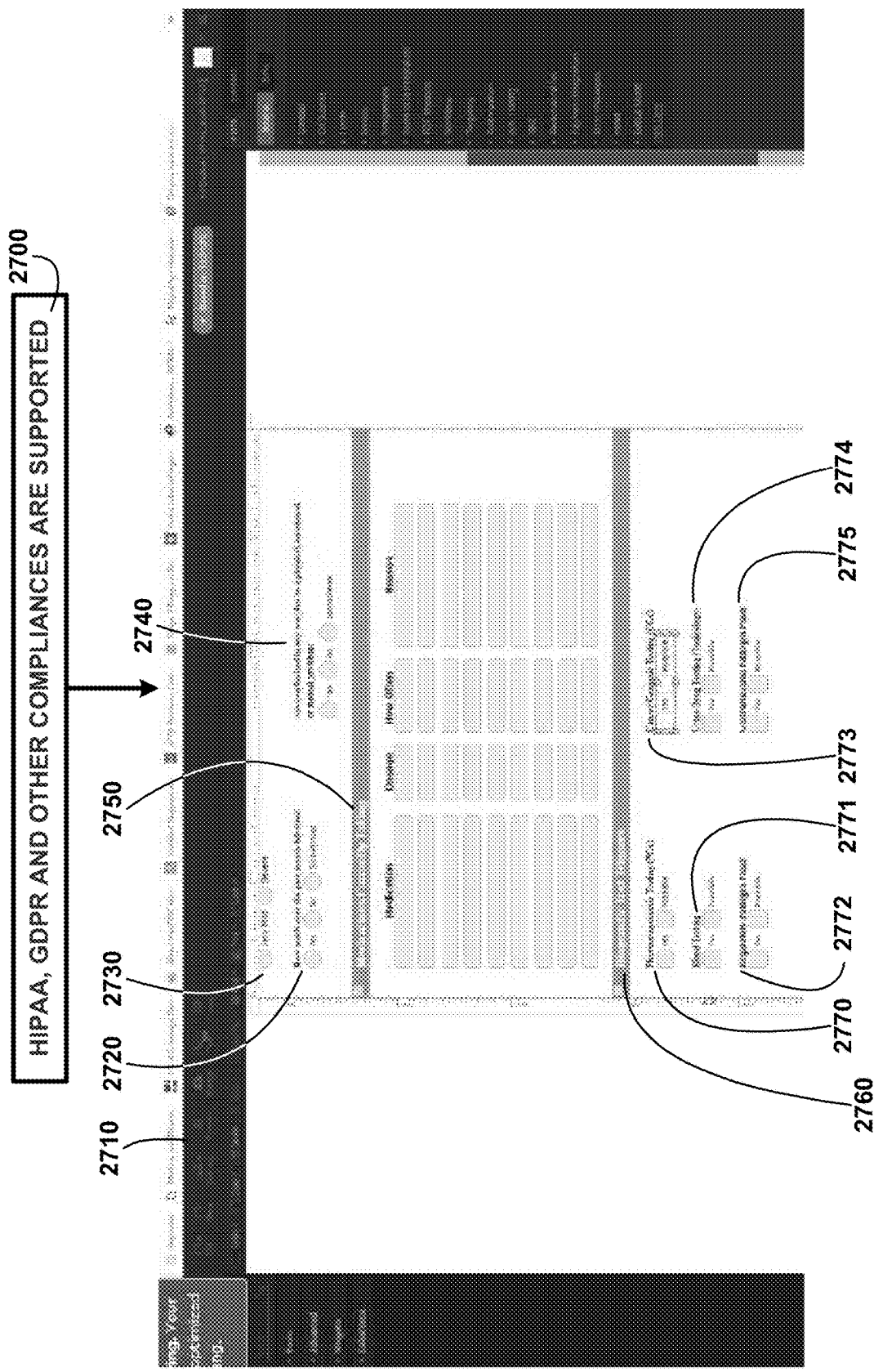
FIG. 27 shows for illustrative purposes only an example of HIPAA, GDPR and other compliances are supported of one embodiment.

HIPAA, GDPR and Other Compliances are Supported:

FIG. 27 shows for illustrative purposes only an example of HIPAA, GDPR and other compliances are supported of one embodiment. FIG. 27 shows HIPAA, GDPR and other compliances are supported 2700 in the customized customer relationship management platform method and devices. A preview 2710 of potential health issues is provided to allow a user to comply with regulations and suggested health care programs described in the Health Insurance Portability and Accountability Act (HIPAA) and General Data Protection Regulation (GDPR) to keep a patient information private. The preview 2710 includes for example a series of questions the user can answer for example how much over the past month felt tired: yes, no, sometimes 2720 very mild, severe 2730 and are you limited in any way due to a physical, emotional, or mental problem: yes, no, sometimes 2740 of one embodiment.

HIPAA, GDPR and other compliances support allows health care companies to comply with the myriad of compliance regulations using a single source product for form creation or conversion, not have to change existing hardware and software and standardize their operations across multiple facilities regardless of location using the customized customer relationship management platform functionality and integration capability.

Figure 28:
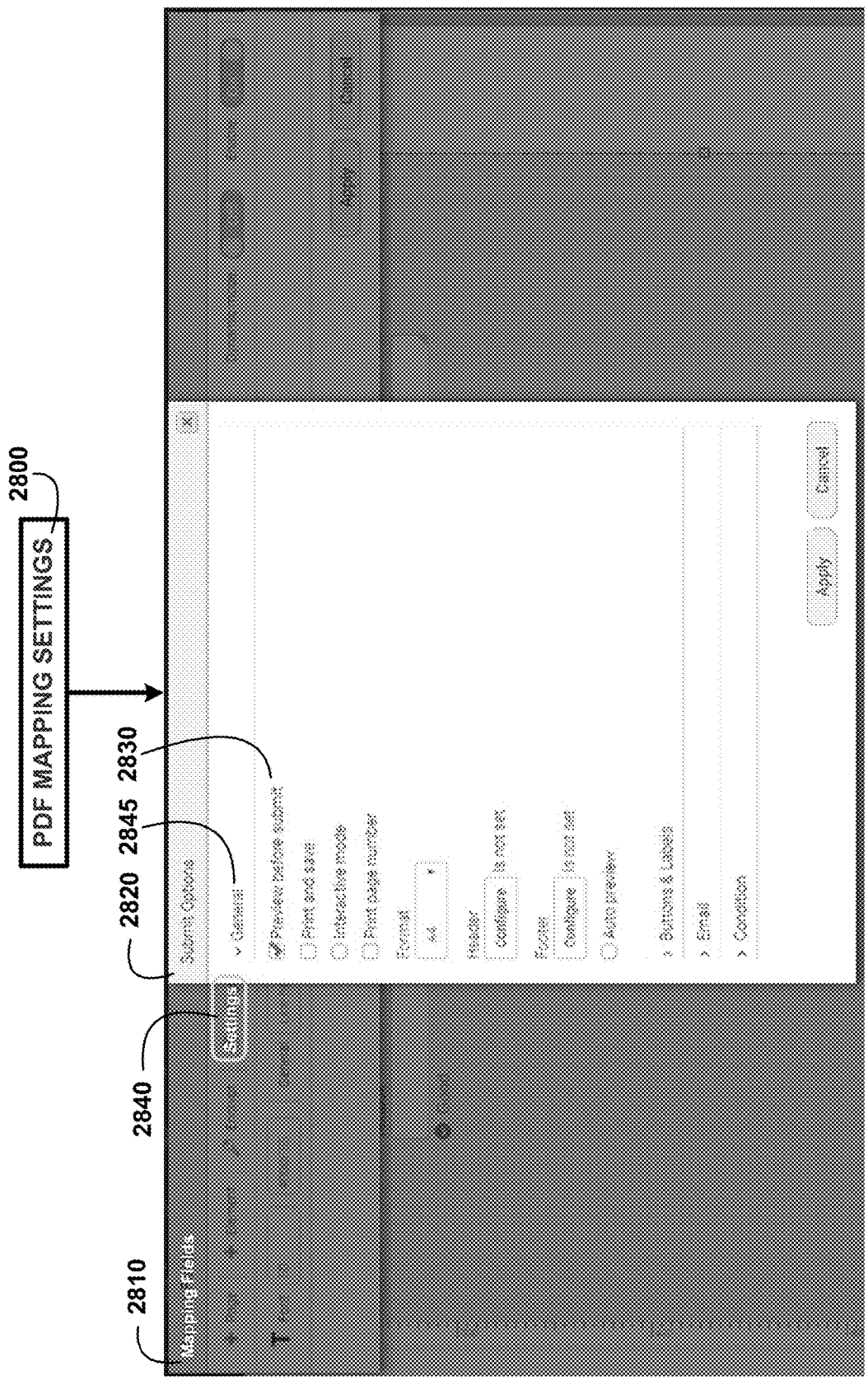
FIG. 28 shows for illustrative purposes only an example of pdf mapping settings of one embodiment.

PDF Mapping Settings:

FIGS. 28-32 show for illustrative purposes only an example of pdf mapping settings of one embodiment. FIG. 28 shows for illustrative purposes only an example of pdf mapping settings of one embodiment. FIG. 28 shows pdf mapping settings 2800 on a mapping fields 2810 webpage. The mapping fields 2810 webpage includes a selection to submit options 2820 for settings 2840 including for example a general 2845 selection to preview before submit 2830 of one embodiment.

Figure 29:
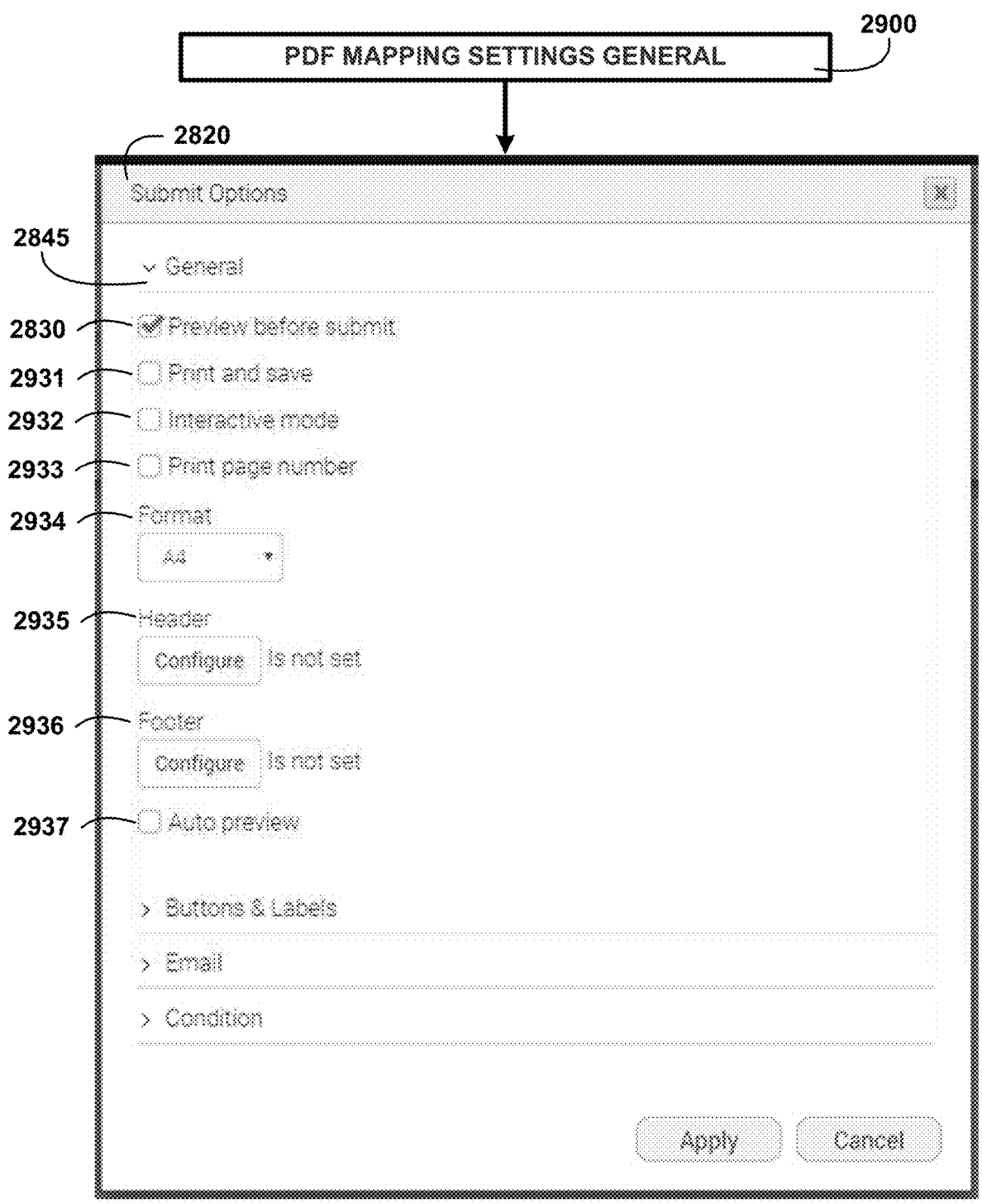
FIG. 29 shows for illustrative purposes only an example of pdf mapping settings general of one embodiment.

Pdf Mapping Settings General:

FIG. 29 shows for illustrative purposes only an example of pdf mapping settings general of one embodiment. FIG. 29 shows pdf mapping settings general 2900 including submit options 2820 of the general 2845 features including preview before submit 2830, print and save 2931, interactive mode 2932, print page number 2933, format 2934 for example A4, header 2935 with an instruction to configure . . . is not set showing it has not been configured, footer 2936 with an instruction to configure . . . is not set showing it has not been configured, and auto preview 2937 of one embodiment.

Figure 30:
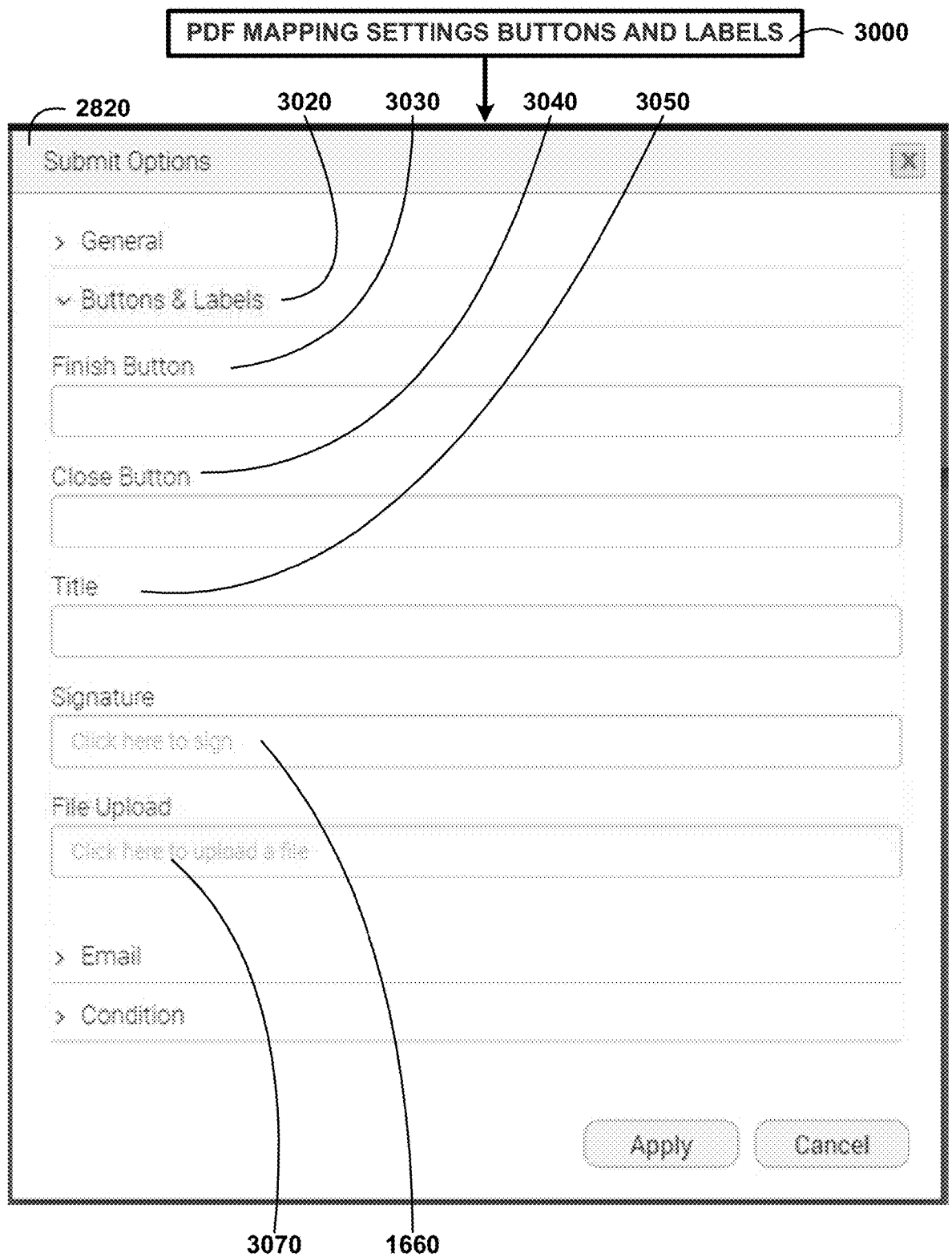
FIG. 30 shows for illustrative purposes only an example of pdf mapping settings buttons and labels of one embodiment.

Pdf Mapping Settings Buttons and Labels:

FIG. 30 shows for illustrative purposes only an example of pdf mapping settings buttons and labels of one embodiment. FIG. 30 shows a pdf mapping settings buttons and labels 3000 feature including the submit options 2820 and a selection menu for buttons & labels 3020. The buttons & labels 3020 selection menu includes finish button 3030, close button 3040, title 3050, signature 1660 with an instruction to click here to sign, and file upload 3070 with an instruction toclick here to upload a file of one embodiment.

Additional settings buttons include features including Add and remove buttons in repeated section, Add script after button completes its task, Enable/Disable condition result options for Checkbox and Radio button, Condition button type allows to manipulate section tabs, Confirmation Mode on button, Disallow items of Picklists in Dropdown, Radio button, Checkbox/Multiple dropdown, Draft button—Hide confirmation, Excess buttons removed from repeated section, Move to a specific page using the Salesforce Action button, button type: Redirect, Page break with flexible next/prev buttons, Repeated section—Show remove button for last, Styles for buttons in Table element including alignment, Text direction buttons in HTML editors, Button—Reset Signature, Option to Ignore Empty Conditions in Action Button—Get, Go to page Button based on Hidden, Button Type: Condition, On click event added to Button, Add and remove buttons in repeated section, Button—Reset Signature, Button Type: Condition, button type: Redirect, On click event added to Button, Repeated section—Show remove button for last, Condition button type allows to manipulate section tabs, Confirmation Mode on button, and Text direction buttons in HTML editors of one embodiment.

Figure 31:
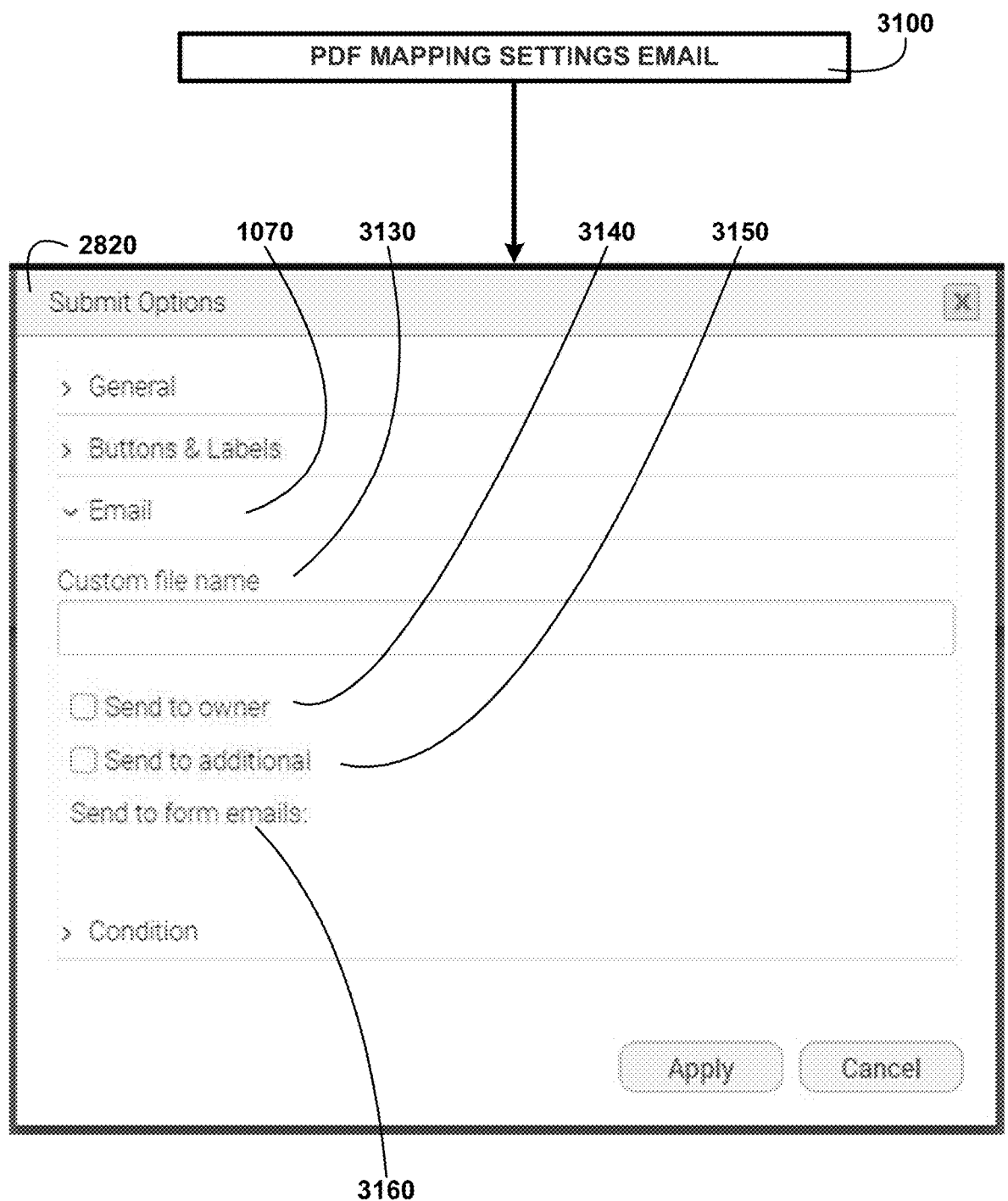
FIG. 31 shows for illustrative purposes only an example of pdf mapping settings email of one embodiment.

Pdf Mapping Settings Email:

FIG. 31 shows for illustrative purposes only an example of pdf mapping settings email of one embodiment. FIG. 31 shows a pdf mapping settings email 3100 feature that includes the submit options 2820 selection. The pdf mapping settings feature email 1070 includes a custom file name 3130, send to owner 3140, send to additional 3150, and send to form emails 3160 of one embodiment.

Figure 32:
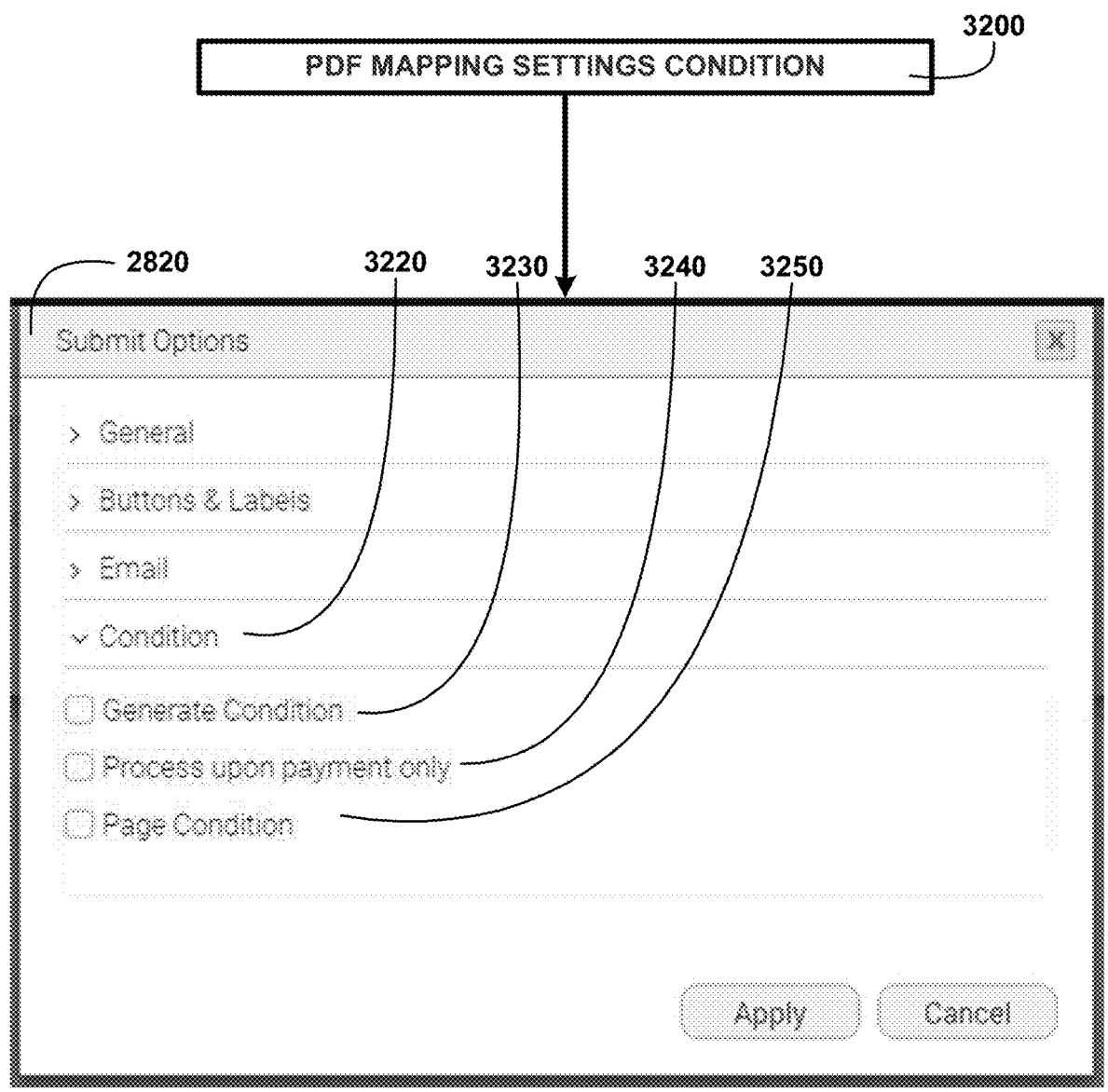
FIG. 32 shows for illustrative purposes only an example of pdf mapping settings condition of one embodiment.

Pdf Mapping Settings Condition:

FIG. 32 shows for illustrative purposes only an example of pdf mapping settings condition of one embodiment. FIG. 32 shows a pdf mapping settings condition 3200 feature including the submit options 2820 selection. A condition 3220 feature includes menu selections to generate condition 3230, process upon payment only 3240 and a page condition 3250 of one embodiment.

PDF Mapping: settings. Configuring Your PDF Settings. No matter what type of PDF you add to your form (Basic, Dynamic, or Auto PDF)—you will need to configure its settings. While the Basic and Dynamic PDF settings are the same, the Auto Pdf has a slightly different set of properties, so we will go over them separately. The Basic/Dynamic PDF Settings 1—Press on the "settings" icon to configure the PDF settings. A Modal window will open then containing the settings, organized in 4 categories: —General—Buttons and Labels—Email—Condition. Please notice that the first category will be open by default.

General properties: —Preview before submit: turning on this checkbox will allow you to present the filler with a preview to his soon-to-be-generated PDF. It will display the template you created and the data the filler entered in it. So, in fact, when the filler hits the submit button a pop up window will open, containing this preview. Only after the filler presses on the "Finish" button in the preview window it will actually submit the form. Just so you know—The PDF preview window contains 4 icons in the top right corner to help the form filler: Plus (for zooming in), minus (for zooming out), clear (for clearing the zoom) and Print (for printing the PDF).

Print and save: turning on this checkbox will add a saving functionality to the print icon. In this case, pressing on the Print icon will open a dialog for print, and once the printing is approved—it will also submit the form. —Interactive mode: This option will only be available when the 'preview before submit' checkbox is turned on. The interactive mode will allow your form fillers to add or edit data inside the PDF preview window. Once this checkbox is turned on you will be able to choose the fields you want to make interactive. —Print page number. If your PDF has more than one page you can turn on this option to add a numbers at the bottom of each page. —Format The default PDF format is A4, however you can choose to change it to Letter. —Header This option can enable you to add a header to the PDF using the editor and HTML. —Footer This option can enable you to add a footer to the PDF using the editor and HTML. —Auto preview This option will automatically open the preview window after the form loads, so the filler will be able to "skip" filling in the form.

Buttons & Labels properties: —Finish/Close button text: if you decide to turn on the 'preview before submit' option, you can change the text on the buttons at the bottom of it. —Title: if you decide to turn on the 'preview before submit' option, you can add a title text to this window. —Signature: When a Signature field is added to the PDF and made interactive (by turning on the 'interactive mode' and adding the signature field to the list of interactive fields), It will have a label below it, containing the default text: "Click here to sign". However you can enter a different text in this input box to replace it. —File upload: When a File upload field is added to the PDF and made interactive (by turning on the 'interactive mode' and adding the File Upload field to the list of interactive fields), It will have a label below it, containing the default text: "Click here to upload a file".

However you can enter a different text in this input box to replace it. Email properties: —Custom file name—Here you can enter a name for the PDF you are now creating. This will be the file name of the PDF attached to the email. —Send to owner/Send to additional/Send to form emails: Checkboxes that determine where this paper form will be sent to. Condition Properties: —Generate Condition: if you decide to turn on this Checkbox you will be allowed to add a condition by which this PDF will be generated. Only if the condition terms are met then the PDF will be generated. —Process upon payment only: turning on this checkbox will make sure that the PDF will be generated only if the payment is executed. —Page Condition: By turning on this option you can set a condition that will make PDF pages hide/show based on the filler's input. PDF Mapping Form Settings. This Category holds the configuration of the PDF Mapping feature. 1—Map Fields by pressing on the "Map Fields" button" you can map your online form on to a paper form scan. Once the window opens you will need to place your online form fields above your paper form, in the right places.

Figure 33:
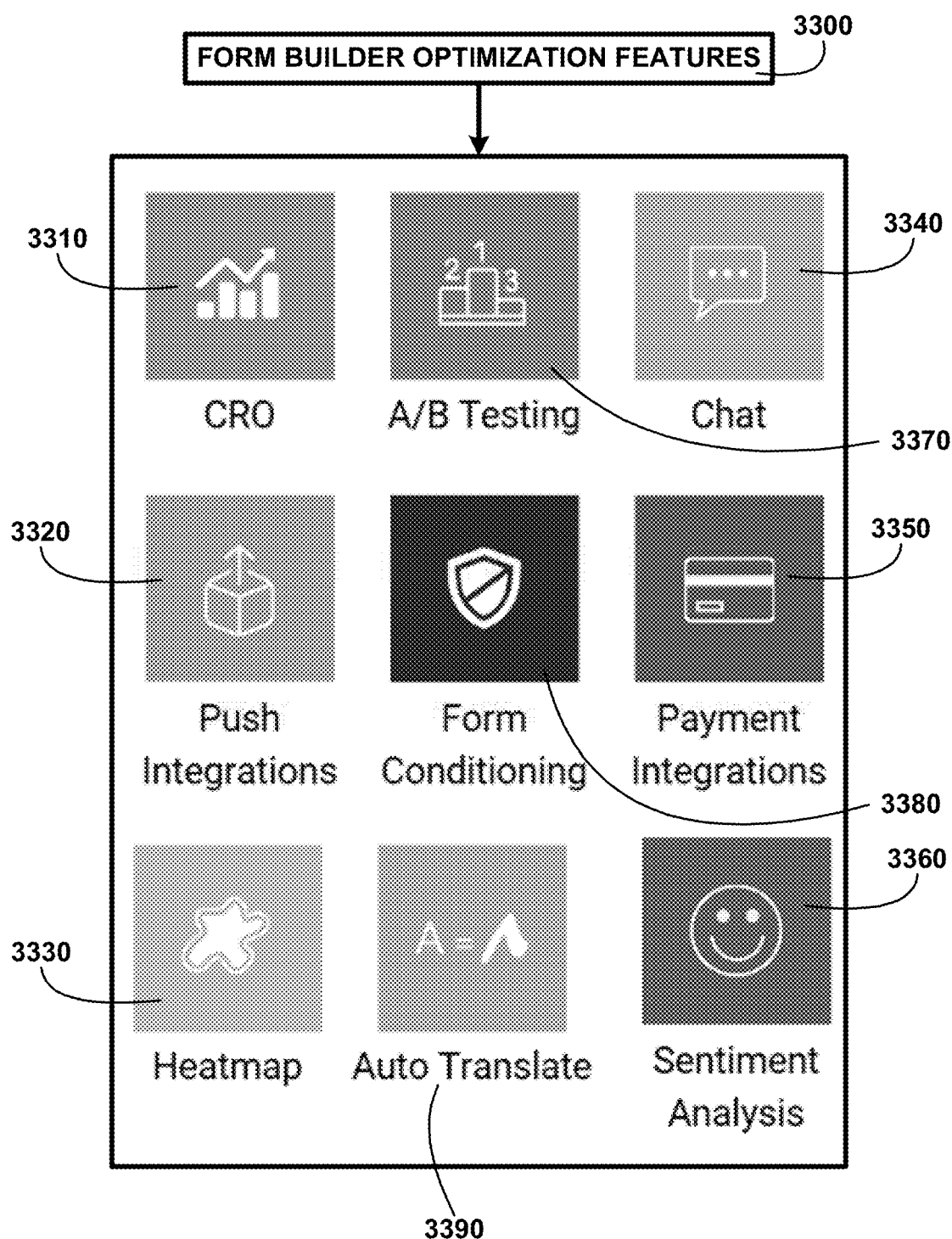
FIG. 33 shows for illustrative purposes only an example of form builder optimization features of one embodiment.

Form Builder Optimization Features:

FIG. 33 shows for illustrative purposes only an example of form builder optimization features of one embodiment. FIG. 33 shows form builder optimization features 3300 includes CRO 3310, Push Integrations 3320, Heatmap 3330, Chat 3340, Payment Integrations 3350, Sentiment Analysis 3360, A/B Testing 3370, Form Conditioning 3380, and Auto Translate 3390 of one embodiment.

Optimization Form Settings. This Category holds the properties related to the optimization of the form. 1—Chats. This property, when turned on, enables you to activate a chat in your form and talk to your form fillers right then and there. Once you turn on this option the chat becomes enabled, However you will need to start the chat from the "My Forms" page. Read more about the Chat 2—Heatmap This property enables you to create a heatmap based on your form.

Once you turn on this checkbox, you start recording the visitors' movements on your form. This creates a graphic image made of colors you can then analyze. In order to view the heatmap created you will need to click on the "View heat map" link in the "My Forms" page Read more about the Heatmap 3—Randomize This property enables you to show the form elements in random order each time the form is loaded by the user. 4—Auto Translate This feature adds a translation option to your published form. Once a user, with a language different from the one set in your form, opens it he will have an option to translate it to his own language or use it as is.

5—Prediction The following property enables you to use the sentiment analysis feature. With this feature you can try to understand the thoughts and intentions of your form fillers. 6—Type of form The following property lets you categorize your form, according to the form types specified in the list. The form type is important because it has a direct influence on the CRO tips you will get. It is good to specify your form type. 9—Autocorrect for Mobile. This option turns on the Mobiles "auto correct" for mobile devices. This option is turned off by default since auto correct in mobiles can interfere with the form filling process. 10—Show Valid Indicator This option is turned on by default. It makes sure that each time a form filler enters a form field correctly, a green v icon will appear next to it, to indicate approval. If you wish to hide these indicators, you can do so easily by turning off this checkbox.

11—Don't save the data. Data entered in your form is stored by default, which later allows you to export it, analyze it etc. However, if you wish to stop saving the data you can do so by turning off this option. 12—Generate barcode This property allows you to generate a barcode.

Custom Translation:

If you are creating an online form that needs to be displayed in several languages, you can use our Auto Translate optimization to easily have it presented to your foreign users with in their native language. However, in some cases you may find the automatic translation insufficient or not precise enough. You may be using technical terms, or even simple words with multiple meanings and need to translate things yourself. This is where our custom translation feature becomes handy. When using this option you can control all the labels, captions, user tips, button text in your form, and you can create different translations to as many languages as you want.

Following is an example of a how to add custom translation to a simple form in French: 1—Enter the form builder and create a new form. 2—Drag a textbox and change its label text to: Nom de la compagnie (which means 'Company Name'). Change the text on your button to "soumettre le formulaire" (which means 'submit form'). 3—In order to have the form translated you must first declare the form's original language (in this case: Frence). Go to "Properties" panel>"Form" tab>"Settings" option>"Personalization" category. 4—Choose "French" in the Language drop down. 5—Now you can add the custom translation. Go to: "Properties" panel>"Form" tab>"Settings" option>"Optimization" category.

6—Turn on the "Custom Translation" checkbox and then press on the "Edit" button below it. 7—Choose a language you would like to translate your form to. For example: English. 8—The fields of the form will now be displayed in small tables, each containing the current field text (in French), and you will need to replace these texts with your english version. For example: you can change 'soumettre le formulaire' text on the button to 'Submit this form now' which has a slight difference in meaning. 9—Press on "Apply" and save the form. 10—Now you can publish your form as URL and see the result: Whenever a translation feature is used in the form (Auto or Custom) a pale blue strip will appears at the top of the web page, saying that the page has been translated. It also gives the user the opportunity to view the form in its original language, if he chooses to of one embodiment.

Figure 34:
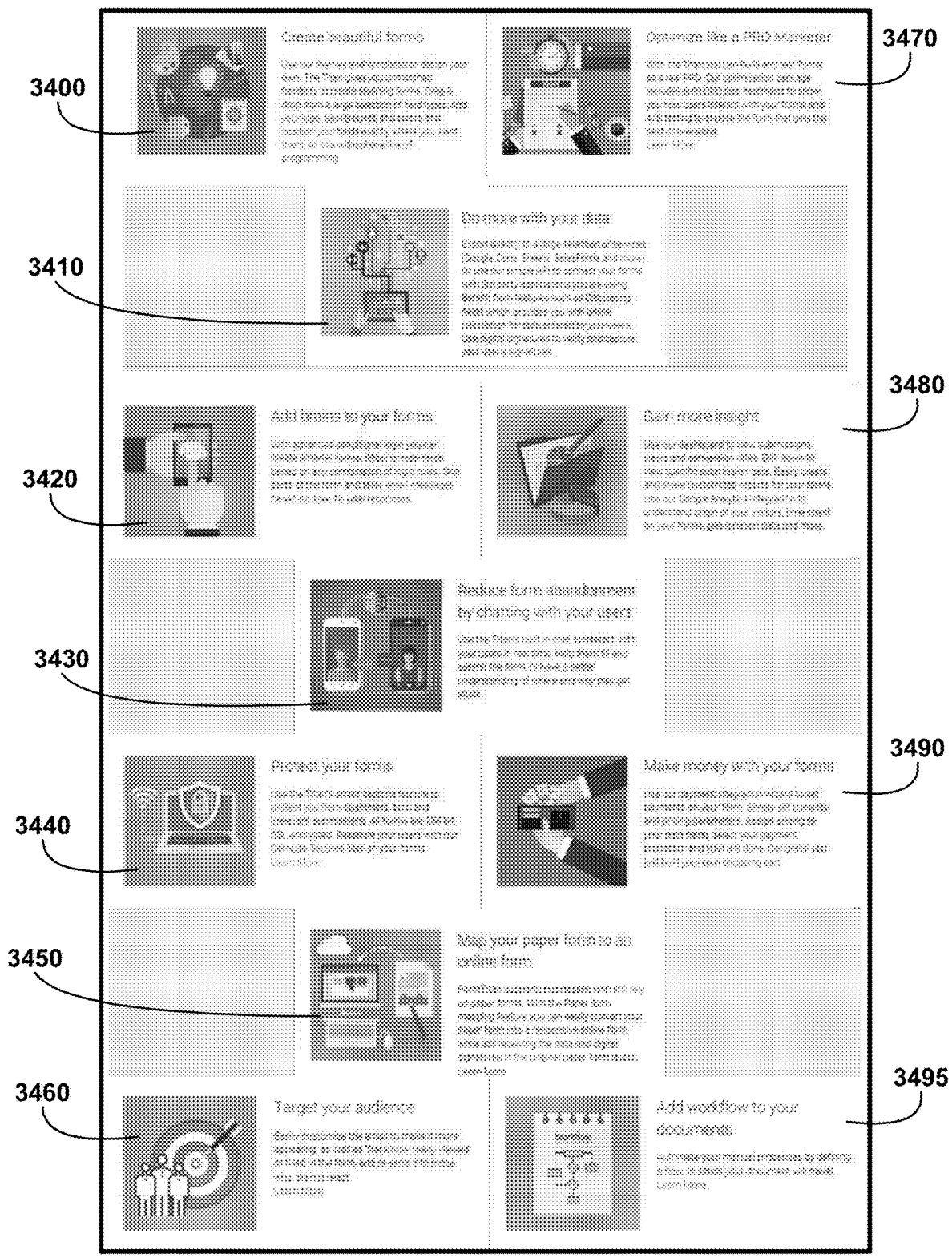
FIG. 34 shows for illustrative purposes only an example of form builder features characteristics of one embodiment.

Form Builder Features Characteristics:

FIG. 34 shows for illustrative purposes only an example of form builder features characteristics of one embodiment. FIG. 34 shows the customized customer relationship management platform method and devices objectives including for example Create beautiful forms 3400, Do more with you data 3410, Add brains to your forms 3420, Reduce form abandonment by chatting with your users 3430, Protect your forms 3440, Map your paper form to an online form 3450, Target your audience 3460, Optimize like a pro marketer 3470, Gain more insight 3480, Make money with your forms 3490, and Add workflow to your documents 3495 of one embodiment.

Each of the form builder features and elements serves a functional purpose. FIG. 34 shows a brief description the characteristics of the features and elements and the general functional purpose behind those features and elements.

Figure 35:
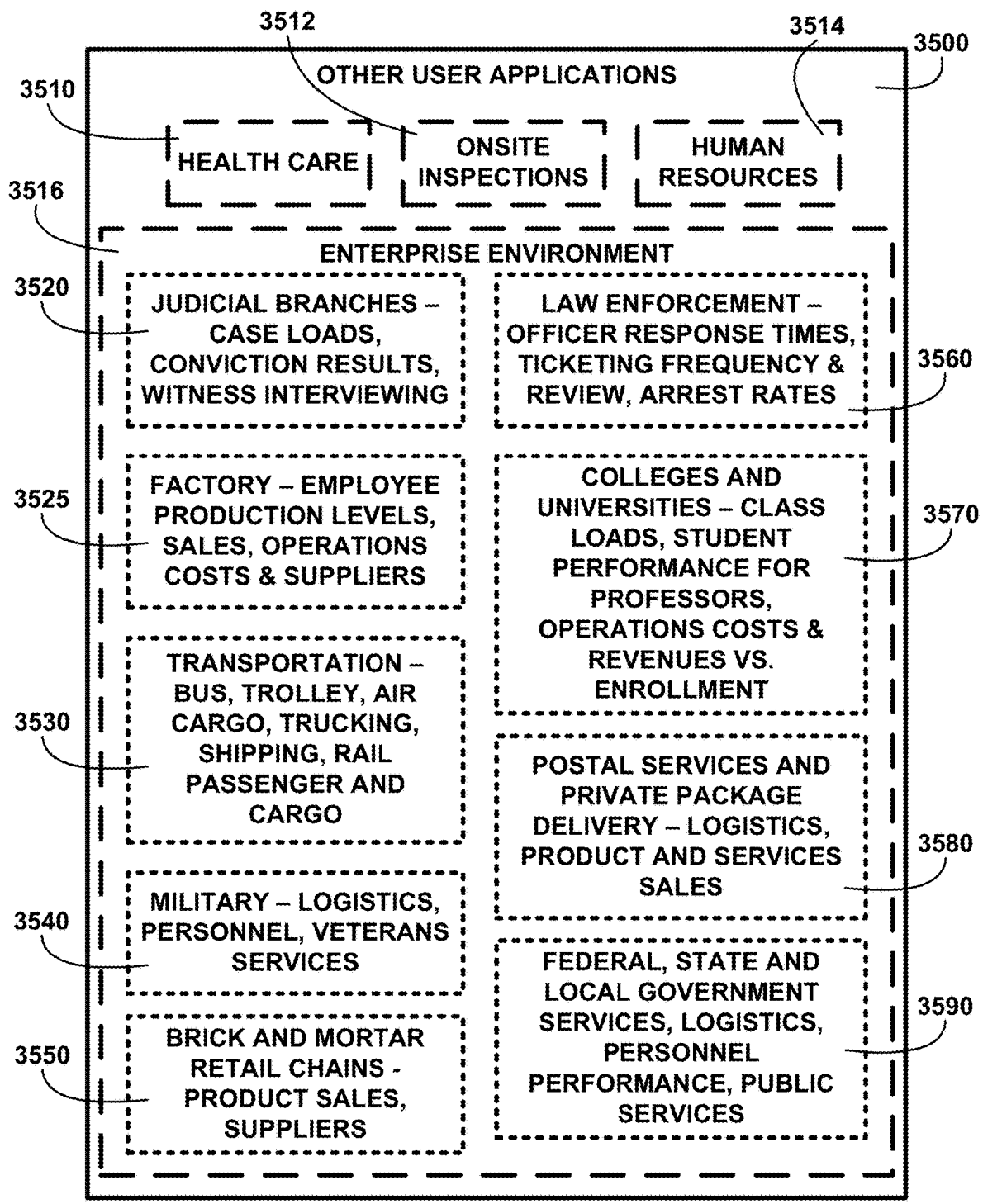
FIG. 35 shows a block diagram of an overview of other user applications of one embodiment.

Other User Applications:

FIG. 35 shows a block diagram of an overview of other user applications of one embodiment. FIG. 35 shows other user applications 3500 including health care 3510, onsite inspections 3512, and human resources 3514. Additional applications in an enterprise environment 3516 include judicial branches—case loads, conviction results, witness interviewing 3520, factory—employee production levels, sales, operations costs & suppliers 3525, transportation—bus, trolley, air cargo, trucking, shipping, rail passenger and cargo 3530, military—logistics, personnel, veterans services 3540, brick and mortar retail chains—product sales, suppliers 3550, law enforcement—officer response times, ticketing frequency & review, arrest rates 3560, colleges and universities—class loads, student performance for professors, operations costs & revenues vs. enrollment 3570, postal services and private package delivery—logistics, product and services sales 3580, and federal, state and local government services, logistics, personnel performance, public services 3590 of one embodiment.

FIG. 35 shows other user applications where the customized customer relationship management platform functionality and integration capability can be an added asset to reduce cost and improvement management tools. The other user applications can include Health Care, Onsite Inspections, and Human Resources. Many industries in the Enterprise Environment can adapt forms or create forms to improve data collection including Judicial Branches—Case Loads, Conviction Results, Witness Interviewing; Factory—Employee Production Levels, Sales, Operations Costs & Suppliers; Transportation—Bus, Trolley, Air Cargo, Trucking, Shipping, Rail Passenger and Cargo; Military—Logistics, Personnel, Veterans Services; Brick and Mortar Retail Chains—Product Sales, Suppliers; Law Enforcement—Officer Response Times, Ticketing Frequency & Review, Arrest Rates; Colleges and Universities—Class Loads, Student Performance for Professors, Operations Costs & Revenues vs. Enrollment; Postal Services and Private Package Delivery—Logistics, Product and Services Sales; and Federal, State and Local Government Services, Logistics, Personnel Performance, Public Services.

Figure 36:
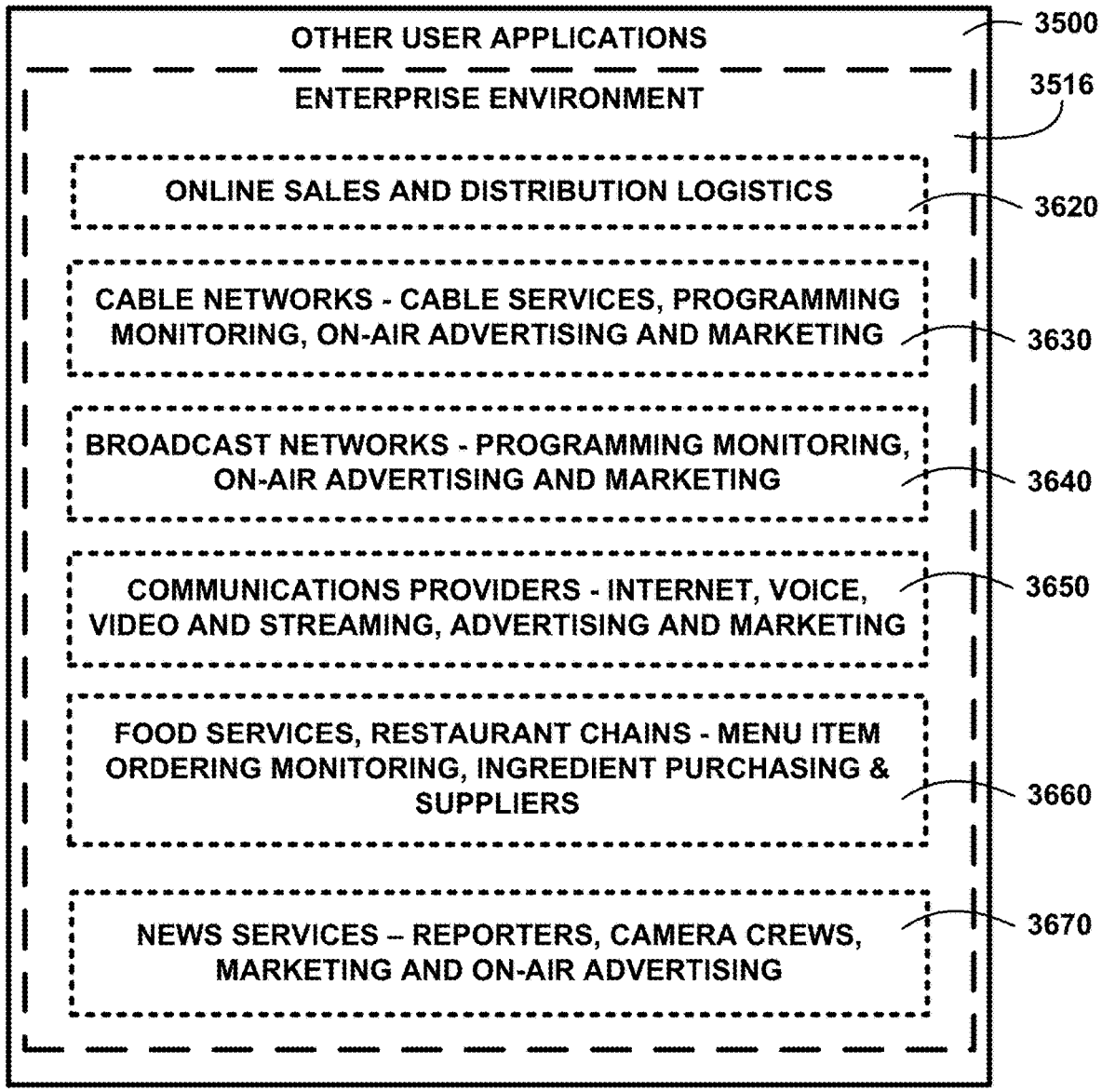
FIG. 36 shows a block diagram of an overview of other user applications enterprise environment of one embodiment.

Other User Applications Enterprise Environment:

FIG. 36 shows a block diagram of an overview of other user applications enterprise environment of one embodiment. FIG. 36 shows other user applications 3500 in an enterprise environment 3516 include online sales and distribution logistics 3620, cable networks—cable services, programming monitoring, on-air advertising and marketing 3630, broadcast networks—programming monitoring, on-air advertising and marketing 3640, and communications providers—internet, voice, video and streaming, advertising and marketing 3650 of one embodiment.

FIG. 36 shows additional other user applications in an Enterprise Environment including Online Sales and Distribution Logistics; Cable Networks—Cable Services, Programming Monitoring, On-Air Advertising and Marketing; Broadcast Networks—Programming Monitoring, On-Air Advertising and Marketing; Communications Providers—Internet, Voice, Video and Streaming, Advertising and Marketing; Food Services, Restaurant Chains—Menu Item Ordering Monitoring, Ingredient Purchasing & Suppliers; and News Services—Reporters, Camera Crews, Marketing and On-Air Advertising.

Figure 37A:
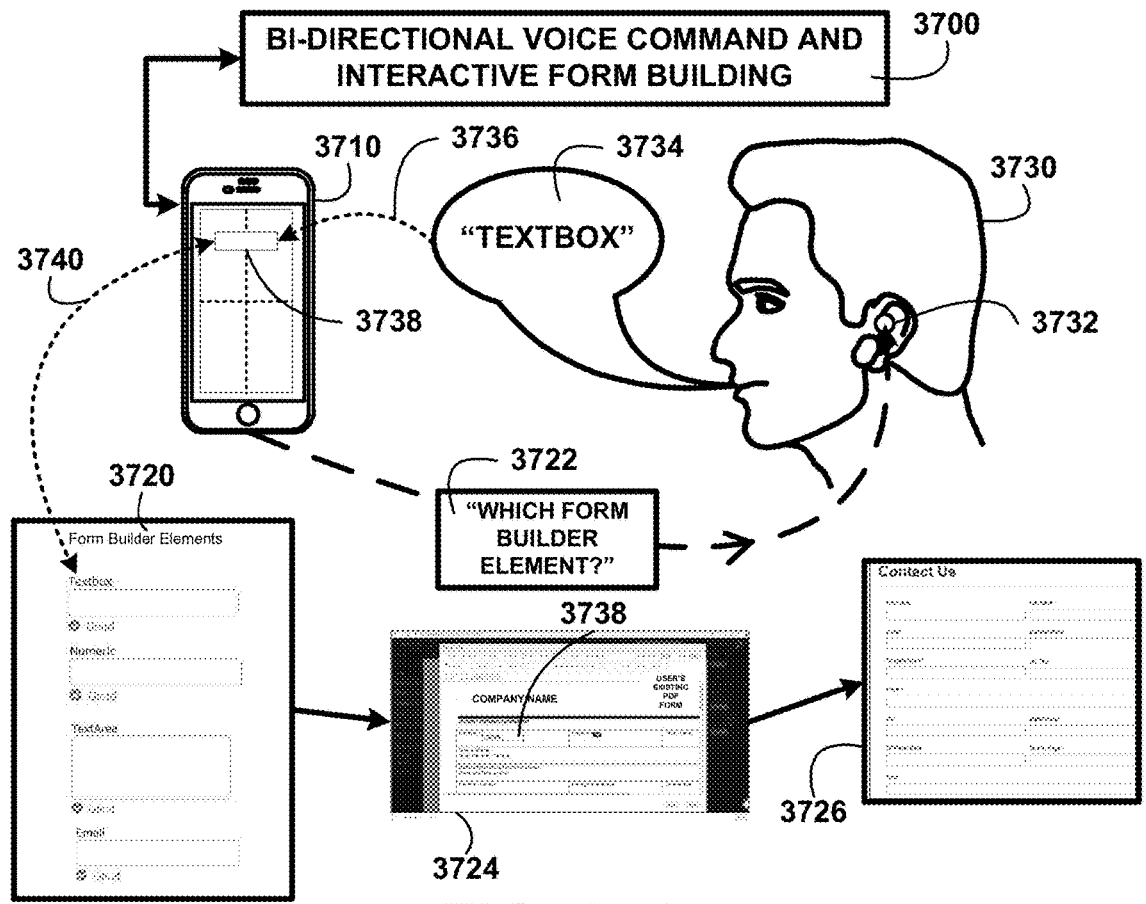
FIG. 37A shows for illustrative purposes only an example of bi-directional voice command and interactive form building elements of one embodiment.

Bi-Directional Voice Command and Interactive Form Building Elements:

FIG. 37A shows for illustrative purposes only an example of bi-directional voice command and interactive form building elements of one embodiment. FIG. 37A shows bi-directional voice command and interactive form building 3700. The customized customer relationship management platform method and devices is accessible through a user smart phone 3710 internet connection to the customized customer relationship management platform method and devices digital servers using a FormTitan digital application installed on a user digital device including the user smart phone 3710. In this example the user opens form builder elements 3720 while creating interactive user's existing pdf form mapping fields 3724. The FormTitan digital application includes an audio text reader to transmit an audible question "which form builder element?" 3722 to the user 3730 through a hands-free ear piece 3732. In response to the audible question regarding the contact us 3726 mapping fields selection the user 3730 conveys the user's verbal response is "text box" 3734. The user's verbal response is received by the smart phone 3736 FormTitan digital application. The FormTitan application enters a textbox onto the user's existing pdf form mapping fields display 3738. The FormTitan application selects a textbox from the form builder elements per the user's verbal command 3740 of one embodiment.

FIG. 37A shows a customized customer relationship management platform user employing the voice element of the form builder. The mini mode has converted the form builder customization screen to fit on the user smart phone screen. The voice has audibly read the elements available and asks the user "which form builder element?". The user listens to the possible selections using for example a Bluetooth device. The user then responds speaking into the smart phone microphone with the "textbox" selection. Upon receiving a element selection the form builder places a textbox element in the body of the form of one embodiment.

Figure 37B:
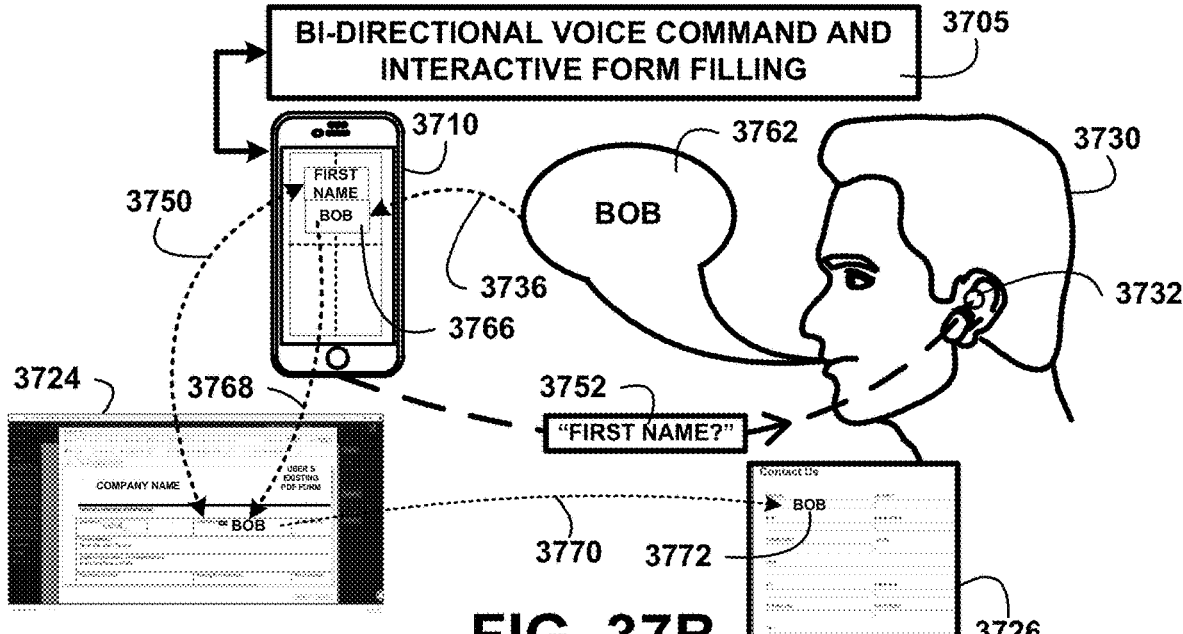
FIG. 37B shows for illustrative purposes only an example of bi-directional voice command and interactive form building data of one embodiment.

Bi-Directional Voice Command and Interactive Form Building Data:

FIG. 37B shows for illustrative purposes only an example of bi-directional voice command and interactive form building data of one embodiment. FIG. 37B shows bi-directional voice command and interactive form filling 3705 using the user smart phone 3710 to fill in the user's existing pdf form mapping fields 3724 contact us 3726 data. The user 3730 hears through the hands-free ear piece 3732 a FormTitan application process to the next data entry for example first name 3750. The FormTitan digital application an audio text reader transmits an audible question "first name?" 3752. A user's verbal response is "Bob" 3762. The user's verbal response is received by the smart phone 3736 and the FormTitan application enters "bob" in the textbox 3766. Additionally the FormTitan application shows "Bob" in the user's existing pdf form mapping fields display 3768. The FormTitan application automatically displays the first name entry 3770. The contact form shows the first name "Bob" on the contact us form 3772 in the first name text box of one embodiment.

FIG. 37B shows in another embodiment the voice element could be asking a user form filler for his name "first name" according to the data element on the form. The user form filler responds with his first name "Bob". The validated audible response is converted into text and entered in the designated textbox on the responsive form. In another embodiment the user form filler could be speaking another language and the Auto Translate feature can translate the response into the language designated on the form of one embodiment.

Figure 38:
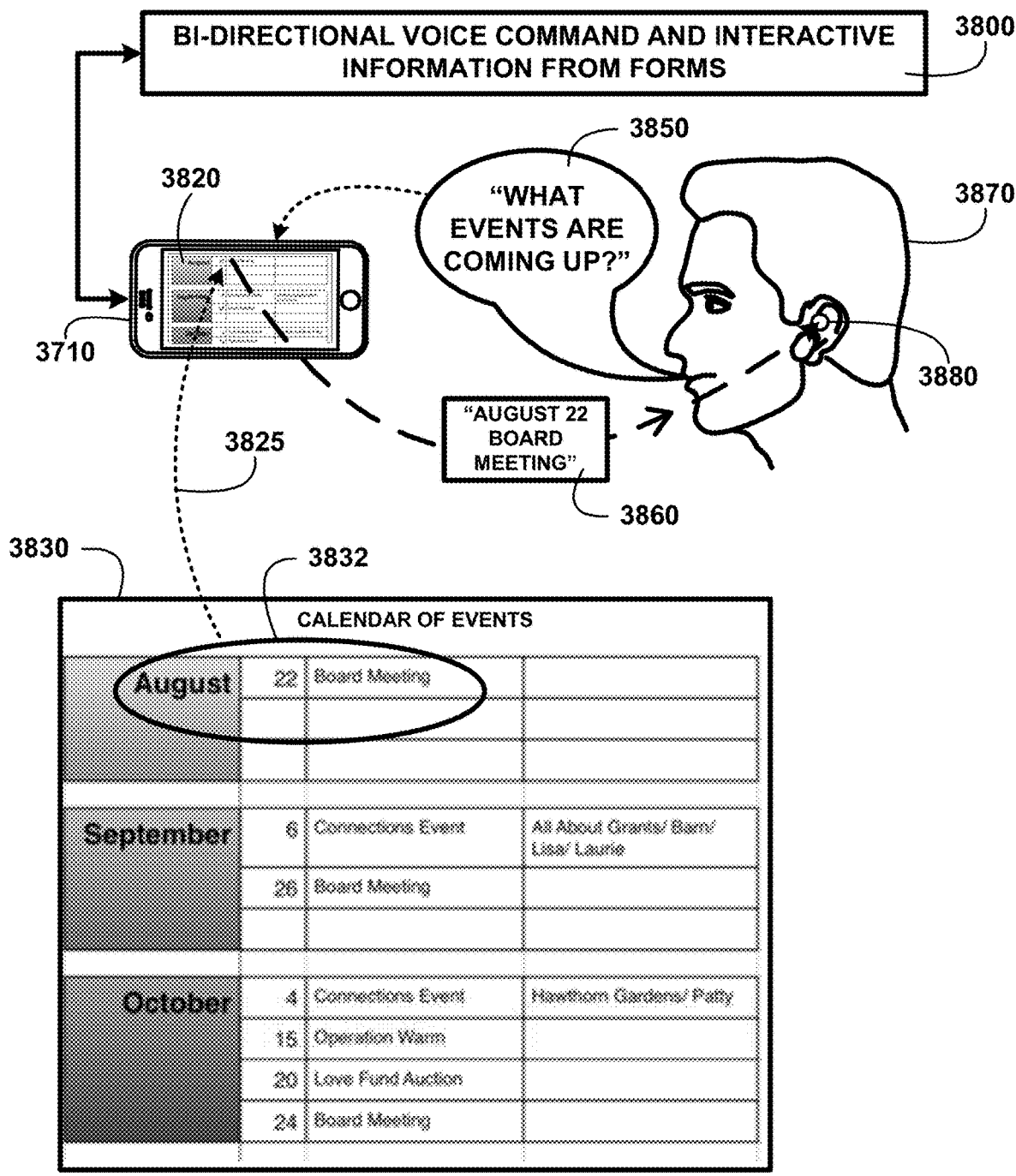
FIG. 38 shows for illustrative purposes only an example of bi-directional voice command and interactive information from forms of one embodiment.

Bi-Directional Voice Command and Interactive Information from Forms:

FIG. 38 shows for illustrative purposes only an example of bi-directional voice command and interactive information from forms of one embodiment. FIG. 38 shows bi-directional voice command and interactive information from forms 3800. The user makes a verbal query request 3870, "what events are coming up?" 3850 on the user smart phone 3710. The FormTitan application displays the user's calendar of events 3830 on the smart phone. The the FormTitan application searches the user's calendar of events 3830 for the next event data 3832. The FormTitan application displays the user's calendar of events 3830 on the smart phone 3710 "august 22 board meeting" 3825. The FormTitan application using the text reader transmits an audible message to the user of the next event "august 22 board meeting" 3860. The user 3870 using a hands-free ear piece 3880 hears the FormTitan application audible message of one embodiment.

FIG. 38 shows a customized customer relationship management platform user employing the voice element of the form builder to query a calendar of events. The user speaks the question "what events are coming up?" into the microphone of his smart phone which is connected to the platform. The voice element reads aloud the next event on the calendar of events resulting from the voice activated query. The voice element responds audibly that the next event is an "August 22 Board Meeting".

Integration Example with Salesforce:

FIGS. 39-49 show for illustrative purposes only an example of integration example with Salesforce of one embodiment.

Figure 39:
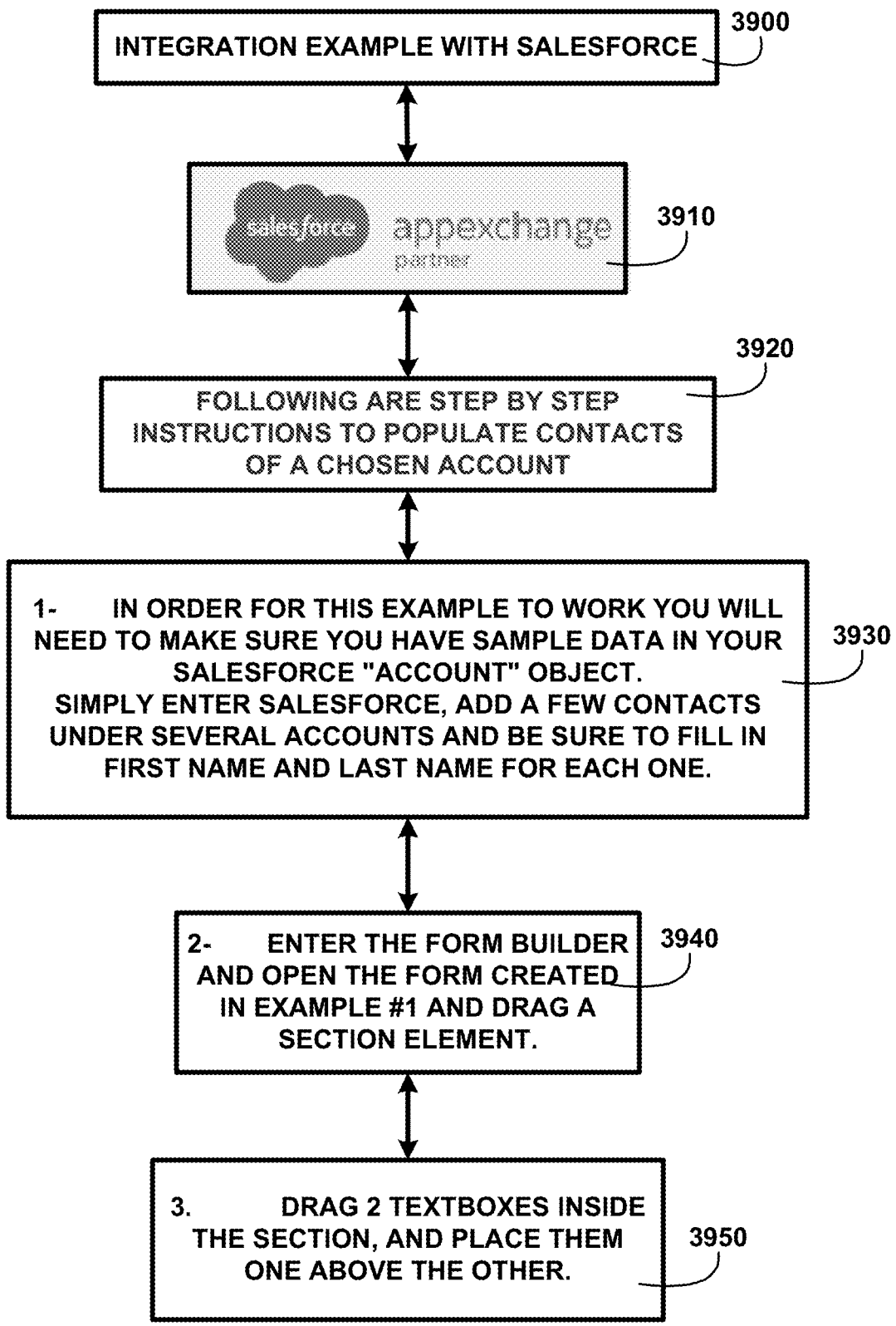
FIG. 39 shows a block diagram of an overview of integration example with Salesforce of one embodiment.

Integration Example with Salesforce:

FIG. 39 shows a block diagram of an overview of integration example with Salesforce of one embodiment. FIG. 39 shows an integration example with Salesforce 3900. The Salesforce app 3910 is accessed using the integrated Salesforce platform. The following are step by step instructions to populate contacts of a chosen account 3920. Step 1—simply enter Salesforce, add a few contacts under several accounts and be sure to fill in first name and last name for each one 3930. Step 2—enter the form builder and open the form created in example #1 and drag a section element 3940. Step 3—drag 2 textboxes inside the section, and place them one above the other 3950 of one embodiment.

Figure 40:
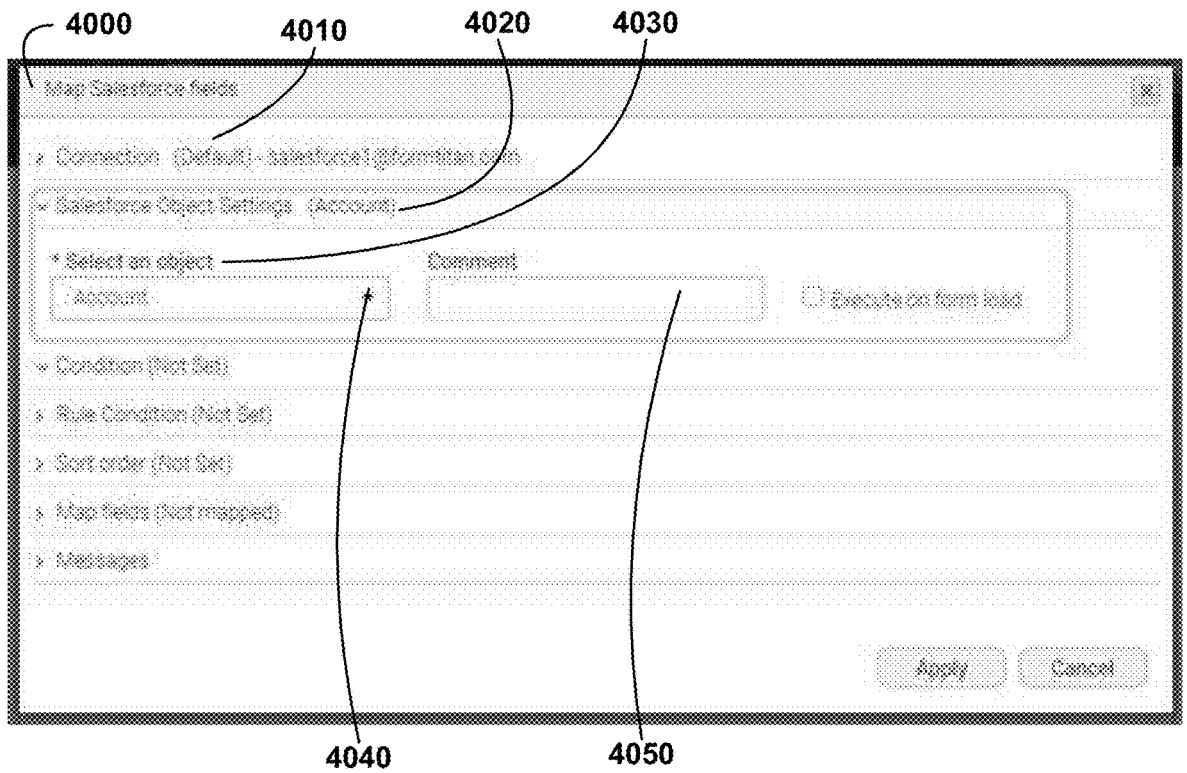
FIG. 40 shows for illustrative purposes only an example of integration Salesforce object settings of one embodiment.

Integration Salesforce Object Settings:

FIG. 40 shows for illustrative purposes only an example of integration Salesforce object settings of one embodiment. FIG. 40 shows a process to map Salesforce fields 4000. A user makes a connection (default) Salesforce1@FormTitan.com 4010. The user opens Salesforce object settings (account) 4020 and proceeds to select an object 4030 in an account 4040 and enter a comment 4050 of one embodiment.

Figure 41:
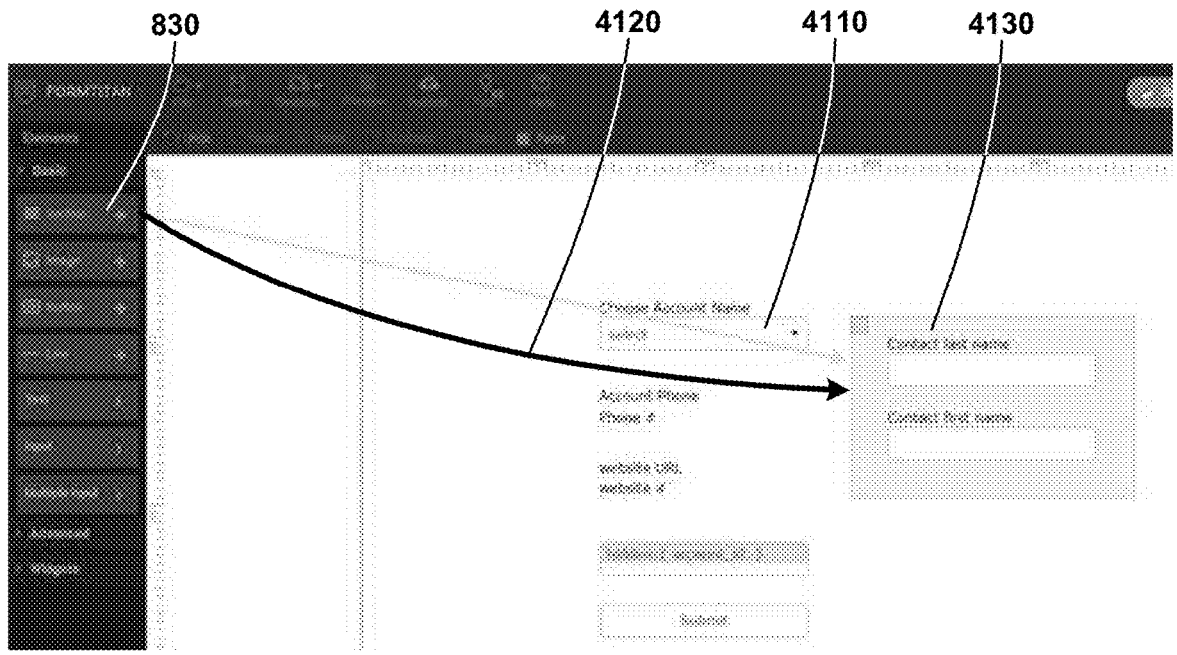
FIG. 41 shows for illustrative purposes only an example of integration setting Salesforce section of one embodiment.

Integration Setting Salesforce Section:

FIG. 41 shows for illustrative purposes only an example of integration setting Salesforce section of one embodiment. FIG. 41 shows the selection of section 830 that displays a choose account name select drop down 4110 for a user to select a name from a section selection 4120 including a contact last name 4130 of one embodiment.

Figure 42:
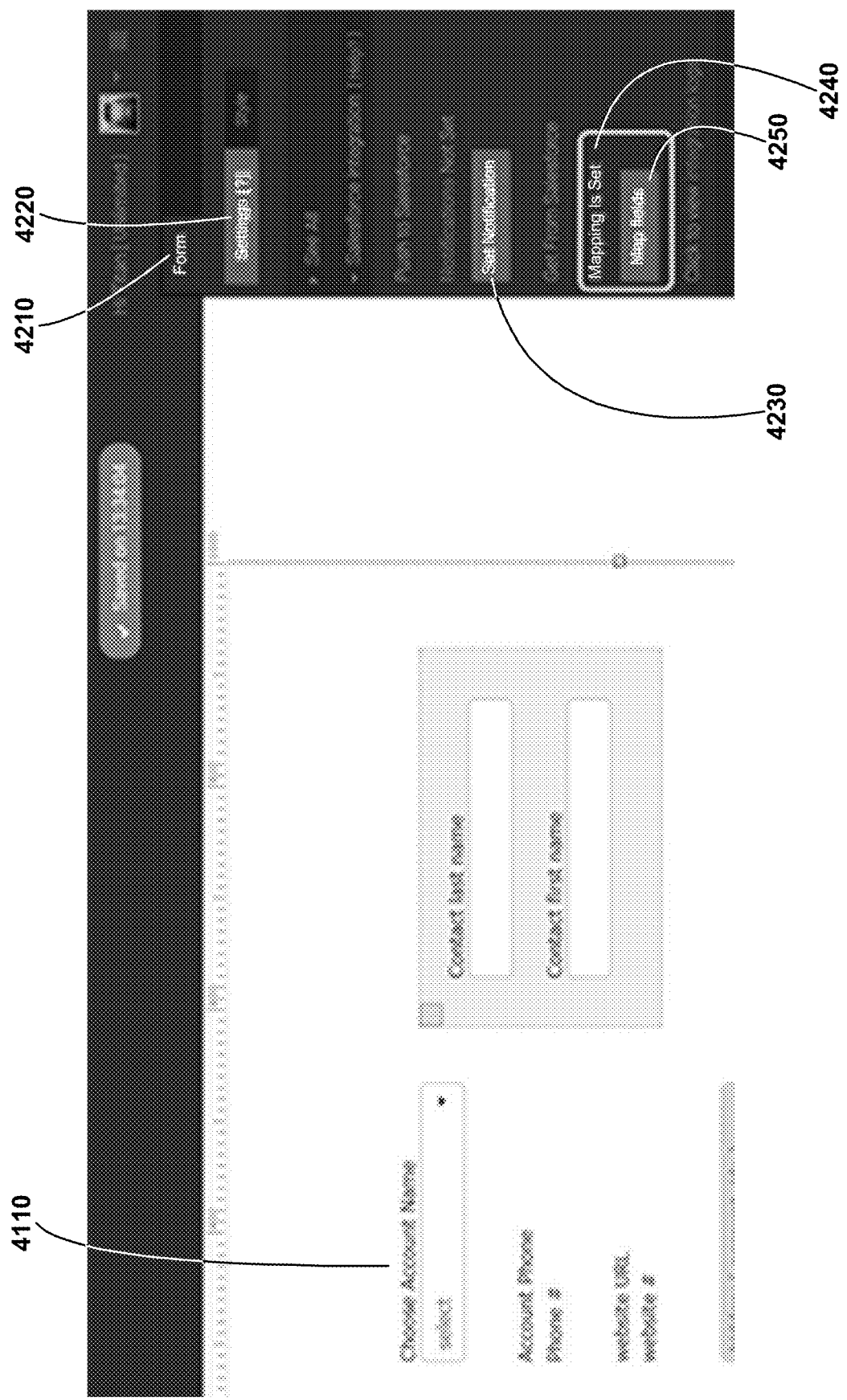
FIG. 42 shows for illustrative purposes only an example of integration setting Salesforce fields of one embodiment.

Integration Setting Salesforce Fields:

FIG. 42 shows for illustrative purposes only an example of integration setting Salesforce fields of one embodiment. FIG. 42 shows a webpage where a user can select a choose account name select drop down 4110 to select an account name. Under the form 4210 a user proceeds to settings [?] 4220 to set notification 4230. Once the notification is enter the mapping is set 4240 in the map fields 4250 of one embodiment.

Figure 43A:
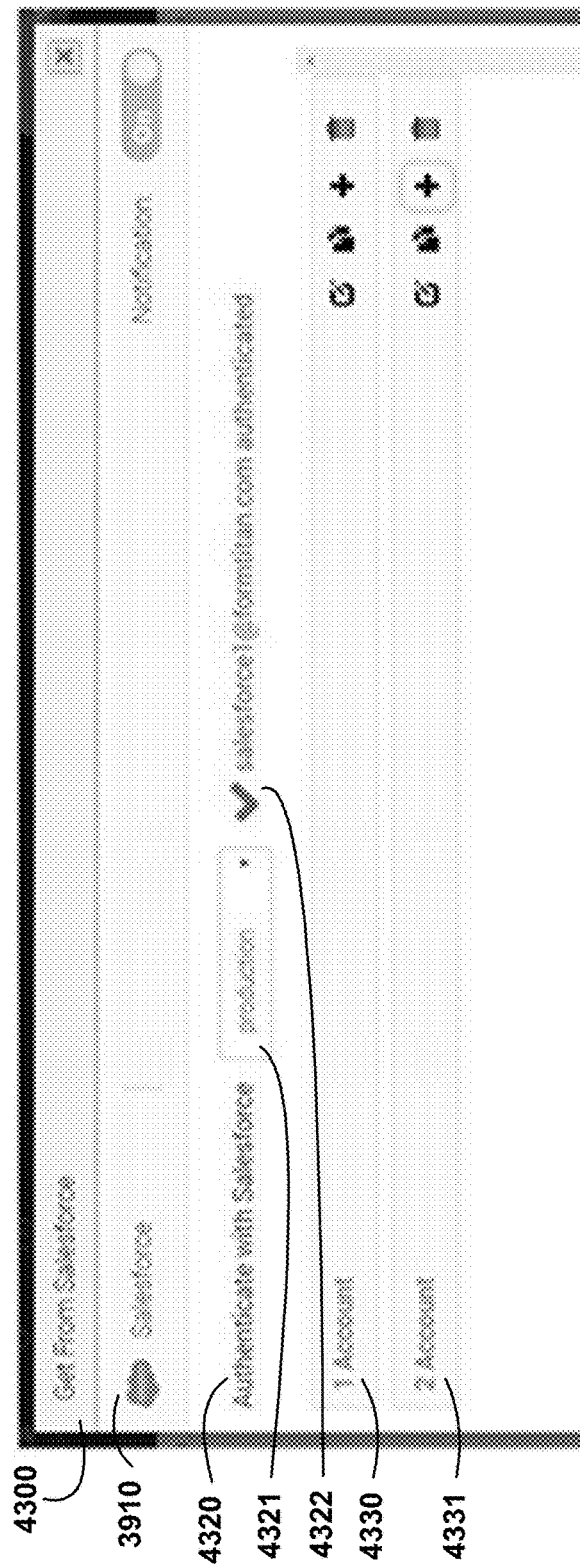
FIG. 43A shows for illustrative purposes only an example of integration get from Salesforce of one embodiment.

Integration Get from Salesforce:

FIG. 43A shows for illustrative purposes only an example of integration get from Salesforce of one embodiment. FIG. 43A shows a Get from Salesforce 4300 feature for integrated use with the Salesforce app 3910. When the Salesforce app 3910 is selected a process on the customer relationship management platform network 210 of FIG. 2 performs an action to authenticate with Salesforce 4320 an a production 4321 operation. The customer relationship management platform network 210 of FIG. 2 finds Salesforce1@FormTitan.com authenticated 4322. The user then selects for example 1 account 4330 or 2 account 4331 of one embodiment.

Figure 43B:
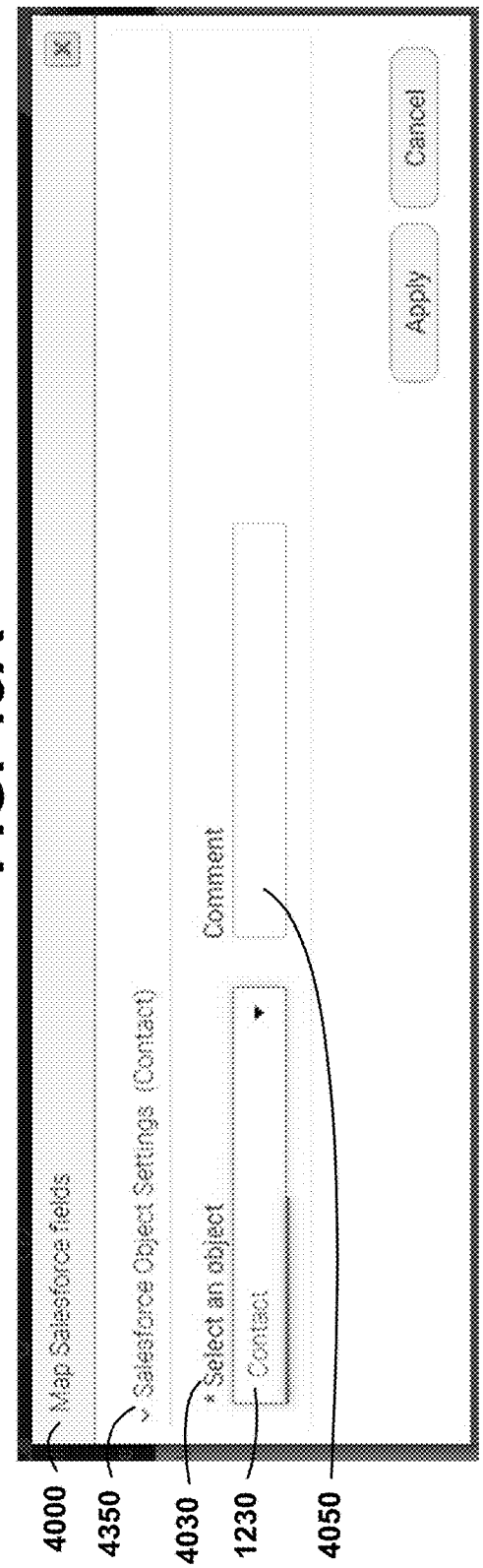
FIG. 43B shows for illustrative purposes only an example of integration map Salesforce fields of one embodiment.

Integration Map Salesforce Fields:

FIG. 43B shows for illustrative purposes only an example of an integration map of Salesforce fields of one embodiment. FIG. 43B shows map Salesforce fields 4000 including Salesforce object settings (contact) 4350. The select an object 4030 includes the contact 1230 and a comment 4050 entry textbox of one embodiment.

Figure 44:
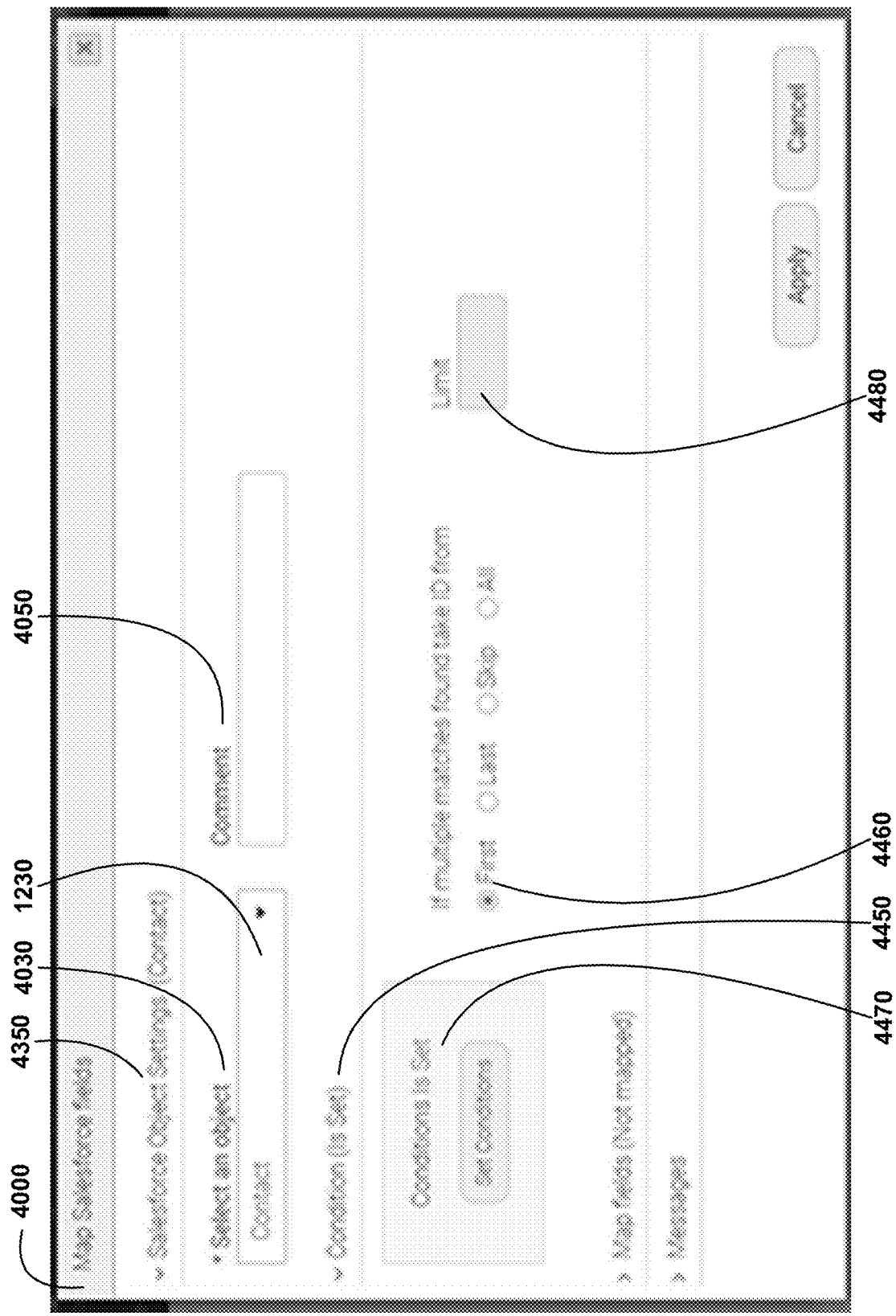
FIG. 44 shows for illustrative purposes only an example of integration map Salesforce object settings of one embodiment.

Integration Map Salesforce Object Settings:

FIG. 44 shows for illustrative purposes only an example of an integration Salesforce map object settings of one embodiment. FIG. 44 shows a webpage for map Salesforce fields 4000 including Salesforce object settings (contact) 4350. The user can select an object 4030 for example the contact 1230 where the user can enter a comment 4050. The user can see displayed that a condition is set 4450 when the user set conditions first 4460 referring to a first name and the display indicates conditions is set 4470 and the user can set a limit 4480 as a condition of one embodiment.

Integration Salesforce Condition:

FIG. 45 shows for illustrative purposes only an example of integration Salesforce condition of one embodiment. FIG. 45 shows a Salesforce condition 4500 webpage with an account ID drop down 4510 to select an account that meets a condition in a drop down for example an equals drop down 4520 in a #2 account drop down 4530 and matching account ID drop down 4510 selection of one embodiment.

Integration Salesforce Mapping Corresponding Fields:

FIG. 46 shows for illustrative purposes only an example of integration Salesforce mapping corresponding fields of one embodiment. FIG. 46 shows Salesforce mapping 4600 including a filter: first 4610 and how it is to show: please choose drop down 4660 using the drop down. A form field 4620 first name 4650 selection from a Salesforce field 4640 contact first name 4630 can be selected as the filter condition of one embodiment.

Integration Salesforce Mapping Contact:

FIG. 47 shows for illustrative purposes only an example of integration Salesforce mapping contact of one embodiment. FIG. 47 shows a Salesforce mapping—#2.1 to select a contact 4700 filter: last 4705. A form field 4620 contact last name 4130 can be selected from a Salesforce field 4640 last name 4740 of one embodiment.

Integration Salesforce Get Contact:

FIG. 48 shows for illustrative purposes only an example of integration Salesforce get contact of one embodiment. FIG. 48 shows a Get from Salesforce 4300 operation using the Salesforce app 3910. The authenticate with Salesforce 4320 can for example use a production drop down 4830 to obtain a Salesforce1@FormTitan.com authenticated 4322 notice. The user selects 1 account 4330 or 2 account 4331. In this example the user selects the 2 account 4331 drop down to get a 2.1 contact 4870 to receive a notification: 4880 of one embodiment.

Figure 49:
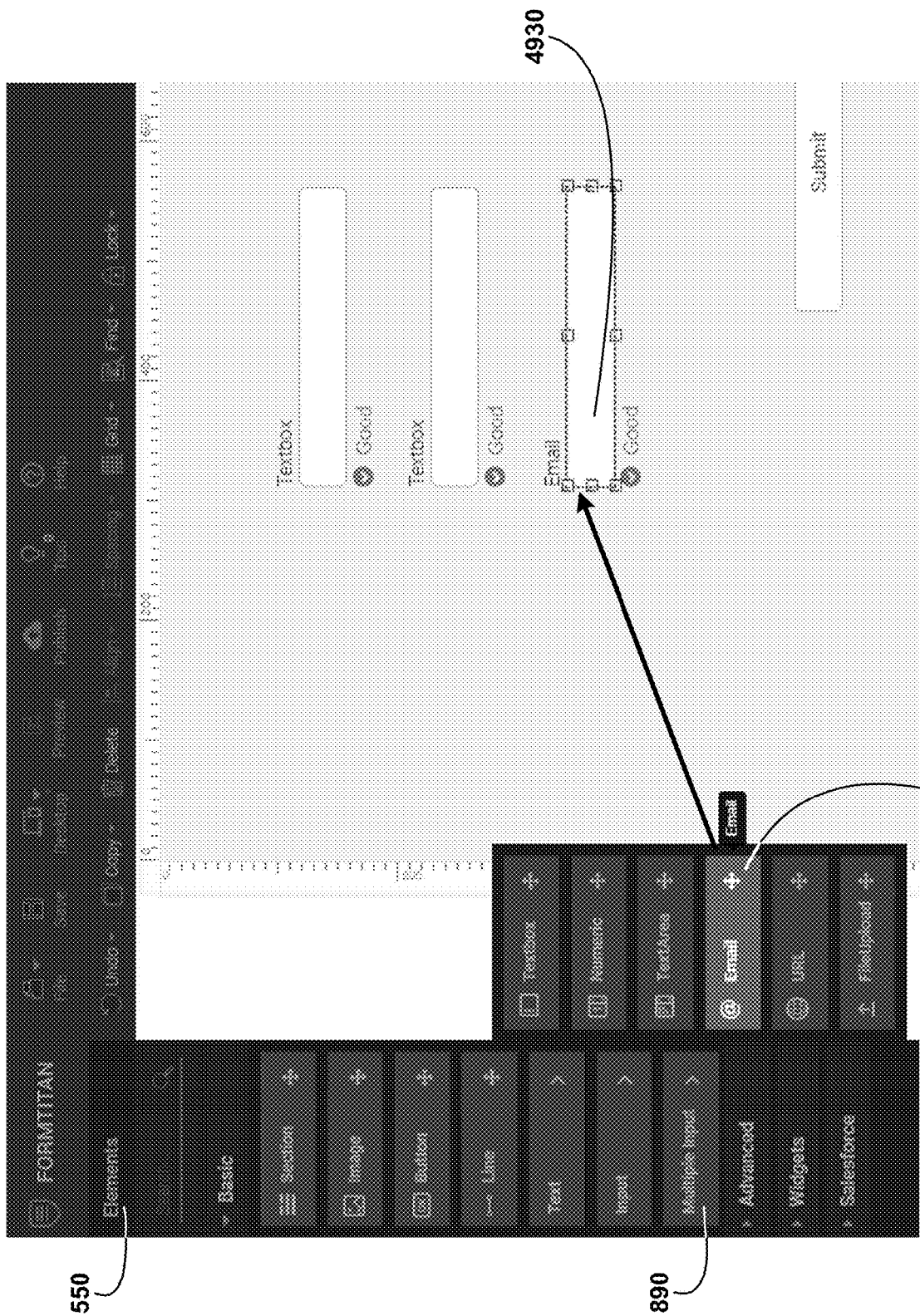
FIG. 49 shows for illustrative purposes only an example of integration Salesforce email of one embodiment.

Integration Salesforce Email:

FIG. 49 shows for illustrative purposes only an example of integration Salesforce email of one embodiment. FIG. 49 shows a user selecting from the elements 550 multiple input 890 feature email 1070. An email input box 4930 is used by the user to enter an email address. A good indicates the quality of the email entry of one embodiment.

An integration example with Salesforce wherein a user uses a Salesforce app. Following are step by step instructions to populate contacts of a chosen account: 1—In order for this example to work you will need to make sure you have sample data in your Salesforce "account" object. Simply enter Salesforce, add a few contacts under several accounts and be sure to fill in first name and last name for each one. 2—Enter the form builder and open the form we created in example #1. Drag a section element. 3 drag 2 textboxes inside the section, and place them one above the other.

Integration Salesforce Object Settings:

Salesforce Push Category-Salesforce Object Settings When the "Map Salesforce fields" window opens for the first time, only two configuration categories will be visible: the "Connection" category and "Salesforce Object Settings" category. Even though this is the second category it will be the one that is open by default, since it is the basis for the entire integration—this is where you choose which Salesforce object will be dealt with in this integration line. So go ahead and choose your object. This category contains three fields: 1—'Select an object' dropdown—this dropdown contains all of the Salesforce objects—just select the one you want to sync with. This is a mandatory field—you cannot proceed without choosing an object. 2—'Comment' textbox—This field is not required and will not be visible to the form filler—It is for your purposes only. The comment allows you to add a short description to the integration line you are now creating and help you recognize it in the future. 3—"Use in custom button" checkbox—Turning on this checkbox will enable you to use a Salesforce Action button as trigger instead of the regular submit button. Read all about using the Salesforce action button for push of one embodiment.

Integration Setting Salesforce Section:

A Salesforce action button can easily be added to your form to get/push data right then and there, without having to submit the form. However, when setting the button to act on a repeated section it applies to all of the data in all of the repeated lines. If you wish to have your form filler press on the custom button in a specific repeated line and have it apply to this line only—you can easily do so. Follow these steps: —Create a new blank form 2—Drag a section element and make it wider. 3—Drag a textbox, a numeric and a button into the section 4—Change the textbox label to: account Go to 'Properties' panel>'Element' tab>'Settings' option>'Basic' category>Label 5—Change the numeric label to num 6—Change the button text to: push this item now 7—Select the section and make it Repeated. Go to 'Properties' panel>'Element' tab>'Settings' option>'Basic' category>Repeated 8—Now configure the Salesforce push integration 'Properties' panel>'Form' tab>'Settongs' option>'Salesforce integration' category>'Push to Salesforce'—Press on the 'Set notofication' button—Authenticate with Salesforce—Choose the account object: Account—Turn on the 'Use in custom button' checkbox—In the 'Action' category—leave the 'Create' option selected—Map the fields: Account Name→account Num>num—Press 'apply', then 'Finish' and save the form. 9—Select the 'button' and change its type to 'Salesforce Action'. 10—Press on the 'Set' button to have the integration line work with your custom button. 11—Open the 'process push or get' dropdown and select the Salesforce action. 12—Press on 'Add' and it will be added to a table above. 13—Turn on the 'Execute per repeated item' checkbox 14—Press 'Apply' and save your form 15—Now it's time to test your form: —First select your Section and change your visible items to 2 and turn on the 'Populate items' checkbox—Publish it as URL—Enter the first item line in the section: an account name and number: test 1, 1 and test 2, 2. —Press on "Add" and enter another item line with data: test 3, 3—Choose a specific line (for example second line) and press on the 'push' button in that line. —Check your Salesforce account and you will see that only that line of data was added as a new record.

Integration Setting Salesforce Fields:

Control which fields on the form will be saved in Salesforce based on action FormTitan Push integration with Salesforce allows you to create new records in Salesforce objects as well as Update existing records. In this demo we will show you: —how to create a lead in Salesforce—and default the company field if its empty. —We will also show you how to prevent update of their name if the action is update.

A bi-directional Salesforce form. FormTitan enables you to: —Read data from Salesforce and have your form fields populated straight from the Salesforce objects in real-time (Aka Get). —Write data to Salesforce objects in order to create a new record, update an existing, or even delete a record (Aka Push). And that's not all . . . you can combine the Get and Push You can Get from multiple Salesforce objects and Push to multiple Salesforce objects and do it all in a single form.

Integration Get from Salesforce:

Salesforce Get Category—Salesforce Object Settings The first time this window will open, only the first two categories will be visible: "Connection" and "Salesforce object setting". The latter will be open by default, since it is the starting point of the integration—this is where you choose your Salesforce object. So even though this is the second category, it will be the one that is open by default. This category contains three fields: 1—'Select an object' dropdown—this dropdown contains all of the Salesforce objects—just select the one you want to sync with. This is a mandatory field—you cannot proceed without choosing an object. 2—'Comment' textbox—This field is not required and will not be visible to the form filler—It is for your purposes only. The comment allows you to add a short description to the integration line you are now creating and help you recognize it in the future. 3—"Execute on form load" checkbox—Turning on this checkbox will execute the get action and populate the fields when the form is loaded. This is of course not a mandatory field and it is turned off by default. When it is not turned on you will be asked to set a condition (in the next category) by which the data will be drawn from Salesforce of one embodiment.

Integration Map Salesforce Fields:

forms Integration with Salesforce Just starting to Integrate forms with Salesforce?—We will show you how easy it is to read data from Salesforce and update it. —populate the account name and account number from Salesforce using Get integration. —Configure a push integration so the filler can update these details and have them sync in real-time.

Fields Order in Salesforce Form One of the options we provide for creating a new form is called 'Salesforce' and it helps you create a form based on a Salesforce object in an automated way. When you choose this option you just need to authenticate with Salesforce, select an object and pick the fields for your form. Once you are done—the form is generated for you on canvas, and all that's left is to play with the styling. In this version, to save you time and efforts, we have added the ability to define the fields order prior to creating the form.

Integration Salesforce Mapping Corresponding Fields:

Extended support when mapping Get with Salesforce lookup fields up till now when trying to fetch a Lookup name from Salesforce you could only map to its record ID, and since the ID is of no interest to your form fillers you would need to create formula fields in Salesforce to get the Lookup's name, or use more 'Get' actions to reach this data. In this version we've enabled you to map the same Lookup only now you can reach any related field three levels deep. (a field in the same level, and 2 levels above it). What's great about it is that it can be done in the same Get action, without adding formula fields, without additional Get actions, saving you time and API calls.

For example: The 'Case' object in Salesforce contains a 'Contact name' lookup, that shows which contact is the owner of this case. Until now, when using the "Get" integration mapping you could only fetch the Contact ID, so you were forced to create a formula that was pulling the account name based on this account id. As of this version this is absolutely not required and you can simply use the same mapping object in your Salesforce integration to choose any of the related fields that the lookup field possess and have it nested up to 3 levels deep! For example: when setting up your Get integration mapping to 'Contact' object fields, You can now also fetch the Parent Account name (which is a Lookup) from within the 'Contact' object: You could easily go from Contact to accountid to parentaccountid and then to account name of one embodiment.

Integration Salesforce Mapping Contact:

Create multiple contacts and cases in Salesforce. utilize the section control to create multiple Salesforce objects. We will show you how to: —to enable your form filler to create an account through the form. —how to allow the filler to create contacts under this account. —and how to enable him to create cases under a contact. in order to do this we will show you: —how to build the form, —how to use the Section element to create a multiple items container. —how to make the section repeated, so the filler can add items— how to configure the Salesforce Push integration so the 3 objects are associated in a parent-child relationship. —and also how to test this form, once it is set up of one embodiment.

Integration Salesforce Email:

a PDF based on Salesforce data and send it via custom email. PDF Our PDF mapping allows you to take the values entered in your form fields and generate a PDF document that contains them. So you see . . . the PDF option is available. Find out how to use the PDF mapping PDF based on Salesforce data The PDF draws its field values from the form. It makes no difference if the filler entered the field values himself or if they were populated from Salesforce automatically—the value found in the field is the one used. So regarding a PDF based on data from Salesforce—this is also possible. The only thing you will need to do is to set up a Get integration in order to populate the fields in your form. Read all about our Salesforce Get integration.

Send PDF via custom email When you configure the PDF mapping you have three checkboxes that enable you to have it sent via mail to the form owner, form filler and additional emails. If the 'form filler' checkbox is turned on, for example, then the PDF document is added as an attachment to the email currently set up for the filler. Please note that there is no email sent to the form filler by default, so you will need to make this option active. In addition—It does not matter if you use the default email or the customized email—because the PDF will be attached to both.

Pdf Block Condition Elements:

FIGS. 50-60 show for illustrative purposes only an example of pdf block condition elements of one embodiment.

Figure 50:
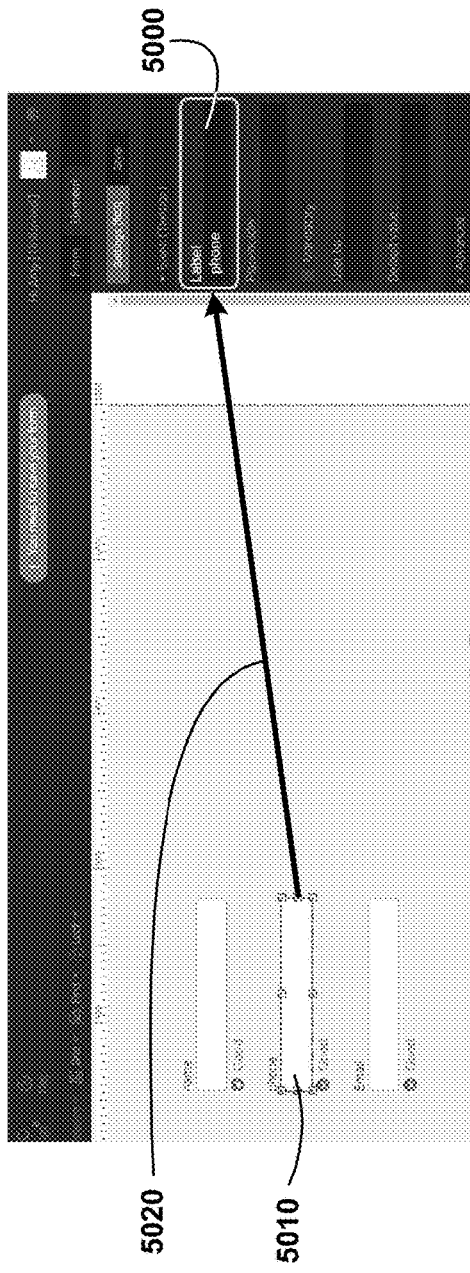
FIG. 50 shows for illustrative purposes only an example of pdf block condition elements of one embodiment.

Pdf Block Condition Elements:

FIG. 50 shows for illustrative purposes only an example of pdf block condition elements of one embodiment. FIG. 50 shows a label phone 5000 element selection where a user enters a phone number in a phone input text box 5010. The phone input is converted into a label automatically 5020 of one embodiment.

Figure 51:
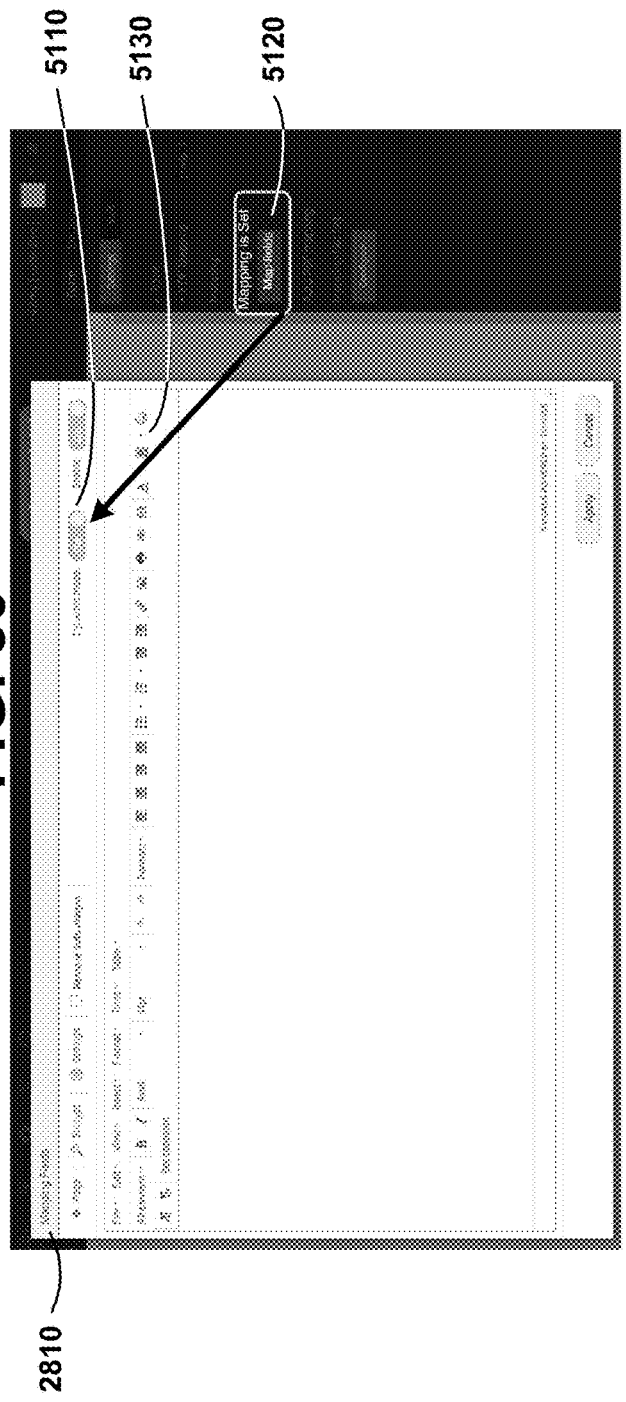
FIG. 51 shows for illustrative purposes only an example of pdf block condition dynamic mode of one embodiment.

Pdf Block Condition Dynamic Mode:

FIG. 51 shows for illustrative purposes only an example of pdf block condition dynamic mode of one embodiment. FIG. 51 shows mapping fields 2810 where dynamic mode is shown on 5110. A notice shows mapping is set map fields 5120 wherein the mapping is set confirms that the dynamic mode is on 5130 of one embodiment.

Figure 52:
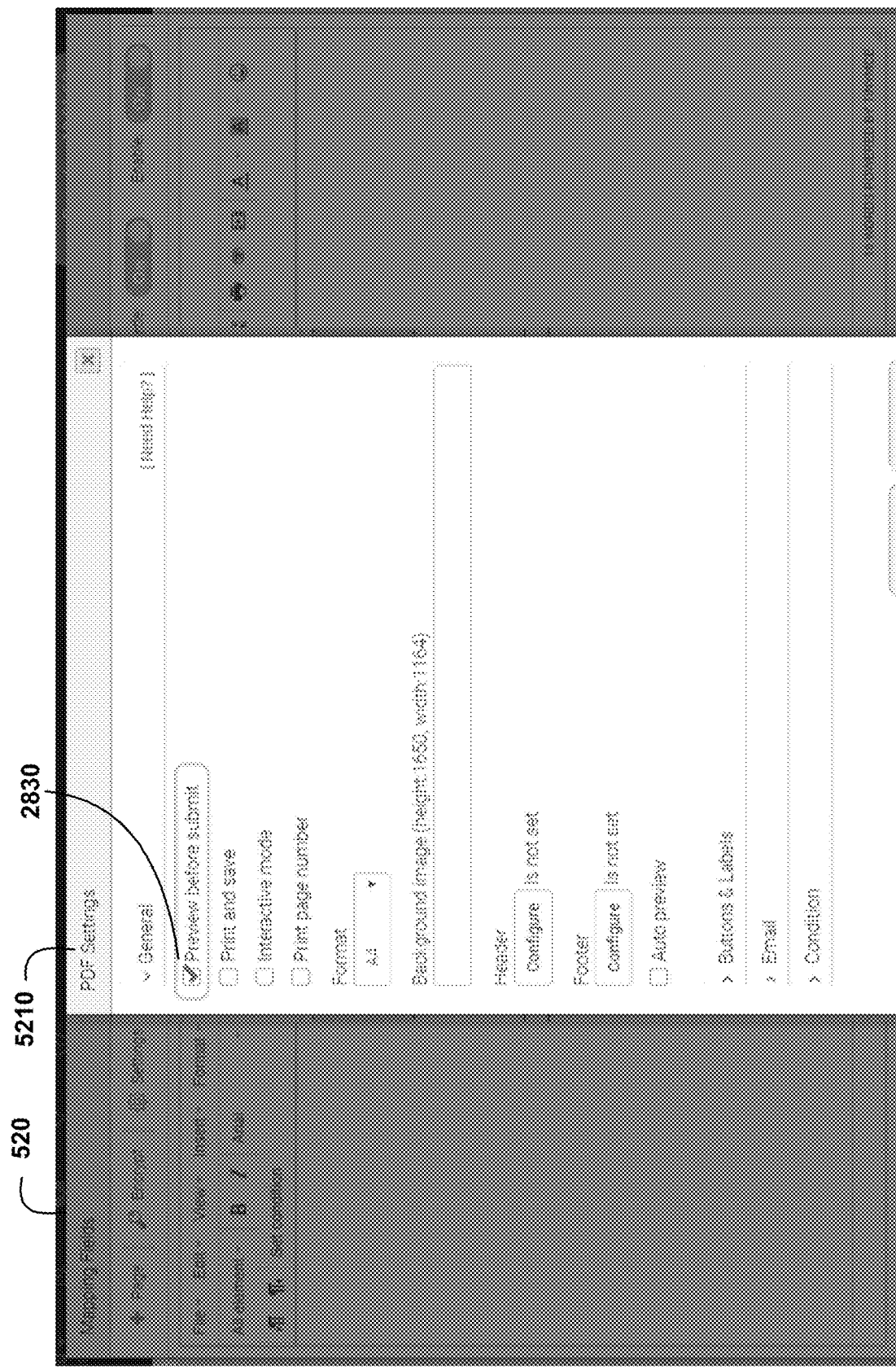
FIG. 52 shows for illustrative purposes only an example of pdf block condition pdf settings of one embodiment.

Pdf Block Condition Pdf Settings:

FIG. 52 shows for illustrative purposes only an example of pdf block condition pdf settings of one embodiment. FIG. 52 shows the mapping fields web page 520 for selection of pdf settings 5210 with an instruction to preview before submit 2830 of one embodiment.

Figure 53:
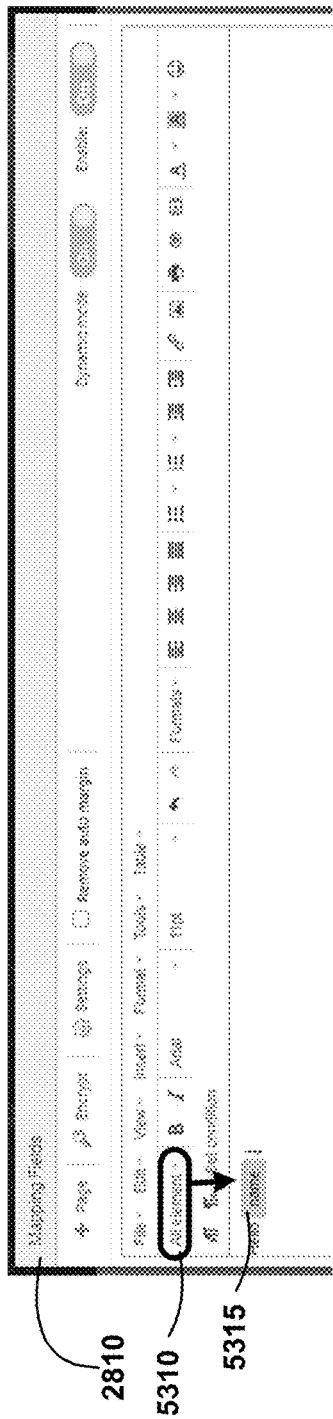
FIG. 53 shows for illustrative purposes only an example of pdf block condition mapping fields all elements of one embodiment.

Pdf Block Condition Mapping Fields all Elements:

FIG. 53 shows for illustrative purposes only an example of pdf block condition mapping fields all elements of one embodiment. FIG. 53 shows mapping fields 2810 where a user can select an all element drop down 5310 and select a field including name 5315 of one embodiment.

Figure 54:
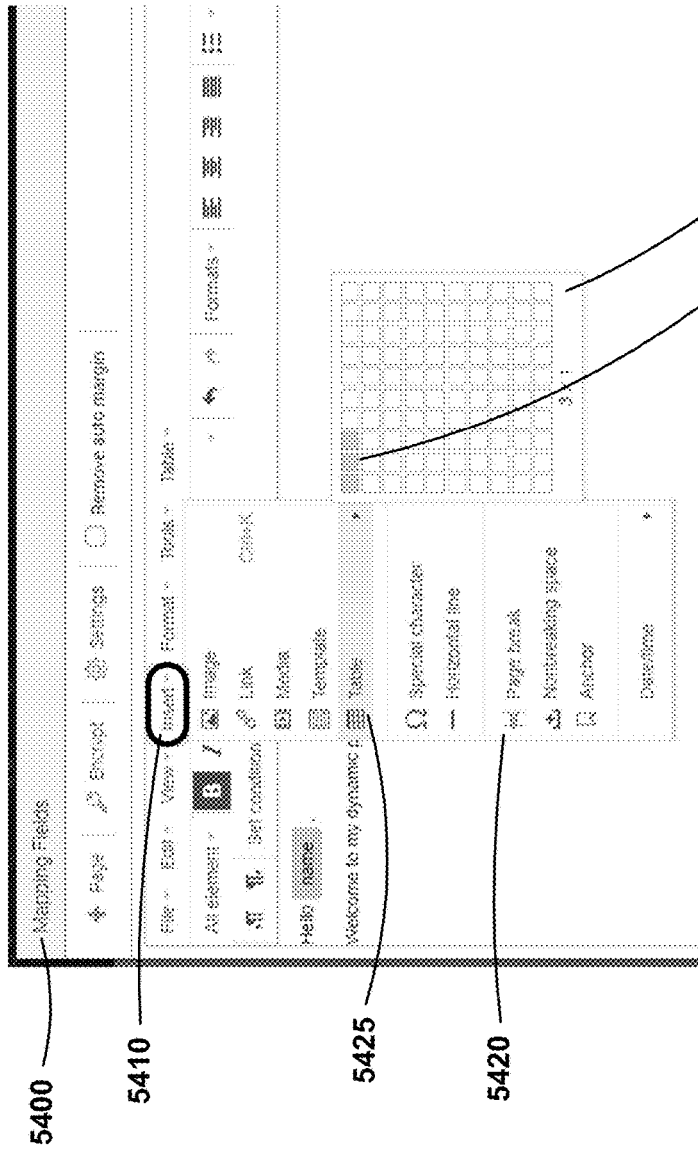
FIG. 54 shows for illustrative purposes only an example of pdf block condition mapping fields table of one embodiment.

Pdf Block Condition Mapping Fields Table:

FIG. 54 shows for illustrative purposes only an example of pdf block condition mapping fields table of one embodiment. FIG. 54 shows the mappings fields 5400 webpage and an insert 5410 feature selection menu that includes a table 5425 with a menu that includes insertion of a page break 5420. Showing is a table grid 5430 where the user highlights a 3×1 page break 5435 for the table of one embodiment.

Figure 55:
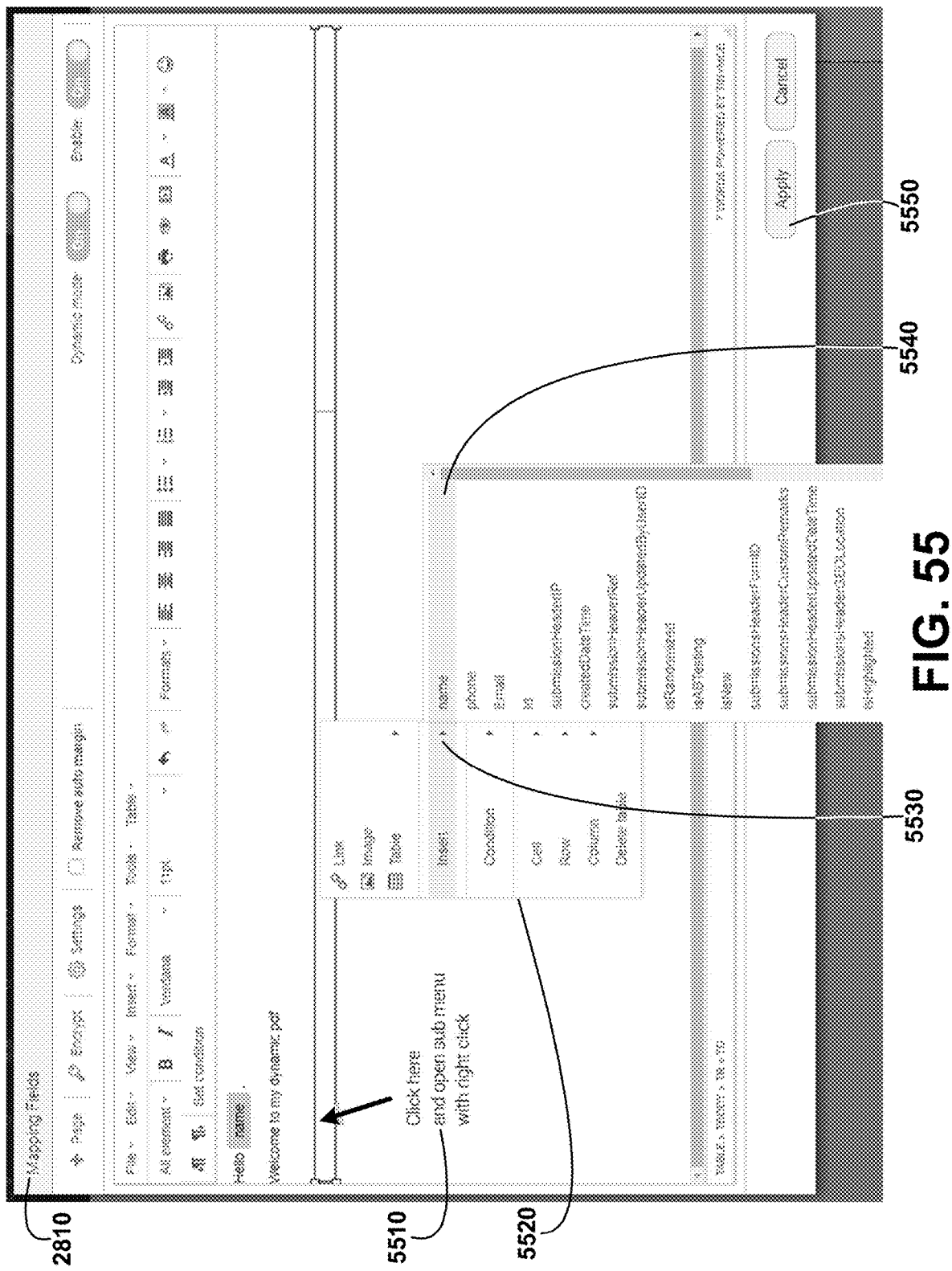
FIG. 55 shows for illustrative purposes only an example of pdf block condition starting mapping fields of one embodiment.

Pdf Block Condition Starting Mapping Fields:

FIG. 55 shows for illustrative purposes only an example of pdf block condition starting mapping fields of one embodiment. FIG. 55 shows mapping fields 2810 with an instruction click here and open sub menu with right click 5510. A sub menu 5520 that includes an insert drop down 5530 and shows a user selected name 5540 that the user can apply 5550 of one embodiment.

Figure 56:
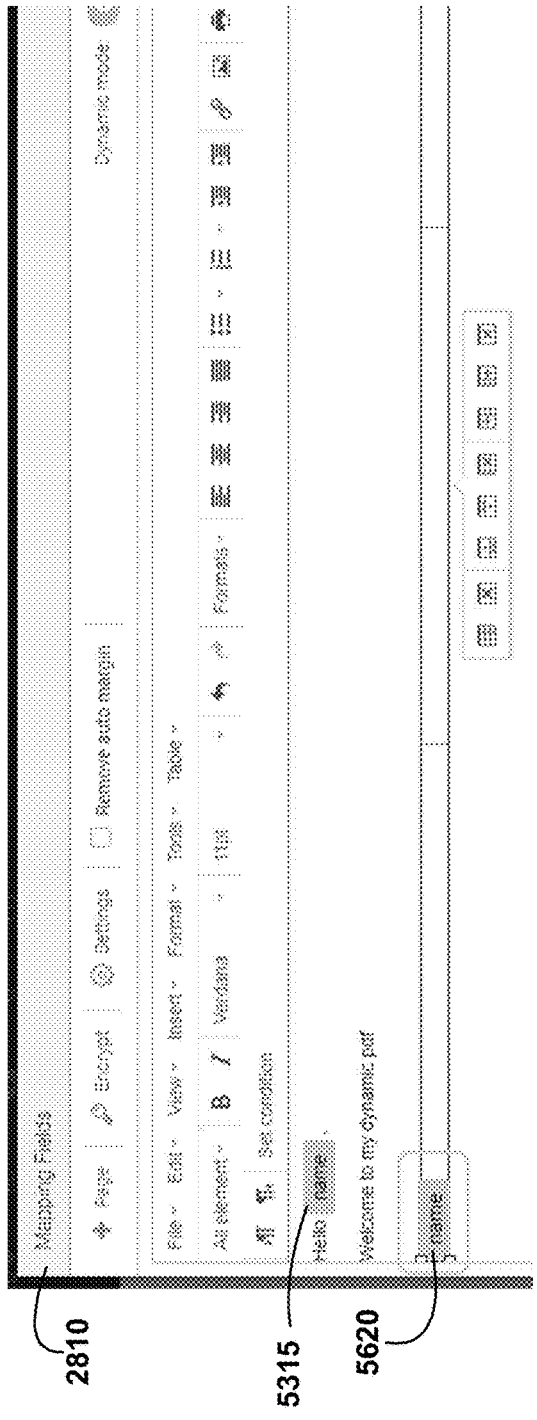
FIG. 56 shows for illustrative purposes only an example of pdf block condition mapping field name of one embodiment.

Pdf Block Condition Mapping Field Name:

FIG. 56 shows for illustrative purposes only an example of pdf block condition mapping field name of one embodiment. FIG. 56 shows the mapping fields 2810 where a name 5315 is displayed and a name insert box 5620 can be entered or automatically inserted from a platform account field of one embodiment.

Figure 57:
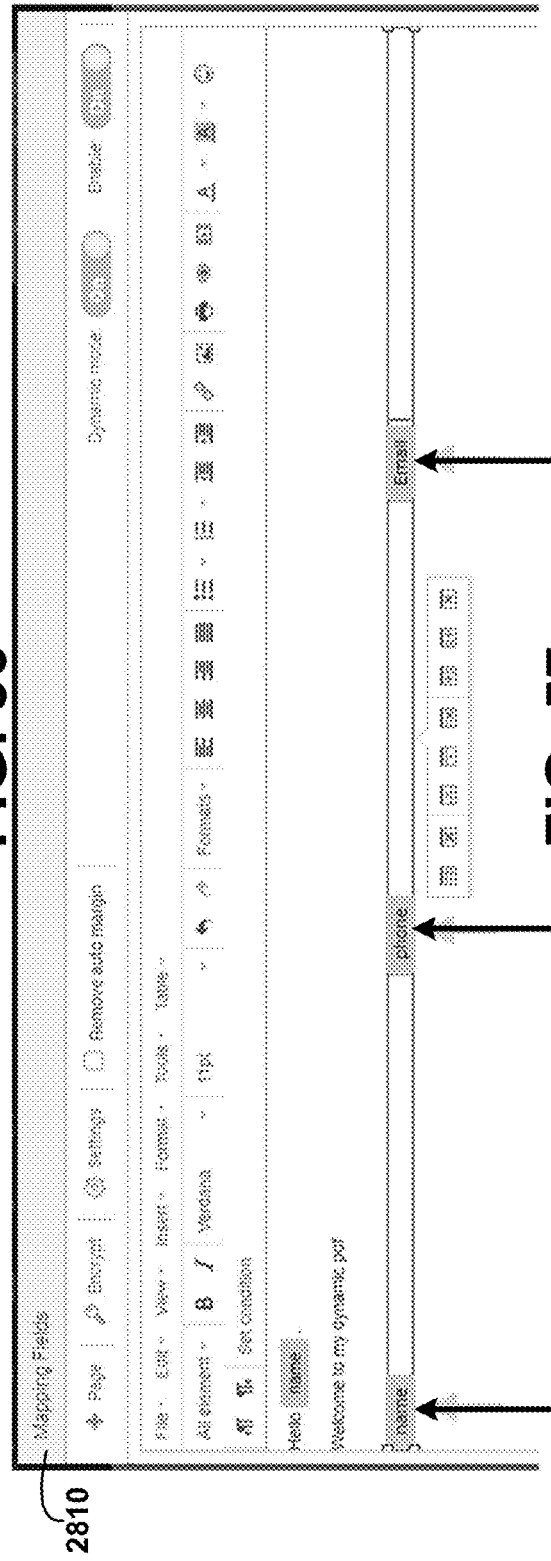
FIG. 57 shows for illustrative purposes only an example of pdf block condition mapping fields of one embodiment.

Pdf Block Condition Mapping Fields:

FIG. 57 shows for illustrative purposes only an example of pdf block condition mapping fields of one embodiment. FIG. 57 shows the mapping fields 2810 where a name entry displays the name 5315, phone 1260 and email 1070 associated with the name entered of one embodiment.

Figure 58:
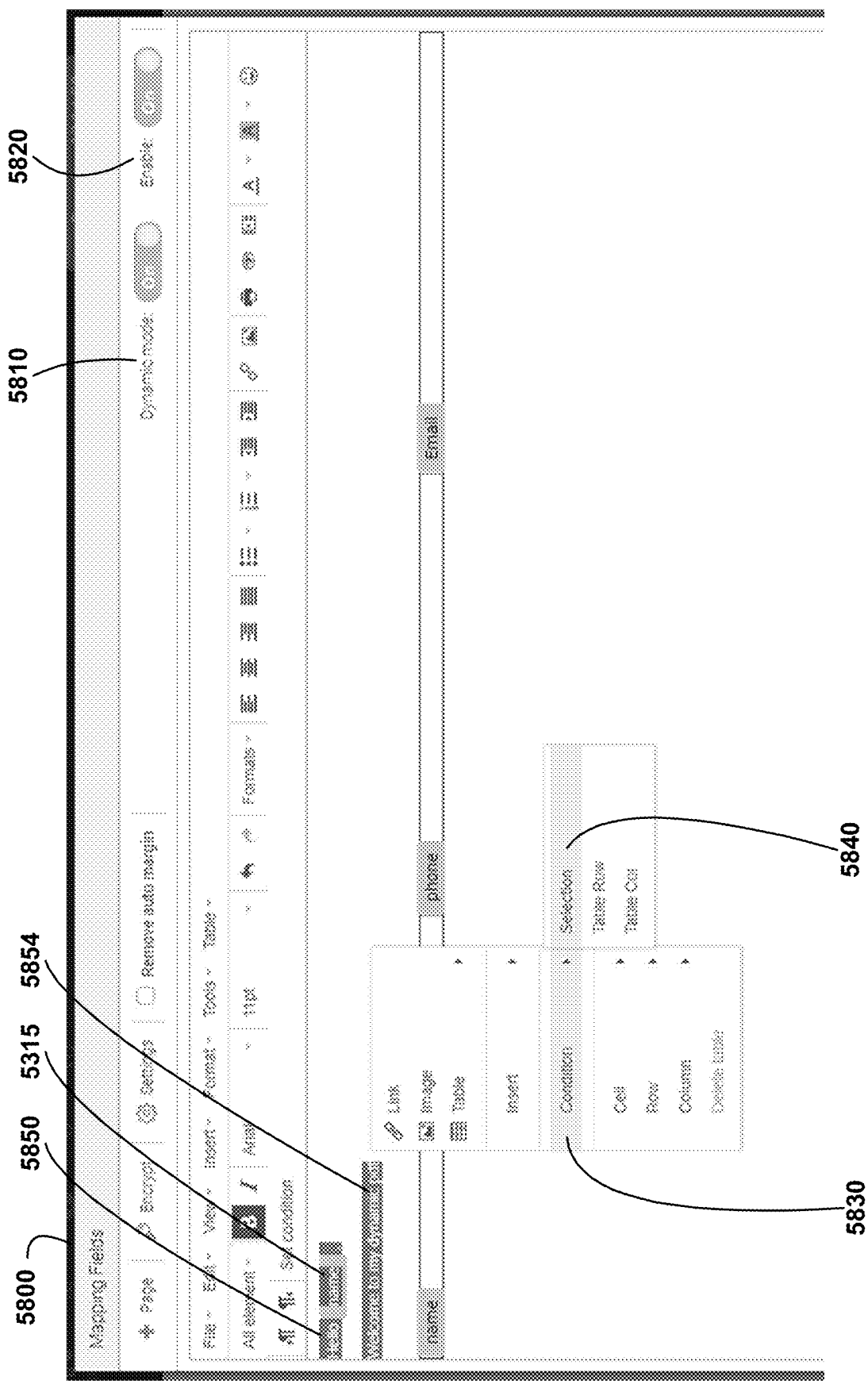
FIG. 58 shows for illustrative purposes only an example of pdf block condition mapping fields selection of one embodiment.

Pdf Block Condition Mapping Fields Selection:

FIG. 58 shows for illustrative purposes only an example of pdf block condition mapping fields selection of one embodiment. FIG. 58 shows a mapping field web page 5800 that a user has setup with a greeting hello 5850, a name 5315 and a salutation welcome to my dynamic pdf 5854. Dynamic mode is on 5810 and enable on 5820 indicates it will be activated as directed in an entry in a condition drop down 5830 selection from the condition drop down sub menu selection table row table col 5840 of one embodiment.

Figure 59:
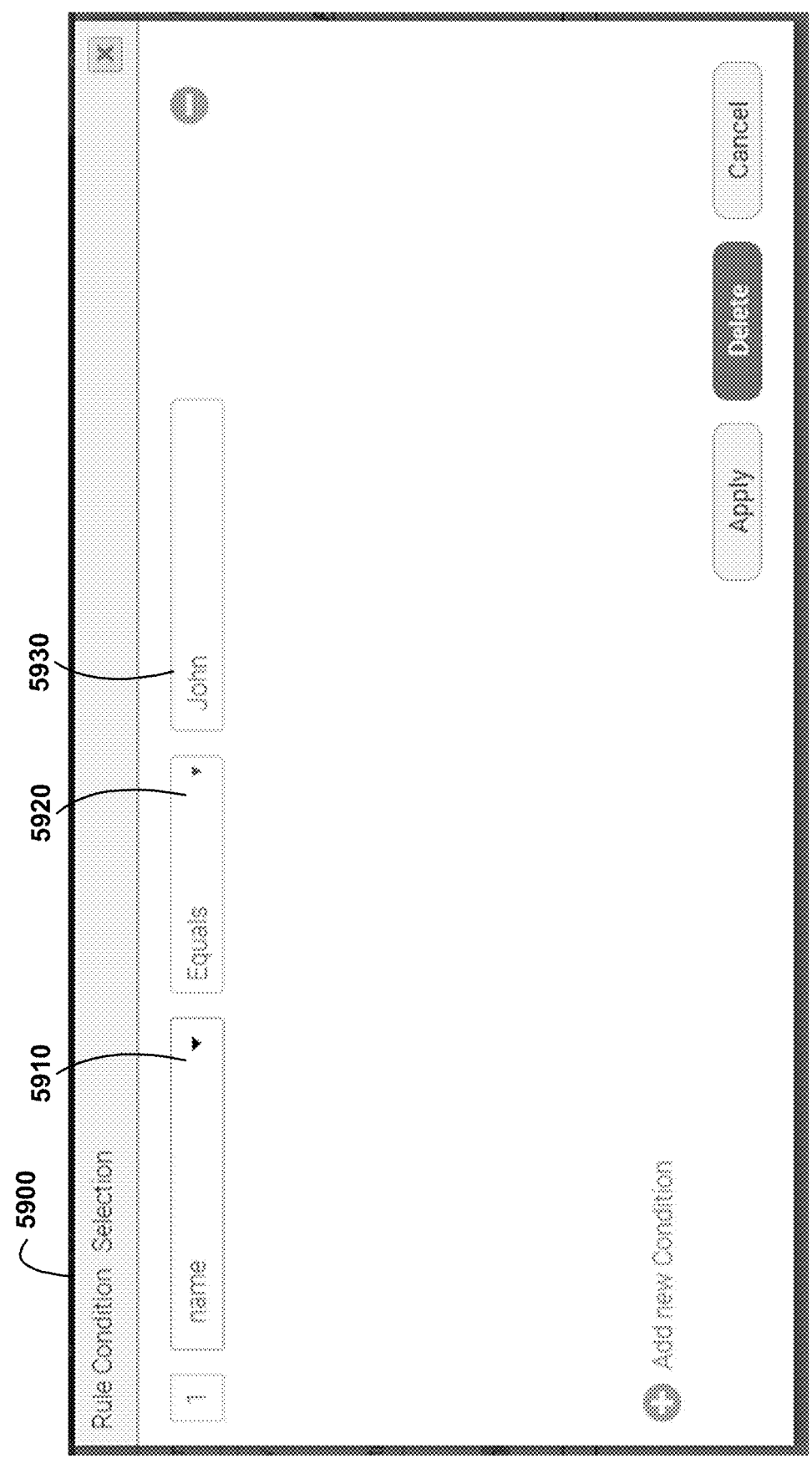
FIG. 59 shows for illustrative purposes only an example of pdf block rule condition selection of one embodiment.

Pdf Block Rule Condition Selection:

FIG. 59 shows for illustrative purposes only an example of pdf block rule condition selection of one embodiment. FIG. 59 shows a rule condition selection 5900 with a name drop down 5910 and condition drop down rules for example equals 5920 john 5930 of one embodiment.

Figure 60:
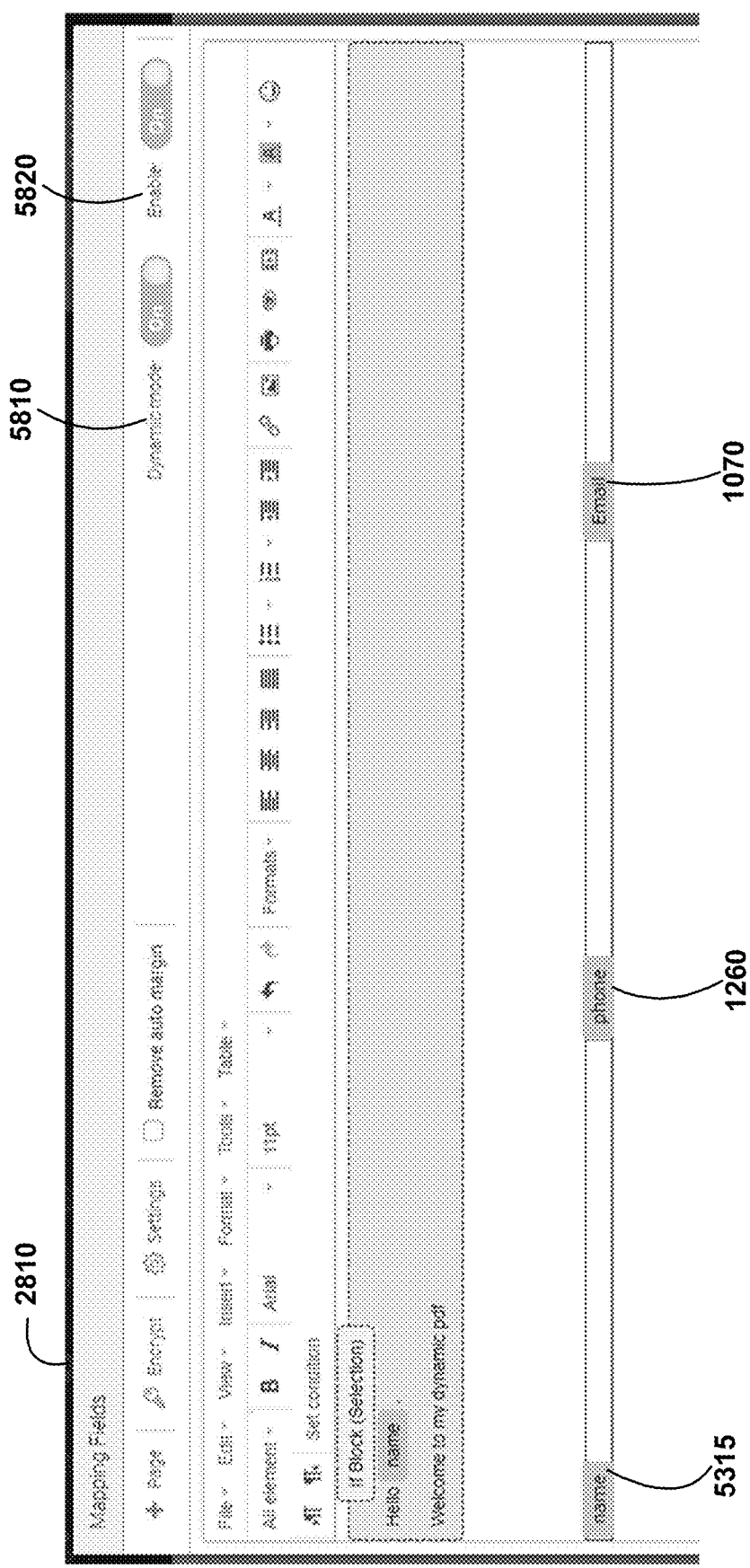
FIG. 60 shows for illustrative purposes only an example of pdf block condition mapping fields dynamic mode settings of one embodiment.

Pdf Block Condition Mapping Fields Dynamic Mode Settings:

FIG. 60 shows for illustrative purposes only an example of pdf block condition mapping fields dynamic mode settings of one embodiment. FIG. 60 shows mapping fields 2810 with dynamic mode on 5810 and enable on 5820 where the greeting and salutation includes a name 5315, phone 1260, and email 1070 of one embodiment.

PDF Block condition. The 'Block condition' is a conditional logic that can be used to show and hide selected parts of the PDF. This option can only be used in the Dynamic PDF mode. The block condition can allow you to set 3 types of conditions: —Selection—to show selected parts in the PDF—Table Col—to show a table column—Table Row—to show a table row. Following is a step-by-step example that will walk you through all 3 types of block condition. All you have to do is: —Create a new simple form—Drag 3 elements: 2 textboxes and an email field—Select each field on canvas and go to the 'Properties' panel>'Element' tab>'Settings' option>'Basic' category>Label—Change their label names to: Name, phone and email. —Create a manual PDF: —Go to 'Properties' panel>'Form' tab>'Settings' option>Press "view more" link>'PDF Mapping' category. —Press on the "Map fields" button and the PDF editor will then open. —Use the toggle to change to the Dynamic mode—Press on the "Settings" icon in the Toolbar and turn on the "Preview before submit" checkbox (in the General category). —Add some text, like: Hello and add the "name field" right after it. So it will now say: Hello name, Add some more text under that, like: Welcome to my dynamic pdf—Add a table with 3 columns (toolbar>insert>table)—Click inside the first column and open a sub menu with a right mouse click—Select Insert and choose the 'Name' field—it will then be inserted into the column—Move to the second column and insert the 'Phone' field into it. —Move to the third column and insert the 'email' field into it. At this point in our example you can create 3 different types of Block conditions: Selection, Table Row, and Table Col.

So following is an example for each type: Selection—Hide/show selected part of the PDF—Select the text you added at the top ("Hello name, . . . )—right click to open the sub menu—Select 'Condition' and then 'Selection'. —Now a window will open for you to configure the condition: Please note that this is a very basic conditional window where the result is always the same and if the condition is met, then the selected item/s will show. —Now Set the following condition: Name equals John and press "apply". This means that if john will be entered in the name field—the text you selected will appear. —You will notice that the selected area is now confined within an "If Block" box. Clicking on the 'If block' title tag will open the condition window for edit. —Press 'Apply' and save the form. —Test the PDF: —Publish the form as URL. —Enter the form: John in the 'name' field, 1234 in the 'phone' field and 'john@test.com' in the email field. —press on submit—The PDF preview will open and the text in the top part of the PDF will appear (because the condition was met). —Now press cancel and change the name to Jill.

Open the preview again and you will not see the text at the beginning of the PDF. Table Col—Hide/show table column—Click inside the third column (with the email in it). —Right click to open your sub menu. —Select 'condition' and then "table col". —Now configure the condition: phone contains 1 This means that if the filler enters a phone number that contains the digit 1 in it—the email cell will show in the PDF table. —Press 'Apply'. —You will now notice that the selected column content is now confined within an "If Block" box. Clicking on the 'If block' title tag will allow you to edit or remove the condition. —Press 'Apply' and save the form. —Test the PDF: —Publish the form as URL. —Enter john, 1234 and john@test.com—Press on submit—The PDF preview will then open and the table will show all 3 columns—Now press 'cancel' and remove the digit 1 in the phone number. Open the PDF preview again and you will not see the third column (with the email).

Table Row—Hide/show table row—Click inside the second column (with the phone in it)—Right click to open your sub menu—Select 'condition' and then "table Row"—Now configure the condition: Name is not empty This means that if the filler enters any name then the table row will show. —Press 'Apply'. —You will also notice that the selected row content is now confined within an "If Block" box. Clicking on the 'If block' title tag will allow you to edit or remove the condition. —Press 'Apply' and save form. —Test the PDF: —Publish the form as URL. —Enter john, 1234 and john@test.com—Press on submit—The PDF preview will then open and the table row will appear. —Now press 'cancel' and remove the value from the Name field—Click submit again and you will not see the table row of one embodiment.

Figure 61:
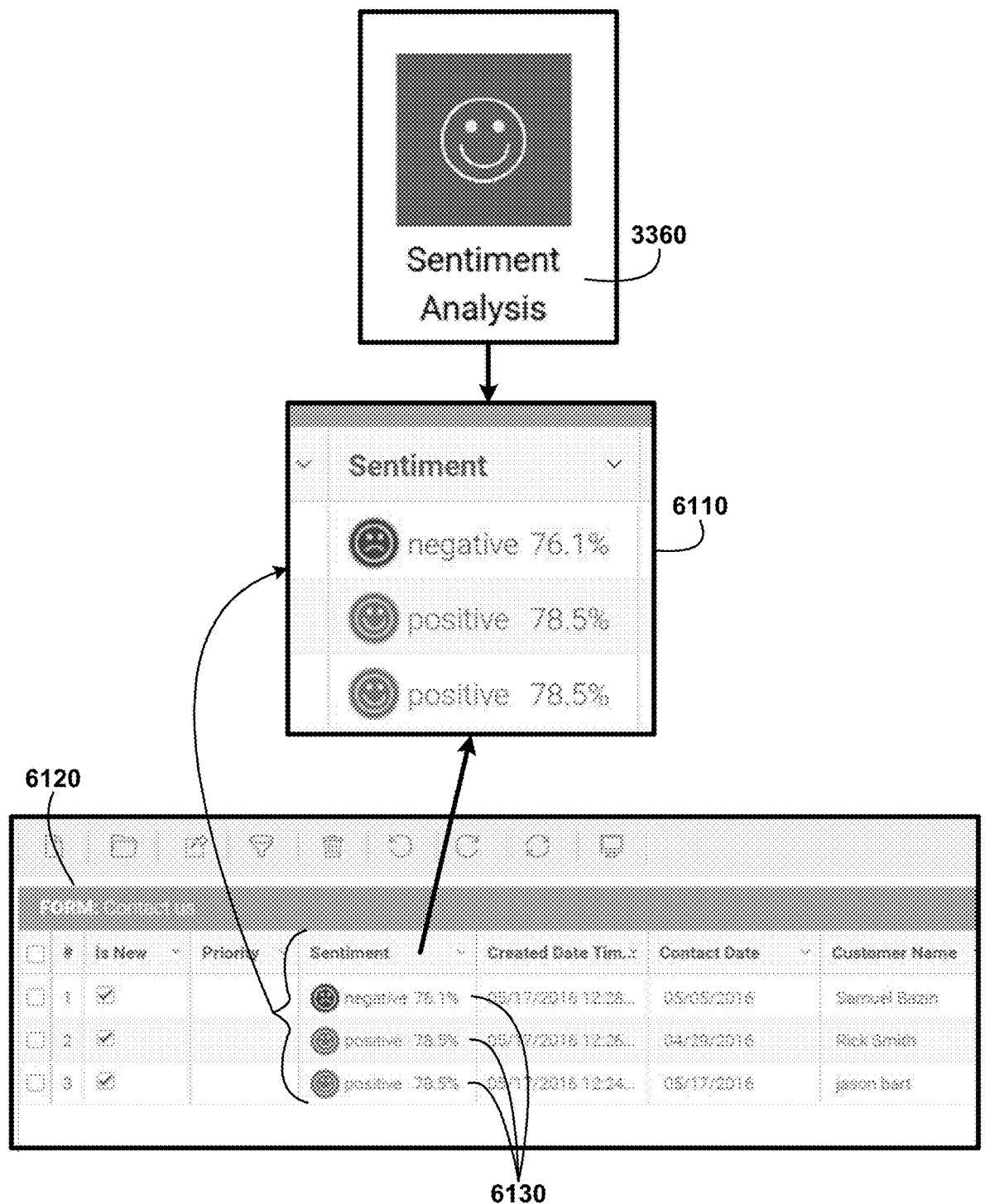
FIG. 61 shows for illustrative purposes only an example of a sentiment analyze feature of one embodiment.

A Sentiment Analyze Feature:

FIG. 61 shows for illustrative purposes only an example of a sentiment analyze feature of one embodiment. FIG. 61 shows a sentiment analysis 3360 feature with a sentiment enlarged view 6110 of results from a form: contact us 6120. The form: contact us 6120 results include sentiments expressed including negative 76.1%, positive 78.5%, and positive 78.5% 6130 of one embodiment.

FormTitan launches the first Form Builder employing sentiment analysis for understanding textual responses. Focusing on conversion rate optimization (CRO), The FormTitan team realized that people need more than a tool to build good looking forms, they want to improve conversion rates. So they built an engine that goes over every newly created form, analyzes it, and provides you with suggestions for changes which would improve conversion rates. If your form has open-ended text fields, FormTitan can employ Sentiment Analysis algorithms to analyze your data. So, for example, it can highlight customers at risk and even use its built-in conditional logic to notify those in charge of customer retention or show a predefined message to such users.

Figure 62:
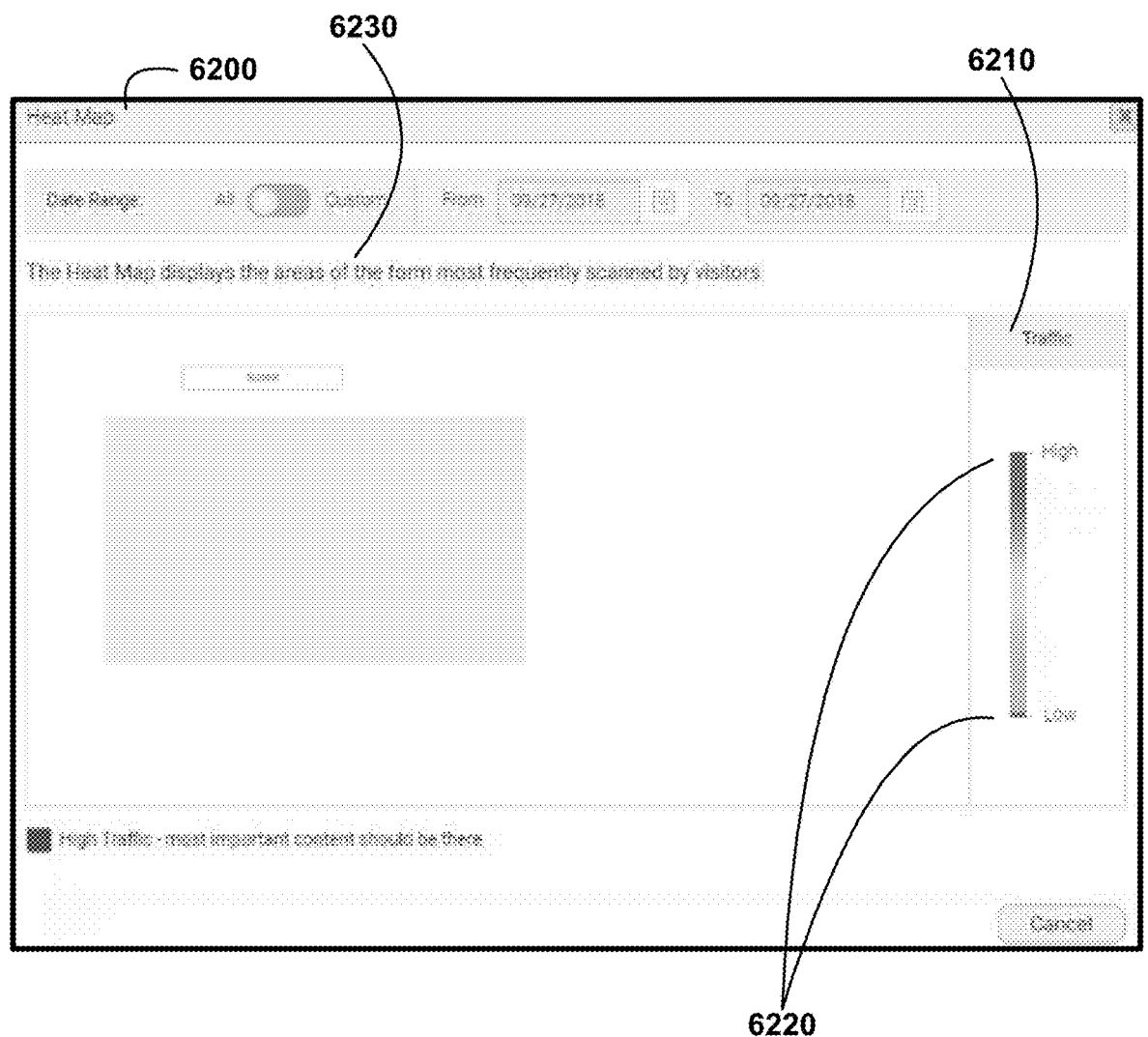
FIG. 62 shows for illustrative purposes only an example of heat map integration of one embodiment.

Heat Map Integration:

FIG. 62 shows for illustrative purposes only an example of heat map integration of one embodiment. FIG. 62 shows a heat map 6200 displayed. The heat map displays the areas of the form most frequently scanned by visitors 6230 to indicate traffic 6210 concentrations. A color scale showing a low to high heat level corresponding to the form area most frequently scanned by visitors in a graphic format 6220 of one embodiment.

Use Heatmap to optimize your form One of the many optimization tools offered by FormTitan is the Heatmap. This feature provides you with a graphical representation of how your visitors move along your Form. It colors the more "active" parts of your form in warmer colors (yellow, orange and red) and shows the areas where the users don't go through as much in cold colors (blue and green). The heatmap draws a kind of map, where you can see where your form fillers spend more time. It helps you understand which parts of your form are the strongest and which are the weakest and place the elements in your form accordingly.

Following are steps to use your heatmap feature: *Please note that this feature requires a license. 1—Open your form in the form builder 2—Go to "Properties" panel>"Form" tab>"Settings">"Optimization" category 3—Turn on the "Heatmap" checkbox and save your form. 4—You can also turn this feature on from the "My Forms" page, by choosing the form on the left and using the toggle in the "form optimization" section to turn it on. 5—Once the feature is turned on, all you have to do is wait. When users start to use your form and fill in data, their movements will be recorded and you will be able to see the resulting map.

Figure 63A:
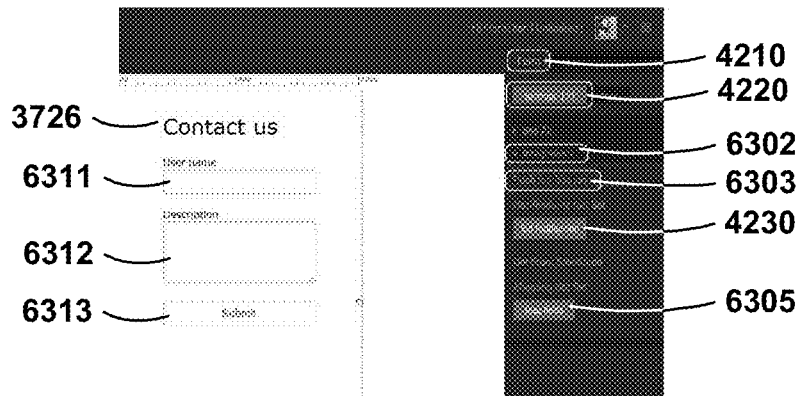
FIG. 63A shows for illustrative purposes only an example of integrating a form platform into form builder of one embodiment.

Integrating a Form Platform into Form Builder:

FIG. 63A shows for illustrative purposes only an example of integrating a form platform into form builder of one embodiment. FIG. 63A shows the form 4210 settings [?] 4220 for integrations 6302 including push notification 6303, set notification 4230 and map fields 4250. The map fields 4250 include contact us 3726, user name 6311, description 6312, and submit 6313 of one embodiment.

Form Builder can integrate multiple applications. These are a variety of calendar/schedulers that can be integrated into a responsive form using FormTitan. A user can create a form to integrate with a calendar application that is responsive by manual entry and voice commands.

Figure 63B:
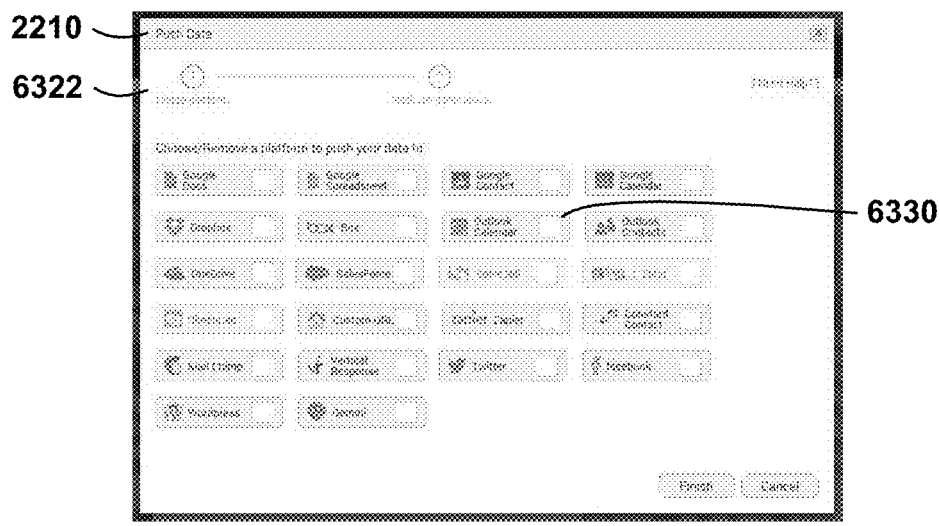
FIG. 63B shows for illustrative purposes only an example of authenticate a form platform of one embodiment.

Authenticate a Form Platform:

FIG. 63B shows for illustrative purposes only an example of authenticate a form platform of one embodiment. FIG. 63B shows using push data 2210 into a selection made using choose platform 6322 for example Outlook Calendar 6330.

An event calendar feature is illustrated with an Salesforce Event Object. Integration with the Salesforce Event Object FormTitan is an online web tool that allows you to create online forms, landing pages and Salesforce forms. The FormTitan form builder can easily integrate with Salesforce event object. Not only does this require no coding skills on your part, but the Salesforce connector is seamless and powerful. Unlike other products, our Salesforce connector not only writes to your Salesforce event object but it can also read from it and populate your online form fields instantly. Furthermore, You can read from multiple objects at a time, with or without dependencies and query your objects based on any value from your form. An Event Object represents an event in the calendar. In the user interface, event and task records are collectively referred to as activities. Usage Use Event to manage calendar appointments.

Figure 63C:
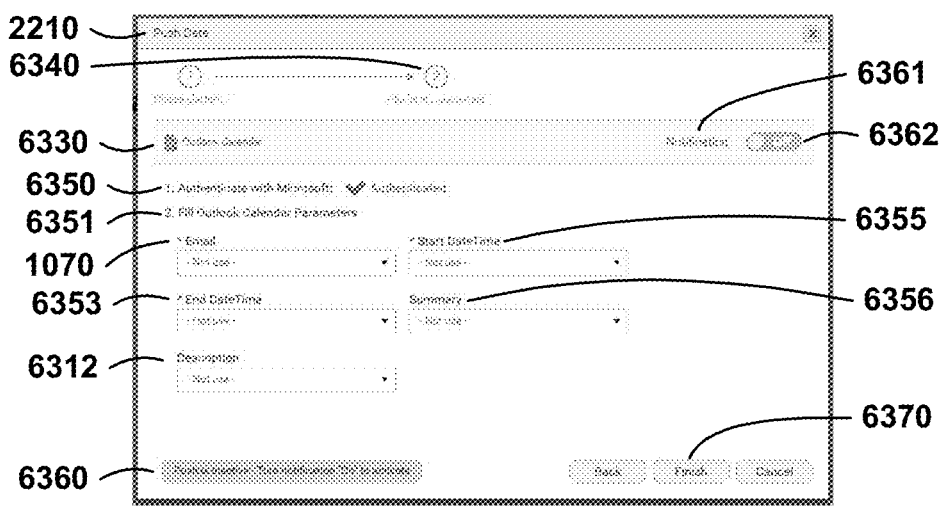
FIG. 63C shows for illustrative purposes only an example of choosing form fields data to push to form platform of one embodiment.

Choosing Form Fields Data to Push to Form Platform:

FIG. 63C shows for illustrative purposes only an example of choosing form fields data to push to form platform of one embodiment. FIG. 63C shows push data 2210 for creating platform parameters 6340 in this example for Outlook Calendar 6330. One platform parameter is 1. authenticate with Microsoft: authenticated 6350. Then the 2. fill Outlook Calendar parameters 6351 selections include email 1070, end datetime 6353, description 6312, start datetime 6355, summary 6356, and finish 6370. Displayed is a notification and instruction that push is inactive—turn notification "on" to activate 6360. A notification 6361 area shows a notification activation switch shown in off 6362 position. A user will turn on the notification toggle and press on "Finish". Once the form is configured to integrate with Outlook Calendar—a user will fill in your form and then a new appointment will be added in your calendar based on your push configuration of one embodiment.

Figure 64:
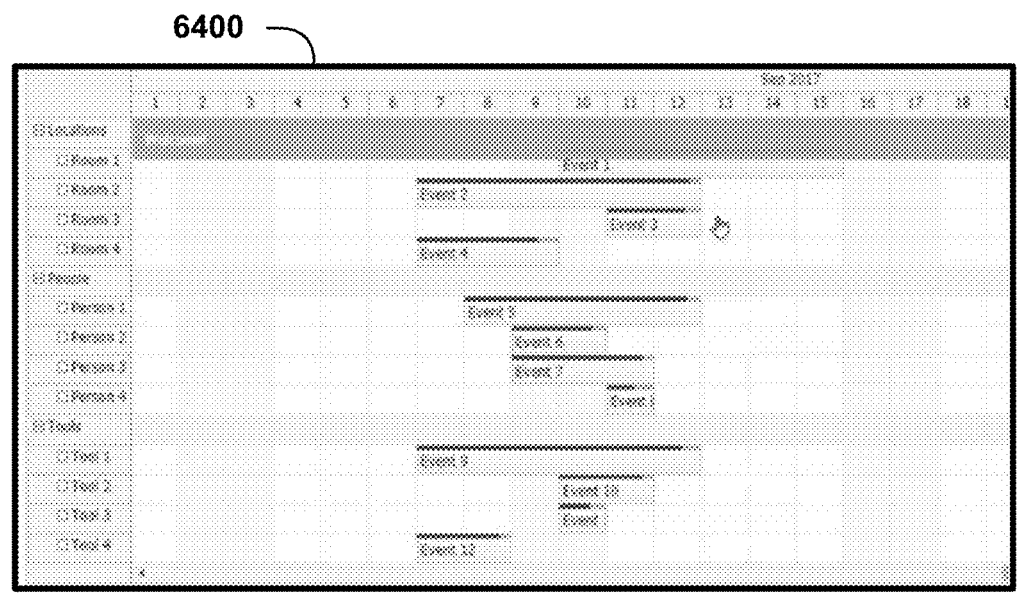
FIG. 64 shows for illustrative purposes only an example of an event calendar feature of one embodiment.

An Event Calendar Feature:

FIG. 64 shows for illustrative purposes only an example of an event calendar feature of one embodiment. FIG. 64 shows an Outlook Calendar event listings 6400 of one embodiment.

Figure 65:
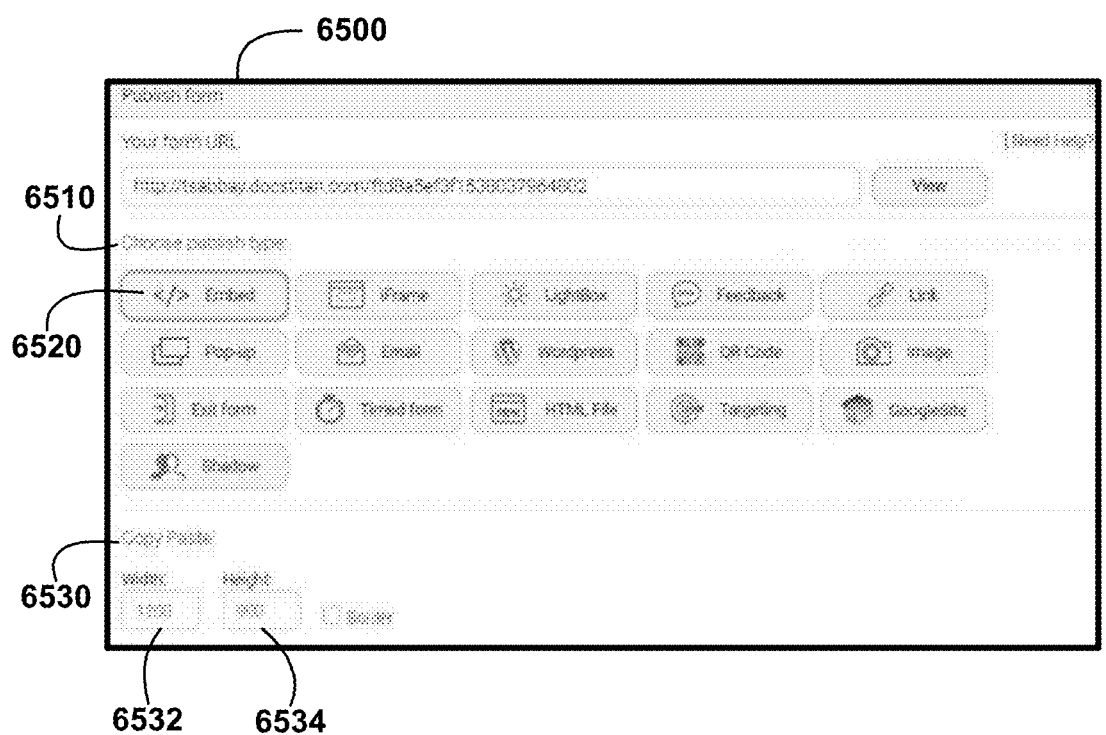
FIG. 65 shows for illustrative purposes only an example of a publish form feature of one embodiment.

A Publish Form Feature:

FIG. 65 shows for illustrative purposes only an example of a publish form feature of one embodiment. FIG. 65 shows a publish form 6500 feature. A user can choose publish type 6510 including </>embed 6520 and copy paste 6530. The area for a publish form section includes user settings for width: for example 1200 6532 and height: for example 900 6534. Other publish features include publish option: Android APK, and Supporting URL parameters in publish options: Embed, Lightbox and Feedback of one embodiment.

Publish Form You have several options for publishing your form. Once you are happy with your form, click on the publish button in the upper toolbar. A publish window will then open with all the publishing options we support.
Simply select the option you need, and a generated code will be created accordingly. Copy the code and paste it in your website, email, blog etc. In addition to all the publish options, the publish window first provides you with the form URL. Clicking on "view" will open the URL in a new browser tab, enabling you to test it, if you wish. Following is a list of all the publishing options supported by the Titan: *In each of the options you can select and modify the properties below (width/height, link text,border, time,traget etc). 1—Embed: Use this option to embed the form within your web page 2—iFrame: Use this option to embed the form within your web page in an inline frame 3—LightBox: Use this option to generate a link that opens the form on the page as lightbox. 4—Feedback: This option adds a button to the bottom right corner of your web page. When pressed—the form opens. You may also choose one of the the 4 button style available. 5—Link: Use this option to generate a direct link to your form 6—PopUp: This option generates a link that when pressed it opens a new pop up window 7—Email: Allows you to send an email containing a link to your form. Simply need to enter your recipient, subject and email body. 8—WordPress: Generate a code that can be embedded in your wordpress site. 9—QR Code: Automatically generate a QR code pointing to your form. 10—Image: This option generates an image of your form, that when clicked it leads to it. 11—Exit Form: This generated code, when inserted in your web page, makes sure that the form will appear if/when the user tries to leave the page. 12—Timed Form: Lets you set a timer (in seconds) for when you would like to make the form appear. 13—HTML File: Generates an HTML code you can use. 14—Targeting: Lets you send your form to a mailing list or phone list. 15—Google Sites: Generates a code you can use in google sites. Read More Following are instructions on how to publish your form: 1—Enter the form builder and open the form you would like to use. 2—Once the form is on canvas, press on the "Publish" icon. 3—Select a publish type and copy the code below.

Figure 66:
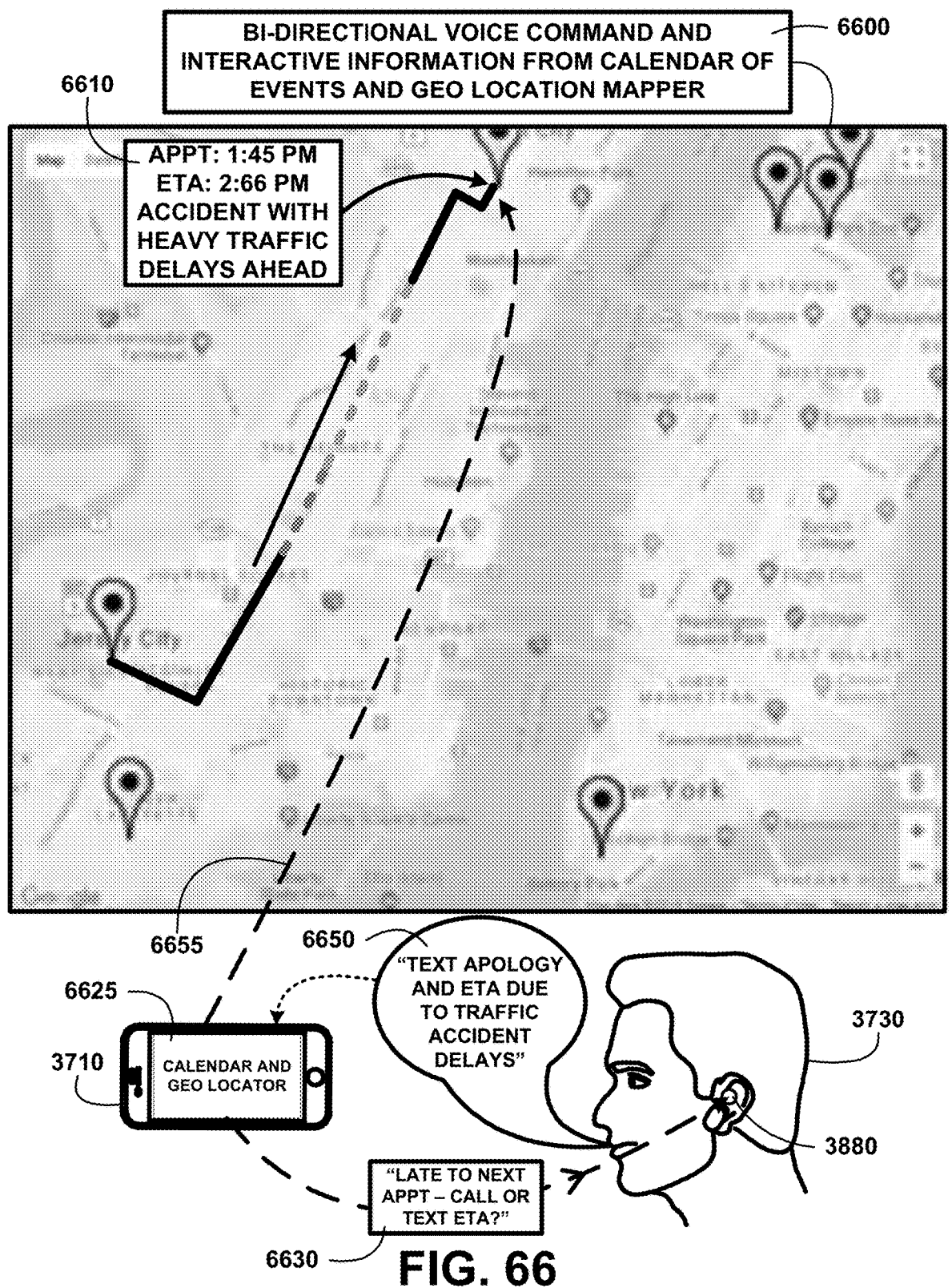
FIG. 66 shows for illustrative purposes only an example of a voice interactive calendar and geo locator of one embodiment.

A Voice Interactive Calendar and Qeo Locator:

FIG. 66 shows for illustrative purposes only an example of a voice interactive calendar and geo locator of one embodiment. FIG. 66 shows bi-directional voice command and interactive information from calendar of events and geo location mapper 6600. The user smart phone 3710 with the FormTitan application installed can display a mapper with information overlays including for example appt: 1:45 pm, ETA: 2:66 pm, accident with heavy traffic delays ahead 6610. A FormTitan network digital processor can calculate the remaining distance to the user's next appointment and estimate arrival time based on projected travel speeds using current traffic conditions. The user smart phone 3710 displays calendar and geo locator 6625. The FormTitan application transmits an audible message "late to next appt—call or text ETA?" 6630 to the user 3730 who may be driving. The user using a hands-free ear piece hears the FormTitan application audible message 3880. The user instructs the application to "text apology and ETA due to traffic accident delays" 6650. The FormTitan application sends a text to the next appoint location 6655 sending the user instructed message of one embodiment.

The bi-directional voice command and interactive information from calendar of events and geo location mapper can greatly assist a user in making their appointments. In this example the voice element notifies the user while driving that his next Appt: 1:45 PM, ETA: 2:10 PM accident with heavy traffic delays ahead from the user's event calendar. On the screen the geo locator shows where his next appointment is and the traffic status acquired from local law enforcement notifications and a calculated ETA based on the distance and reduced speeds.

The voice element asks "late to next appt—call or text eta?". The user instructs the customized customer relationship management platform through the voice element to "text apology and eta due to traffic accident delays". The interactive capacity of the customized customer relationship management platform has allowed the user to get valuable information and assist the user in providing a professional image with his contacts of one embodiment.

Figure 67:
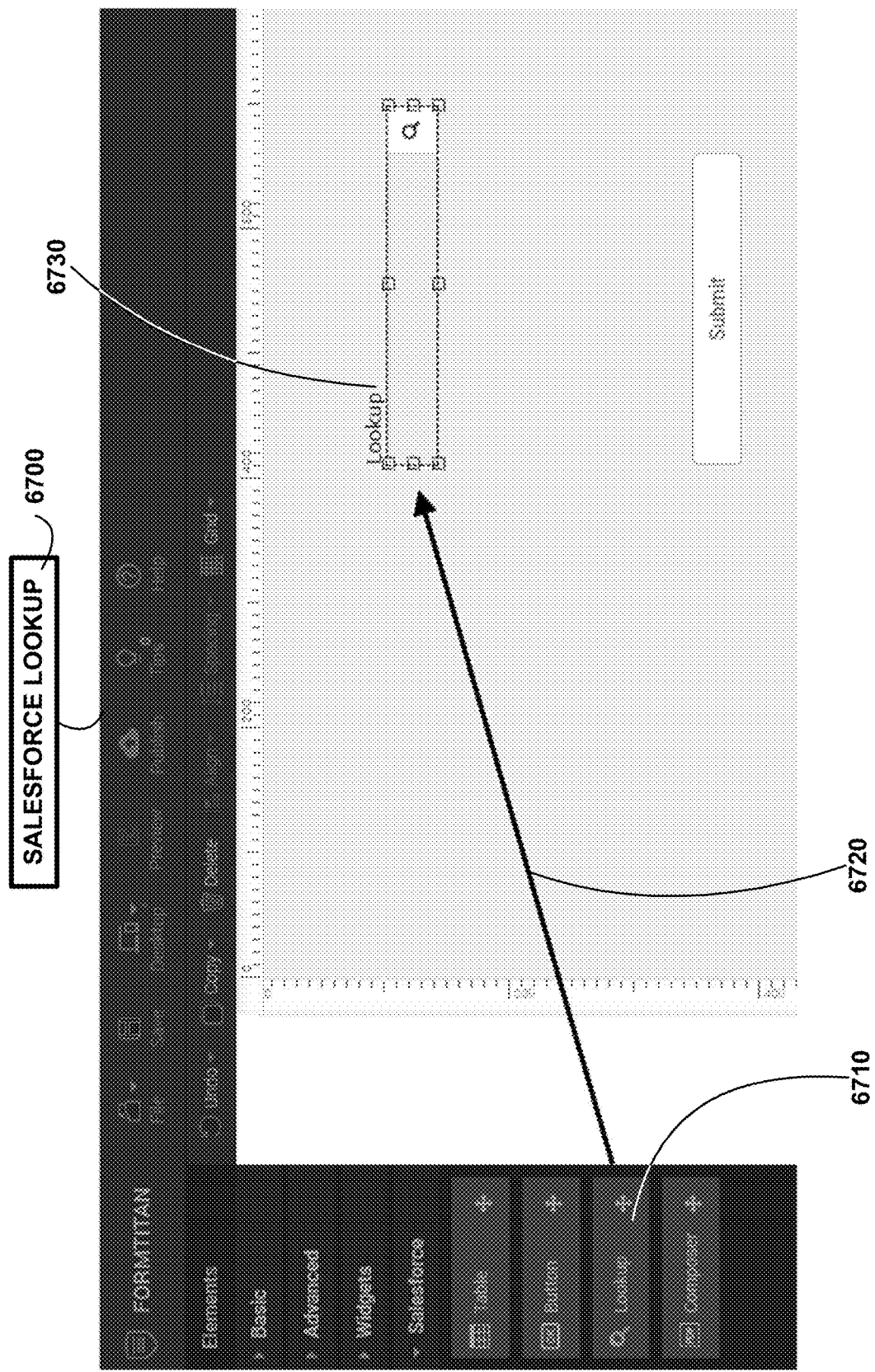
FIG. 67 shows for illustrative purposes only an example of Salesforce lookup of one embodiment.

Salesforce Lookup:

FIG. 67 shows for illustrative purposes only an example of Salesforce lookup of one embodiment. FIG. 67 shows a Salesforce lookup 6700 menu selection lookup 6710 the user can press which opens a lookup text box 6720. The user can enter the data into the lookup text box 6730. Another feature includes Date and Date time format in Table and Lookup of one embodiment.

The Lookup is a special element that is used when you Integrate forms with Salesforce. It allows you to create a search box for your users, enabling them to search inside Salesforce objects and choose an item. When you add a Lookup, all you have to do is set the integration with Salesforce and configure the columns of the lookup results table. Following are steps to use the Lookup element: 1—Enter your form in the form builder 2—Go to "Elements" panel>"Salesforce" category Drag the "Lookup" element onto the canvas. 3—Once the "Lookup" is selected on canvas its properties will open in the panel on the right. (in "Properties" panel>"Element" tab>"Settings" option>"Basic" category>Mapping) Press on the "Set" button. 4—a window will now open, where you will need to configure the Lookup: Authentication First, you will need to authenticate with Salesforce. Configure Salesforce integration Press on the "Configure Salesforce Integration" button" to make the connection between the Lookup and the Salesforce object. This window looks very much alike the regular integration mapping window, only it is designed for the lookup and contains only 4 categories: Connection—this will contain the account you authenticated with earlier, however you can change it if you wish. Salesforce object settings—Select the Salesforce object you want your users to search in. Condition—Set a condition like: Account Name Contains Search box (which means the user will enter text in the searchbox and matching items will be searched for in the "Account Name" field). Sort order—This is not a mandatory, however you can control how the results will be sorted (according to which fields) and if the sorting is Ascending or Descending. Configuring the results table columns The results of the search will be displayed in a table—so now you will be required to set the columns of this table. Open the "Add fields for display" dropdown, choose the fields, one by one, and press "Add". Each field will be displayed in a row and will include: Col—This is the field name Custom label—an input box in which you can enter a different text for the field label (instead of the one specified in the Col) Text & Value—2 sets of vertical radio buttons that control which field will be used for the Text in the results, and which will be used to store the value. Press "Apply" and save the form Now you will be able to publish the form as URL and test it. 5—Testing When your form loads you can either: A-Enter the a text inside the Lookup element and press on the "Search" button. The results will then open in a window according to your search. B—press on the Lookup button to open it, enter a text in the searchbox and press on the 'Search' button. The results will then appear according to your search.

Mapping the Salesforce External Lookup Relationship field to your form field The Salesforce External Lookup Relationship field type is an external lookup relationship links a child standard, custom, or external object to a parent external object. In the following video we will show you how to map your External Lookup Relationship field from Salesforce to your FormTitan form field. A lookup relationship creates a relationship between two records so you can associate them with each other.

Figure 68:
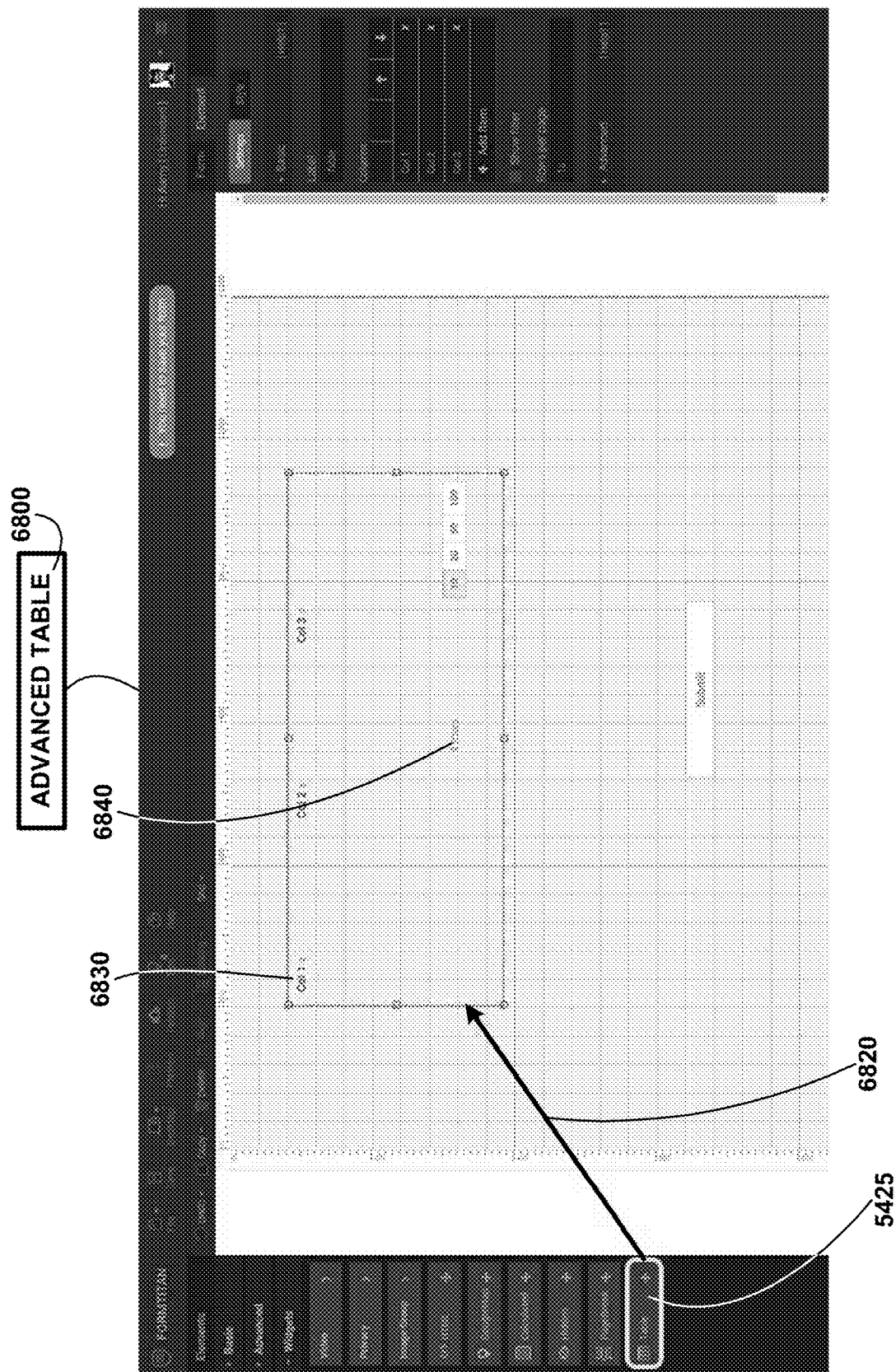
FIG. 68 shows for illustrative purposes only an example of advanced table of one embodiment.

Advanced Table:

FIG. 68 shows for illustrative purposes only an example of advanced table of one embodiment. FIG. 68 shows an advanced table 6800 feature to create a table 5425. A table selection opens a table formatting template 6820 for a user to select a column for example col 1 6830 and select a number of rows for example 4 rows 6840 of one embodiment.

Salesforce Table Working with Salesforce in an organized way. The Salesforce Table is an element you can drag from our "Elements Panel" and use in your form, but It may only be used for working with Salesforce. Since FormTitan enables a BI-Directional integration with Salesforce, you can draw data from Salesforce to your table, and edit that data so it is updated in the Salesforce object. Sure, you can read & write by working with regular elements and sections, however, now it can also be done using a table element.

Simple Table. Since Salesforce works with objects, the table element is built according to it. Once you drag the table element you will only need to set its columns and then configure the Salesforce "Get" integration to populate them—This is the basic use of the table.

Advanced Table. FormTitan Salesforce form builder enables you to create more complex scenarios. You can make the table hierarchical, drawing data with parent-child relationships and also writing to different objects simultaneously.

Simple Table. When using the Table element to create Salesforce forms, you can use the simple table or the advanced table. The "simple table" refers to the most basic table you can create for working with Salesforce. It is not hierarchical—It has a single level, with which you can only "Read" data from Salesforce, and you can do so from only one Salesforce object. In order to configure a simple table all you will need is to change the table's "Basic" settings and set the "Get" integration. The "Advanced table", in comparison, is more powerful. It refers to a hierarchical table, that enables you to work with multiple Salesforce objects. and allows you to "Read" from Salesforce objects as well as "write" to Salesforce objects.

Creating a simple table is easy—just follow these steps: 1—Enter a new/your form in the form builder 2—Drag a table element from "Elements" panel>Widgets>Table 3—Enlarge the table on canvas using the resizing handles 4 Once selected, the table's properties will open in the "Properties" panel (on the right side) 5—Change the default column values from Col1, Col2, Col3 to the Salesforce object fields you would like to display in the table. For example: if you wish to display information from the "Account" Salesforce object you could set the following columns: Account Name, Account Phone, Account Website.*

Please notice that this table is "Flat", it has no hierarchy and its columns can belong to only one Salesforce object. 6—You can, of course, add more columns, or remove columns according to your requirements. 7—You can add a filter row to the table, just below the headers, to help the user search for specific data—by turning on the "Show filter" checkbox. 8—Change the table style—the table's appearance, just like any FormTitan element, can be easily altered in the Element style. Go to: "Properties" panel>"Element" tab>Style" option> and open the "Apply style to" drop down. Choose the part of the table you would like to apply your style to. Weather it is to the table in general, to the rows, header etc. 9—make the style changes in the relevant categories. For example: Choose "Table" in the "Apply style to" dropdown, and specify a pale blue color in the background. 10—All that is left to do now is to connect this table to the Salesforce object. Go to the "Properties" panel>"Form" tab>"Settings">open the "Salesforce Integration" category Notice that there are two sections here: the top one is "Push to Salesforce", in which you configure the "writing" operations (creating, updating, upserting, deleting data in Salesforce objects). and the bottom section is "Get from Salesforce", in which you configure the "Reading" from Salesforce objects. Choose the in the "Get from Salesforce" section and press on the "Map Fields" button. 11—Authenticate with Salesforce and press on the "Add object" button 12—Choose the Salesforce object you would like to "read" from. In this case: Account. 13—Turn on the "execute on form load" checkbox—this will "pull" the data from Salesforce and populate the form once the form is loading. 14—There is no need to set a condition in this case, however, we will choose to display "All" matches found. As well as limit the number of accounts we show to 200. 15—Map the form fields (in this case, your table columns) to the Salesforce object fields. And press on "Apply". 16—You will see that a single integration line has been created. (you can edit it using the edit icon on the right). Press on "Apply" and save the form. 17—Publish your form to see the result. Press on the "Publish" icon in the main toolbar above Press on the "View" button to see the form. 18—And this is the published form—with the data populated straight from Salesforce—in real-time.

Advanced Table. When creating online forms for Salesforce with the Table element you can create a simple table, that only allows to read data from Salesforce, work with in a flat mode (with no hierarchy) and connect to only one Salesforce object, FormTitan still provides the capability to create a more powerful table which allows you to: 1—Read from Salesforce objects as well as write to Salesforce objects. 2—work with many Salesforce object at once. 3—work with hierarchy—data that has parent-child relationships. Create as many levels as you want in the table. A table is considered advanced once you start adding to the "simple" table—adding levels, adding Salesforce objects, adding "writing" to Salesforce objects.

Creating an advanced table is done in 3 phases: First Phase: Creating the table, it's levels and columns Second Phase: Setting up the Salesforce integration Third Phase: Setting filler permissions to View, Edit, Add, Delete, Export data First Phase: Creating the table, it's levels and columns 1—Enter a new/your form in the form builder 2—Drag a table element from "Elements" panel>Widgets>Table 3—Enlarge the table on canvas using the resizing handles. 4—Once selected, the table's properties will open in the "Properties" panel (on the right side). 5—Change the default column values from Col1, Col2, Col3 to the Salesforce object fields you would like to display in the table. For example: if you wish to display information from the "Account" Salesforce object you could set the following columns: Account Name, Account Phone, Account Website.

Please notice that this is the configuration for the first level of the table—displaying the parent object data. 6—You can, of course, add more columns, or remove columns according to your requirements. 7—You can add a filter row to the table, just below the headers, to help the user search for specific data—by turning on the "Show filter" checkbox. 8—Max Rows property allows you to enter a maximum number of rows that can be displayed in the table level. If, for example you set a max number of 10, then the form filler will only be able to add rows to this Table level until it reaches the max number. After that—the "Add" button will become disabled. 9—The 'Rows per page' property allows you to define how many rows will the table display in each page. 10—Change the table style—the table's appearance, just like any FormTitan element, can be easily altered in the Element style.

Go to: "Properties" panel>"Element" tab>Style" option> and open the "Apply style to" drop down. Choose the parts of the table you would like to apply your style to one by one. You can change the style of the table in general, the rows, table header, columns and even the modal window of the "Edit"/"Add"/"View"/"Delete" options. 11—make the style changes in the relevant categories. For example: Choose "Table" in the "Apply style to" dropdown, and specify a pale blue color in the background. 12—Ok, so now that the first level is configured you can start creating the next level in the table. Go to "Properties" panel>"Form" tab>"Settings" options>"Advanced" category press on the "Add level" button. a new level will appear on canvas containing the default columns (Col 1, Col 2, Col3) In addition 2 links will now be added inside the table element on canvas, for moving between the levels and also a "Previous" button for the user—to go back to the first level. 13—Set the fields of the child Salesforce object. "Properties" panel>"Element">"Settings" option>"Basic" category>change column names.

For example: if you wish to display the Contacts of each account you could set the following columns: Contact last name, Contact first name, Birth date. Second Phase: Setting up the Salesforce integration 14—Start by going to the Salesforce integration. Go to the "Properties" panel>"Form" tab>"Settings">open the "Salesforce Integration" category *Notice that there are two sections here: the top one is "Push to Salesforce", in which you configure the "writing" operations (creating, updating, upserting, deleting data in Salesforce objects). and the bottom section is "Get from Salesforce", in which you configure the "Reading" from Salesforce objects. Choose the ""Get from Salesforce" section and press on the "Map Fields" button. 15—Authenticate with Salesforce and press on the "Add object" button 16—Start mapping according to your table levels—start from the first level and work your way down.

So the first Salesforce object you would need to "read" from. according to this example is Account. Open the dropdown and choose it. 17—Turn on the "execute on form load" checkbox—this will "pull" the data from Salesforce and populate the table once the form is loading. 18—There is no need to set a condition in this case, however, we will choose to display "All" matches found. As well as limit the number of accounts we show to 200. 19—Map the form fields (in this case, your level #1 table columns) to the Salesforce object fields. And press on "Apply" 20—Once done, you will see that a single integration line has been created. This line, hold your mapping to the first level of the table. (you can edit it using the edit icon on the right). Press on "Apply" and save the form. 21—Now you will need to add the integration for the second level of your table and map your contact fields.

Since we would like to display the contacts belonging to each account in hierarchy, we will need to add the next object as a child of the first object. Press on the "Add object" button located at the bottom of your window. 22—Select the "Contact" object from the drop down. You will now need to add a condition in order to set the parent-child relationship like so: Choose to display "All" matches found. As well as limit the number of accounts we show to 200. 23—And map your contact fields to the Contact object fields in Salesforce. press "Apply". 24—You will now see 2 integration lines. The first is the account line, and the second line, will hold the mapping to the contact object. 25—Publish your form to see the result. Press on the "Publish" icon in the main toolbar above Press on the "View" button to see the form. 26—And this is the published form—with the data populated straight from Salesforce—in real-time. On the left part of the table you will see the columns you set.

On the right part you will see a column called "Next level", which holds buttons that will lead to the data in the second level. Third Phase: Setting filler permissions to View, Edit, Add, Delete, Export data 27—Making table columns editable Now that your table levels are set, and the Salesforce integration configured you can How your filler to "Read" data from Salesforce. If you wish to add more functionality and enable "writing" you can easily do that by setting permissions. "Properties" panel>"Form" tab>"Settings" options>"Advanced" category and turn on the checkboxes according to your needs: —Allow view— this will enable the form filler to view more data than is displayed in the table columns. when you turn on this checkbox a configure button will appear and you will need to press on it. a window will then open listing this level's column names and you will need to turn on the checkboxes of the fields you wish to make viewable. In addition you will be ale to add fields for viewing. —Allow edit—this will enable the form filler to edit the data in this level and by doing so, to update the Salesforce object. when you turn on this checkbox a configure button will appear and you will need to press on it. a window will then open listing this level's column names and you will need to turn on the checkboxes of the fields you wish to make editable.

Allow add—this will enable the form filler to add new data in this level and by doing so, to add data inside the Salesforce object. when you turn on this checkbox a configure button will appear and you will need to press on it. a window will then open listing this level's column names and you will need to turn on the checkboxes of the fields you wish have the user fill in when he wants to create a new item. You can restrict the number of rows in the table by mapping the "MaxRows" property of the table in the GET operation. If you map that then the user can only add rows as long as the total rows in the table are less than the MaxRows set to. —Allow delete—this will enable the form filler to delete data in this level and by doing so, to have the data deleted in the Salesforce object.

Allow Export—this option will allow the form filler to export the data in the current level he is in. When you turn on this checkbox a new "Export" button will be added at the bottom of the table and when the user presses on it the data in the level will be downloaded in CSV. 28—If you want your filler to be able to update the second level of the table you can set the "writing" permissions, just like you did in the first level. (go to "Properties" panel>"Form" tab>"Settings" options>"Advanced" category. and turn on the checkboxes according to your needs) 29—Adding fields to the View/Edit/Add windows (in addition to the column fields) While you want your table to stay compact and show only the most important fields, you may want to have fields added to the Add/Edit modal windows so they may also be updated. Adding a field is easy—all you have to do is choose it from the dropdown below and press on "Add".

Once you add a field to the Add/Edit window you have 3 options: 1—The field will be added to the specific window and its data loaded from Salesforce. Once you add a field its default mode will be to load the data from Salesforce and you will indeed see that the "Load data" checkbox is turned on. 2—The field will be added to the specific window and its data will be loaded from a selected field in your form. In order to do this you will need to turn on the "Map value" checkbox (this will remove the "load data" checkbox).

A dropdown will then appear on the right containing fields from the form. Read more about loading a selected field from Salesforce 3—The field will be added to the specific window and its data will be loaded from a field within your Table. In order to do this you will need to turn on the "Map value" checkbox. A dropdown will then appear on the right containing the object in Level 1, and once selected another dropdown will appear so you can select the field you want to map to. Read more about loading the field from your Salesforce Table 30—If you have a hidden field in your form, you will be able to store the relevant record ID in it—the record ID of the viewed record, the edited record or the added record (depending on which window you are doing this from). Read more about Map record ID to hidden 31—Now go and test your form again: If you have added the permission to edit or delete the items in the table—you will also see 2 more columns, containing links to edit & delete. If you have added the permission to add a new item—an "Add" button will be added at the bottom of your table.

Populating your Salesforce data in a Table element. Mapping the Salesforce fields to your FormTitan Table element. Populating data from Salesforce inside your online form is easy—all you have to do is use the integration and map the Sf fields to the fields in your form. But what if you wish to display the data in a table? is this possible? Well, yes—it is. FormTitan has a table element especially for working with Salesforce. Following are the steps to draw Salesforce data into your FormTitan table element: 1—Drag a table element ("Elements panel">"Widgets" category>"Table") 2—Configure the column headers (In the "Properties panel">"Element">"Settings") 3—Change the table size and styles (In the "Properties panel">"Element">"Style") 4—at this point you can also hide the table filter and decide how many rows you want to be displayed per page. 5—Integrate with Salesforce to draw data (In the "Properties panel" >"Form">"Settings">"Salesforce Integration" category>"Get") 6—Push on the "Get" button and authenticate with Salesforce. 7—choose the "account" object, 8—Turn on the "Execute on form load" checkbox 9—Choose the "All" option in the "If multiple matches found take ID from" field. and give a limit number (in this case: 300) 10—Map the fields and press "Apply" 11—an integration "Get" line will be created. 12—Press on "Finish" and save the form 13—Publish your form as URL to test it. You will see the your Salesforce accounts are displayed inside the table when the page loads. Populating into formTitan elements. Salesforce data can also be populate into other form elements such as: Dropdowns or radio buttons (for Picklists), Textboxes, Text area, paragraph (for Text area rich), Date, repeatable sections etc. Data can be populated on form load, but it can also be dynamically populated upon a trigger.

Figure 69:
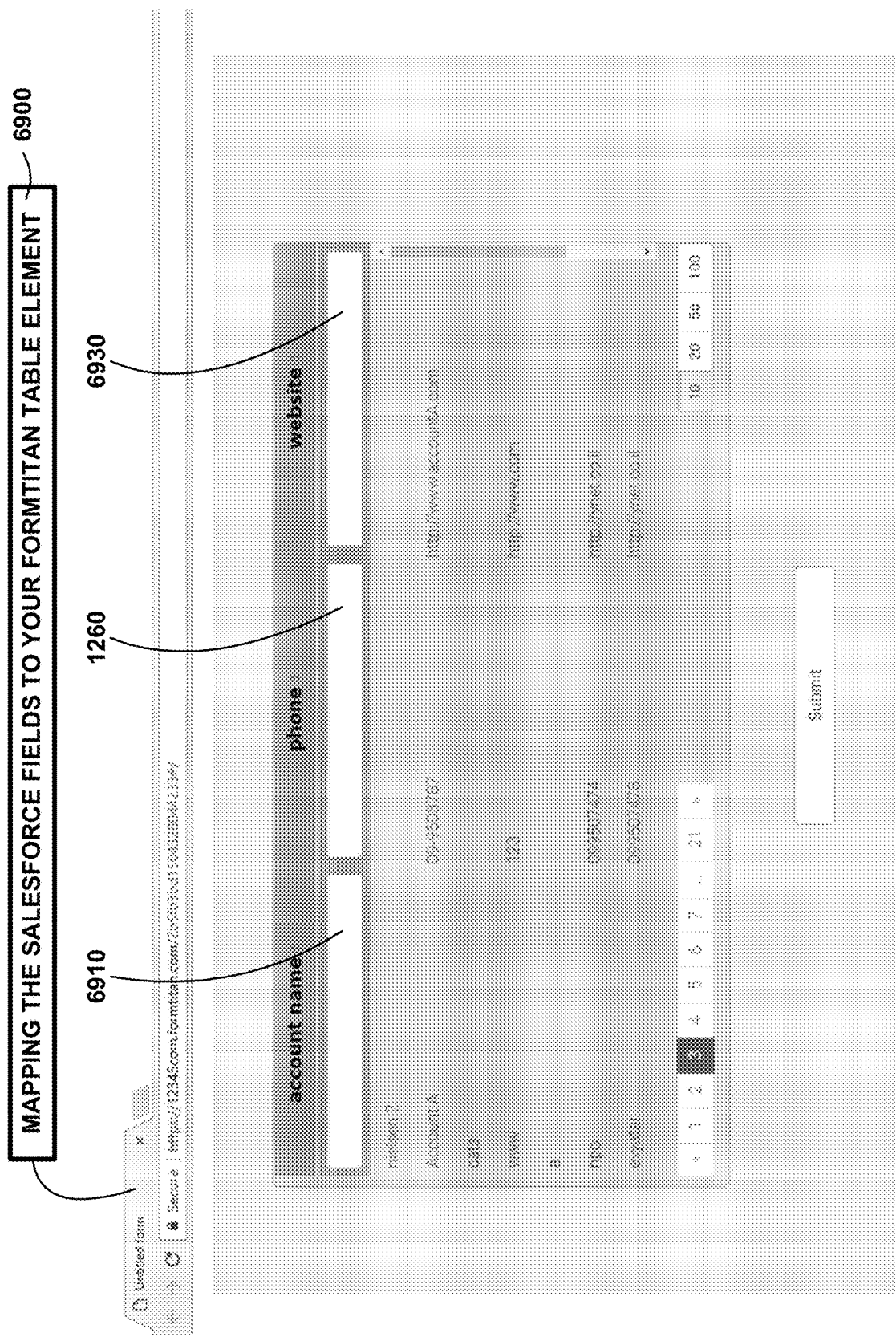
FIG. 69 shows for illustrative purposes only an example of mapping the Salesforce fields to your FormTitan table element of one embodiment.

Mapping the Salesforce Fields to Your FormTitan Table Element:

FIG. 69 shows for illustrative purposes only an example of mapping the Salesforce fields to your FormTitan table element of one embodiment. FIG. 69 shows mapping the Salesforce fields to your FormTitan table element 6900. The user can use an untitled form to select an account name 6910, phone 1260 and website 6930. FIG. 69 shows below a corresponding reference list of accounts matching the selected account name 6910, phone 1260 and website 6930 of one embodiment.

Populating your Salesforce data into a Table with hierarchy Last updated Apr. 23 2018 Mapping the Salesforce fields to your FormTitan hierarchical Table element In the previous post we have seen that FormTitan makes it possible to populate your Salesforce data in a table element. Well . . . there's more. The Table element can be made hierarchical by adding additional levels to it. Practically speaking, when a grid is initially displayed to your user it shows the results of the first level, for example: accounts details. The user can then decide to focus on a certain row in the grid and drill down to view the second level (by pressing on an arrow link of the relevant row). For example: The user is shown a list of accounts.

He picks one and he is then shown all the contacts belonging to this account. This is easy to set up—We'll show you how! Following are the steps to draw Salesforce data into your FormTitan hierarchical table element: 1—Drag a table element ("Elements panel">"Widgets" category>"Table") 2—Configure the column headers (In the "Properties panel">"Element">"Settings") 3—Change the table size and styles (In the "Properties panel">"Element">"Style") 4—you can also hide the table filter and decide how many rows you want to be displayed per page. 5—Now you will need to add another level. In the "Properties panel">"Element">"Settings">Advanced>press on "Add level" button. Once the button is pressed you will see that the the previous level columns will be replaced on canvas by the new level's default columns (Col 1, Col 2, Col 3) and you will need to configure the new level's columns: Contact Last Name and Contact First Name. (delete the third column).

Please notice that Level links are added on canvas, to the bottom of the grid on the left. These links will allow you to move between the table's levels on canvas. 6—Integrate with Salesforce to draw data into the grid (In the "Properties panel">"Form">"Settings">"Salesforce Integration" category>"Get") 7—Press on the "Get" button and authenticate with Salesforce. 8—Choose the "account" object. 9—Turn on the "Execute on form load" checkbox. (this will draw the accounts once the form is loaded) 10—Choose the "All" option in the "If multiple matches found take ID from" field and enter a limit number (in this case: 300) 11—Map the fields (account name, phone and website) and press "Apply" 12—a "Get" integration line will be created. 13—Press on the "Add object" button and choose the "Contact" object. (this ithe object you want to read from in order to populate fields in level 2 of the grid) 14—Set a condition: Account ID Equals fld2 Level 1 RecordID Choose the "All" option in the "If multiple matches found take ID from" field. and enter a limit number (in this case: 300) 15—Map the fields: Last name and First name and press "Apply" 16—another "Get" integration line will be created and there will be two. 17—Press on "Apply" and save the form 18—Publish your form as URL to test it. You will see the your Salesforce accounts are displayed inside the table when the page loads—this is the first level. 19—Press on the "Arrow" link in a certain account row to drill down and see its contacts. Watch how to populate your data into the Table element with hierarchy: Populating into formTitan elements Salesforce data can also be populate into other form elements such as: Dropdowns or radio buttons (for Picklists), Textboxes, Text area, paragraph (for Text area rich), Date, repeatable sections etc. Data can be populated on form load, but it can also be dynamically populated upon a trigger.

Changing the Salesforce Table Styles When you want to add a Salesforce Table to your form, all you need to do is drag a single element called "Salesforce Table" on to the canvas. However it is important to understand that the the Table has a few parts in terms of style (like header, rows, modal windows etc) and so we need to choose which part to apply the style to. After you choose a part you can easily change its style using our regular style categories: Font, Background, Size & Position, Margin, Padding, Alignment, order and CSS Name. Following are examples of how to change the style of each part: 1—Enter your form in the form builder 2—Drag a Table element from the "Elements" panel>"Salesforce" category. 3—When the Table is selected Go to "Properties Panel">"Element" tab>"Style" Option Table 4—Open the "Apply style to" dropdown and Choose the "Table" option This option allows you to change the style of the entire table in general Changing font, background, size, etc will effect the Table as a whole. Row 4—Open the "Apply style to" dropdown and Choose the "Row" option This option allows you to change the style of the all the grid rows Style changes will effect only the table rows.

Alternative row 4—Open the "Apply style to" dropdown and Choose the Alternative Row" option This option will enable you to have alternating row style. It will effect every second row in the grid. Header 4—Open the "Apply style to" dropdown and Choose the "Header" option This option allows you to change the style of the table header. Add Button 4—Open the "Apply style to" dropdown and Choose the "Add Button" option This option will allow you to change the style of the Add Button, that appears at the bottom of the Table. You can change its size, colors, border, padding alignment etc. Export Button 4—Open the "Apply style to" dropdown and Choose the "Export Button" option This option will allow you to change the style of the Export Button, that appears at the bottom of the Table.

You can change its size, colors, border, padding alignment etc. Next Button 4—Open the "Apply style to" dropdown and Choose the "Next Button" option This option will allow you to change the style of the Next Button, that appears inside the Table, in its own column. You can change its size, colors, border, padding alignment etc. Previous Button 4—Open the "Apply style to" dropdown and Choose the "Previous Button" option This option will allow you to change the style of the Previous Button, that appears at the bottom of the Table in a child level. You can change its size, colors, border, padding alignment etc.

Modal Header 4—Open the "Apply style to" dropdown and Choose the "Modal Header" option If you allow your form filler to update data through the table: View, Edit, Delete and Add data, all this will be done in modal windows. You can change the windows style of these 4 modal windows. This option will allow you to change the style of the Modal window title Modal body 4—Open the "Apply style to" dropdown and Choose the "Modal Body" option If you allow your form filler to update data through the table: View, Edit, Delete and Add data, all this will be done in modal windows. You can change the windows style of these 4 modal windows.

This option will allow you to change the style of the Modal window title (in the 4 modal windows) Modal button Apply 4—Open the "Apply style to" dropdown and Choose the "Modal Button Apply" option If you allow your form filler to update data through the table: View, Edit, Delete and Add data, all this will be done in modal windows. You can change the windows style of these 4 modal windows. This option will allow you to change the style of the Modal Apply Button (in the 4 modal windows) Modal button Cancel 4—Open the "Apply style to" dropdown and Choose the "Modal Button Cancel" option If you allow your form filler to update data through the table: View, Edit, Delete and Add data, all this will be done in modal windows.

You can change the windows style of these 4 modal windows. This option will allow you to change the style of the Modal Cancel Button (in the 4 modal windows) Col 4—Open the "Apply style to" dropdown and Choose the "Col" name option (in our example we did not change the default names of the Columns and that is why we have "Col1", "Col2", "Col3", however after you change your column names they will be the ones listed in the "Apply style to" dropdown). This option allows you to change the style of the a column in the table: its color, its width etc. Next Level 4—Open the "Apply style to" dropdown and Choose the "Next Level" option. This option allows you to change the style of the Next Level column in the table.

Executing Salesforce actions after Edit/Add in Salesforce Table. The Salesforce Table windows are used to allow the form fillers to Edit and Add data, However, they can also be used as a trigger, leading up to other Salesforce actions. How does this work exactly? All you have to do is: —create a new Get or Push action—Link this action to the Edit or Add window, so it will run after the record is updated or created. In this example we will: —Create a form with a table and a full name field. —

The Table will load your accounts from Salesforce when the form opens. —The filler will be required to enter a contact name in the full name field. —After he updates an account via "Edit" window—this will trigger the contact's creation in Salesforce. Follow the steps: 1—Create a new blank form 2—Drag a Salesforce Table element 3—Configure the columns: Account name, Phone, Website 4—Set the Salesforce Get integration to populate the table fields. —Go to 'Properties' panel>'Form' tab>'Settings' option>'Salesforce Integration' category>Get from Salesforce—Press on 'Map fields' button—Authenticate with Salesforce—Add object: Account—Turn on the 'Execute on form load' checkbox—Choose 'All' in the 'if multiple matches found' radio button and enter a limit of 100. —Map the fields: Account name→Account Name Phone→Account Phone Website→Website 5—Drag a Full Name element to the form 6—Create a Push integration that will create a new contact in Salesforce from the values entered in the 'full name' field: —Authenticate with Salesforce—Choose object: Contact—Add comment: Create contact after Edit—Turn on the 'Use in custom button' checkbox—Action: Create—Map fields: Last name-→Full Name Last Name First name→Full Name First Name—Press 'Apply' and save the form 7—Select the Table element on canvas. Go to 'Properties' panel>'Element' tab>'Settings' option>'Advanced' category. Turn on the 'Allow Edit' checkbox and press on the 'Configure' button below it. 8—Make the fields editable: Account name, Phone, Website by turning on the checkboxes 9—Press on the 'Configure' button of the 'Execute Salesforce actions' option. And choose the action that will run after edit.

In this example it's called: Contact(create)—Create contact after Edit.'—Press on the "Add" button, and the action will now be displayed in the table above. —Press 'Apply' and save your form. 10—Now test your form: —Publish it as URL—Wait till the accounts are loaded in the Table—Fill in a full name for the test (for example: Snow White)—Now choose an account in the table and press on 'Edit' icon—Make a small change and save it. —You will now see that the Push action is running after the Update was completed. —check your Salesforce account and you will find that an Account was updated (done from the Table Edit window) and a new contact was created (Snow White).

Salesforce Table inline editing When you are using the Salesforce Table in your form you can allow your form fillers to edit the data. You can let them update information by pressing on the 'edit' icon and editing the data in the 'Edit' modal window and you can also let them edit the data inline. Inline Editing means that the form filler can simply click inside a table cell and it will become editable. Following are the steps to configure Inline editing in your Table. 1—Drag a Salesforce Table on to your canvas 2—Enter the following columns: Account Name, Account Phone, Account Website 3—Set the Salesforce get integration to draw 100 accounts when the form loads—Authenticate with Salesforce—Select the object: Account—Turn on the 'Execute on form load' checkbox—Choose the 'All' option in the 'If multiple matches found take ID from' radio button And set a limit number of 100—Set the mapping: Account Name→Account Name Account Phone→Account Phone Account Website Website Press 'Apply' and save the form 4—Select the table on canvas and go to its 'Advanced settings'

5—Turn on the "Allow inline editing" checkbox 6—Press on the 'configure' button and set the editable fields 7—Turn on the 'Editable' checkbox in each field you want your filler to edit inline 8—You can also add a placeholder text for this field, that will show when the filler clicks to edit. 9—Press 'Apply' and test the form. 10—Now test your form Publish it as URL Click inside the first account's phone field—see how it becomes editable. Change the phone number to 8888888 and it will then be updated in the Table as well as in your Salesforce account. Please note—This feature is included in our 'Advanced tools', which is not included in every license. Find out which license includes the 'Advanced tools' in our Pricing page.

When your filler is updating or adding a record through the Salesforce table you can have certain fields taken from the table field values instead of asking the filler to enter values in them again. All you have to do is: 1—Sign in to your FormTitan account. 2—Enter your form in the form builder. 3—Choose the relevant table level, by clicking on the level link on canvas 4—Go to table settings>Advanced and open the Add/Edit modal window 5—Choose the Salesforce field you would like to update from the dropdown at the bottom and pressing on 'Add'. 6—Turn on the 'Map value' checkbox. Open the dropdown and choose the parent object and then the field you want to take the value from **Please note that when you open the mapping dropdown you will see not only the parent objects of the table levels but also the form fields, which will enable you to use a form field for your push.

Storing the record ID that was used in the View/Edit/Add Salesforce table modals. The Salesforce Table has 3 modal windows you can activate and allow your form fillers to view a record, edit it or add a new record. When you configure the window (let's take the 'Edit' window, for example) you need to specify which of the table columns will be editable. And you can also have the record ID of the edited item stored in a hidden field and use this after that for form logic. This can also be done in the View and Add windows. Following is an example showing how to Set up the Edit window and store the record ID of the Edited item. Here are the steps: 1—Create a new blank form 2—Drag a Salesforce Table element 3—Configure the columns: Account name, Phone, Website 4—Now drag a hidden field below the Table Go to 'Properties' panel>'Element' tab>'Settings' option>'Basic' category and change its name to: edit_id 5—Set the Salesforce Get integration to populate the table fields: —Go to 'Properties' panel>'Form' tab>'Settings' option>'Salesforce Integration' category>Get from Salesforce—Press on 'Map fields' button—Authenticate with Salesforce—Add object: Account—Turn on the 'Execute on form load' checkbox—Choose 'All' in the 'if multiple matches found' radio button and enter a limit of 100. —Map the fields: Account name→Account Name Phone→Account Phone Website→Website—Press 'Apply' and save the form 6—Select the Table element on canvas. Go to 'Properties' panel>'Element' tab>'Settings' option>'Advanced' category. Turn on the 'Allow Edit' checkbox and press on the 'Configure' button below it. 7—Turn on the 'Editable' checkboxes of your 3 column fields so the filler will be able to update their values.

8—Open the 'Map record ID to HIDDEN' dropdown and choose the hidden: edit_id 9—Press 'Apply' and save the form. 10—Now test your form: —First make your hidden field visible for this check Go to 'Properties' panel>'Form' tab>'Settings' option>(View more)>'Debug mode' category>turn on the 'show hidden fields' checkbox—publish the form as URL—press on the 'Edit' icon to update a record and change something in one of the fields. When the update action is done you will see that the hidden field is populated with the record ID.

Populating your Salesforce data in a Table element. Mapping the Salesforce fields to your FormTitan Table element Populating data from Salesforce inside your online form is easy—all you have to do is use the integration and map the Sf fields to the fields in your form. But what if you wish to display the data in a table? is this possible? Well, yes—it is. FormTitan has a table element especially for working with Salesforce. Following are the steps to draw Salesforce data into your FormTitan table element: 1—Drag a table element ("Elements panel">"Widgets" category>"Table") 2—Configure the column headers (In the "Properties panel">"Element">"Settings") 3—Change the table size and styles (In the "Properties panel">"Element">"Style") 4—at this point you can also hide the table filter and decide how many rows you want to be displayed per page.

5—Integrate with Salesforce to draw data (In the "Properties panel">"Form">"Settings">"Salesforce Integration" category>"Get") 6—Push on the "Get" button and authenticate with Salesforce. 7—choose the "account" object, 8—Turn on the "Execute on form load" checkbox 9—Choose the "All" option in the "If multiple matches found take ID from" field. and give a limit number (in this case: 300) 10—Map the fields and press "Apply" 11—an integration "Get" line will be created. 12—Press on "Finish" and save the form 13—Publish your form as URL to test it. You will see the your Salesforce accounts are displayed inside the table when the page loads. Watch how to populate your data into the Table element Populating into formTitan elements Salesforce data can also be populate into other form elements such as: Dropdowns or radio buttons (for Picklists), Textboxes, Text area, paragraph (for Text area rich), Date, repeatable sections etc. Data can be populated on form load, but it can also be dynamically populated upon a trigger.

Populating your Salesforce data into a Table with hierarchy. Mapping the Salesforce fields to your FormTitan hierarchical Table element In the previous post we have seen that FormTitan makes it possible to populate your Salesforce data in a table element. Well . . . there's more. The Table element can be made hierarchical by adding additional levels to it. Practically speaking, when a grid is initially displayed to your user it shows the results of the first level, for example: accounts details. The user can then decide to focus on a certain row in the grid and drill down to view the second level (by pressing on an arrow link of the relevant row). For example: The user is shown a list of accounts. He picks one and he is then shown all the contacts belonging to this account. This is easy to set up—We'll show you how! Following are the steps to draw Salesforce data into your FormTitan hierarchical table element: 1—Drag a table element ("Elements panel">"Widgets" category>"Table") 2—Configure the column headers (In the "Properties panel">"Element">"Settings") 3—Change the table size and styles (In the "Properties panel">"Element">"Style") 4—you can also hide the table filter and decide how many rows you want to be displayed per page. 5—Now you will need to add another level. In the "Properties panel">"Element">"Settings">Advanced>press on "Add level" button.

Once the button is pressed you will see that the the previous level columns will be replaced on canvas by the new level's default columns (Col 1, Col 2, Col 3) and you will need to configure the new level's columns: Contact Last Name and Contact First Name. (delete the third column). *Please notice that Level links are added on canvas, to the bottom of the grid on the left. These links will allow you to move between the table's levels on canvas. 6—Integrate with Salesforce to draw data into the grid (In the "Properties panel">"Form">"Settings">"Salesforce Integration" category>"Get") 7—Press on the "Get" button and authenticate with Salesforce. 8—Choose the "account" object. 9—Turn on the "Execute on form load" checkbox. (this will draw the accounts once the form is loaded) 10—Choose the "All" option in the "If multiple matches found take ID from" field and enter a limit number (in this case: 300) 11—Map the fields (account name, phone and website) and press "Apply" 12—a "Get" integration line will be created. 13—Press on the "Add object" button and choose the "Contact" object. (this ithe object you want to read from in order to populate fields in level 2 of the grid) 14—Set a condition: Account ID Equals fld2 Level 1 RecordID Choose the "All" option in the "If multiple matches found take ID from" field. and enter a limit number (in this case: 300) 15—Map the fields: Last name and First name and press "Apply" 16—another "Get" integration line will be created and there will be two. 17—Press on "Apply" and save the form 18—Publish your form as URL to test it. You will see the your Salesforce accounts are displayed inside the table when the page loads—this is the first level. 19—Press on the "Arrow" link in a certain account row to drill down and see its contacts.

Populating into formTitan elements. Salesforce data can also be populate into other form elements such as: Dropdowns or radio buttons (for Picklists), Textboxes, Text area, paragraph (for Text area rich), Date, repeatable sections etc. Data can be populated on form load, but it can also be dynamically populated upon a trigger.

Storing the record ID that was used in the View/Edit/Add Salesforce table modals. The Salesforce Table has 3 modal windows you can activate and allow your form fillers to view a record, edit it or add a new record. When you configure the window (let's take the 'Edit' window, for example) you need to specify which of the table columns will be editable. And you can also have the record ID of the edited item stored in a hidden field and use this after that for form logic. This can also be done in the View and Add windows. Following is an example showing how to Set up the Edit window and store the record ID of the Edited item. Here are the steps: 1—Create a new blank form 2—Drag a Salesforce Table element 3—Configure the columns: Account name, Phone, Website 4—Now drag a hidden field below the Table Go to 'Properties' panel>'Element' tab>'Settings' option>'Basic' category and change its name to: edit_id 5—Set the Salesforce Get integration to populate the table fields: —Go to 'Properties' panel>'Form' tab>'Settings' option>'Salesforce Integration' category>Get from Salesforce—Press on 'Map fields' button—Authenticate with Salesforce—Add object: Account—Turn on the 'Execute on form load' checkbox—Choose 'All' in the 'if multiple matches found' radio button and enter a limit of 100. —Map the fields: Account name→Account Name Phone→Account Phone Website→Website—Press 'Apply' and save the form 6—Select the Table element on canvas. Go to 'Properties' panel>'Element' tab>'Settings' option>'Advanced' category. Turn on the 'Allow Edit' checkbox and press on the 'Configure' button below it. 7—Turn on the 'Editable' checkboxes of your 3 column fields so the filler will be able to update their values. 8—Open the 'Map record ID to HIDDEN' dropdown and choose the hidden: edit_id 9—Press 'Apply' and save the form. 10—Now test your form: —First make your hidden field visible for this check Go to 'Properties' panel>'Form' tab>'Settings' option> (View more)>'Debug mode' category>turn on the 'show hidden fields' checkbox—publish the form as URL—press on the 'Edit' icon to update a record and change something in one of the fields. When the update action is done you will see that the hidden field is populated with the record ID.

Salesforce Table inline editing. When you are using the Salesforce Table in your form you can allow your form fillers to edit the data. You can let them update information by pressing on the 'edit' icon and editing the data in the 'Edit' modal window and you can also let them edit the data inline. Inline Editing means that the form filler can simply click inside a table cell and it will become editable. Following are the steps to configure Inline editing in your Table. 1—Drag a Salesforce Table on to your canvas 2—Enter the following columns: Account Name, Account Phone, Account Website 3—Set the Salesforce get integration to draw 100 accounts when the form loads—Authenticate with Salesforce—Select the object: Account—Turn on the 'Execute on form load' checkbox—Choose the 'All' option in the 'If multiple matches found take ID from' radio button And set a limit number of 100—Set the mapping: Account Name→Account Name Account Phone→Account Phone Account Website→Website—Press 'Apply' and save the form 4—Select the table on canvas and go to its 'Advanced settings'

5—Turn on the "Allow inline editing" checkbox 6—Press on the 'configure' button and set the editable fields 7—Turn on the 'Editable' checkbox in each field you want your filler to edit inline 8—You can also add a placeholder text for this field, that will show when the filler clicks to edit. 9—Press 'Apply' and test the form. 10—Now test your form Publish it as URL Click inside the first account's phone field—see how it becomes editable. Change the phone number to 8888888 and it will then be updated in the Table as well as in your Salesforce account. Please note—This feature is included in our 'Advanced tools', which is not included in every license. Find out which license includes the 'Advanced tools' in our Pricing page.

When your filler is updating or adding a record through the Salesforce table you can have certain fields taken from the table field values instead of asking the filler to enter values in them again. All you have to do is: 1—Sign in to your FormTitan account. 2—Enter your form in the form builder. 3—Choose the relevant table level, by clicking on the level link on canvas 4—Go to table settings>Advanced and open the Add/Edit modal window 5—Choose the Salesforce field you would like to update from the dropdown at the bottom and pressing on 'Add'. 6—Turn on the 'Map value' checkbox. Open the dropdown and choose the parent object and then the field you want to take the value from **Please note that when you open the mapping dropdown you will see not only the parent objects of the table levels but also the form fields, which will enable you to use a form field for your push.

Figure 70:
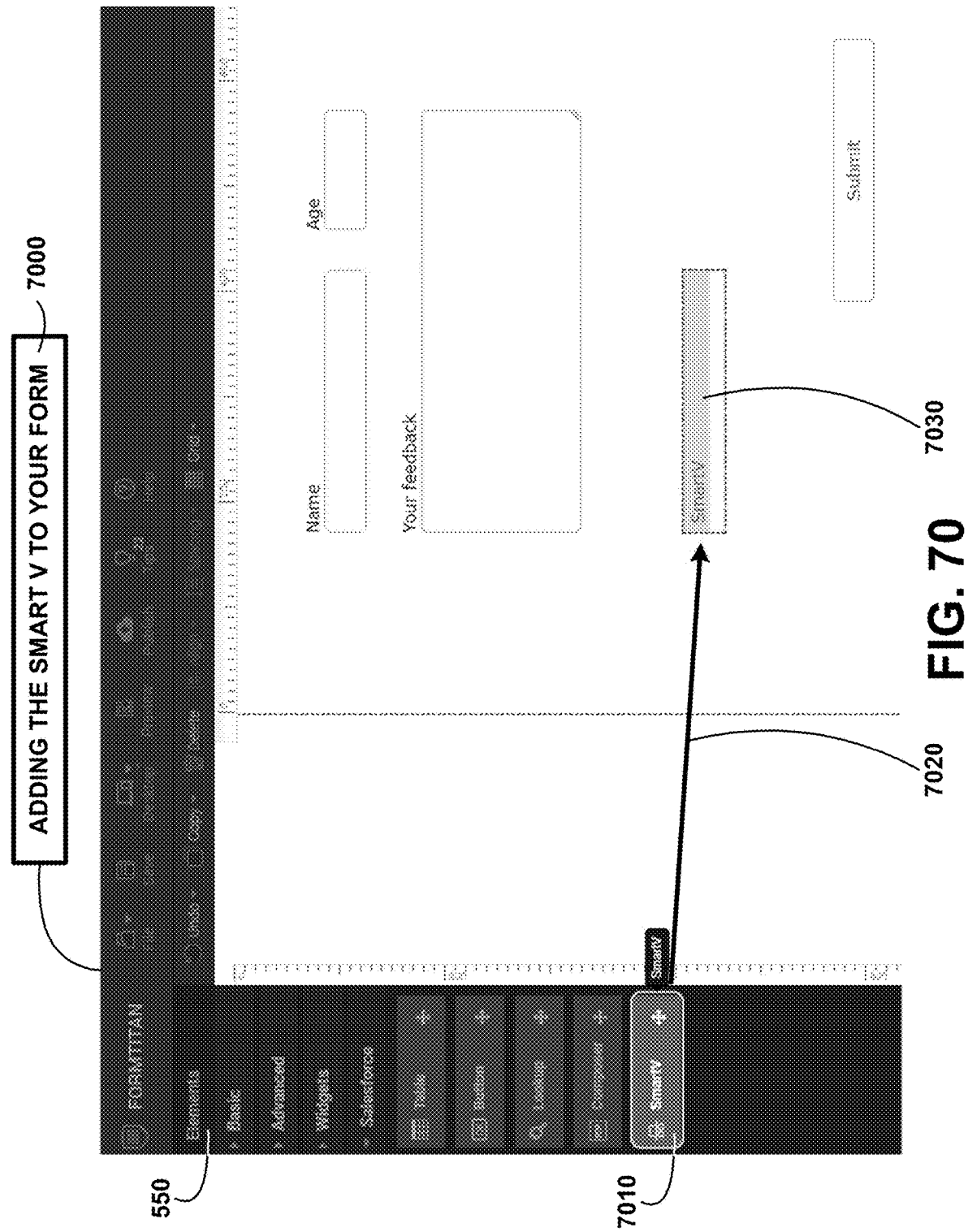
FIG. 70 shows for illustrative purposes only an example of adding the Smart V to your form of one embodiment.

Adding the Smart V to Your Form:

FIG. 70 shows for illustrative purposes only an example of adding the Smart V to your form of one embodiment. FIG. 70 shows adding the Smart V to your form 7000. Under elements 550 the user can select Smart V 7010. Selecting the Smart V button opens a Smart V text box 7020. The user makes an entry into the Smart V text box 7030. Other features for Smart V include a Registration link in Smart V, Smart V customizations, Smart V logout, Smart V session configurations, Smart V supports special characters, Changing the Smart V window background color, and Date field format in Smart V of one embodiment.

How to add the Smart V to your form Adding the smart V to your form Following are steps to add a SmartV to your form: 1—Enter your form in the fom builder. 2—Drag a Smart V element from "Elements panel">"Salesforce">"SmartV" 3—Go to "Properties" panel>"Element" tab>"Settings" option>"Basic" category 4—Press on the "Map fields" button to configure your validation. 5—Since the validation is done based on the data in your Salesforce account you will first need to authenticate with Salesforce. 6—Once authenticated press on the "Configure Salesforce integration" button. 7—Choose the Salesforce object you would like to use for this validation—in this example: Contact. 8—Select the fields for the validation by choosing them from the "Add field for display" dropdown, and then press on "Add" button. Please note that you must add an "email" field here so an email with a secret code could be sent to the form filler later on, in the second step of the validation. In this example we have added the following fields from the Salesforce contact object: Email, First name, Secret, Contact ID, Last name.

9—These fields will now be displayed in a table that contains 3 important columns: Email, Value and Secret. You will now have to choose: —which of the the fields will be used for drawing the email address (we chose "email")—which of the fields will be used to hold returned value (we chose "contact id")—which of the fields will be used to store your secret code (we chose "secret") 10—Once this is done press on "Apply" and save your fom. 11—In order to do check this LIVE you will need to create a test contact in your Salesforce account. Beforehand and make sure it contains: —You first and last name, —a "Secret" field (create a custom text field for this)—your email address (so that the code is sent to you) You will now see the Smart validation window. Choose a real contact from your Salesforce account and enter its details in this window: the email address, first name and last name. 12—Publish your form as "URL" to test it. You will now see the Smart Validation window.

Enter the email, last name and first name of your Test Contact. You will now see a second window, in which you will be required to enter a code. 13 Go to your inbox and copy the code that was sent to you. 14—Paste this code in the window and submit—and the form will open right after.

How to customize your Smart V. Customizing the smart V in your form If you look at the Smart V properties you will see that in addition to its main "Mapping" option (used to set up the Smart V) there are other properties as well—in this post we will review what they are and how to use them. Shared Session, Enabled Session, Captions, Email Settings. Shared Session The idea behind this feature is that instead of configuring the same Smart V a few times in multiple forms, you can have it set up only one time and then share this configuration with your other forms. How does this work? Let's say you have 3 different forms: Form A, Form B and Form C.

In order to have all forms work with the same Smart V login window you will need to do the following: 1—Drag a smart V element in Form A. Set the mapping, configure the captions, email, session length and save the form. 2—Drag a smart V element in Form B. and turn on the "Shared Session" checkbox. Press on the "Select form" button to choose the form containing the Smart V settings—in this case: Form A. 3—Do same as in the previous bullet: only in Form C. The result is that all 3 forms will now share the same Smart V session. and that any change in the settings of this session in Form A will also affect the other 2 forms.

Enabled Session This property enables you to set a time frame (in minutes) for your Smart V session. This means that after the form filler enters the secret code and accesses the form his session will be active for this time period, and he will be able to come and go as he pleases without having to enter his details in the Smart V again. Steps to change session length: 1—Turn on the "Enabled Session" checkbox 2—Enter the number of minutes you want the session to last 3—Save the form Logout from Session If you have set a Session for your Smart V, you can also add a Logout button to allow your filler to sign out of the session if he wishes to. In order to do this you will simply need to: —Drag a button element to your canvas—Change its type to SmartV Logout Disable 2FA This property will enable you to change the Smart V from a 2 verification element to a 1 verification process, where the filler will be asked to identify by entering his details, without having to provide a secret code. All you need to do is turn on the 'Disable 2FA' and the Smart v will be changed (to a 1FA . . . ). Captions This property will enable you to customize the texts in the Smart V login window. you will be able to change the header, the labels and error messages. Steps to change your Smart V captions: 1—Press on the "Edit" button. 2—Change the texts to your liking and press 'Apply'. 3—Save the form.

Email Settings This property will allow you to customize the email sent to the form filler, containing his secret code for the Smart V. Steps to change the Email settings: 1—Press on "Email Settings" 2—You will be able to customize the following: —"Disable email notification"—By turning on this checkbox you can cancel the email that is sent to the form filler (containing the secret code). In this situation the code will only be stored in the Salesforce field you mapped for the secret. (Read more about it: How to add Smart V—bullet #9)—"From Name"—Enter a name that will appear as "Sender" in the email you send. —"Reply To"— Enter an email address you would like your recipients to reply to. —"Subject"—We provide a default subject that contains the Secret code, but you can add to it or change it altogether. —"Body"—We also provide a default text for the email body. This also contains the secret code and the form URI. Again—you can change it as you wish. 3—Press on "Apply" After making the changes. 4—Save the form. Background color This property will allow you to customize the Smart V window background, which is by default a shade of black. Simply enter a different Hex Color Code and save your form.

Figure 71:
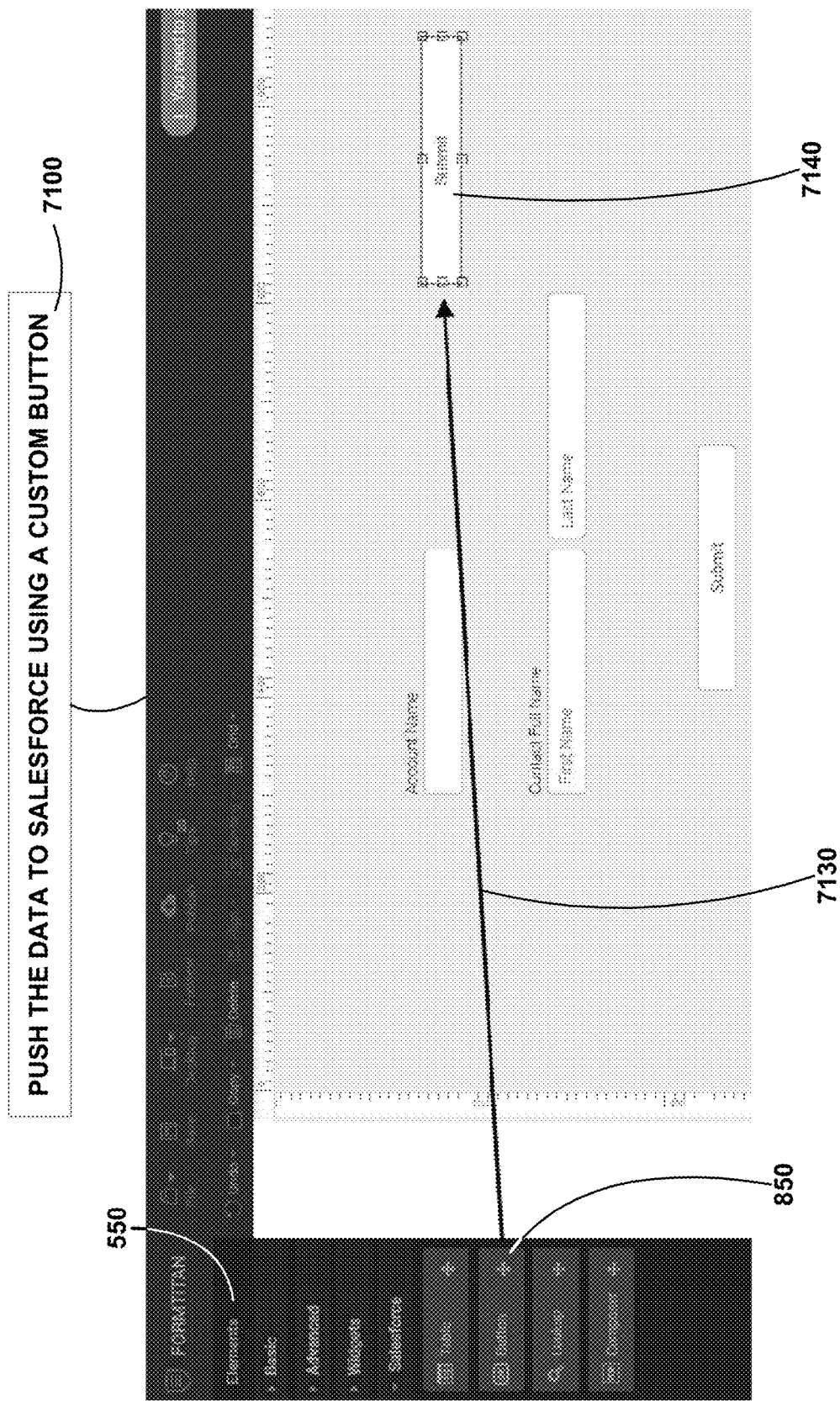
FIG. 71 shows for illustrative purposes only an example of push the data to Salesforce using a custom button of one embodiment.

Push the Data to Salesforce Using a Custom Button:

FIG. 71 shows for illustrative purposes only an example of push the data to Salesforce using a custom button of one embodiment. FIG. 71 shows a feature to push the data to Salesforce using a custom button 7100. Under elements 550 the user can select button 850 on the menu. The button selection opens an input box 7130. For example the button selection can create a submit button 7140 for a form of one embodiment.

How do I use the Salesforce Action button for Push? Last updated Feb. 8 2018 Push the data to Salesforce using a custom button Custom Salesforce buttons are buttons designed especially for working with Salesforce. They are located in the "Elements panel" under "Salesforce" category and their purpose is to allow users to push the data to Salesforce without having to submit the form. Following is an example of how to add two custom buttons to the form: one to push data to the "Account" object, and the other to push data to the "Contact" object. Follow the steps: 1—Create a new blank form in the form builder 2—Drag a textbox. Change its label to "Account Name". Drag a full name element and change its label to "Contact full name". 3—Go to "Properties" panel>"Form" tab>"Settings">Salesforce integration">Push—authenticate with Salesforce 4—You will now need to configure 2 push lines: the first for account and the second for contact. Account—In the "Salesforce object settings" category—choose the "Account" object— Turn on the "Use in custom button" checkbox—this will make this push triggered by a custom button—In the "Action" category—The default action is "create"—leave it as is—map your fields—in this case only one (account name)

5—Contact—Now press on "Add object" button to add the contact. —In the "Salesforce object settings" category— choose the "Contact" object—Turn on the "Use in custom button" checkbox—Map the contact fields and save it all You will now see 2 lines of push: 6—Add the custom buttons to your form—Drag a button from "Elements" panel>"Salesforce" category>"Button" Place it next to the account textbox—a window will open and you will need to connect this button to the right action: Open the "Process push" dropdown, choose "Account (create) and press on "Add" button next to it—Press on "Apply"—Select the button on canvas and change the text on it to "Push account". (in "Properties" panel>"Element">"Settings">"General")

Please note—if you are working on a multi-page form then another field will be added to this window: 'Go to Page' dropdown. Using this field you can add another functionality to this Action button, so it doesn't just push data to Salesforce, but it also moves the form filler to a different page after that. Read how to do this 7—Drag another button from "Elements" panel>"Salesforce" category>"Button" Place it next to the account textbox—configure this button in the same way you did with the previous button. —a window will open and you will need to connect this button to the right action: Open the "Process push" dropdown, choose "Account (create) and press on "Add" button next to it— Press on "Apply"—Select the button on canvas and change the text on it to "Push contact". (in "Properties" panel>"Element">"Settings">"General") 8—Save the form Now publish the form as URL to check it. Enter an account name and press on the custom Salesforce button next to it—Enter your Salesforce account and check that this data was added in the Account object. Enter a contact name and press on the custom Salesforce button next to it—Enter your Salesforce account and check that this data was added in the contact object.

Redirect in Custom Push/Get With Action Button When you use the Salesforce Action button to create a custom Push or Get you don't have to submit the form because the action button acts as trigger. If you wish to have your form redirect to another URL after this custom Get or Push—you can easily add this functionality in your Action button configuration. Example Following is an example to show you how to redirect your form after a custom Get: In this example the filler will enter an account name and press on the custom button, and based on the account he entered the phone umber will be drawn and a URL will be stored in the form's hidden field—all this populated from the Salesforce 'Account' object.

After this, the form will redirect to a different URL (in this case another FormTitan published form) based on the URL in the hidden field and params will also be added at the end of the URL to pre-fill some fields in it. Before starting—create test data*—In order to follow this example you will need to create some test data: A—In your FormTitan account—Create a new blank form—call it "test redirect"—we will redirect our main form to it. —drag a textbox in it. Change its label text to "Account" and check what its Field ID is. (When it is selected on canvas you will see its ID inside the "Settings" tab)—Press on the "Publish" icon in the top toolbar and copy the form URL. (so we can redirect to it) B—In your Salesforce account—set up a test record in the "Account" object—create a new account, Give it a name, a phone number and insert the URL from the previous bullet in the Account Description field.

Create your main form with a custom Get 1—Create a new blank form. 2—In the form builder—Give your form a name: custom get ("Properties" panel>Form>Settings>General>Basic>General) 3—Drag the following elements on to the canvas: —Textbox—for account field (From "Element" panel>"Basic" category>"Input" sub category>Textbox)—Textbox—for phone field (From "Element" panel>"Basic" category>"Input" sub category>Textbox)—hidden field—to store a URL (From "Element" panel>"Widgets" category>Hidden) 4—Select the first textbox and change its label text to: Account Select the second textbox and change its label text to: Phone Select the hidden field and change its name to: id_URL 5—Delete the default submit button, which is already on canvas. 6—Create a Salesforce Get integration: —Go to "Properties panel">"Form" tab>"Salesforce Integration">Get from Salesforce—Push on the "Map fields" button—Authenticate with Salesforce—Choose an object: Account and turn on the "Use in custom button" checkbox—Set a condition: Account name equals account—Map the fields: Phone→Account Phone id_URL→Account Description 7—Drag a Salesforce Action button (From "Element" panel>"Salesforce" category>Button) Once on canvas, the configuration window will open and you will need to map the custom button to your Get action—Open the "process push" dropdown and chose the "Account (Get)" option. —Press on the "add" button and the action will be added in the grid at the top. —Turn on the "Redirect after finish" checkbox—this will open a few fields you will need to set: —Url: Choose the form field you would like to draw the URL from (in this case we will take the URL from the hidden field, which is mapped to the account description field in Salesforce). —Open in: you will be able choose between Self and Parent. —Set parameters—you can choose parameters that will be added to the URL in order to pre-fill fields in the form. In this case we will turn on the Press on the "Set parameters" button and Turn on the "Use" checkbox in the rows of the fields you would like to prefill. Enter a Param name—in this case we will use the ID of the field you want to pre-fill in the form you redirected to: fld2 8—Select the button and change the text on the button to: Get Now 9—Now test your form: —Publish it as URL and test it—Enter the name of the test account in Salesforce—you will now see the phone number populated based on it—the form will redirect automatically to the test form you created and you will see that the first textbox was prefilled. —If you look closely at the URL you will see it is the same one you inserted in your Salesforce account, and the params are added at the end of it.

Custom Salesforce buttons in a Multi-page Form. Custom Salesforce button pushes data and moves filler to different page This post is very similar to the one about "How to use the custom Salesforce button". The only difference is that in this post we will show you how to use the Action button in a multi page form. In the multi page form this button can not only push data to Salesforce but it can also move the form filler to the next/previous page.

Following is an example of to show you how it's done. 1—Create a new blank form in the form builder 2—Drag a textbox. Change its label to "Account Name". 3—Go to "Properties" panel>"Form" tab>"Settings">Salesforce integration">Push—authenticate with Salesforce 4—You will now need to configure the push integration—In the "Salesforce object settings" category—choose the "Account" object—Turn on the "Use in custom button" checkbox—this will make this push triggered by a custom button (an Action button)—In the "Action" category—The default action is "create"—leave it as is—map your fields—in this case only one (account name)—You will now see one integration line was created—Press on "Apply" 5—Save the form. 6—Add the custom buttons to your form—Drag a button from "Elements" panel>"Salesforce" category>"Button" Place it next to the account textbox—a window will open and you will need to connect this button to the right action: Open the "Process push" dropdown, choose "Account (create) and press on "Add" button next to it—Press on "Apply"-Select the button on canvas and change the text on it to "Push account". (in "Properties" panel>"Element">"Settings">"General")

Please note—When you are working on a multi-page form then another field will be added to this window: 'Go to Page' dropdown. Using this field you can add another functionality to this Action button, so it doesn't just push data to Salesforce, but it also moves the form filler to a different page after that. —Select the option "Next Page" in the dropdown. 7—Save the form Now publish the form as URL to check it. Enter an account name and press on the custom Salesforce button next to it—See that you are forwarded to the next page in the form. Also, enter your Salesforce account and check that this data was added in the Account object.

Triggering your Salesforce actions from a page break. The page break trigger is a new option to run your Salesforce actions, and it works in multi page forms. Up till now you could have your "Get" and "Push" actions either triggered on load (when the form opened), on submit (when the form was sent) or when a custom Salesforce Action button was pressed. This new option makes the page break buttons act as triggers. It can help make the overall flow of the form faster. What's special about the multi page form is that loading all the pages data in one go is not a necessity because the user can only view one page at a time anyway, so if you break down your Salesforce actions per page you can cut your loading time short. In order to use this option, all you have to do is: —Select the page break element in a specific page, and attach the sf actions to this page by setting your integration lines as—and making them work via custom button (which in our case means the page break buttons). —Define when the trigger will work: —If it will work only the first time you reach the page (this is the default trigger)—

Figure 72:
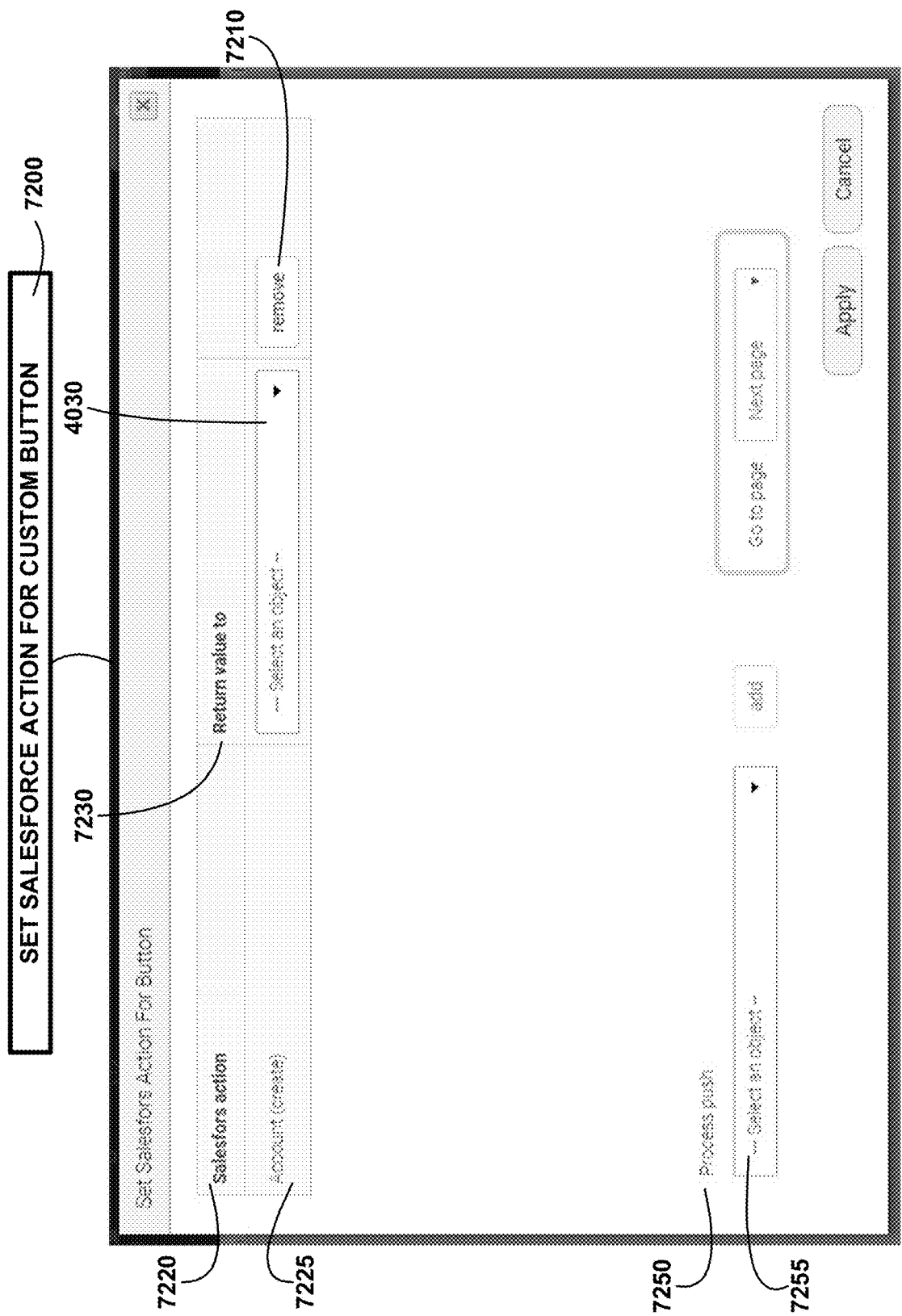
FIG. 72 shows for illustrative purposes only an example of set Salesforce action for custom button of one embodiment.

If it will work only if you arrive at the page from a Next button—If it will work only if you arrive at the page from a Back button—If it will work every time you reach the page. When you add a page break to your form the default trigger state in all the form pages is "Load first time". But this can be changed to one of the other options listed above.
Set Salesforce Action for Custom Button:

FIG. 72 shows for illustrative purposes only an example of set Salesforce action for custom button of one embodiment. FIG. 72 shows the user can set Salesforce action for custom button 7200. A set Salesforce action for button web page shows a Salesforce action 7220 a user can select including account (create) 7225, remove 7210, return value to 7230, select an object 4030, process push 7250 and select an object 7255 of one embodiment.

A Salesforce action button can easily be added to your form to get/push data right then and there, without having to submit the form. However, when setting the button to act on a repeated section it applies to all of the data in all of the repeated lines. If you wish to have your form filler press on the custom button in a specific repeated line and have it apply to this line only—you can easily do so. Follow these steps: 1—Create a new blank form 2—Drag a section element and make it wider. 3—Drag a textbox, a numeric and a button into the section 4—Change the textbox label to: account Go to 'Properties' panel>'Element' tab>'Settings' option>'Basic' category>Label 5—Change the numeric label to num 6—Change the button text to: push this item now 7—Select the section and make it Repeated. Go to 'Properties' panel>'Element' tab>'Settings' option>'Basic' category>Repeated 8—Now configure the Salesforce push integration 'Properties' panel>'Form' tab>'Settongs' option>'Salesforce integration' category>'Push to Salesforce'—Press on the 'Set notofication' button—Authenticate with Salesforce—Choose the account object: Account—Turn on the 'Use in custom button' checkbox—In the 'Action' category—leave the 'Create' option selected—Map the fields: Account Name-→account Num>num—Press 'apply', then 'Finish' and save the form. 9—Select the 'button' and change its type to 'Salesforce Action'.

10—Press on the 'Set' button to have the integration line work with your custom button. 11—Open the 'process push or get' dropdown and select the Salesforce action. 12—Press on 'Add' and it will be added to a table above. 13—Turn on the 'Execute per repeated item' checkbox 14—Press 'Apply' and save your form 15—Now it's time to test your form: —First select your Section and change your visible items to 2 and turn on the 'Populate items' checkbox—Publish it as URL—Enter the first item line in the section: an account name and number: test 1, 1 and test 2, 2. —Press on "Add" and enter another item line with data: test 3, 3—Choose a specific line (for example second line) and press on the 'push' button in that line. —Check your Salesforce account and you will see that only that line of data was added as a new record.
Additional Features:

Voice recognition can be added to the bi-directional voice command and interactive form building. Recognizing the user's voice when employing the voice element of the form builder feature of the customized customer relationship management platform provides an additional level of security. If a voice analyzer of the customized customer relationship management platform does not match the current voice being received to the voice analysis of the authorized user then it closes the form builder and proceeds to another security check.

Iris recognition can be added to the customized customer relationship management platform security features. The user for example can use the camera of a smart phone for capturing their iris image. The captured iris image is processed against the authorized user iris image stored by the customized customer relationship management platform security features. A positive match processes the request to the form builder, if not no access is provided.

The iris recognition must be passed positively to allow a user to use their eye movements to navigate the form using eye commands to create the form and/or fill in the form. The eye commands can move for example a textbox element on the form to a user desired position. The eye command can be used to select a form input element and the voice command to make the input audibly when filling out the form.

Human gestures, like hand movements can be tracked using a proximity sensor, accelerometer and gyroscope to for example change form pages, zoom in and out, change the form builder feature for a next operation and other user desired operations.

Computer vision and video recognition of facial expressions can be captured for example using a smart phone camera. The captured facial expressions can be incorporated in the sentiment analyze feature and used separately for navigating a form or features selection. A raise eyebrow can for example be given an operation selection by the user which is stored and can then be used by the user to for example visually focus on the submit button then raise an eyebrow to activate a clic to submit the form.

A user who has created a number of forms using the form builder and activate a machine learning feature. The machine learning feature can analyze for each type of form the common elements selected and placement position in the form. The user can then automate an initial form creation to include in the chosen position those common elements. This saves time for the user and reduces the duplication of effort to arrive at a the same or similar form layout.

The customized customer relationship management platform application can configure for example a smart phone accelerometer for motion sensing the phone position for example portrait or landscape to activate the mini mode display sizing conversion to fit the phone positioning. The accelerometer may also be used for adjusting augmented reality apps for example in a help situation where a user is chatting with a FormTitan associate and an augmented reality app is allowing the associate to follow the user's selections, positioning of an element and other movements in real time directly to better assist the user in understanding where they may have been incorrectly using the form builder feature. The accelerometer is also used to measure a user driving speed to estimate an ETA to a meeting site as described in FIG. 66.

The accelerometer may also be used activate features. For example the user can select a smart phone physical movement for example a quick side to side shaking movement to activate a publish form feature. The user for example could select a top to bottom shaking movement to activate a form submit button.

A magnetometer for example in a smart phone senses where a phone is in physical space. It is used in mapping a user's location and travel. The magnetometer is used with an accelerometer and GPS unit to determine where a user is located.

A smart phone digital barometer coupled with a meteorological app can alert a user if in their travels they may encounter inclement weather changes. This could cause delays in the meeting scheduled. Gather barometric data on a remote user's location may also explain a remote users difficulties in a clear connection using the customized customer relationship management platform application as there may be for example lighting storms in the area that are disrupting internet, cellular or WI-FI communications.

Biometrics can be integrated into the customized customer relationship management platform application to using sensors to provide levels of enhanced security by capturing and validating human related metrics including Finger Print recognition, IRIS (eye) scanning and full facial recognition. Additionally, biometric sensors can be used to collect a user's heart rate and SpO2 (the estimate of arterial oxygen saturation) for use within a vendors 'health' application form and in the sentiment analysis.

Cognitive services can be integrated with the customized customer relationship management platform and application. Cognitive services can include for example Vision-Image-processing algorithms to smartly identify, caption and moderate user and other pictures; Speech-Convert spoken audio into text, use voice for verification, or add speaker recognition to your app; Knowledge-Map complex information and data in order to solve tasks such as intelligent recommendations and semantic search; Search-Add Bing Search APIs to your apps and harness the ability to comb billions of webpages, images, videos, and news with a single API call; and Language-Allow your apps to process natural language with pre-built scripts, evaluate sentiment and learn how to recognize what users want.

Because the Cognitive Services APIs harness the power of machine learning, we were able to bring advanced intelligence into our product without the need to have a team of data scientists on hand. Enhance security with a face. Use the Face API to verify a selfie for smart authentication. Signing in with visual identity verification is becoming an additional security layer for many industries. Microsoft's Face API can compare portraits giving it amazing flexibility in uncontrolled scenarios. Express dramatic moments in an instant. Quickly retrieve surprised, happy, or sad celebrity images out of millions by combining multiple APIs. Search through video frames to pull out the perfect moment for your content. Never let an abundance of untagged footage be a deterrent for your ability to serve up contextual content when you need it. Engage customers through chat. Bring together cognitive service APIs and Bot Framework to engage your audience on a whole new level. Build a bot that embodies your brand, addresses your customers' main questions and escalates to a human operator if needed.

Enable great voice interactions with speech customization. With the custom speech service you can build great voice interactions between your systems and your users. Enhance speech recognition using background noise reduction and complex technical word training. Emotion preview with the Emotion API takes a facial expression in an image as an input, and returns the confidence across a set of emotions for each face in the image, as well as bounding box for the face, using the Face API. Computer vision—this feature returns information about visual content found in an image. Use tagging, descriptions, and domain-specific models to identify content and label it with confidence.

Language understanding preview-language understanding provides simple tools that enable you to build your own language models, which allow any application or bot to understand your commands and act accordingly. Speaker recognition-Identify who is speaking. Input audio of the unknown speaker is paired against a group of selected speakers, and in the case there is a match found, the speaker's identity is returned. Cognitive services employ Artificial Intelligence (AI) can include integrating 3rd party applications including for example Microsoft AI Platform Services that compose intelligent applications, customized to your organization's availability, security, and compliance requirements. Infrastructure Services and tools backed by best-of-breed infrastructure enterprise grade security, availability, compliance and manageability. Tools can include for example leveraging a set of comprehensive tools and frameworks to build, deploy and operationalize AI products and services at scale.

Integrating $3^{rd}$ party applications can include cloud computing including Azure cloud platform, Azure securityRely on a trusted cloud security foundation, Azure global infrastructureAchieve global reach and support local compliance, Featured Explore, Virtual MachinesProvision Windows and Linux virtual machines in seconds, Windows Virtual DesktopDeliver a virtual desktop experience to any device at cloud scale, Azure SQL DatabaseManaged relational SQL Database as a service, App ServiceQuickly create powerful cloud apps for web and mobile, Azure Cosmos DBGlobally distributed, multi-model database for any scale, Machine LearningOpen and elastic AI development spanning the cloud and the edge, Azure Kubernetes Service (AKS)Simplify the deployment, management, and operations of Kubernetes, FunctionsProcess events with serverless code, Cognitive ServicesAdd smart API capabilities to enable contextual interactions, and Blockchain WorkbenchConnect your blockchain to the cloud without the heavy lifting.

Integrating $3^{rd}$ party applications can include applications using artificial intelligence capabilities including Cognitive ServicesAdd smart API capabilities to enable contextual interactions, Azure Bot ServiceIntelligent, serverless bot service that scales on demand, Azure DatabricksFast, easy, and collaborative Apache Spark-based analytics platform, Machine LearningOpen and elastic AI development spanning the cloud and the edge, Cognitive Services—Search APIsHarness the ability to comb billions of webpages, images, videos, and news with a single API call, Cognitive Services—Language APIsProcess natural language with pre-built scripts, evaluate sentiment, and learn to recognize intent, Cognitive Services—Vision APIsUse Image-processing algorithms to smartly identify, caption and moderate your pictures, Cognitive Services—Speech APIsConvert speech to text or text to speech, translate text or audio, or add speaker recognition to your app, and Cognitive Services—Knowledge APIsMap information and data in order to solve complex tasks.

Integrating $3^{rd}$ party applications can include Analytics Analytics Gather, store, process, analyze, and visualize data of any variety, volume, or velocity, SQL Data WarehouseElastic data warehouse as a service with enterprise-class features, Azure DatabricksFast, easy, and collaborative Apache Spark-based analytics platform, HDInsightProvision cloud Hadoop, Spark, R Server, HBase, and Storm clusters, Data FactoryHybrid data integration at enterprise scale, made easy, Machine Learning Open and elastic AI development spanning the cloud and the edge, Stream Analytics Real-time data stream processing from millions of IoT devices, Data Lake Analytics Distributed analytics service that makes big data easy, Azure Analysis ServicesEnterprise-grade analytics engine as a service, and Event HubsReceive telemetry from millions of devices.

Integrating $3^{rd}$ party applications can include Compute Compute Access cloud compute capacity and scale on demand—and only pay for the resources you use, Virtual MachinesProvision Windows and Linux virtual machines in seconds, Virtual Machine Scale SetsManage and scale up to thousands of Linux and Windows virtual machines, Azure Kubernetes Service (AKS)Simplify the deployment, management, and operations of Kubernetes, FunctionsProcess events with serverless code, Service FabricDevelop microservices and orchestrate containers on Windows or Linux, App ServiceQuickly create powerful cloud apps for web and mobile, Container InstancesEasily run containers on Azure without managing servers, BatchCloud-scale job scheduling and compute management, and Azure Batch AIEasily experiment and train your deep learning and AI models in parallel at scale.

Integrating 3$^{rd}$ party applications can include Containers Containers Develop and manage your containerized applications faster with integrated tools, Azure Kubernetes Service (AKS)Simplify the deployment, management, and operations of Kubernetes, Container InstancesEasily run containers on Azure without managing servers, Service FabricDevelop microservices and orchestrate containers on Windows or Linux, Container RegistryStore and manage container images across all types of Azure deployments, App ServiceQuickly create powerful cloud apps for web and mobile, Web App for ContainersEasily deploy and run containerized web apps that scale with your business, and BatchCloud-scale job scheduling and compute management.

Integrating 3$^{rd}$ party applications can include Databases Databases Support rapid growth and innovate faster with secure, enterprise-grade, and fully managed database services, Azure Cosmos DBGlobally distributed, multi-model database for any scale, Azure SQL DatabaseManaged relational SQL Database as a service, Azure Database for MySQLManaged MySQL database service for app developers, Azure Database for PostgreSQLManaged PostgreSQL database service for app developers, Azure Database for MariaDBManaged MariaDB database service for app developers, SQL Server on Virtual MachinesHost enterprise SQL Server apps in the cloud, SQL Data WarehouseElastic data warehouse as a service with enterprise-class features, Azure Database Migration ServiceSimplify on-premises database migration to the cloud, and Redis CachePower applications with high-throughput, low-latency data access.

Integrating 3$^{rd}$ party applications can include Developer Tools Developer Tools Build, manage, and continuously deliver cloud applications—using any platform or language, Visual StudioThe powerful and flexible environment for developing applications in the cloud, Visual Studio CodeA powerful, lightweight code editor for cloud development, SDKsGet the SDKs and command-line tools you need, Azure DevOpsServices for teams to share code, track work, and ship software, CLIsBuild, deploy, diagnose, and manage multi-platform, scalable apps and services, Azure Pipelines-Continuously build, test, and deploy to any platform and cloud, Azure Lab ServicesSet up labs for classrooms, trials, development and testing, and other scenarios, Azure DevTest LabsQuickly create environments using reusable templates and artifacts, and Developer tool integrationsUse the development tools you know—including Eclipse, IntelliJ, and Maven—with Azure.

Integrating 3$^{rd}$ party applications can include DevOps DevOps Deliver innovation faster with simple, reliable tools for continuous delivery, Azure DevOpsServices for teams to share code, track work, and ship software, Azure Pipelines-Continuously build, test, and deploy to any platform and cloud, Azure BoardsPlan, track, and discuss work across your teams, Azure ReposGet unlimited, cloud-hosted private Git repos for your project, Azure ArtifactsCreate, host, and share packages with your team, Azure Test PlansTest and ship with confidence with a manual and exploratory testing toolkit, Azure DevTest LabsQuickly create environments using reusable templates and artifacts, and DevOps tool integrationsUse your favorite DevOps tools with Azure.

Integrating 3$^{rd}$ party applications can include Identity Identity Manage user identities and access to protect against advanced threats across devices, data, apps, and infrastructure, Azure Active DirectorySynchronize on-premises directories and enable single sign-on, Azure Active Directory B2CConsumer identity and access management in the cloud, Azure Active Directory Domain ServicesJoin Azure virtual machines to a domain without domain controllers, and Azure Information ProtectionBetter protect your sensitive information—anytime, anywhere.

Integrating 3$^{rd}$ party applications can include Integration Integration Seamlessly integrate on-premises and cloud-based applications, data, and processes across your enterprise, Logic AppsAutomate the access and use of data across clouds without writing code, Service BusConnect across private and public cloud environments, API Management-Publish APIs to developers, partners, and employees securely and at scale, Event GridGet reliable event delivery at massive scale.

Integrating 3$^{rd}$ party applications can include Internet of Things Internet of Things Bring IoT to any device and any platform, without changing your infrastructure, IoT Hub-Connect, monitor and manage billions of IoT assets, IoT EdgeExtend cloud intelligence and analytics to edge devices, IoT CentralExperience the simplicity of SaaS for IoT, with no cloud expertise required, IoT solution acceleratorsCreate fully customizable solutions with templates for common IoT scenarios, Azure SphereSecurely connect MCU-powered devices from the silicon to the cloud, Time Series InsightsExplore and analyze time-series data from IoT devices, Azure MapsSimple and secure location APIs provide geospatial context to data, FunctionsProcess events with serverless code, and Event GridGet reliable event delivery at massive scale.

Integrating 3$^{rd}$ party applications can include Management Management and Governance Simplify, automate, and optimize the management and compliance of your cloud resources, Microsoft Azure portalBuild, manage, and monitor all Azure products in a single, unified console, Cloud ShellStreamline Azure administration with a browser-based shell, Azure AdvisorYour personalized Azure best practices recommendation engine, Azure BackupSimple and reliable server backup to the cloud, Cost ManagementOptimize what you spend on the cloud, while maximizing cloud potential, Azure PolicyImplement corporate governance and standards at scale for Azure resources, Azure MonitorHighly granular and real-time monitoring data for any Azure resource, Azure Site RecoveryOrchestrate protection and recovery of private clouds, and SchedulerRun your jobs on simple or complex recurring schedules.

Integrating 3$^{rd}$ party applications can include Media Media Deliver high-quality video content anywhere, any time, and on any device, Media ServicesEncode, store, and stream video and audio at scale, EncodingStudio grade encoding at cloud scale, Azure Media PlayerA single layer for all your playback needs, Live and On-Demand StreamingDeliver content to virtually all devices with scale to meet business needs, Media AnalyticsUncover insights from video files with speech and vision services, Content ProtectionSecurely deliver content using AES, PlayReady, Widevine, and Fairplay, Video IndexerUnlock video insights.

Integrating 3$^{rd}$ party applications can include Microsoft Azure Stack Microsoft Azure Stack. Microsoft Azure Stack is an extension of Azure—bringing the agility and innovation of cloud computing to your on-premises environment and enabling the only hybrid cloud that allows you to build and deploy hybrid applications anywhere. We bring together the best of the edge and cloud to deliver Azure services anywhere in your environment.

Integrating $3^{rd}$ party applications can include Migration Migration Simplify and accelerate your migration to the cloud, Azure MigrateEasily discover, assess, right-size, and migrate your on-premises VMs to Azure, Azure Site RecoveryOrchestrate protection and recovery of private clouds, Azure Database Migration ServiceSimplify on-premises database migration to the cloud, Data BoxSecure, ruggedized appliance for Azure data transfer, and Cost ManagementOptimize what you spend on the cloud, while maximizing cloud potential.

Integrating $3^{rd}$ party applications can include Mobile Mobile Build and deploy cross-platform and native apps for any mobile device, Mobile AppsBuild and host the backend for any mobile app, Notification HubsSend push notifications to any platform from any back end, Visual Studio App CenterShip apps faster by automating application lifecycles, XamarinCreate cloud-powered mobile apps faster, Azure MapsSimple and secure location APIs provide geospatial context to data, and API AppsEasily build and consume Cloud APIs.

Integrating $3^{rd}$ party applications can include Networking Networking Connect cloud and on-premises infrastructure and services to provide your customers and users the best possible experience, Virtual NetworkProvision private networks, optionally connect to on-premises datacenters, Load BalancerDeliver high availability and network performance to your applications, Application GatewayBuild secure, scalable, and highly available web front ends in Azure, VPN GatewayEstablish secure, cross-premises connectivity, Azure DNSHost your DNS domain in Azure, Content Delivery NetworkEnsure secure, reliable content delivery with broad global reach, Azure DDoS ProtectionProtect your applications from Distributed Denial of Service (DDoS) attacks, Traffic ManagerRoute incoming traffic for high performance and availability, and Azure Front Door ServiceScalable, security-enhanced delivery point for global, microservice-based web applications.

Integrating $3^{rd}$ party applications can include Security Security Protect your enterprise from advanced threats across hybrid cloud workloads, Security CenterUnify security management and enable advanced threat protection across hybrid cloud workloads, Key VaultSafeguard and maintain control of keys and other secrets, Application GatewayBuild secure, scalable, and highly available web front ends in Azure, Azure Information ProtectionBetter protect your sensitive information—anytime, anywhere, VPN GatewayEstablish secure, cross-premises connectivity, Azure Active DirectorySynchronize on-premises directories and enable single sign-on, Azure DDoS ProtectionProtect your applications from Distributed Denial of Service (DDoS) attacks, and Azure Advanced Threat ProtectionDetect and investigate advanced attacks on-premises and in the cloud.

Integrating $3^{rd}$ party applications can include Storage Storage Get secure, massively scalable cloud storage for your data, apps, and workloads, StorageDurable, highly available, and massively scalable cloud storage, Blob StorageREST-based object storage for unstructured data, Archive StorageIndustry leading price point for storing rarely accessed data, Queue StorageEffectively scale apps according to traffic, File StorageFile shares that use the standard SMB 3.0 protocol, Disk StoragePersistent, secured disk options supporting virtual machines, Azure Data Lake StorageMassively scalable data lake storage, Data BoxSecure, ruggedized appliance for Azure data transfer, and Storage ExplorerView and interact with Azure Storage resources.

Integrating $3^{rd}$ party applications can include Web Web Build, deploy, and scale powerful web applications quickly and efficiently, Web AppsQuickly create and deploy mission critical web apps at scale, API ManagementPublish APIs to developers, partners, and employees securely and at scale, Content Delivery NetworkEnsure secure, reliable content delivery with broad global reach, Azure SearchFully-managed search-as-a-service, and Azure SignalR ServiceAdd real-time web functionalities easily. Integrating $3^{rd}$ party applications can include cognitive services with apps, websites and bots with intelligent algorithms to see, hear, speak, understand and interpret your user needs through natural methods of communication.

The customized customer relationship management platform method and devices includes other features, elements and form building features including Add company info to billing, Add script after button completes its task, Address populating google map—Additions, Address validation for New Zealand and Australia, Advanced Field Conditional Logic, Allow alignment in the Calculated field, Allow Calculator to use First or Last name of fullname, Allscripts integration, Area selection, Auto focus in Lookup search box, Auto position for section with tabs, Billing—update Tranzila token from billing, Calendar supports Russian and Hebrew, Categories added to My Forms, category in form settings: Head, category in get: Meta caching, changing instance Confirmation message, Condition and Value rule based on word count, Condition based on advanced values, Conditional mapping in Repeated and Files, Convert lead to contact, Currency format in payment integration, Custom value rule messages, Cut Action, Date and DateTime Additions, Debug Mode for checking hidden fields, Disallow items of Picklists in Dropdown, Radio button, Checkbox/Multiple dropdown, Display full error details for users, Document generation (single/bulk) directly from Salesforce, Draft button—Hide confirmation, Dropdown—Advanced navigation mode, Dropdown default selection, Dropdown for dynamic navigation in multi page forms, DST Support, Edit Hidden field value in my submission, Effected by, Effected by option Extended, Element Type Displayed in Basic Settings, Element: Slider, Elements Search, Else added to the Conditional mapping, Empty options in Dependency Picklist, Enabled and Disabled for Lookup Condition, Enter Key moves to next field like tab, Enter key working in Duplicate form, Entry duplication, Excess buttons removed from repeated section, Executing actions after Delete in Salesforce Table, Executing actions after View/Edit/Add in Salesforce Table, Export added to Salesforce Table, Export more than 1000 submissions, Field Condition/Value redesign and enhancement, Field tag, File upload additions, File upload compression, File upload new properties, File upload size limit in Value rule, File upload size limit is increased to 30 MB, filter to Editors, filter to Field Dropdowns, Find action supports Page Break, Form Builder layout made lighter, form settings category: Debug Mode, Form settings: fields affecting and fields effected by, Form URL starting with a number, Function mode to String Calculated Field, Geo localization for Address and Google map, Go to page Button based on Hidden, Google map based on input of address, Hebrew country list in Address field, Hidden field new system value: browser, Hidden Fields Can Be Resized, Hidden fields in auto-layout for tablet and mobile, Hidden fields in Custom editors, hover/selected effects for section, HTML mode for emails, Ignore Mandatory for Debug, Image capture orientation, Image slider auto play with interval, in form settings: Google map API CODE, Inline editing in the Salesforce Table, language to custom translation: Chinese, likert type: dropdown, Limit number of rows in a Salesforce table based on parameters, limit:ip whitelist, Link to Draft form in my submissions, Linkable columns in Lookup, links in Dashboard/My-forms, Lookup—add placeholder, Mapping only reference fields in your Table, Multi Dropdown placeholder, Multi Picklist Include/Exclude with OR operator, My account—new tab: mail, My submissions—export limits, My submissions automatically refreshed after action from Sub menu, Open Redirect in modal window, Optimized CSS compilation, option for spacing: Make same space, option in Conditional logic: Force execution, option to Hide the error summary modal window, options for Bulk Apply in Condition, options to Field Condition Results, Page break Triggers in multi page forms, Page break with flexible next/prev buttons, Parameters added to Redirect URL option in Form Condition, Pass submission id in hyperlink with parameter, Populate Date Time fields with Parameters from URL, Populate items in Section (for Number of visible items), Populate Lookup field from URL, Predefined lists including all languages—Hebrew, all languages, world countries, USA states, marital status, and months of the year (long), Progress indicator—Gradient, Property for Hidden: Use system value, Property in Account Settings: Compressed mode, property in Section: Repeat margin, Purchasing a license via Tranzila is open to Israelis, Reading field values from an external script, Resized modal windows in my submissions, Save and resume—returns to the same page, Save and resume in Hebrew, Search with Lookup, Section overflow—scroll, Section Repeat with mapped data, Set order of fields in sf table view window, Set Time in Time and Date Time fields, Set Value From, Set values in fields from scripts, Setting a default year for date/datetime fields, Setting current date/time as default values in Date/Time fields, Show Hidden Fields in Debug Mode showing all fields, Show item number in repeated section, Silent mode property added to the Inline Edit window, Star rating supported in Calculated field, Submission ID in mapping of nested child, Support for Dependency Picklist, Supporting MailChimp Version 3.0, Supporting Slider Disable/Enable/Read only, system value in Hidden: IP, tab added to My account: Company info, thank you message box title text, Tooltip for disabled text fields, Tooltip style properties including Tooltip Label color, Tooltip Background color, Font size and Font family, Tooltip supports CSS, Upgrading our servers, Uploading/Downloading modal added to submissions page, Use mask value, User Requests, Using parameters to reach a specific page in multi page form, Using the Short State name in Address mapping, Value rule—Min count of words, Value Rule: Address Validation, Versatile Section, When form is updated show asterisk in browser tab, and work mode: Mini of one embodiment.

Figure 73:
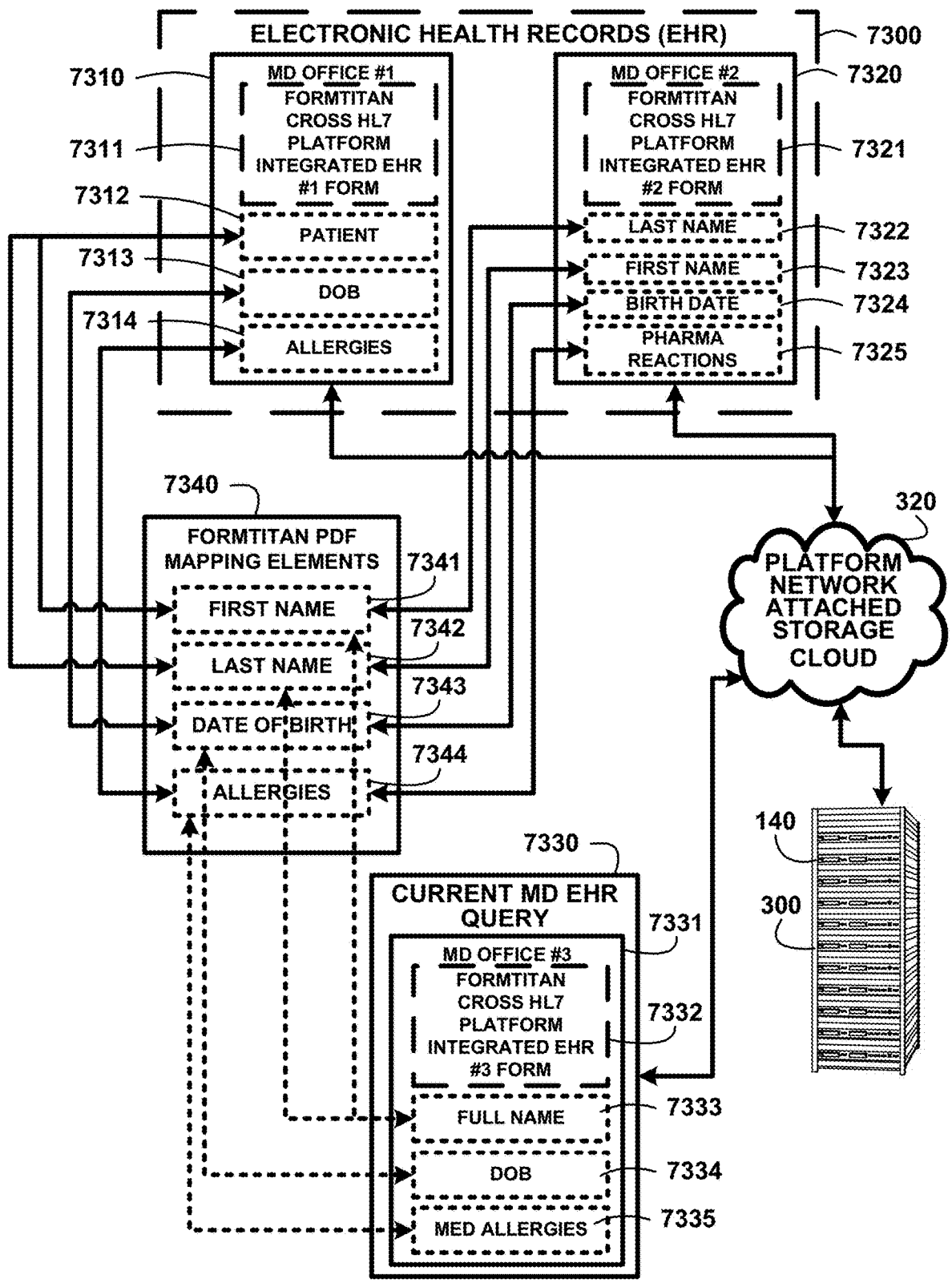
FIG. 73 shows for illustrative purposes only an example of an HL7 EHR cross platform application of one embodiment.

HL7 EHR Cross Platform Application:

FIG. 73 shows for illustrative purposes only an example of an HL7 EHR cross platform application of one embodiment. FIG. 73 shows the cross platform integration 140 an application for HL7 electronic health records (EHR) using custom FormTitan created forms from three different medical office. A MD office #1 7310 FormTitan cross HL7 platform integrated EHR #1 form 7311 includes patient data for example patient 7312, DOB 7313 and allergies 7314. A MD office #2 7320 FormTitan cross HL7 platform integrated EHR #2 form 7321 includes the same patient data however listed under different title and in a different sequence for example last name 7322, first name 7323, birth date 7324 and pharma reactions 7325.

A current MD EHR query 7330 for the electronic health records for the same patient data is made by MD office #3 7331. MD office #3 7331 has created a FormTitan cross HL7 platform integrated EHR #3 form 7332. The FormTitan cross HL7 platform integrated EHR #3 form 7332 from the MD office #3 7331 includes the same patient data however listed under different title and in a different sequence for example full name 7333, DOB 7334, and med allergies 7335. The current MD EHR query 7330 would normally not be able to automatically transfer the patient data to a non-FormTitan form as the listing titles would not match. The MD office #3 staff would have to download the other forms and manually enter the patient data from the non-FormTitan forms.

In this exampled instance since all of the forms were created using FormTitan the current MD EHR query 7330 routed through the platform network attached storage cloud 320 can use the customized customer relationship management platform network 300 network server to access the electronic health records (EHR) 7300. The customized customer relationship management platform network 300 network server can perform a search for the existing EHR FormTitan forms records. The network server using the FormTitan pdf mapping elements 7340 used when the two existing FormTitan cross HL7 platform integrated EHR #1 form 7311 and FormTitan cross HL7 platform integrated EHR #2 form 7321 were created can determine the matching FormTitan pdf mapping elements 7340 for example first name 7341, last name 7342, date of birth 7343 and allergies 7344. The data from the existing matching records can be assigned to the FormTitan pdf mapping elements 7340 used to create the FormTitan cross HL7 platform integrated EHR #3 form 7332.

The retrieval of matching EHR record data and automatic assignment and entry into corresponding FormTitan pdf mapping elements 7340 of a FormTitan cross HL7 platform integrated EHR form saves time and potential typographic errors for and MD office. The EHR data can includes other patient information including driver license, address, SSN where applicable, other patient ID data, heath insurance provider and other information included in the patient EHR that the current MD needs to provide the patient with appropriate health care treatment of one embodiment.

Figure 74:
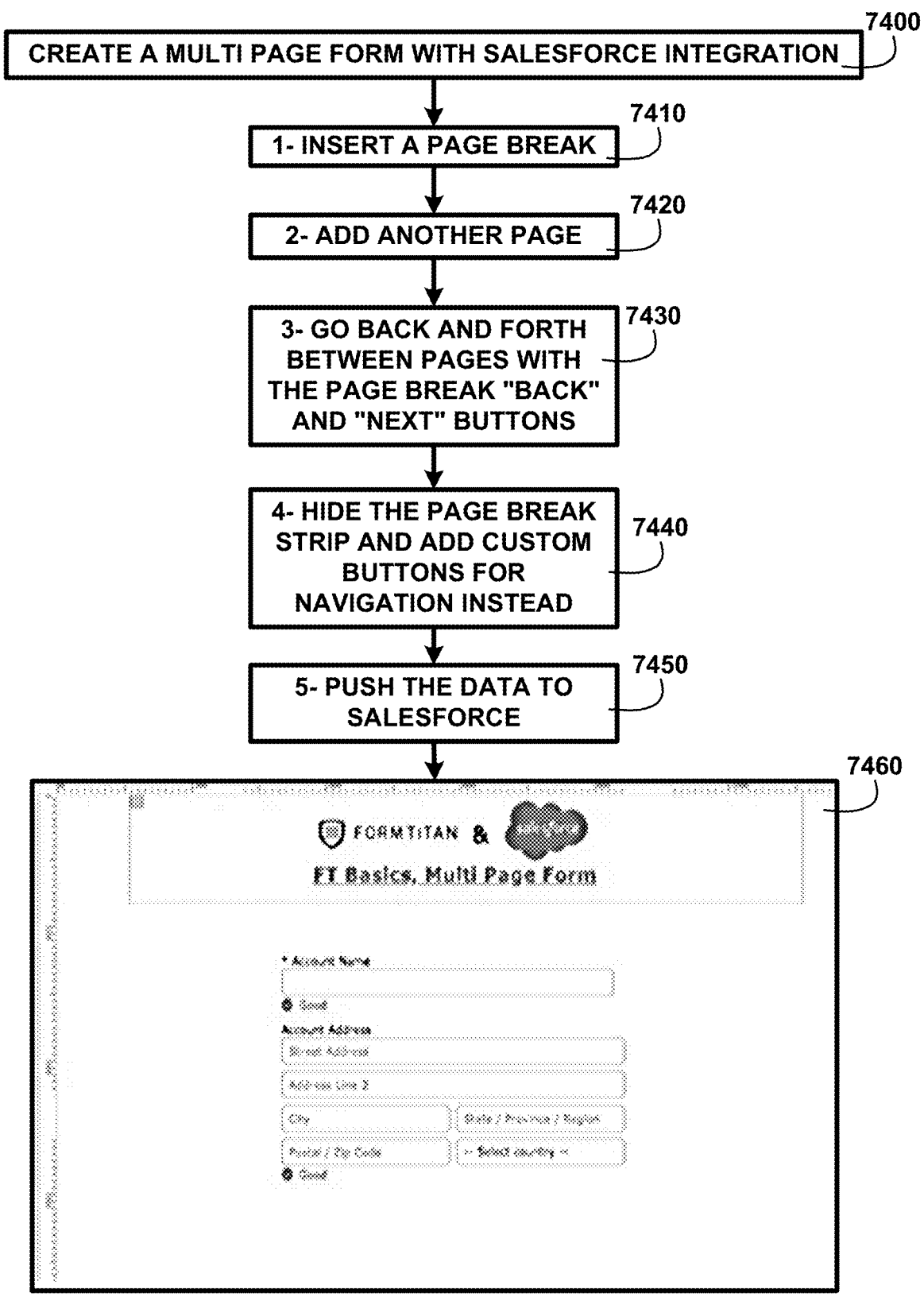
FIG. 74 shows for illustrative purposes only an example of a multi page form with Salesforce integration of one embodiment.

A Multi Page Form with Salesforce Integration:

FIG. 74 shows for illustrative purposes only an example of a multi-page form with Salesforce integration of one embodiment. FIG. 74 shows steps to create a multi-page form with Salesforce integration 7400. Step 1—insert a page break 7410 button inserts a page break. Step 2—add another page 7420 begins the addition of multiple pages. Step 3—go back and forth between pages with the page break "back" and "next" buttons 7430 allows a user to add as many pages as the user wants. Step 4—hide the page break strip and add custom buttons for navigation instead 7440 allows a user to hide the display of the page break strip. Adding custom buttons for navigation allows the user to navigate through the multi-page form easier. Step 5—push the data to Salesforce 7450 allows the user to push the data entered in each of the multi-pages into the user's Salesforce account. The steps have allowed the user to create a FT basics multi-page form as shown in the image shown FT basics, multi page form 7460 of one embodiment.

Figure 75:
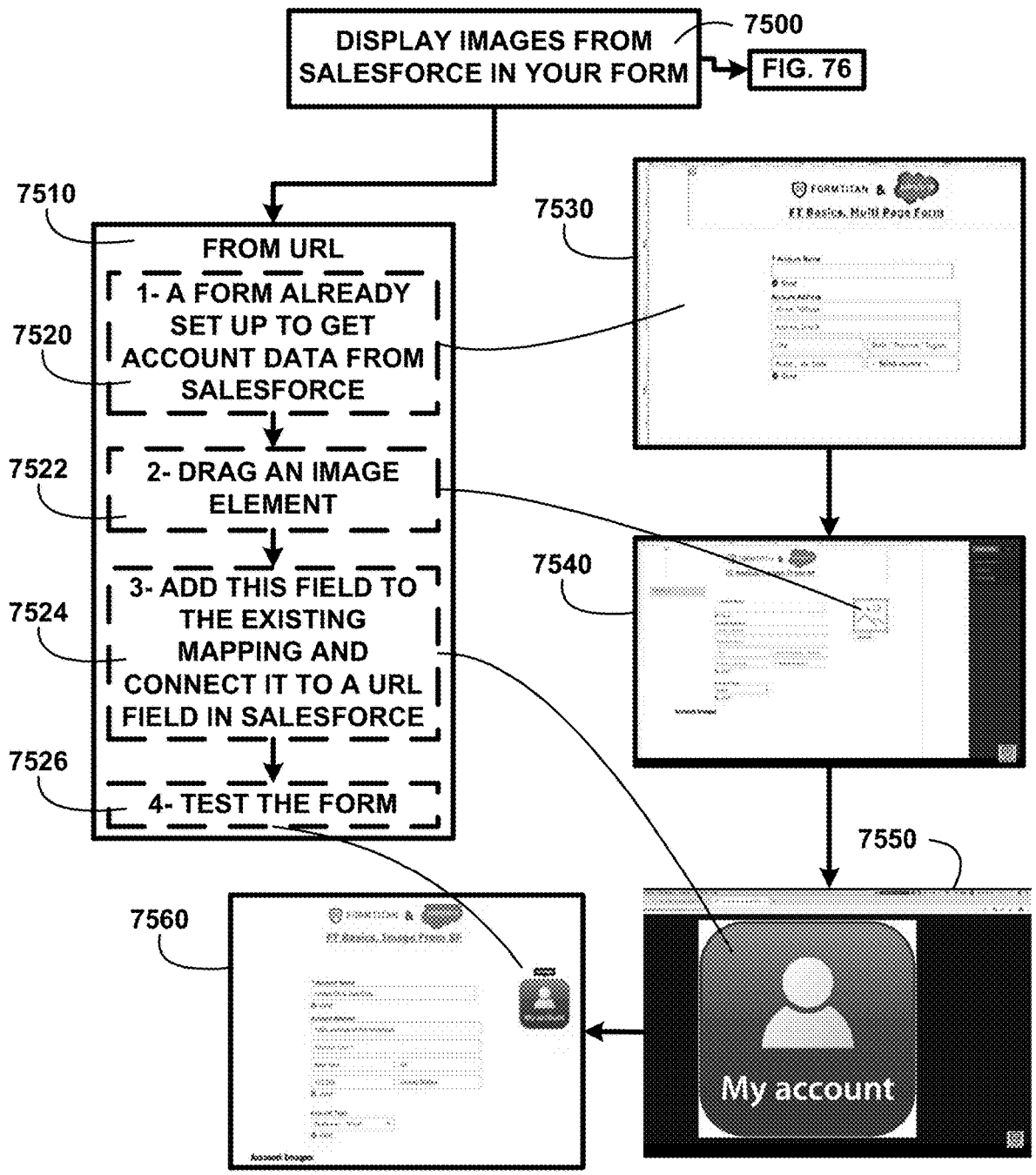
FIG. 75 shows for illustrative purposes only an example of display images from Salesforce in your form of one embodiment.
Figure 76:
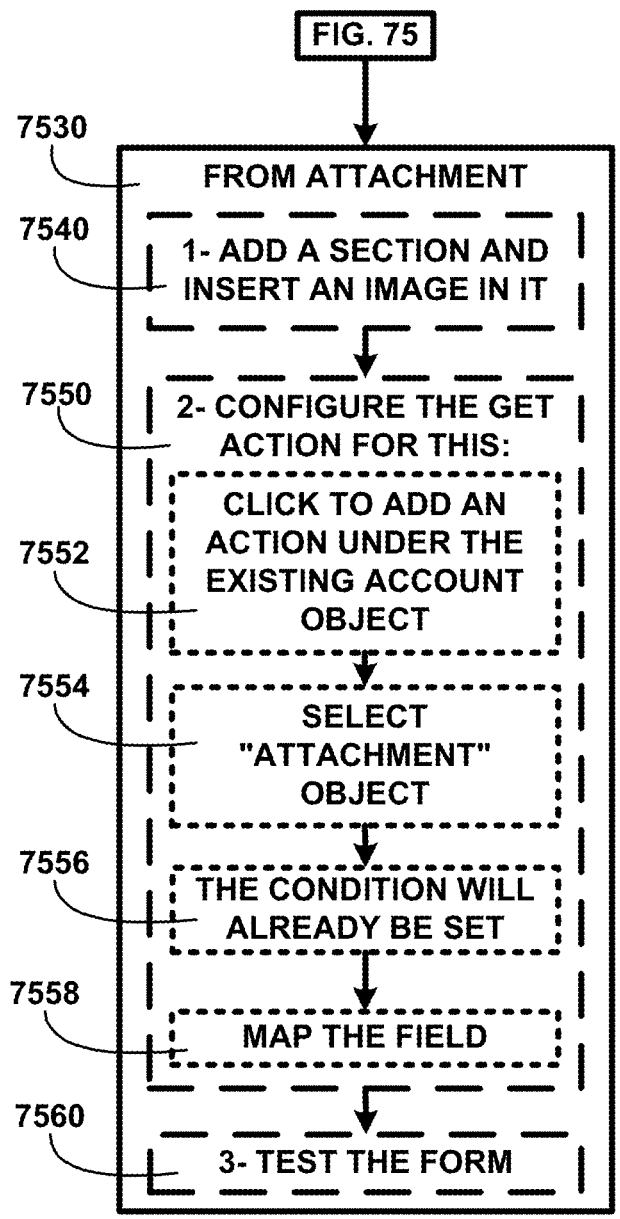
FIG. 76 shows a block diagram of an overview of display images from Salesforce attachment in a form of one embodiment.

Display Images from Salesforce in Your Form:

FIG. 75 shows for illustrative purposes only an example of display images from Salesforce in your form of one embodiment. FIG. 75 shows the steps to display images from Salesforce in your form 7500. A description of images from an attachment Is shown in FIG. 76. Images may come from URL 7510 images that can be captured. The steps for inserting an image from a URL include step 1—a form already set up to get account data from Salesforce 7520 wherein the form is a FT basics, multi page form 7530. Step 2—drag an image element 7522 places a placeholder where the user desires the image on the form. The image element 7540 is showing on the form page. Step 3—add this field to the existing mapping and connect it to a URL field in Salesforce 7524. A user may wish to add their my account image 7550 which can be selected from a file or URL site. Step 4—test the form 7526 allows the user to see the image selected on the FT basics, image from Salesforce 7560 of one embodiment.

Display Images from Salesforce Attachment in a Form:

FIG. 76 shows a block diagram of an overview of display images from Salesforce attachment in a form of one embodiment. FIG. 76 shows a continuation from FIG. 75 describing displaying an image from attachment 7530. The process includes step 1—add a section and insert an image in it 7540. The user follows step 2-configure the get action for this: 7550. The user will click to add an action under the existing account object 7552, select "attachment" object 7554 wherein the condition will already be set 7556 and then map the field 7558. With those steps completed the user can follow step 3—test the form 7560 to confirm the image is attached of one embodiment.

Figure 77:
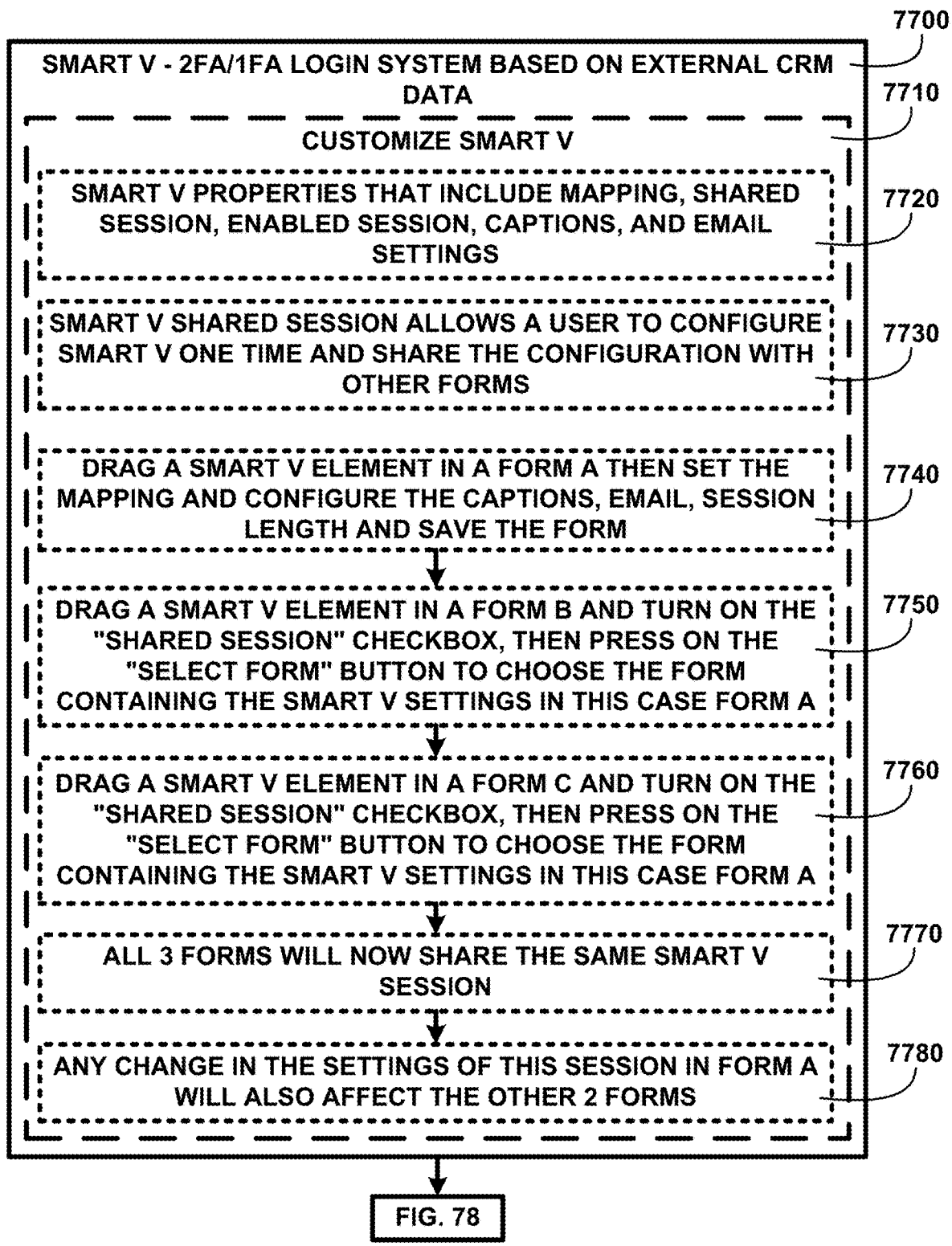
FIG. 77 shows a block diagram of an overview of a Smart V—2FA/1FA login system based on external CRM data of one embodiment.

Smart V—2FA/1FA Login System Based on External CRM Data:

FIG. 77 shows a block diagram of an overview of a Smart V—2FA/1FA login system based on external CRM data of one embodiment. FIG. 77 shows a SmartV-2FA/1FA login system based on external CRM data 7700. A user can customize Smart V 7710 for use in a FormTitan form to add Smart V properties that include mapping, shared session, enabled session, captions, and email settings 7720. A Smart V shared session allows a user to configure Smart V one time and share the configuration with other forms 7730. The user can drag a Smart V element in a form A then set the mapping and configure the captions, email, session length and save the form 7740. The user can drag a Smart V element in a form B and turn on the "shared session" checkbox, then press on the "select form" button to choose the form containing the Smart V settings in this case form A 7750. A user can drag a Smart V element in a form C and turn on the "shared session" checkbox, then press on the "select form" button to choose the form containing the Smart V settings in this case form A 7760. All 3 forms will now share the same Smart V session 7770. Any change in the settings of this session in form A will also affect the other 2 forms 7780. The description of Smart V continue in FIG. 78 of one embodiment.

Figure 78:
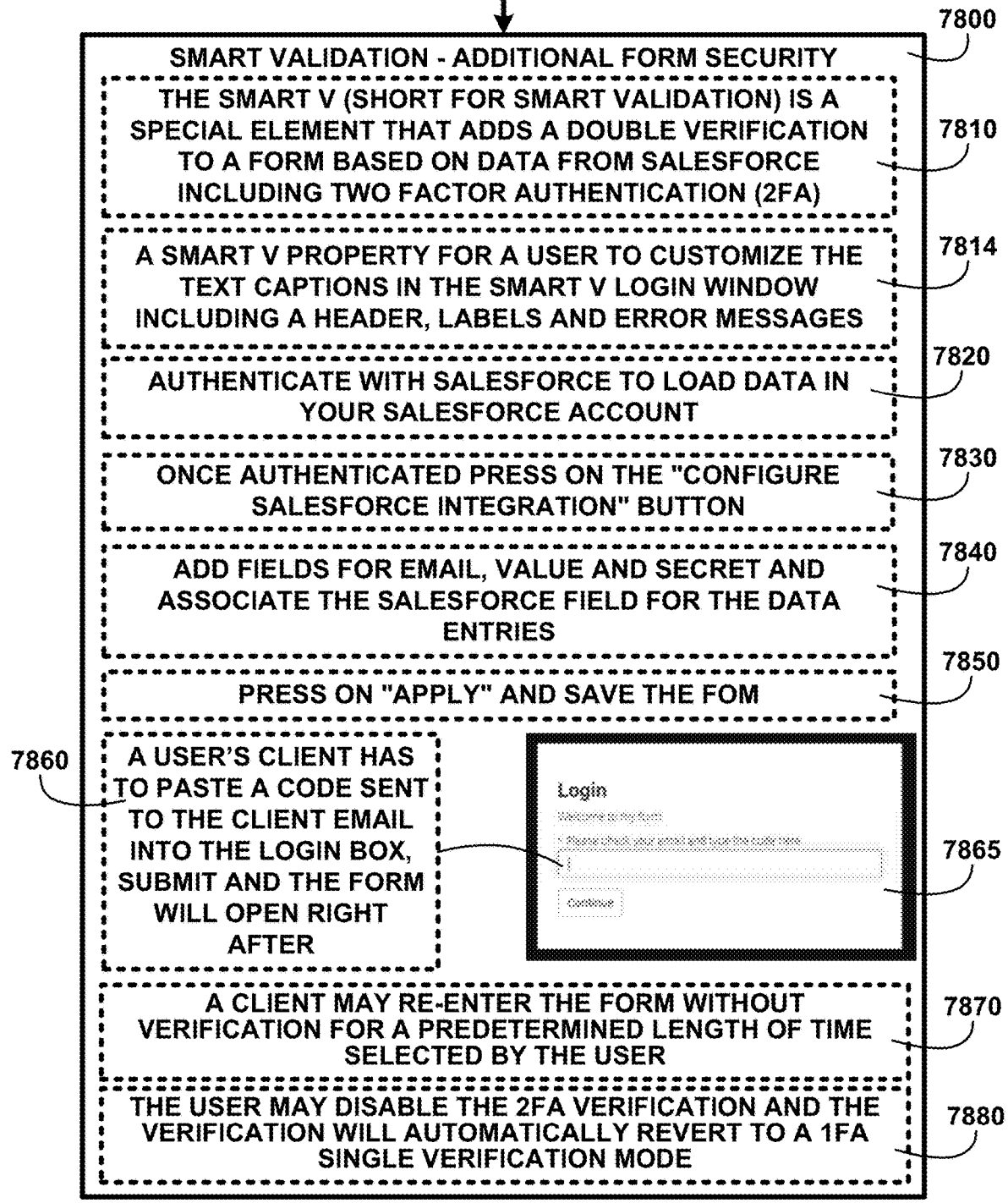
FIG. 78 shows for illustrative purposes only an example of Smart Validation—additional form security of one embodiment.

Smart Validation—Additional Form Security:

FIG. 78 shows for illustrative purposes only an example of Smart Validation—additional form security of one embodiment. FIG. 78 shows a continuation from FIG. 77. Smart V provides a user with Smart Validation—additional form security 7800. The Smart V (short for Smart Validation) is a special element that adds a double verification to a form based on data from Salesforce including two factor authentication (2FA) 7810. A Smart V property for a user to customize the text captions in the Smart V login window including a header, labels and error messages 7814. The user must authenticate with Salesforce to load data in your Salesforce account 7820. The user can once authenticated press on the "configure Salesforce integration" button 7830. The user can add fields for email, value and secret and associate the Salesforce field for the data entries 7840. The user will then press on "apply" and save the form 7850

A user's client has to paste a code sent to the client email into the login box, submit and the form will open right after 7860. The Login 7865 page of the form shows the box where the client enters the code. A client may re-enter the form without verification for a predetermined length of time selected by the user 7870. The user may disable the 2FA verification and the verification will automatically revert to a 1FA single verification mode 7880 of one embodiment.

Bi Directional, Real-Time Integration with Salesforce:

FIG. 79 shows a block diagram of an overview of bi directional, real-time integration with Salesforce of one embodiment. FIG. 79 shows a bi directional, real-time integration with Salesforce 7900 element that a user can add to a form. Bi directional, real-time integration is used to allow data to sync in all the relevant places, to help maintain a clean database, prevent data duplication, provide the most up to date information and free a user from manual data entry 7910. Data integration is setting up automatic record creation within the user CRM whenever a potential lead fills out the user website contact form 7920. The bi directional, real-time integration with Salesforce 7900 element can be used to draw contact details from a user Salesforce account and have the contact details populated in the form fields, so if the user is already listed in the user CRM the contact would not have to type in their details again 7930. Two different operations are incorporated into the integration setup 7940. One operation is reading data from Salesforce objects, which is called "GET" 7942. The other operation is writing data to Salesforce objects, which is called "PUSH" 7944. A user may create a form which only GETS data, or a form that only PUSHES data or combine the two operations and create a dual integration form 7950. The user may also use a special table element for working with Salesforce wherein the user sets up the special table configured to only retrieve the "GET" side of the integration, and the "PUSH" side of the integration is created automatically based on the "GET" data 7960 of one embodiment.

Figure 80:
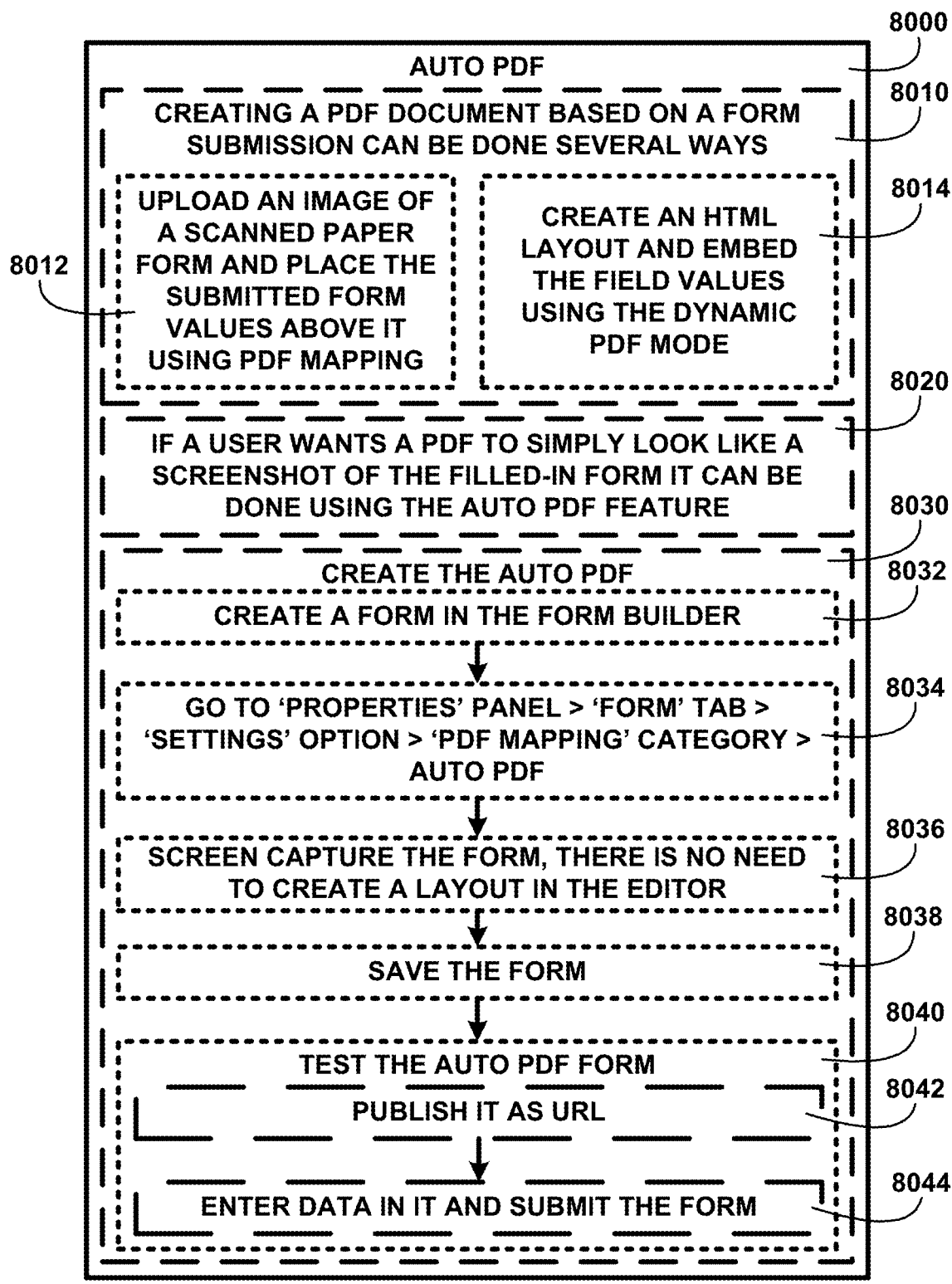
FIG. 80 shows a block diagram of an overview of an auto pdf element of one embodiment.

An Auto Pdf Element:

FIG. 80 shows a block diagram of an overview of an auto pdf element of one embodiment. FIG. 80 shows an auto pdf 8000 element for creating a pdf document based on a form submission can be done several ways 8010. One way a user can create a pdf document is to upload an image of a scanned paper form and place the submitted form values above it using pdf mapping 8012. Another way a user can create a pdf document is to create an html layout and embed the field values using the dynamic pdf mode 8014. PDF modes include a PDF Interactive mode that allows a filler to enter and edit the entered data from within a PDF preview window. This allows the filler to perform inline editing of the PDF data from within the PDF preview, without having to return to the form. Once the filler approves the PDF in the preview window the filler would submit the form and generate the PDF.

If a user wants a pdf to simply look like a screenshot of the filled-in form it can be done using the auto pdf feature 8020. A user can create the auto pdf 8030 using the following steps including create a form in the form builder 8032. A user will go to 'properties' panel>'form' tab>'settings' option>'pdf mapping' category>auto pdf 8034. The user can screen capture the form, there is no need to create a layout in the editor 8036 then save the form 8038. Upon completion the user can test the auto pdf form 8040 using a step to publish it as URL 8042. The user can then enter data in it and submit the form 8044 of one embodiment.

Figure 81:
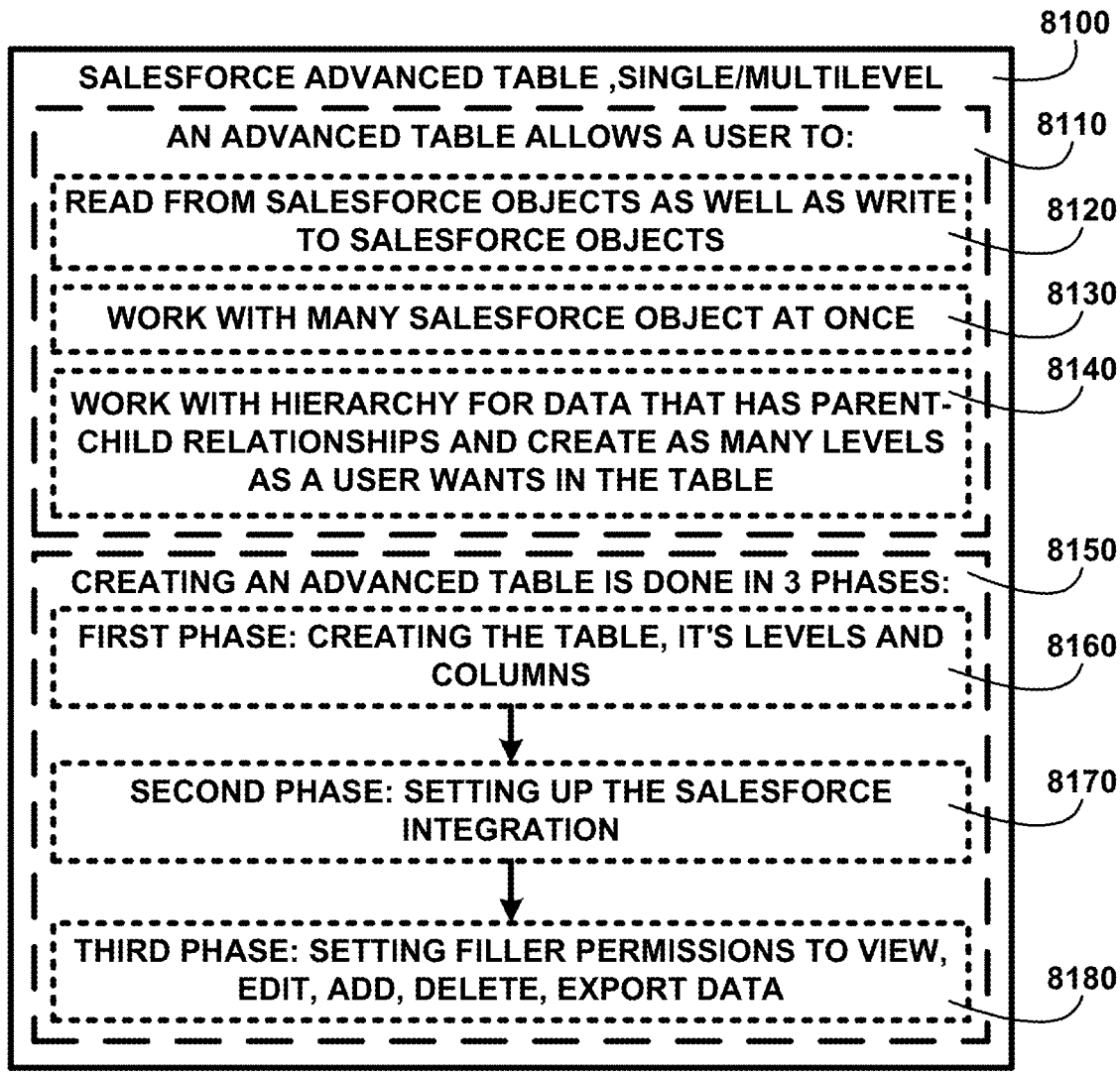
FIG. 81 shows a block diagram of an overview of a Salesforce advanced table, single/multilevel of one embodiment.

Salesforce Advanced Table, Single/Multilevel:

FIG. 81 shows a block diagram of an overview of Salesforce advanced table,single/multilevel of one embodiment. FIG. 81 shows a Salesforce advanced table,single/multilevel 8100 element. An advanced table allows a user to: 8110 read from Salesforce objects as well as write to Salesforce objects 8120, work with many Salesforce object at once 8130 and work with hierarchy for data that has parent-child relationships and create as many levels as a user wants in the table 8140. The user can perform steps for creating an advanced table is done in 3 phases: 8150. A first phase: creating the table, its levels and columns 8160. A second phase: setting up the Salesforce integration 8170. A third phase: setting filler permissions to view, edit, add, delete, export data 8180.

The First Phase: Creating the table, it's levels and columns 8160 includes the following steps 1—Enter a new/or existing form in the form builder. Step 2—Drag a table element from "Elements" panel>Widgets>Table. Step 3—Enlarge the table on canvas using the resizing handles. Step 4—Once selected, the table's properties will open in the "Properties" panel (on the right side). Step 5—Change the default column values from Col1, Col2, Col3 to the Salesforce object fields a user would like to display in the table. For example: if a user wishes to display information from the "Account" Salesforce object a user could set the following columns: Account Name, Account Phone, Account Website. *Please notice that this is the configuration for the first level of the table—displaying the parent object data. Step 6—A user can, of course, add more columns, or remove columns according to a user's requirements. Step 7—You can add a filter row to the table, just below the headers, to help the user search for specific data—by turning on the "Show filter" checkbox. Step 8—Max Rows property allows a user to enter a maximum number of rows that can be displayed in the table level. If, for example a user set a max number of 10, then the form filler will only be able to add rows to this Table level until it reaches the max number. After that—the "Add" button will become disabled. Step 9—The 'Rows per page' property allows a user to define how many rows will the table display in each page. Step 10—Change the table style—the table's appearance, just like any FormTitan element, can be easily altered in the Element style. Go to: "Properties" panel>"Element" tab>Style" option> and open the "Apply style to" drop down. Choose the parts of the table to apply a style to one by one. A user can change the style of the table in general, the rows, table header, columns and even the modal window of the "Edit"/"Add"/"View"/"Delete" options. Step 11—make the style changes in the relevant categories. For example: Choose "Table" in the "Apply style to" dropdown, and specify a pale blue color in the background. Step 12—Ok, so now that the first level is configured a user can start creating the next level in the table. Go to "Properties" panel>"Form" tab>"Settings" options>"Advanced" category press on the "Add level" button. a new level will appear on canvas containing the default columns (Col 1, Col 2, Col3) In addition 2 links will now be added inside the table element on canvas, for moving between the levels and also a "Previous" button for the user—to go back to the first level. And Step 13—Set the fields of the child Salesforce object. "Properties" panel>"Element">"Settings" option>"Basic" category>change column names. For example: if a user wishes to display the Contacts of each account a user could set the following columns: Contact last name, Contact first name, Birth date of one embodiment.

The Second Phase: Setting up the Salesforce integration 8170 includes additional steps including Step 14—Start by going to the Salesforce integration. Go to the "Properties" panel>"Form" tab>"Settings">open the "Salesforce Integration" category. Notice that there are two sections here: the top one is "Push to Salesforce", in which a user configures the "writing" operations (creating, updating, upserting, deleting data in Salesforce objects). and the bottom section is "Get from Salesforce", in which a user configures the "Reading" from Salesforce objects. Choose the ""Get from Salesforce" section and press on the "Map Fields" button. Step 15—Authenticate with Salesforce and press on the "Add object" button. Step 16—Start mapping according to the selected table levels—start from the first level and work down. So the first Salesforce object a user would need to "read" from. according to this example is Account. Open the dropdown and choose it. Step 17—Turn on the "execute on form load" checkbox—this will "pull" the data from Salesforce and populate the table once the form is loading. Step 18—There is no need to set a condition in this case, however, we will choose to display "All" matches found. As well as limit the number of accounts we show to 200. Step 19—Map the form fields (in this case, level #1 table columns) to the Salesforce object fields. And press on "Apply". Step 20—Once done, a user will see that a single integration line has been created. This line holds the mapping to the first level of the table. (a user can edit it using the edit icon on the right). Press on "Apply" and save the form. Step 21—Now a user will need to add the integration for the second level of the table and map the contact fields. Since we would like to display the contacts belonging to each account in hierarchy, we will need to add the next object as a child of the first object. Press on the "Add object" button located at the bottom of the window. Step 22—Select the "Contact" object from the drop down. You will now need to add a condition in order to set the parent-child relationship like so: Choose to display "All" matches found. As well as limit the number of accounts we show to 200. Step 23'And map the contact fields to the Contact object fields in Salesforce. press "Apply". Step 24—You will now see 2 integration lines. The first is the account line, and the second line, will hold the mapping to the contact object. Step 25—Publish the form to see the result. Press on the "Publish" icon in the main toolbar above Press on the "View" button to see the form. And Step 26—And this is the published form—with the data populated straight from Salesforce—in real-time. On the left part of the table a user will see the columns the user set. On the right part a user will see a column called "Next level", which holds buttons that will lead to the data in the second level of one embodiment.

The Third Phase: Setting filler permissions to View, Edit, Add, Delete, Export data 8170 includes Step 27—Making table columns editable Now that the table levels are set, and the Salesforce integration configured a user can allow a filler to "Read" data from Salesforce. If a user wishes to add more functionality and enable "writing" a user can easily do that by setting permissions. "Properties" panel>"Form" tab>"Settings" options>"Advanced" category and turn on the checkboxes according to the needs: —Allow view—this will enable the form filler to view more data than is displayed in the table columns. when a user turns on this checkbox a configure button will appear and a user will need to press on it. a window will then open listing this level's column names and a user will need to turn on the checkboxes of the fields a user wishes to make viewable. In addition a user will be able to add fields for viewing. —Allow edit—this will enable the form filler to edit the data in this level and by doing so, to update the Salesforce object. When a user turns on this checkbox a configure button will appear and a user will need to press on it. a window will then open listing this level's column names and a user will need to turn on the checkboxes of the fields a user wishes to make editable. —Allow add—this will enable the form filler to add new data in this level and by doing so, to add data inside the Salesforce object. when a user turn on this checkbox a configure button will appear and a user will need to press on it. a window will then open listing this level's column names and a user will need to turn on the checkboxes of the fields a user wishes have the user fill in when he wants to create a new item. You can restrict the number of rows in the table by mapping the "MaxRows" property of the table in the GET operation. If a user maps that then the user can only add rows as long as the total rows in the table are less than the MaxRows set to. —Allow delete—this will enable the form filler to delete data in this level and by doing so, to have the data deleted in the Salesforce object. —Allow Export—this option will allow the form filler to export the data in the current level he is in. When a user turns on this checkbox a new "Export" button will be added at the bottom of the table and when the user presses on it the data in the level will be downloaded in CSV. Step 28—If a user wants a filler to be able to update the second level of the table a user can set the "writing" permissions, just like a user did in the first level. (go to "Properties" panel>"Form" tab>"Settings" options>"Advanced" category. and turn on the checkboxes according to the needs). Step 29—Adding fields to the View/Edit/Add windows (in addition to the column fields) While a user wants the table to stay compact and show only the most important fields, a user may want to have fields added to the Add/Edit modal windows so they may also be updated. Adding a field is easy—all a user has to do is choose it from the dropdown below and press on "Add". Once a user adds a field to the Add/Edit window a user will have 3 options: 1—The field will be added to the specific window and its data loaded from Salesforce. Once a user add a field its default mode will be to load the data from Salesforce and s will indeed see that the "Load data" checkbox is turned on.

2—The field will be added to the specific window and its data will be loaded from a selected field in the form. In order to do this a user will need to turn on the "Map value" checkbox (this will remove the "load data" checkbox). A dropdown will then appear on the right containing fields from the form. Read more about loading a selected field from Salesforce. 3—The field will be added to the specific window and its data will be loaded from a field within the Table. In order to do this a user will need to turn on the "Map value" checkbox. A dropdown will then appear on the right containing the object in Level 1, and once selected another dropdown will appear so a user can select the field a user wants to map to. Step 30—If a user has a hidden field in the form, a user will be able to store the relevant record ID in it—the record id of the viewed record, the edited record or the added record (depending on which window a user is doing this from). And Step 31—Now go and test the form again: If a user has added the permission to edit or delete the items in the table—a user will also see 2 more columns, containing links to edit & delete. If a user has added the permission to add a new item—an "Add" button will be added at the bottom of the table of one embodiment.

Figure 82:
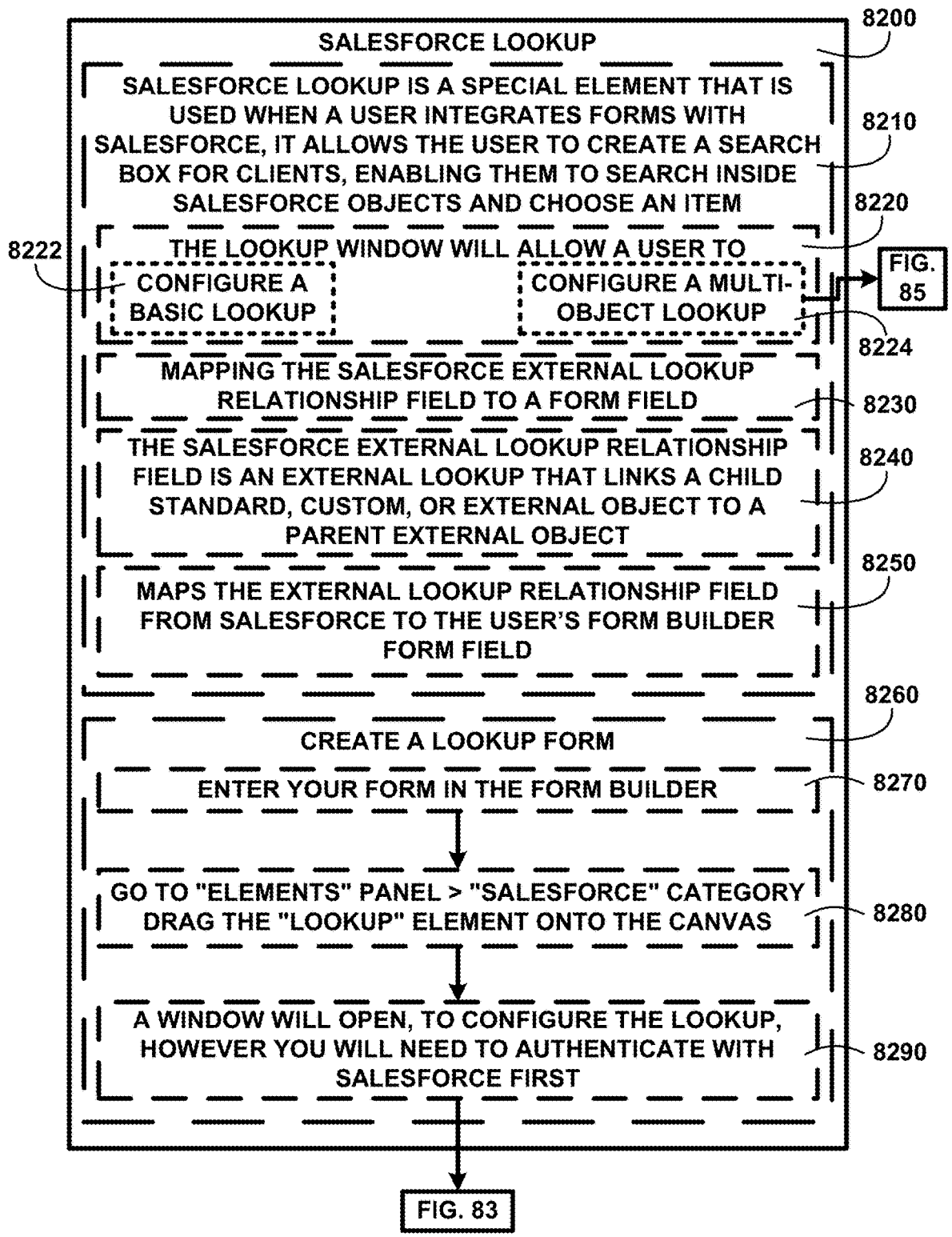
FIG. 82 shows a block diagram of an overview of a Salesforce lookup of one embodiment.

Salesforce Lookup:

FIG. 82 shows a block diagram of an overview of Salesforce lookup of one embodiment. FIG. 82 shows Salesforce lookup 8200 is an element of the FormTitan form builder a user may customize their form by using for particular tasks. Salesforce lookup is a special element that is used when a user integrates forms with Salesforce, it allows the user to create a search box for clients, enabling them to search inside Salesforce objects and choose an item 8210. The lookup window will allow a user to 8220 configure a basic lookup 8222 and/or configure a multi-object lookup 8224 as described in FIG. 85. The user can follow these steps to set up a Salesforce lookup. A user will perform mapping the Salesforce external lookup relationship field to a form field 8230. The Salesforce external lookup relationship field is an external lookup that links a child standard, custom, or external object to a parent external object 8240. The user maps the external lookup relationship field from Salesforce to the user's form builder form field 8250 to create a lookup form 8260. A user will then enter the form in the form builder 8270 and go to "elements" panel>"Salesforce" category drag the "lookup" element onto the canvas 8280. A window will open, to configure the lookup, however the user will need to authenticate with Salesforce first 8290. The descriptions continue on FIG. 83 of one embodiment.

Figure 83:
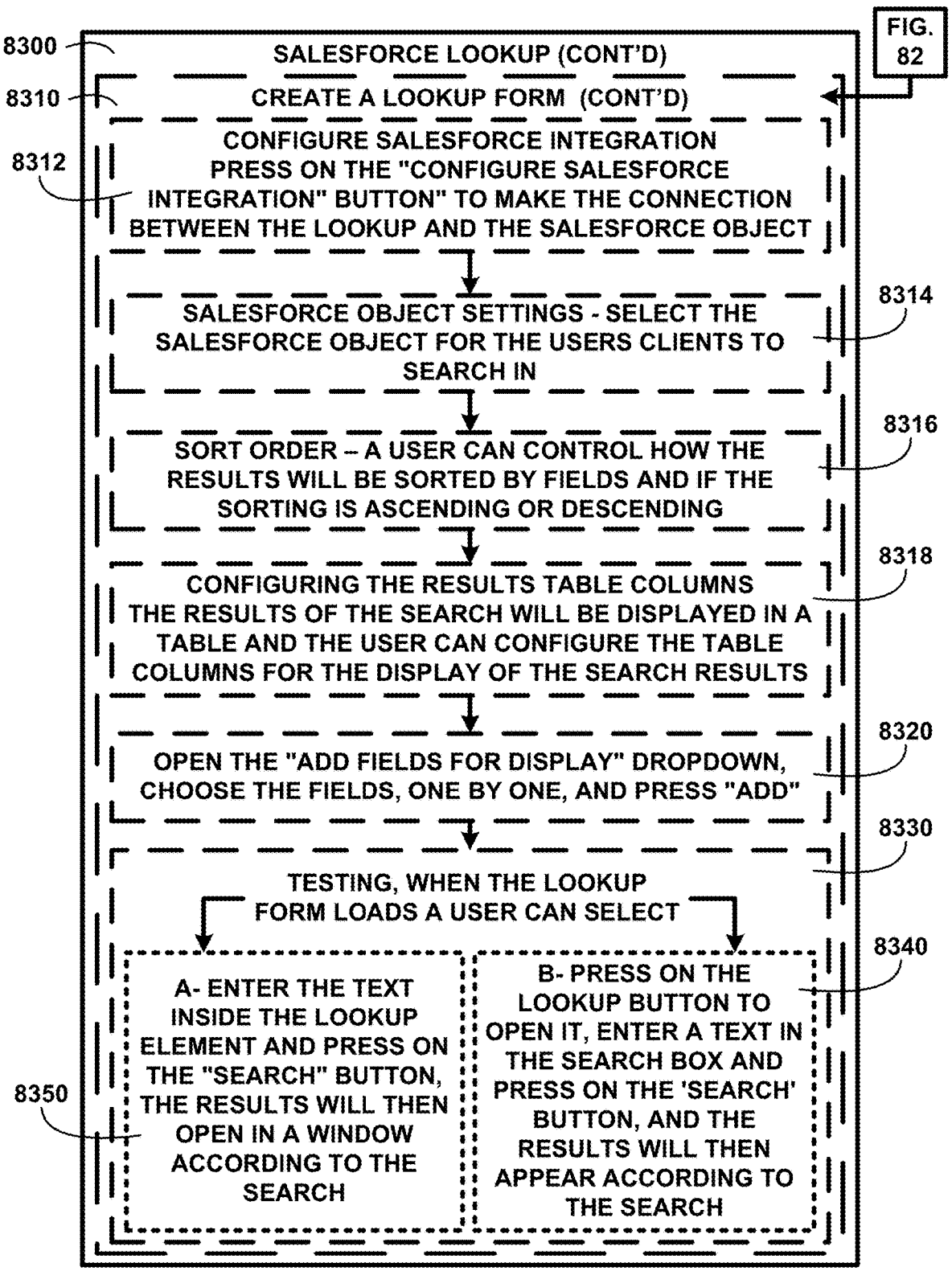
FIG. 83 shows a block diagram of an overview of create a lookup form of one embodiment.

Create a Lookup Form:

FIG. 83 shows a block diagram of an overview of a process to create a lookup form of one embodiment. FIG. 83 shows the Salesforce lookup (cont'd) 8300 from FIG. 82 and the create a lookup form (cont'd) 8310. A user to configure Salesforce integration press on the "configure Salesforce integration" button" to make the connection between the lookup and the Salesforce object 8312. A Salesforce object settings—select the Salesforce object for the users clients to search in 8314. The user can add a sort order—a user can control how the results will be sorted by fields and if the sorting is ascending or descending 8316. A user continues configuring the results table columns the results of the search will be displayed in a table and the user can configure the table columns for the display of the search results 8318. The user will open the "add fields for display" dropdown, choose the fields, one by one, and press "add" 8320. A user can perform testing, when the lookup form loads a user can select 8330 from two choices. On choice is A—enter the text inside the lookup element and press on the "search" button, the results will then open in a window according to the search 8350 and the other choice is B— press on the lookup button to open it, enter a text in the search box and press on the 'search' button, and the results will then appear according to the search 8340 of one embodiment.

Figure 84:
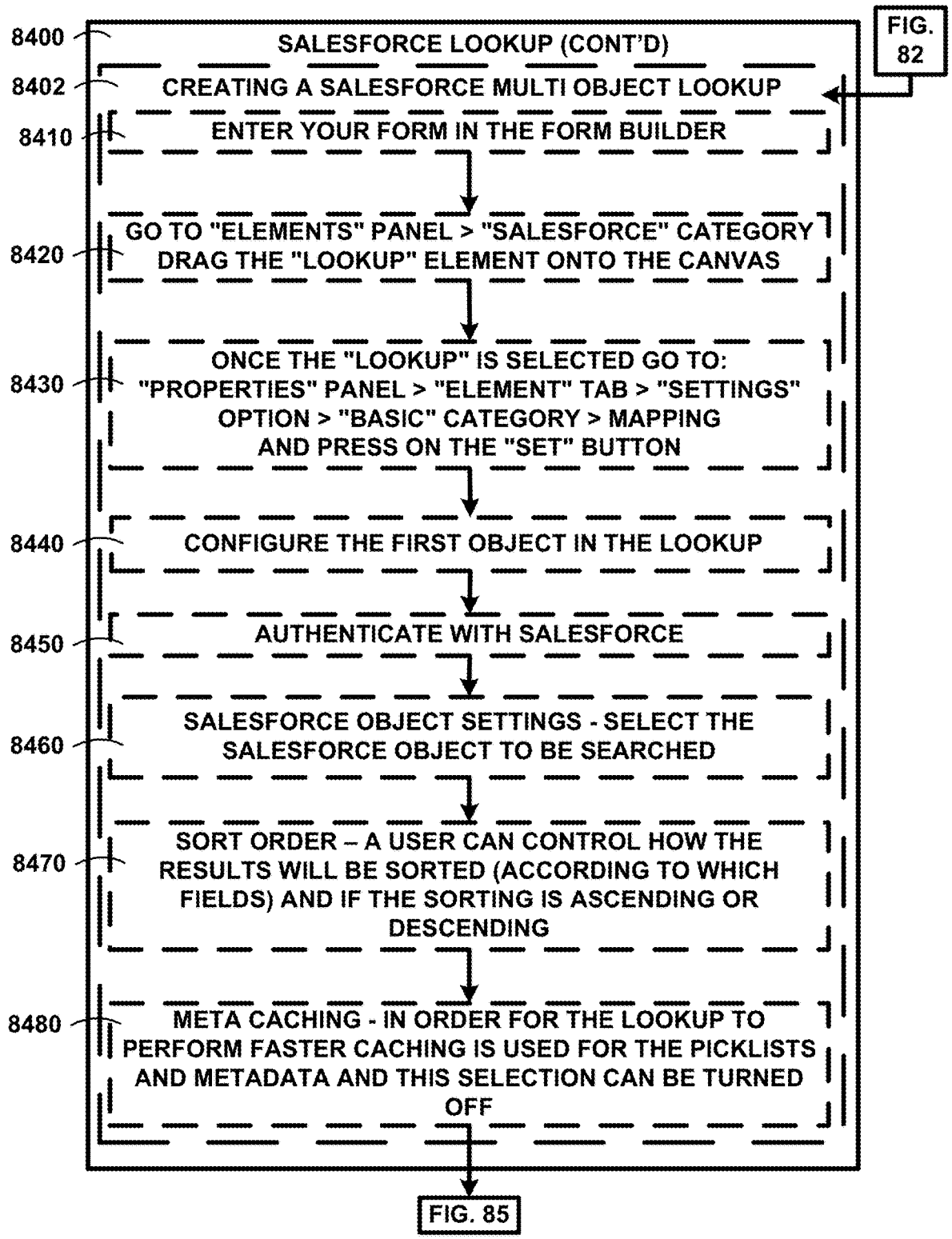
FIG. 84 shows a block diagram of an overview of a Salesforce multi object lookup of one embodiment.

A Salesforce Multi Object Lookup:

FIG. 84 shows a block diagram of an overview of a Salesforce multi object lookup of one embodiment. FIG. 84 shows the Salesforce lookup (cont'd) 8400 from FIG. 82 for creating a Salesforce multi object lookup 8402. A user will enter the form in the form builder 8410 then go to "elements" panel>"Salesforce" category drag the "lookup" element onto the canvas 8420. Once the "lookup" is selected go to: "properties" panel>"element" tab>"settings" option>"basic" category>mapping and press on the "set" button 8430 to configure the first object in the lookup 8440. A user will authenticate with Salesforce 8450 and using the Salesforce object settings—select the Salesforce object to be searched 8460. A user may include a sort order—a user can control how the results will be sorted (according to which fields) and if the sorting is ascending or descending 8470. FormTitan uses meta caching—in order for the lookup to perform faster caching is used for the picklists and metadata and this selection can be turned off 8480. The descriptions continue in FIG. 85 of one embodiment.

Figure 85:
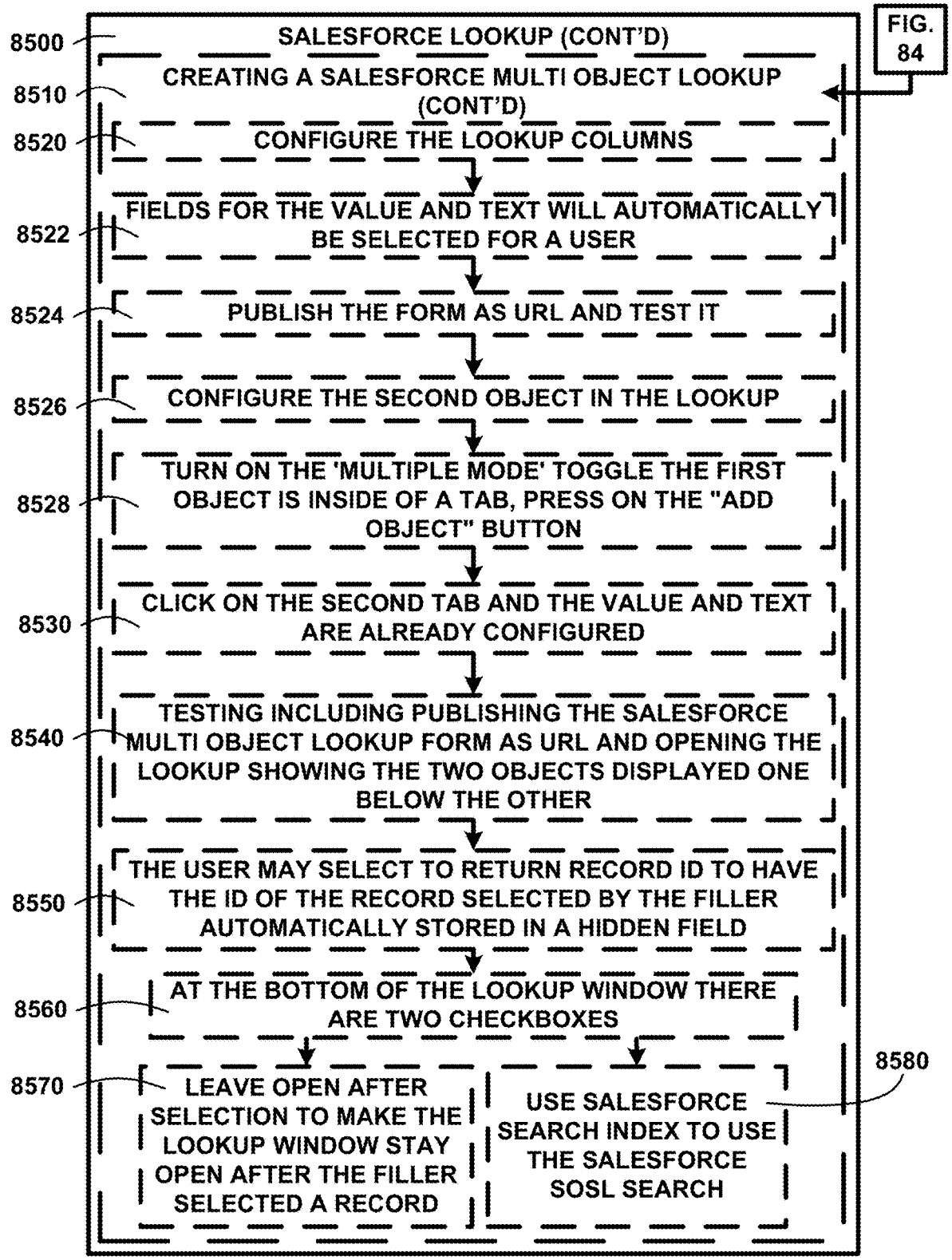
FIG. 85 shows a block diagram of an overview of creating a Salesforce multi object lookup (cont'd) of one embodiment.

Creating a Salesforce Multi Object Lookup:

FIG. 85 shows a block diagram of an overview of creating a Salesforce multi object lookup (cont'd) of one embodiment. FIG. 85 shows the Salesforce lookup (cont'd) 8500 from FIG. 84 for creating a Salesforce multi object lookup 8510. A user will configure the lookup columns 8520 and fields for the value and text will automatically be selected for a user 8522. The user will then publish the form as URL and test it 8524. The user continues to configure the second object in the lookup 8526. After configuring the second object the user will turn on the 'multiple mode' toggle the first object is inside of a tab, press on the "add object" button 8528. The user will click on the second tab and the value and text are already configured 8530. The user will continue testing including publishing the Salesforce multi object lookup form as URL and opening the lookup showing the two objects displayed one below the other 8540. The user may select to return record ID to have the ID of the record selected by the filler automatically stored in a hidden field 8550. At the bottom of the lookup window there are two checkboxes 8560. The two checkboxes allows the user to make a selection to leave open after selection to make the lookup window stay open after the filler selected a record 8570 and to use Salesforce search index to use the Salesforce SOSL search 8580 to make the search faster and increase the search results of one emobodiment.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A method, comprising:
providing a website interface within a customizable application builder with non-line by line coding visualization tools for an application creation user;
providing a form builder for creating at least one form using at least one component of the non-line by line coding visualization tools configured to integrate bi-directional form data with a third party customer relationship management platform and including at least one form element for receiving the form data input from an end user, each associated with a conditional rule builder, an auto pdf mapping tool, a manual pdf mapping tool and at least two dynamic pdf mapping tools;
wherein the bi-directional form data includes application creation user and end user controls for getting and pushing data between the third party customer relationship management platform and the form before submission of the form;
wherein upon submission of the form, the auto pdf mapping tool is configured to automatically generate a pdf form representing a replicated html version of the form, including integrating form elements and form input from the end user;
wherein the manual pdf mapping tool includes non-line by line coding visualization tools that allows the application creation user to drag and drop form elements onto a predetermined pdf template file, wherein upon submission of the form, the manual pdf mapping tool automatically generates a customizable pdf of the form that includes the customizable form elements with the form input from the end user;
wherein the dynamic pdf mapping tool includes non-line by line coding visualization tools that allows the application creation user to drag and drop form elements onto a blank editable html template or edit the html of the blank html template, wherein upon submission of the form, the dynamic pdf mapping tool dynamically generates a customizable pdf of the form that includes the customizable form elements with the form input from the end user; and
wherein the at least one form element includes a customizable smart validation element configured to provide end users with at least one login for accessing information associated with the integrated bi-directional form data of the third party customer relationship management platform that is an alternative login to an administrative login of the third party customer relationship management platform.

2. The method of claim 1, further comprising using user selected smart phone physical movement for activating features including a quick side to side shaking movement to activate a publish form feature and a top to bottom shaking movement to activate a form submit button.

3. The method of claim 1, further comprising integrating third party applications includes augmented reality apps for interactive operations with others, search APIs for combining content from webpages, images, videos, and news into a form, language apps for processing natural language with pre-built scripts, evaluate sentiment and learn how to recognize what users want, cloud apps for data management operations, cognitive services apps and other apps.

4. The method of claim 1, further comprising providing the at least one form element including a voice control element configured to allow the text of a user's form to be spoken to a filler pronouncing the names of the fields and their user tips out loud and wherein the voice control element for receiving a filler's spoken input, recognize the filler's speech, enter the filler's oral text in the input boxes of the form, create a new blank form and drag a textbox element and a numeric element into a form.

5. The method of claim 1, further comprising providing the at least one form element including a conditional logic element configured to affect fields, sections and pages in a form: to hide/show, enable/disable, set values and use value rules to determine what values the fields should or should not accept.

6. The method of claim 1, further comprising using the customizable application builder with non-line by line coding visualization tools for creating a cross platform integration application for third party health level seven electronic health records using the customized customer relationship management platform created forms.

7. The method of claim 1, further comprising using at least one form element configured for auto save/push and auto pull selections when selected in settings to automatically save the data entered in the customizable application builder and also simultaneously in a customer relationship management platform integrated system including third party customer relationship management integrated platforms without a user having to enter any additional commands.

8. The method of claim 1, further comprising using at least one form element configured for adding a smart validation element that adds a double verification to a form based on data from third party customer relationship management integrated platforms including two factor authentication (2FA) wherein a user's client has to paste a code sent to the client email into the login box before the form will open.

9. The method of claim 1, further comprising using at least one form element configured for smart real-time integrations, bidirectional third party customer relationship management integrated platforms and dynamic customer relationship management platform real-time integrations and also including settings including auto save/push, auto pull, auto translate, custom translate, and phone survey.

10. The method of claim 1, further comprising using at least one form element configured for creating a third party customer relationship management integrated platform single or multi object lookup and for using an advanced third party customer relationship management integrated platform table configured for a single or multilevel table for displaying the third party customer relationship management integrated platform single or multi object lookup search results.

11. An apparatus, comprising:
a website interface within a customizable application builder with non-line by line coding visualization tools for an application creation user;
at least one device for creating user forms in a pdf format for receiving form input from an end user, each associated with a conditional rule builder, an auto pdf mapping tool, a manual pdf mapping tool and at least two dynamic pdf mapping tools;
at least one form element configured with a customizable smart validation element configured for providing end users with at least one login for accessing information associated with the integrated bi-directional form data of a third party customer relationship management platform;
wherein the customizable smart validation element is an alternative login to an administrative login of the third party customer relationship management platform;
wherein the at least two dynamic pdf mapping tools are configured to include in-line and on-screen writing and editing capabilities by the end user after the form is submitted to allow dynamic changes to the pdf;
a digital device application for user mobile interaction including a mini mode element wherein a work area will have a maximum width of 180px for use on digital devices with narrow display screens; and
a digital memory device for storing user customer relationship management platform data and including an indexing system used for a user customer relationship management platform application single or multi object lookup element to allow a user to search for one or more objects in the customer relationship management platform data.

12. The apparatus of claim 11, further comprising at least one a voice control element configured to allow text of a user's form to be spoken to a filler pronouncing names of the fields out loud.

13. The apparatus of claim 11, further comprising at least one device for creating user forms in a pdf format configured to include a pdf Interactive mode for inline editing of pdfs from a pdf preview window.

14. The apparatus of claim 11, further comprising at least one device for creating codes for use with a smart validation two factor authentication (2FA) security system wherein a user may disable the 2FA verification and the verification will automatically revert to a 1FA single verification mode.

15. The apparatus of claim 11, further comprising at least one device for creating user forms in a pdf format configured to perform a screen capture of a user existing form, and converting it to a fillable pdf form.

16. An apparatus, comprising:
a customized customer relationship management platform network including at least one server configured to automatically send and receive new and updated user customer relationship management platform data to at least one third party digital device application without user input;
at least one device for creating user pdf forms using user customer relationship management platform data configured to perform a screen capture of a user existing form, and converting it to a fillable pdf form;
wherein the customized customer relationship management platform includes a dynamic pdf editor configured to allow a user to enter content in the dynamic pdf editor with in-line and on-screen writing and editing capabilities by the end user after the form is submitted but before a final pdf of the form is created to allow the final pdf form to include the entered content;
at least one form element configured with a customizable smart validation element configured for providing users with an alternative login to an administrative login of a third party customer relationship management platform; and
a digital device for converting user mobile interaction with a customer relationship management platform application wherein a work area will have a maximum width of 180px for use on digital devices with narrow display screens.

17. The apparatus of claim 16, further comprising at least one device configured for smart real-time integrations, automatic bidirectional third party customer relationship management integrated platform and dynamic customer relationship management platform real-time integrations and also including settings including auto save/push, auto pull, auto translate, custom translate, and phone survey for automatically sending and receiving new and updated user customer relationship management platform data.

18. The apparatus of claim 16, further comprising at least one a voice control element configured to allow text of a user's form to be spoken to a filler pronouncing names of the fields out loud using a language selected by the filler.

19. The apparatus of claim 16, further comprising the customized customer relationship management platform network configured for a cross platform integration application for health level seven electronic health records using the customized customer relationship management platform created forms.

20. The apparatus of claim 16, further comprising the at least one device for creating user pdf forms configured to include a conditional logic element configured to affect fields, sections and pages in a form: to hide/show, enable/disable, set values and use value rules to determine what values the fields should or should not accept.

* * * * *